US008623375B2

(12) United States Patent
Crowe et al.

(10) Patent No.: US 8,623,375 B2
(45) Date of Patent: Jan. 7, 2014

(54) CHIMERIC OSPA GENES, PROTEINS, AND METHODS OF USE THEREOF

(75) Inventors: Brian A. Crowe, Leobendorf (AT); Ian Livey, Vienna (AT); Maria O'Rourke, Vienna (AT); Michael Schwendinger, Neusiedl Am See (AT)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/107,787

(22) Filed: May 13, 2011

(65) Prior Publication Data

US 2011/0293652 A1    Dec. 1, 2011

Related U.S. Application Data

(60) Provisional application No. 61/334,901, filed on May 14, 2010.

(51) Int. Cl.
| | | |
|---|---|---|
| A61K 39/40 | (2006.01) | |
| A61K 39/116 | (2006.01) | |
| C12N 15/63 | (2006.01) | |
| C12N 1/19 | (2006.01) | |
| C12P 21/02 | (2006.01) | |
| C07K 14/20 | (2006.01) | |

(52) U.S. Cl.
USPC ............... 424/190.1; 424/234.1; 530/350

(58) Field of Classification Search
None
See application file for complete search history.

(56) References Cited

U.S. PATENT DOCUMENTS

| 4,179,337 A | 12/1979 | Davis et al. |
| 4,376,110 A | 3/1983 | David et al. |
| 4,816,567 A | 3/1989 | Cabilly et al. |
| 4,855,283 A | 8/1989 | Lockhoff et al. |
| 4,877,612 A | 10/1989 | Berger et al. |
| 5,234,784 A | 8/1993 | Aslam et al. |
| 5,252,714 A | 10/1993 | Harris et al. |
| 5,585,089 A | 12/1996 | Queen et al. |
| 5,688,512 A | 11/1997 | Bergstrom et al. |
| 5,693,762 A | 12/1997 | Queen et al. |
| 5,777,095 A | 7/1998 | Barbour et al. |
| 5,942,236 A | 8/1999 | Lobet et al. |
| 6,083,722 A | 7/2000 | Bergstrom et al. |
| 6,143,872 A | 11/2000 | Barbour et al. |
| 6,183,986 B1 | 2/2001 | Bergstrom et al. |
| 6,203,798 B1 | 3/2001 | Bergstrom et al. |
| 6,248,562 B1 | 6/2001 | Dunn et al. |
| 6,676,942 B1 | 1/2004 | Lobet et al. |
| 7,008,625 B2 | 3/2006 | Dattwyler et al. |
| 7,094,391 B1 | 8/2006 | Barbour et al. |
| 2009/0326200 A1 | 12/2009 | Luft et al. |
| 2010/0292096 A1 | 11/2010 | Luft et al. |

FOREIGN PATENT DOCUMENTS

| EP | 0109942 B1 | 5/1984 |
| EP | 0231039 B1 | 8/1987 |
| EP | 0401384 B1 | 12/1990 |
| EP | 0598816 B1 | 6/1994 |
| EP | 0711563 B1 | 5/1996 |
| EP | 0726955 B1 | 8/1996 |
| EP | 1080109 B1 | 3/2001 |
| EP | 1311682 B1 | 5/2003 |
| EP | 1939294 A1 | 7/2008 |
| GB | 2189141 A | 10/1987 |
| WO | WO-90/04411 A1 | 5/1990 |
| WO | WO-92/14488 A1 | 9/1992 |
| WO | WO 9304175 A1 * | 3/1993 |
| WO | WO-97/28818 A1 | 8/1997 |
| WO | WO-99/10494 A2 | 3/1999 |
| WO | WO-99/30733 A1 | 6/1999 |
| WO | WO-02/16421 A2 | 2/2002 |
| WO | WO 0216422 A2 * | 2/2002 |
| WO | WO-2006/014292 A2 | 2/2006 |
| WO | WO-2008/101667 A1 | 8/2008 |
| WO | WO-2009/131665 A1 | 10/2009 |
| WO | WO-2009/135118 A2 | 11/2009 |

OTHER PUBLICATIONS

Dykuizen et al. (PNAS vol. 90, pp. 10163-10167).*
Altschul et al., Basic local alignment search tool. *J. Mol. Biol.* 215:403-10 (1990).
Batzer et al., Enhanced evolutionary PCR using oligonucleotides with inosine at the 3'-terminus. *Nucleic Acid Res.* 19:5081 (1991).
Bayer et al., Protein biotinylation. *Meth. Enzym.* 184:138-163 (1990).
Benach et al., A murine IgM monoclonal antibody binds an antigenic determinant in outer surface protein A, an immundominant basic protein of the Lyme disease spirochete. *J. Immunol.* 140: 265-72 (1988).
Bergstrom et al., Molecular analysis of linear plasmid-encoded major surface proteins, OspA and OspB, of the Lyme disease spirochaete *Borrelia burgdorferi*. *Molec. Microbiol.* 3:479-86 (1989).
Bouchon et al., Analysis of the lapidated recombinant outer surface protein A from *Borrelia burgdorferi* by mass spectrometry. *Anal. Biochem.* 246: 52-61 (1997).
Chu et al., SV40 DNA transfection of cells in suspension: analysis of efficiency of transcription and translation of T-antigen. *Gene* 13:197-202 (1981).
Correction: A vaccine consisting of recombinant *Borrelia burgdorferi* outer-surface protein a to prevent lyme disease. *N. Engl. J. Med.* 339:571 (1998).
de Silva et al., *Borrelia burgdorferi* OspA is an arthropod-specific transmission-blocking Lyme disease vaccine. *J. Exp. Med.* 183: 271-5 (1

(56) References Cited

OTHER PUBLICATIONS

Ding et al., Structural identification of a key protective B-cell epitope in Lyme disease antigen OspA. *J. Mol. Biol.* 302: 1153-64 (2000).
Engels et al., Gene synthesis. *Angew. Chem. Intl. Ed.* 28:716-734 (1989).
Erdile et al., Role of attached lipid in immunogenicity of *Borrelia burgdorferi* OspA. *Infect. Immun.* 61: 81-90 (1993).
Fix, Strategies for delivery of peptides utilizing absorption-enhancing agents. *J. Pharm. Sci.* 85:1282-5 (1996).
Francis et al., Protein modification and fusion proteins. Focus on Growth Factors 3:4-10 (1992).
Gern et al., Immunization with a polyvalent OspA vaccine protects mice again Ioxides ricinus tick bites infected by *Borrelia burgdorferi* ss, *Borrelia garinii* and *Borrelia afzelii*. *Vaccine* 15:1551-7 (1997).
Geysen et al., Use of peptide synthesis to probe viral antigens for epitopes to a resolution of a single amino acid. *Proc. Natl. Acad. Sci. USA* 81:3998-4002 (1984).
Golde et al., The Lyme disease vaccine candidate outer surface protein A (OspA) in a formulation compatible with hman use protects mice against natural tick transmission of *B. burgdorferi*. *Vaccine* 13:435-41 (1995).
Golde et al., Reactivity with a specific epitope of outer surface protein A predicts protection from infection with the Lyme disease spirochete, *Borrelia burgdorferi*. *Infect. Immun.* 65: 882-9 (1997).
Graham et al., A new technology for the assay of infectivity of human adenovirus 5 DNA. *Virology* 52:456-67 (1973).
Gross et al., Identification of LFA-1 as a candidate autoantigen in treatment-resistant Lyme arthritis. *Science* 281:703-6 (1998).
Guerdoux-Jamet et. al., Using codon usage to predict genes origin: is the *Escherichia coli* outer membrane a patchwork of products from different genomes? *DNA Res.* 4:257-65 (1997).
Henikoff et al., Amino acid substitution matrices from protein blocks. *Proc. Natl. Acad. Sci. USA* 89:10915-9 (1992).
Hoogenboom et al., By-passing mmunization. Human antibodies from synthetic repertoires of germline VH gene segments rearranged in vitro. *J. Mol. Biol.* 227:381-8 (1991).
Houghten et al., General method for the rapid solid-phase synthesis of large numbers of peptides: Specificity of antigen-antibody interaction at teh level of individual amino acids. *Proc. Natl. Acad. Sci. USA* 82: 5131-5 (1985).
Howe et al., Organization of genes encoding two outer membrane proteins of the Lyme disease agent *Borrelia burgdorferi* within a single transcriptional unit, *Infect. Immun.* 54:207-12 (1986).
Jiang et al., Purification of *Borrelia burgdorferi* outer surface protein A (OspA) and analysis of antibody binding domains. *Clin. Diagn. Lab. Immunol.* 1:406-12 (1994).
Jiang et al., Cross-antigenicity between the major surface proteins (ospA and ospB) and other proteins of *Borrelia burgdorferi*. *J. Immunol.* 144: 284-9 (1990).
Jones et al., Replacing the complementarity determining regions in a human antibody with those from a mouse. *Nature* 321 :522-5 (1986).
Karlin et al., Applications and statistics for multiple high-scoring segments in molecular sequences. *Proc. Natl. Acad. Sci. USA* 90:5873-7 (1993).
Keller et al., Safety and immunogenicity of a recombinant outer surface protein A Lyme vaccine. *JAMA* 271:1764 8 (1994).
Kohler et al., Continuous cultures of fused cells secreting antibody of predefined specificity. *Nature* 256:495-7 (1975).
Koide et al., Structure-based design of a second-generation Lyme disease vaccine based on a C-terminal fragment of *Borrelia burdorferi* OspA. *J. Mol. Biol.* 350:290-9 (2005).
Kozbor, A human hybrid myeloma for production of human monoclonal antibodies. *J. Immunol.* 133:3001-5 (1984).
Lakey et al., Enhanced production of recombinant Mycobacterium tuberculosis antigens in *Escherichia coli* by replacement of low-usage codons. *Infect. Immun.* 68:233-8 (2000).
Li et al., Crystal structure of Lyme disease antigen outer surface protein A complexed with an Fab. *Proc. Nati. Acad. Sci. USA* 94:3584-9 (1997).
Lovrich et al., Abilities of OspA proteins from different seroprotective groups of *Borrelia burgdorferi* to protect hamsters from infection. *Infect. Immun.* 63:2113-9 (1995).
Luft et al., Approaches toward the directed design of a vaccine against *Borrelia burgdorferi*. *J. Infect. Dis.* 185(Suppl. 1): S46-51 (2002).
Makoff et al., Expression of tetanus toxin fragment C in *E. coli*: High level expression by removing rare codons. *Nucl. Acids Res.* 17:10191-202 (1989).
Marks et al., By-passing immunization: Human antibodies from V-gene libraries displayed on phage. *J. Mol. Biol.* 222:581-97 (1991).
Merrifield et al., Solid phase peptide synthesis: The synthesis of a tetrapeptide. *J. Am. Chem. Soc.* 85:2149-54 (1963).
Morrison et al., Chimeric human antibody molecules: Mouse antigen-binding domains with human constant region domains. *Proc. Natl. Acad. Sci. USA* 81:6851-5 (1985).
Needleman et al., A general method applicable to the search for similarities in the amino acid sequqnece of two proteins. *J. Mol. Biol.* 48:443-53 (1970).
Ohtsuka et al., An alternative approach to deoxyoligonucleotides as hybridization probes by insertion of deoxyinosine at ambiguous codon positions. *J. Biol. Chem.* 260:2605-8 (1985).
Oliyai et al., Prodrugs of peptides and proteins for improved formulation and delivery. *Ann. Rev. Pharmacol. Toxicol.* 32:521-44 (1993).
Pal et al., Inhibition of *Borrelia burgdorferi*-tick interactions in vivo by outer surface protein A antibody. *J. Immunol.* 166: 7398-403 (2001).
Pearson et al., Improved tools for biological sequence comparison. *Proc. Natl. Acad. Sci. USA* 85:2444-8 (1988).
Riechmann et al., Reshaping human antibody for therapy. *Nature* 332:323-7 (1988).
Rossolini et al., Use of deoxyinosine-containing primers vs degenerate primers for polymerase chain reaction based on ambiguous sequence information. *Mol. Cell. Probes* 8:91-8 (1994).
Sigal et al., A vaccine consisting of recombinant *Borrelia burgdorferi* outer-surface protein A to prevent Lyme disease. Recombinant Outer-Surface Protein A Lyme Disease Vaccine Study Consortium. *N. Engl. J. Med.* 339:216-22 (1998).
Smith et al., Comparison of biosequences. *Adv. Appl. Math.* 2: 482-9 (1981).
Steere et al., Vaccination against Lyme disease with recombinant *Borrelia burgdorferi* outer-surface lipoprotein A with adjuvant. Lyme disease vaccine study group. *N. Engl. J. Med.* 339: 209-15 (1998).
Studier et al., Use of bacteriophage T7 RNA polymerase to direct selective high-level expression of cloned genes. *J. Mol. Biol.* 189:113-30 (1986).
Sutcliffe et al., Antibodies that react with predetermined sites on proteins. *Science* 219:660-6 (1983).
Takahashi et al., Induction of CD8+ cytotoxic T cells by immunization with purified HIV-1 envelope protein in ISCOMs. *Nature* 344:873-5 (1990).
Towbin, Electrophoretic transfer of proteins from polyacrylamide gels to nitrocellulose sheets: procedure and some applications. *Proc. Natl. Acad. Sci. USA* 76:4350-6 (1979).
Van Hoecke et al., Evaluation of the safety, reactogenicity and immunogenicity of three recombinant outer surface protein (OspA) Lyme vaccines in healthy adults. *Vaccine* 14:1620-6 (1996).
Verhoeyen et al., Reshaping human antibodies: Grafting an antilysozyme activity. *Science* 239:1534-6 (1988).
Will et al., Sequence analysis of ospA genes shows homogeneity within *Borrelia burgdorferi sensu stricto* and *Borrelia afzelii* strains but reveals major subgroups within the *Borrelia garinii* species. *Med. Microbiol. Immunol.* 184:73-80 (1995).
Wilske et al., An OspA serotyping system for *Borrelia burgdorferi* based on reactivity with monoclonal antibodies and OspA sequence analysis. *J. Clin. Microbiol.* 31:340-50 (1993).
International Search Report and Written Opinion of the International Searching Authority, PCT/US2011/036533, dated Sep. 23, 2011.
International Search Report and Written Opinion of the International Searching Authority, PCT/US2011/036525, dated Jul. 20, 2011.

* cited by examiner

Fig. 2

```
  1  MRLLIGFALA  LALIGCAQKG  AESIGSVSVD  LPGEMKVLVS  KEKDKNGKYD
 51  LIATVDKLEL  KGTSDKNNGS  GVLEGVKTNK  SKVKLTISDD  LGQTTLEVFK
101  EDGKTLVSKK  VTSKDKSSTE  EKFNEKGEVS  EKIITMADGT  RLEYTGIKSD
151  GTGKAKYVLK  NFTLEGKVAN  DKTTLEVKEG  TVTLSMNISK  SGEVSVELND
201  TDSSAATKKT  AAWNSKTSTL  TISVNSKKTT  QLVFTKQDTI  TVQKYDSAGT
251  NLEGTAVEIK  TLDELKNALK
```

(SEQ ID NO: 2)

Fig. 3A

```
     +1      M   R   L     L   I   G     F   A   L     A   L   A     L   I   G   C
             NdeI
             ~~~~~~
       1   CATATGCGTC  TGTTGATCGG  CTTTGCTCTG  GCGCTGGCTC  TGATCGGCTG
           GTATACGCAG  ACAACTAGCC  GAAACGAGAC  CGCGACCGAG  ACTAGCCGAC

+1      A   Q   K     G   A   E   S     I   G   S     V   S   V     D   L   P
      51   CGCACAGAAA  GGTGCTGAGT  CTATTGGTTC  CGTTTCTGTA  GATCTGCCCG
           GCGTGTCTTT  CCACGACTCA  GATAACCAAG  GCAAAGACAT  CTAGACGGGC

+1   G   E   M   K     V   L   V     S   K   E     D   K   N     G   K   Y
     101   GTGAAATGAA  GGTTCTGGTG  AGCAAAGAAA  AAGACAAGAA  CGGCAAGTAC
           CACTTTACTT  CCAAGACCAC  TCGTTTCTTT  TTCTGTTCTT  GCCGTTCATG

+1      D   L   I     A   T   V   D     K   L   E     L   K   G     T   S   D   K
     151   GATCTCATCG  CAACCGTCGA  CAAGCTGGAG  CTGAAAGGTA  CTTCTGATAA
           CTAGAGTAGC  GTTGGCAGCT  GTTCGACCTC  GACTTTCCAT  GAAGACTATT

+1      N   N   G     S   G   V     L   E   G   V     K   T   N     K   S   K
     201   AAACAACGGC  TCTGGTGTGC  TGGAGGGCGT  CAAAACTAAC  AAGAGCAAAG
           TTTGTTGCCG  AGACCACACG  ACCTCCCGCA  GTTTTGATTG  TTCTCGTTTC

+1  V   K   L   T     I   S   D     D   L   G     Q   T   T   L     E   V   F
             HindIII
             ~~~~~~
     251   TAAAGCTTAC  GATCTCTGAC  GATCTCGGTC  AGACCACGCT  GGAAGTTTTC
           ATTTCGAATG  CTAGAGACTG  CTAGAGCCAG  TCTGGTGCGA  CCTTCAAAAG +1      K   E   D   G     K   T   L     V   S   K     K   V   T   S     K   D   K
     301   AAAGAGGATG  GCAAGACCCT  CGTGTCCAAA  AAAGTAACTT  CCAAAGACAA
           TTTCTCCTAC  CGTTCTGGGA  GCACAGGTTT  TTTCATTGAA  GGTTTCTGTT +1      S   S   T     E   E   K     F   N   E   K     G   E   V     S   E   K
     351   GTCCTCTACG  GAAGAAAAAT  TCAACGAAAA  AGGTGAGGTG  TCTGAAAAGA
           CAGGAGATGC  CTTCTTTTTA  AGTTGCTTTT  TCCACTCCAC  AGACTTTTCT +1   I   I   T   M     A   D   G     T   R   L     E   Y   T   G     I   K   S
     401   TCATCACCAT  GGCAGACGGC  ACCCGTCTTG  AATACACCGG  TATTAAAAGC
           AGTAGTGGTA  CCGTCTGCCG  TGGGCAGAAC  TTATGTGGCC  ATAATTTTCG +1      D   G   T     G   K   A   K     Y   V   L     K   N   F     T   L   E   G
                KpnI
                ~~~~~~
     451   GATGGTACCG  GTAAAGCGAA  ATATGTTCTG  AAAAACTTCA  CTCTGGAAGG
           CTACCATGGC  CATTTCGCTT  TATACAAGAC  TTTTTGAAGT  GAGACCTTCC +1      K   V   A     N   D   K     T   T   L   E     V   K   E     G   T   V
     501   CAAAGTGGCT  AATGATAAAA  CCACCTTGGA  AGTCAAGGAA  GGCACCGTTA
           GTTTCACCGA  TTACTATTTT  GGTGGAACCT  TCAGTTCCTT  CCGTGGCAAT
```

Fig. 3B

```
      +1  T   L   S   M    N   I   S    K   S   G    E   V   S    V   E   L   N
     551  CTCTGAGCAT  GAATATCTCC  AAATCTGGTG  AAGTTTCCGT  TGAACTGAAC
          GAGACTCGTA  CTTATAGAGG  TTTAGACCAC  TTCAAAGGCA  ACTTGACTTG

+1  D   T   D    S   S   A   A    T   K   K    T   A   A    W   N   S   K
                                                                       EcoRI
                                                                       ~~~~~~
     601  GACACTGACA  GCAGCGCTGC  GACTAAAAAA  ACTGCAGCGT  GGAATTCCAA
          CTGTGACTGT  CGTCGCGACG  CTGATTTTTT  TGACGTCGCA  CCTTAAGGTT

+1      T   S   T    L   T   I    S   V   N   S    K   K    T   Q   L
     651  AACTTCTACT  TTAACCATTA  GCGTTAACAG  CAAAAAAACT  ACCCAGCTGG
          TTGAAGATGA  AATTGGTAAT  CGCAATTGTC  GTTTTTTTGA  TGGGTCGACC

+1  V   F   T    K   Q   D   T    I   T   V    Q   K   Y    S   A   G
     701  TGTTCACTAA  ACAAGACACG  ATCACTGTGC  AGAAATACGA  CTCCGCAGGC
          ACAAGTGATT  TGTTCTGTGC  TAGTGACACG  TCTTTATGCT  GAGGCGTCCG

+1  T   N   L    E   G   T   A    V   E   I    K   T    L   D   E   L   K
     751  ACCAACTTAG  AAGGCACGGC  AGTCGAAATT  AAAACCCTTG  ATGAACTGAA
          TGGTTGAATC  TTCCGTGCCG  TCAGCTTTAA  TTTTGGGAAC  TACTTGACTT

+1  N   A   L   K   *
                          Bpu1102I  BamHI
                          ~~~~~~~~~~~~~~
     801  AAACGCGCTG  AAATAAGCTG  AGCGGATCC
          TTTGCGCGAC  TTTATTCGAC  TCGCCTAGG
``` lipB sOspA 1/2$^{251}$ – nucleotide sequence (SEQ ID NO: 1), and amino acid sequence (SEQ ID NO: 2; complementary nucleotide sequence (SEQ ID NO: 48)

Fig. 4

```
  1  MRLLIGFALA  LALIGCAQKG  AESIGSVSVD  LPGGMTVLVS  KEKDKNGKYS
 51  LEATVDKLEL  KGTSDKNNGS  GTLEGEKTNK  SKVKLTIADD  LSQTKFEIFK
101  EDAKTLVSKK  VTLKDKSSTE  EKFNEKGETS  EKTIVMANGT  RLEYTDIKSD
151  GSGKAKYVLK  DFTLEGTLAA  DGKTTLKVTE  GTVVLSMNIL  KSGEITVALD
201  DSDTTQATKK  TGKWDSNTST  LTISVNSKKT  KNIVFTKEDT  ITVQKYDSAG
251  TNLEGNAVEI  KTLDELKNAL
```

(SEQ ID NO: 4)

Fig. 5A

```
    +1      M   R   L   L   I   G   F   A   L   A   L   A   L   I   G   C
         NdeI
         ~~~~~~
  1     CATATGCGTC  TGTTGATCGG  CTTTGCTCTG  GCGCTGGCTC  TGATCGGCTG
        GTATACGCAG  ACAACTAGCC  GAAACGAGAC  CGCGACCGAG  ACTAGCCGAC

+1      A   Q   K   G   A   E   S   I   G   S   V   S   V   D   L   P
 51     CGCACAGAAA  GGTGCTGAGT  CTATTGGTTC  CGTTTCTGTA  GATCTGCCCG
        GCGTGTCTTT  CCACGACTCA  GATAACCAAG  GCAAAGACAT  CTAGACGGGC

+1  G   G   M       T   V   L   V       S   K   E   K       D   N       G   K   Y
101     GTGGCATGAC  CGTTCTGGTC  AGCAAAGAAA  AAGACAAAAA  CGGTAAATAC
        CACCGTACTG  GCAAGACCAG  TCGTTTCTTT  TTCTGTTTTT  GCCATTTATG

+1  S   L   E       A   T   V   D       K   L       E   L   K   G       T   S   D   K
                                        HindIII
                                        ~~~~~~
151     AGCCTCGAGG  CGACCGTCGA  CAAGCTTGAG  CTGAAAGGCA  CCTCTGATAA
        TCGGAGCTCC  GCTGGCAGCT  GTTCGAACTC  GACTTTCCGT  GGAGACTATT +1      N   N   G       S   G   T       L   E   G   E       K   T   N       K   S   K
201     AAACAACGGT  TCCGGCACCC  TGGAAGGTGA  AAAAACTAAC  AAAAGCAAAG
        TTTGTTGCCA  AGGCCGTGGG  ACCTTCCACT  TTTTTGATTG  TTTTCGTTTC +1  V   K   L   T       I   A   D       D   L   S       Q   T   K   F       E   I   F
251     TGAAACTGAC  CATTGCTGAT  GACCTCAGCC  AGACCAAATT  CGAAATTTTC
        ACTTTGACTG  GTAACGACTA  CTGGAGTCGG  TCTGGTTTAA  GCTTTAAAAG +1      K   E   D       A   K   T   L       V   S   K       K   V   T       L   K   D   K
301     AAAGAAGATG  CCAAAACCTT  AGTATCCAAA  AAAGTGACCC  TGAAAGACAA
        TTTCTTCTAC  GGTTTTGGAA  TCATAGGTTT  TTTCACTGGG  ACTTTCTGTT +1      S   S   T       E   E   K       F   N   E   K       G   E   T       S   E   K
351     GTCCTCTACC  GAAGAAAAAT  TCAACGAAAA  GGGTGAAACC  TCTGAAAAAA
        CAGGAGATGG  CTTCTTTTTA  AGTTGCTTTT  CCCACTTTGG  AGACTTTTTT +1  T   I   V   M       A   N   G       T   R   L       E   Y   T   D       I   K   S
                                        KpnI
                                        ~~~~~~~
401     CCATCGTAAT  GGCAAATGGT  ACCCGTCTGG  AATACACCGA  CATCAAAAGC
        GGTAGCATTA  CCGTTTACCA  TGGGCAGACC  TTATGTGGCT  GTAGTTTTCG +1      D   G   S       G   K   A   K       Y   V   L       K   D   F   T       L   E   G
451     GATGGCTCCG  GCAAAGCCAA  ATACGTTCTG  AAAGACTTCA  CCCTGGAAGG
        CTACCGAGGC  CGTTTCGGTT  TATGCAAGAC  TTTCTGAAGT  GGGACCTTCC +1      T   L   A       A   D   G   K       T   T   L       K   V   T       E   G   T
501     CACCCTCGCT  GCCGACGGCA  AAACCACCTT  GAAAGTTACC  GAAGGCACTG
        GTGGGAGCGA  CGGCTGCCGT  TTTGGTGGAA  CTTTCAATGG  CTTCCGTGAC
```

Fig. 5B

```
     +1  V   V   L   S    M   N   I    L   K   S    G   E   I   T    V   A   L
    551  TTGTTTTAAG  CATGAACATC  TTAAAATCCG  GTGAAATCAC  CGTTGCGCTG
         AACAAAATTC  GTACTTGTAG  AATTTTAGGC  CACTTTAGTG  GCAACGCGAC

+1  D   D   S    D   T   T    Q   A   T    K   K   T    G   K   W   D   S
    601  GATGACTCTG  ACACCACTCA  GGCCACTAAA  AAAACCGGCA  AATGGGATTC
         CTACTGAGAC  TGTGGTGAGT  CCGGTGATTT  TTTTGGCCGT  TTACCCTAAG

+1       N   T   S    T   L   T    I   S   V   N    S   K   K    T   K   N
                                                EcoRI
                                                ~~~~~~~
    651  TAACACTTCC  ACTCTGACCA  TCAGCGTGAA  TTCCAAAAAA  ACTAAAAACA
         ATTGTGAAGG  TGAGACTGGT  AGTCGCACTT  AAGGTTTTTT  TGATTTTTGT

+1  I   V   F   T    K   E   D    T   I   T    V   Q   K   Y    D   S   A
    701  TCGTGTTCAC  CAAAGAAGAC  ACCATCACCG  TCCAGAAATA  CGACTCTGCG
         AGCACAAGTG  GTTTCTTCTG  TGGTAGTGGC  AGGTCTTTAT  GCTGAGACGC

+1  G   T   N    L   E   G   N    A   V   E    I   K   T    L   D   E   L
    751  GGCACCAACC  TCGAAGGCAA  CGCAGTCGAA  ATCAAAACCC  TGGATGAACT
         CCGTGGTTGG  AGCTTCCGTT  GCGTCAGCTT  TAGTTTTGGG  ACCTACTTGA

+1  K   N   A    L   K   *
                              Bpu1102I    BamHI
                              ~~~~~~~~~~~~~~~~~
    801  GAAAAACGCT  CTGAAATAAG  CTGAGCGGAT  CC
         CTTTTTGCGA  GACTTTATTC  GACTCGCCTA  GG
``` lipB sOspA 6/4 – nucleotide sequence (SEQ ID NO: 3), and amino acid sequence (SEQ ID NO: 4); complementary nucleotide sequence (SEQ ID NO: 49)

Fig. 6

```
  1  MRLLIGFALA  LALIGCAQKG  AESIGSVSVD  LPGGMKVLVS  KEKDKNGKYS
 51  LMATVEKLEL  KGTSDKNNGS  GTLEGEKTNK  SKVKLTIAED  LSKTTFEIFK
101  EDGKTLVSKK  VTLKDKSSTE  EKFNEKGEIS  EKTIVMANGT  RLEYTDIKSD
151  KTGKAKYVLK  DFTLEGTLAA  DGKTTLKVTE  GTVTLSMNIS  KSGEITVALD
201  DTDSSGNKKS  GTWDSDTSTL  TISKNSQKTK  QLVFTKENTI  TVQNYNRAGN
251  ALEGSPAEIK  DLAELKAALK
```

(SEQ ID NO: 6)

Fig. 7A

```
     +1      M   R   L   L   I   G   F   A   L   A   L   A   L   I   G   C
             NdeI
             ~~~~~~
      1   CATATGCGTC TGTTGATCGG CTTTGCTTTG GCGCTGGCTT TAATCGGCTG
          GTATACGCAG ACAACTAGCC GAAACGAAAC CGCGACCGAA ATTAGCCGAC

+1      A   Q   K       G   A   E       S   I   G   S       V   S   V       D   L   P
     51   TGCACAGAAA GGTGCTGAGT CTATTGGTTC CGTTTCTGTA GATCTGCCCG
          ACGTGTCTTT CCACGACTCA GATAACCAAG GCAAAGACAT CTAGACGGGC

+1   G   G   M       V   L   V       S   K   E       K   D   K       G   K   Y
    101   GGGGTATGAA AGTTCTGGTA AGCAAAGAAA AAGACAAAAA CGGTAAATAC
          CCCCATACTT TCAAGACCAT TCGTTTCTTT TTCTGTTTTT GCCATTTATG

+1      S   L   M       A   T   V   E       K   L   E       L   K   G       T   S   D   K
    151   AGCCTGATGG CAACCGTAGA AAAGCTGGAG CTTAAAGGCA CTTCTGATAA
          TCGGACTACC GTTGGCATCT TTTCGACCTC GAATTTCCGT GAAGACTATT

+1      N   N   G       S   G   T       L   E   G   E       K   T   N       K   S   K
    201   AAACAACGGT TCTGGCACCC TGGAAGGTGA AAAAACTAAC AAAAGCAAAG
          TTTGTTGCCA AGACCGTGGG ACCTTCCACT TTTTTGATTG TTTTCGTTTC

+1   V   K   L   T       I   A   E       D   L   S       K   T   T   F       E   I   F
             HindIII
             ~~~~~~
    251   TAAAGCTTAC TATTGCTGAG GATCTGAGCA AAACCACCTT TGAAATCTTC
          ATTTCGAATG ATAACGACTC CTAGACTCGT TTTGGTGGAA ACTTTAGAAG +1      K   E   D       G   K   T   L       V   S   K       K   V   T       L   K   D   K
    301   AAAGAAGATG GCAAAACTCT GGTATCTAAA AAAGTAACCC TGAAAGACAA
          TTTCTTCTAC CGTTTTGAGA CCATAGATTT TTTCATTGGG ACTTTCTGTT +1      S   S   T       E   E   K       F   N   E   K       G   E   I       S   E   K
    351   GTCTTCTACC GAAGAAAAAT TCAACGAAAA GGGTGAAATC TCTGAAAAAA
          CAGAAGATGG CTTCTTTTTA AGTTGCTTTT CCCACTTTAG AGACTTTTTT +1   T   I   V   M       A   N   G       T   R   L       E   Y   T   D       I   K   S
                                  KpnI
                                  ~~~~~~~~
    401   CTATCGTAAT GGCAAATGGT ACCCGTCTGG AATACACCGA CATCAAAAGC
          GATAGCATTA CCGTTTACCA TGGGCAGACC TTATGTGGCT GTAGTTTTCG +1      D   K   T       G   K   A   K       Y   V   L       K   D   F       T   L   E   G
    451   GATAAAACCG GCAAAGCTAA ATACGTTCTG AAAGACTTTA CTCTGGAAGG
          CTATTTTGGC CGTTTCGATT TATGCAAGAC TTTCTGAAAT GAGACCTTCC +1      T   L   A       A   D   G       K   T   T   L       K   V   T       E   G   T
    501   CACTCTGGCT GCTGACGGCA AAACCACTCT GAAAGTTACC GAAGGCACTG
          GTGAGACCGA CGACTGCCGT TTTGGTGAGA CTTTCAATGG CTTCCGTGAC
```

Fig. 7B

```
    +1  V   T   L   S     M   N   I     S   K   S     G   E   I     T   V   L
    551 TTACTCTGAG CATGAACATT TCTAAATCCG GCGAAATCAC CGTTGCACTG
        AATGAGACTC GTACTTGTAA AGATTTAGGC CGCTTTAGTG GCAACGTGAC

+1  D   D   T     D   S   S   G     N   K   K     S   G   T     W   D   S   D
    601 GATGACACTG ACTCTAGCGG CAATAAAAAA TCCGGCACCT GGGATTCTGA
        CTACTGTGAC TGAGATCGCC GTTATTTTTT AGGCCGTGGA CCCTAAGACT

+1      T   S   T     L   T   I     S   K   N   S     Q   K   T     K   Q   L
                                                                            PvuII
                                                                            ~~~~~~
    651 TACTTCTACT TTAACCATTA GCAAAAACAG CCAGAAAACT AAACAGCTGG
        ATGAAGATGA AATTGGTAAT CGTTTTTGTC GGTCTTTTGA TTTGTCGACC

+1  V   F   T   K     E   N   T     I   T   V     Q   N   Y   N     R   A   G
    701 TATTCACCAA AGAAAACACT ATCACCGTAC AGAACTATAA CCGTGCAGGC
        ATAAGTGGTT TCTTTTGTGA TAGTGGCATG TCTTGATATT GGCACGTCCG

+1  N   A   L     E   G   S   P     A   E   I     K   D   L     A   E   L   K
    751 AATGCGCTGG AAGGCAGCCC GGCTGAAATT AAAGATCTGG CAGAGCTGAA
        TTACGCGACC TTCCGTCGGG CCGACTTTAA TTTCTAGACC GTCTCGACTT

+1  A   A   L   K   *
                        Bpu1102I  BamHI
    801 AGCCGCTTTG AAATAAGCTG AGCGGATCC
        TCGGCGAAAC TTTATTCGAC TCGCCTAGG
``` lipB sOspA 5/3 – nucleotide sequence (SEQ ID NO: 5), and amino acid sequence (SEQ ID NO: 6); complementary nucleotide sequence (SEQ ID NO: 50)

Fig. 9

5' sequence of lipidated constructs (SEQ ID NO: 31)
Amino acid sequence (SEQ ID NO: 33)
Complementary nucleotide sequence (SEQ ID NO: 51)

```
+1      M   R   L    L   I   G    F   A   L    A   L   A   L    I   G   C    A   Q   K
        NdeI
        ~~~~~
1    CATATGCGTC  TGTTGATCGG  CTTTGCTCTG  GCGCTGGCTC  TGATCGGCTG  CGCACAGAAA
     GTATACGCAG  ACAACTAGCC  GAAACGAGAC  CGCGACCGAG  ACTAGCCGAC  GCGTGTCTTT
```

5' sequence of non- lipidated constructs (SEQ ID NO: 32)
Amino acid sequence (SEQ ID NO: 34)
Complementary nucleotide sequence (SEQ ID NO: 52)

```
+1      M                                                              A   Q   K
        NdeI
        ~~~~~
1    CATATG**  ******  ******  ******  ********  *GCAC AGAAA
     GTATAC**  ******  ******  ******  ********  *CGTG TCTTT
```

| Lane | Construct / sample | Induced[1] |
|---|---|---|
| 2 | High Marker | - |
| 3 | Low Marker | - |
| 4 | WCB[2] lipB sOspA 1/2[251] | - |
| 5 | WCB lipB sOspA 1/2[251] | + |
| 6 | PC[3] sOspA 1/2[251] | - |
| 7 | PC sOspA 1/2[251] | + |
| 8 | - | - |
| 9 | WCB lipB sOspA 5/3 | - |
| 10 | WCB lipB sOspA 5/3 | + |
| 11 | PC sOspA 5/3 | - |
| 12 | PC sOspA 5/3 | + |
| 13 | - | - |
| 14 | WCB lipB sOspA 6/4 | - |
| 15 | WCB lipB sOspA 6/4 | + |
| 16 | PC sOspA 6/4 | - |
| 17 | PC sOspA 6/4 | + |
| 18 | High Marker | - |
| 19 | Low Marker | - |

[1] Induced for 3 hours with 1mM IPTG, - implies not induced
[2] WCB; working cell bank
[3] PC; Primary cells
* OspA

Fig. 14

Cloning of *de Novo* synthesis products

```
|_____|___|          |___|_____|
Kpn I          Pvu II  EcoR I     EcoR I  Pvu II      BamH I

Kpn I – EcoR I fragment          EcoR I – BamH I fragment
```

Digestion with P*vu* II

```
|_____|              |_____|
Kpn I              Pvu II         Pvu II           BamH I
                            ↓
```

Ligation to Kpn I/ BamHI digested vector

```
|_____|_____|
Kpn I             Pvu II            BamH I
```

Required sequence in final lipB sOspA 5/3 construct (SEQ ID NO: 35); complementary nucleotide sequence (SEQ ID NO: 53)

```
                              PvuII
671                          ~~~~~                         720
GCAAAAACAG CCAGAAAACT AAACAGCTGG TATTCACCAA AGAAAACACT
CGTTTTTGTC GGTCTTTTGA TTTGTCGACC ATAAGTGGTT TCTTTTGTGA
```

**Oligos for 3' terminal of *Kpn* I – *Eco*R I fragment (incorporating external *Eco*R I site) (SEQ ID NO: 36); complementary nucleotide sequence (SEQ ID NO: 54)**

```
GCAAAAACAG CCAGAAAACT AAACAGCTGGG
CGTTTTTGTC GGTCTTTTGA TTTGTCGACCCTTAA
```

**Oligos for 5' terminal of EcoR I – BamH I fragment (incorporating external *Eco*R I site) (SEQ ID NO: 37); complementary nucleotide sequence (SEQ ID NO: 55)**

```
AATTC AAACAGCTGG TATTCACCAA AGAAAACACT
    G TTTGTCGACC ATAAGTGGTT TCTTTTGTGA
```

Fig. 15

Alignment highlighting the amino acid change in lipB sOspA 1/2$^{251}$ (SEQ ID NO: 39) and the PCR primer sequences (SEQ ID NOs: 21 and 41) used to introduce the change.

lipB OspA 1/2 mod (SEQ ID NO: 38); consensus sequence (SEQ ID NO: 40)

```
                            719                                                      774
                              I  T  V  Q  K  Y  D  S  A  G  T  N  L  E  G  T  A  V
   lipB OspA 12 mod   (701) ▓▓▓▓▓▓▓▓▓▓▓▓▓▓▓▓▓▓▓▓▓AAC▓▓▓▓▓▓▓▓▓▓▓▓▓▓▓▓▓▓▓▓▓▓▓▓▓▓▓
   lipB sOspA 1/2 251 (700) ▓▓▓▓▓▓▓▓▓▓▓▓▓▓▓▓▓▓▓▓▓GCA▓▓▓▓▓▓▓▓▓▓▓▓▓▓▓▓▓▓▓▓▓▓▓▓▓▓▓
         Consensus   (701) GATCACTGTGCAGAAATACGACTCC   GGCACCAACTTAGAAGGCACGGCAGTC Internal forward primer →          AATACGACTCCGCAGGCACC    (SEQ ID NO: 21)
Internal reverse primer →          CGSCTCCGCAGGCACCAA      (SEQ ID NO: 41)
External forward primer → bp 1 to 21 + NdeI site
External reverse primer → bp 808 to 828 = BamH I site
```

Fig. 16A

Alignment of OspA sequence of Blip OspA BPBP/A1 with the modified molecule lipB sOspA 1/2[251].

```
          M   R   L    L   I   G   F    A   L   A    L   A   L    I   G   C   A
   1    ATGAGATTAT TAATAGGATT TGCTTTAGCG TTAGCTTTAA TAGGATGTGC
   1    ATGCGTCTGT TGATCGGCTT TGCTCTGGCG CTGGCTCTGA TCGGCTGCGC

Q   K   G    A   E   S    I   G   S    V   S   V   D    L   P   G
  51    ACAAAAAGGT GCTGAGTCAA TTGGATCCGT TCAGTAGAT TTGCCTGGTG
  51    ACAGAAAGGT GCTGAGTCTA TTGGTTCCGT TCTGTAGAT CTGCCCGGTG

E   M   K   V    L   V   S    K   E   K    D   K   N   G    K   Y   D
 101    AAATGAAAGT TCTTGTAAGC AAAGAAAAAG ACAAAAACGG CAAGTACGAT
 101    AAATGAAGGT TCTGGTGAGC AAAGAAAAAG ACAAGAACGG CAAGTACGAT

L   I   A    T   V   D   K    L   E   L    K   G   T    S   D   K   N
 151    CTAATTGCAA CAGTAGACAA GCTTGAGCTT AAAGGAACTT CTGATAAAAA
 151    CTCATCGCAA CCGTCGACAA GCTGGAGCTG AAAGGTACTT CTGATAAAAA

N   G   S    G   V   L    E   G   V   K    T   N   K    S   K   V
                                                                      HindIII
                                                                      ~
 201    CAATGGATCT GGAGTACTTG AAGGCGTAAA AACTAACAAA AGTAAAGTAA
 201    CAACGGCTCT GGTGTGCTGG AGGGCGTCAA AACTAACAAG AGCAAAGTAA K   L   T   I    S   D   D    L   G   Q    T   T   L   E    V   F   K
          HindIII
          ~~~~~
 251    AATTAACAAT TTCTGACGAT CTAGGTCAAA CCACACTTGA AGTTTTCAAA
 251    AGCTTACGAT CTCTGACGAT CTCGGTCAGA CCACGCTGGA AGTTTTCAAA E   D   G    K   T   L   V    S   K   K    V   T   S    K   D   K   S
 301    GAAGATGGCA AAACACTAGT ATCAAAAAAA GTAACTTCCA AAGACAAGTC
 301    GAGGATGGCA AGACCCTCGT GTCCAAAAAA GTAACTTCCA AAGACAAGTC S   T   E    E   K   F    N   E   K   G    E   V   S    E   K   I
 351    ATCAACAGAA GAAAAATTCA ATGAAAAAGG TGAAGTATCT GAAAAAATAA
 351    CTCTACGGAA GAAAAATTCA ACGAAAAAGG TGAGGTGTCT GAAAAGATCA I   T   M   A    D   G   T    R   L   E    Y   T   G   I    K   S   D
 401    TAACAATGGC AGACGGAACC AGACTTGAAT ACACAGGAAT TAAAAGCGAT
 401    TCACCATGGC AGACGGCACC CGTCTTGAAT ACACCGGTAT TAAAAGCGAT G   T   G    K   A   K   Y    V   L   K    N   F   T    L   E   G   K
          KpnI
          ~~~~~~
 451    GGAACTGGAA AAGCTAAATA TGTTTTAAAA AATTTTACTC TTGAAGGAAA
 451    GGTACCGGTA AAGCGAAATA TGTTCTGAAA AACTTCACTC TGGAAGGCAA V   A   N    D   K   T    T   L   E   V    K   E   G    T   V   T
 501    AGTAGCTAAT GATAAAACAA CATTGGAAGT AAAAGAAGGA ACCGTTACTT
 501    AGTGGCTAAT GATAAAACCA CCTTGGAAGT CAAGGAAGGC ACCGTTACTC
```

Fig. 16B

```
       L   S   M   N      I   S   K      S   G   E      V   S   V   E      L   N   D
551  TAAGTATGAA TATTTCAAAA TCTGGGGAAG TTTCAGTTGA ACTTAATGAC
551  TGAGCATGAA TATCTCCAAA TCTGGTGAAG TTTCCGTTGA ACTGAACGAC

I   D   S      S   A   A   T      K   K   T      A   A   W      N   S   K   T
                                                                    EcoRI
                                                                    ~~~~~~~
601  ACTGACAGTA GTGCTGCTAC TAAAAAAACT GCAGCTTGGA ATTCAAAAAC
601  ACTGACAGCA GCGCTGCGAC TAAAAAAACT GCAGCGTGGA ATTCCAAAAC

S   T   L      T   I   S      V   N   S   K      K   T   T      Q   L   V
651  TTCTACTTTA ACAATTAGTG TTAACAGCAA AAAAACTACA CAACTTGTGT
651  TTCTACTTTA ACCATTAGCG TTAACAGCAA AAAAACTACC CAGCTGGTGT

F   T   K   Q      D   T   I      T   V   Q      K   Y   D   S      A   G   T
701  TTACTAAACA AGACACAATA ACTGTACAAA AATACGACTC CAACGGTACC
701  TCACTAAACA AGACACGATC ACTGTGCAGA AATACGACTC CGCAGGCACC

N   L   E      G   T   A   V      E   I   K      T   L   D      E   L   K   N
751  AATTTAGAAG GCACAGCAGT CGAAATTAAA ACACTTGATG AACTTAAAAA
751  AACTTAGAAG GCACGGCAGT CGAAATTAAA ACCCTTGATG AACTGAAAAA

A   L   K    *
                    Bpu1102I    BamHI
                    ~~~~~~~~~~~~~~
801  CGCTTTAAAA TAA
801  CGCGCTGAAA TAAGCTGAGC GGATCC
```

The top strand is the original sequence (SEQ ID NO: 42) and the bottom strand is the optimized sequence (SEQ ID NO: 43). Amino acid sequence (SEQ ID NO: 2).

Note: Three bases (CAT) at the start of the sequence are not shown, they form part of the *Nde* I site CATATG.

Fig. 17A

Alignment of OspA sequence of Blip OspA KT with the modified molecule lipB sOspA 6/4.

```
        M  R  L     L  I  G     F  A  L     A  L  A  L     I  G  C
  1  ATATGAGATT ATTAATAGGA TTTGCTTTAG CGTTAGCTTT AATAGGATGT
  1  ATATGCGTCT GTTGATCGGC TTTGCTCTGG CGCTGGCTCT GATCGGCTGC

A  Q  K     G  A  E  S     I  G  S     V  S  V     D  L  P  G
 51  GCACAAAAAG GTGCTGAGTC AATTGGATCC GTTTCAGTAG ATTTACCTGG
 51  GCACAGAAAG GTGCTGAGTC TATTGGTTCC GTTTCTGTAG ATCTGCCCGG

G  M  T     V  L  V     S  K  E  K     D  K     N  G  K  Y
101  TGGAATGACA GTTCTTGTAA GTAAAGAAAA AGACAAAGAC GGTAAATACA
101  TGGCATGACC GTTCTGGTCA GCAAAGAAAA AGACAAAAAC GGTAAATACA

S  L  E  A     T  V  D     K  L  E     L  K  G     T  S  D  K
                                   HindIII
                                   ~~~~~~
151  GTCTAGAGGC AACAGTAGAC AAGCTTGAGC TTAAAGGAAC TTCTGATAAA
151  GCCTCGAGGC GACCGTCGAC AAGCTTGAGC TGAAAGGCAC CTCTGATAAA N  N  G     S  G  T  L     E  G  E     K  T     N  K  S  K  V
201  AACAACGGTT CTGGAACACT TGAAGGTGAA AAAACTGACA AAAGTAAAGT
201  AACAACGGTT CCGGCACCCT GGAAGGTGAA AAAACTAACA AAAGCAAAGT K  L  T     I  A  D     D  L  S  Q     T  K  F     E  I  F
251  AAAATTAACA ATTGCTGATG ACCTAAGTCA AACTAAATTT GAAATTTTC
251  GAAACTGACC ATTGCTGATG ACCTCAGCCA GACCAAATTC GAAATTTTCA K  E  D     A  K  T  L     V  S  K  K  V  T     L  K  D  K
301  AAGAAGATGC CAAAACATTA GTATCAAAAA AAGTAACCCT TAAAGACAAG
301  AAGAAGATGC CAAAACCTTA GTATCCAAAA AAGTGACCCT GAAAGACAAG S  S  T     E  E  K  F     N  E  K     G  E  T     S  E  K  T
351  TCATCAACAG AAGAAAAATT CAACGAAAAG GGTGAAACAT CTGAAAAAAC
351  TCCTCTACCG AAGAAAAATT CAACGAAAAG GGTGAAACCT CTGAAAAAAC I  V  M     A  N  G     T  R  L  E     Y  T  D     I  K  S
                    KpnI
                    ~~~~~~~
401  AATAGTAAGA GCAAATGGAA CCAGACTTGA ATACACAGAC ATAAAAAGCG
401  CATCGTAATG GCAAATGGTA CCCGTCTGGA ATACACCGAC ATCAAAAGCG +3 D  G  S     G  K  A  K     Y  V  L     K  D  F     T  L  E  G
451  ATGGATCCGG AAAAGCTAAA GAAGTTTTAA AAGACTTTAC TCTTGAAGGA
451  ATGGCTCCGG CAAAGCCAAA TACGTTCTGA AAGACTTCAC CCTGGAAGGC +3 T  L  A     A  D  G  K     T  T  L     K  V  T     E  G  T  V
501  ACTCTAGCTG CTGACGGCAA AACAACATTG AAAGTTACAG AAGGCACTGT
501  ACCCTCGCTG CCGACGGCAA AACCACCTTG AAAGTTACCG AAGGCACTGT
```

Fig. 17B

```
     +3   V   L   S     M   N   I     L   K   S     G   E   I   T     V   A   L
     551  TGTTTTAAGC    AAGAACATTT    TAAAATCCGG    AGAAATAACA    GTTGCACTTG
     551  TGTTTTAAGC    ATGAACATCT    TAAAATCCGG    TGAAATCACC    GTTGCGCTGG

D   D   S   D     T   T   Q     A   T   K     K   T   G   K     W   D   S
     601  ATGACTCTGA    CACTACTCAG    GCTACTAAAA    AAACTGGAAA    ATGGGATTCA
     601  ATGACTCTGA    CACCACTCAG    GCCACTAAAA    AAACCGGCAA    ATGGGATTCT

N   T   S     T   L   T   I     S   V   N     S   K   K     T   K   N   I
                                                  EcoRI
                                                  ~~~~~~~
     651  AATACTTCCA    CTTTAACAAT    TAGTGTGAAT    AGCAAAAAAA    CTAAAAACAT
     651  AACACTTCCA    CTCTGACCAT    CAGCGTGAAT    TCCAAAAAAA    CTAAAAACAT

V   F   T     K   E   D     T   I   T   V     Q   K   Y     D   S   A
     701  TGTATTTACA    AAAGAAGACA    CAATAACAGT    ACAAAAATAC    GACTCAGCAG
     701  CGTGTTCACC    AAAGAAGACA    CCATCACCGT    CCAGAAATAC    GACTCTGCGG

G   T   N   L     E   G   N     A   V   E     I   K   T     L   D   E   L
     751  GCACCAATCT    AGAAGGCAAC    GCAGTCGAAA    TTAAAACACT    TGATGAACTT
     751  GCACCAACCT    CGAAGGCAAC    GCAGTCGAAA    TCAAAACCCT    GGATGAACTG

K   N   A   L   K   *
                                           BamHI
                                           ~~~~~
     801  AAAAACGCTT    TAAAATAA
     801  AAAAACGCTC    TGAAATAAGC    TGAGCGGATC   C
```

The top strand is the original sequence (SEQ ID NO: 44) and the bottom strand is the optimised sequence (SEQ ID NO: 45). The amino acid sequence (SEQ ID NO: 4).

**Note: A single base (C) at the start of the sequence is not shown, which forms part of the *Nde* I site CATATG.**

Fig. 18A

Alignment of OspA sequence of Blip OspA 5/3 with the modified molecule lipB sOspA 5/3.

```
            M   R   L   L   I   G   F   A   L   A   L   I   G   C
        NdeI
        ~~~~~~
    1   CATATGAGAT TATTAATAGG ATTTGCTTTA GCGTTAGCTT TAATAGGATG
    1   CATATGCGTC TGTTGATCGG CTTTGCTTTG GCGCTGGCTT TAATCGGCTG

A   Q   K   G   A   E   S   I   G   S   V   S   V   D   L   P
   51   TGCACAAAAA GGTGCTGAGT CAATTGGATC CGTTTCAGTA GATTTACCTG
   51   TGCACAGAAA GGTGCTGAGT CTATTGGTTC CGTTTCTGTA GATCTGCCCG

G   G   M   K   V   L   V   S   K   E   K   D   K   N   G   K   Y
  101   GTGGAATGAA AGTTCTTGTA AGTAAAGAAA AAGACAAAGA TGGTAAATAC
  101   GGGGTATGAA AGTTCTGGTA AGCAAAGAAA AAGACAAAAA CGGTAAATAC

S   L   M   A   T   V   E   K   L   E   L   K   G   T   S   D   K
  151   AGTCTAATGG CAACAGTAGA AAAGCTTGAG CTTAAAGGAA CTTCTGATAA
  151   AGCCTGATGG CAACCGTAGA AAAGCTGGAG CTTAAAGGCA CTTCTGATAA

N   N   G   S   G   T   L   E   G   E   K   T   N   K   S   K
  201   AAACAACGGT TCTGGAACAC TTGAAGGTGA AAAAACTGAC AAAAAGTAAAG
  201   AAACAACGGT TCTGGCACCC TGGAAGGTGA AAAAACTAAC AAAAGCAAAG

V   K   L   T   I   A   E   D   L   S   K   T   T   F   E   I   F
            HindIII
            ~~~~~~
  251   TAAAATTAAC AATTGCTGAG GATCTAAGTA AAACCACATT TGAAATCTTC
  251   TAAAGCTTAC TATTGCTGAG GATCTGAGCA AAACCACCTT TGAAATCTTC K   E   D   G   K   T   L   V   S   K   K   V   T   L   K   D   K
  301   AAAGAAGATG GCAAAACATT AGTATCAAAA AAAGTAACCC TTAAAGACAA
  301   AAAGAAGATG GCAAAACTCT GGTATCTAAA AAAGTAACCC TGAAAGACAA S   S   T   E   E   K   F   N   E   K   G   E   I   S   E   K
  351   GTCATCAACA GAAGAAAAAT TCAACGAAAA GGGTGAAATA TCTGAAAAAA
  351   GTCTTCTACC GAAGAAAAAT TCAACGAAAA GGGTGAAATC TCTGAAAAAA T   I   V   M   A   N   G   T   R   L   E   Y   T   D   I   K   S
                                KpnI
                                ~~~~~~~
  401   CAATAGTAAG AGCAAATGGA ACCAGACTTG AATACACAGA CATAAAAAGC
  401   CTATCGTAAT GGCAAATGGT ACCCGTCTGG AATACACCGA CATCAAAAGC D   K   T   G   K   A   K   Y   V   L   K   D   F   T   L   E   G
  451   GATAAAACCG GAAAAGCTAA AGAAGTTTTA AAAGACTTTA CTCTTGAAGG
  451   GATAAAACCG GCAAAGCTAA ATACGTTCTG AAAGACTTTA CTCTGGAAGG T   L   A   A   D   G   K   T   T   L   K   V   T   E   G   T
  501   AACTCTAGCT GCTGACGGCA AAACAACATT GAAAGTTACA GAAGGCACTG
  501   CACTCTGGCT GCTGACGGCA AAACCACTCT GAAAGTTACC GAAGGCACTG
```

Fig. 18B

```
        V   T   L   S     M   N   I     S   K   S     G   E   I     T   V   L
551   TTACTTTAAG CAAGAACATT TCAAAATCCG GAGAAATAAC AGTTGCACTT
551   TTACTCTGAG CATGAACATT TCTAAATCCG GCGAAATCAC CGTTGCACTG

D   D   T     D   S   S   G     N   K   K     S   G   T     W   D   S   D
601   GATGACACTG ACTCTAGCGG CAATAAAAAA TCCGGAACAT GGGATTCAGA
601   GATGACACTG ACTCTAGCGG CAATAAAAAA TCCGGCACCT GGGATTCTGA

T   S   T     L   T   I     S   K   N   S     Q   K   T     K   Q   L
                                                                            PvuII
                                                                            ~~~~~
651   TACTTCTACT TTAACAATTA GTAAAAACAG TCAAAAAACT AAACAACTTG
651   TACTTCTACT TTAACCATTA GCAAAAACAG CCAGAAAACT AAACAGCTGG

V   F   T   K     E   N   T     I   T   V     Q   N   Y   N     R   A   G
701   TATTCACAAA AGAAAACACA ATAACAGTAC AAAACTATAA CAGAGCAGGC
701   TATTCACCAA AGAAAACACT ATCACCGTAC AGAACTATAA CCGTGCAGGC

N   A   L     E   G   S   P     A   E   I     K   D   L     A   E   L   K
751   AATGCGCTTG AAGGCAGCCC AGCTGAAATT AAAGATCTTG CAGAGCTTAA
751   AATGCGCTGG AAGGCAGCCC GGCTGAAATT AAAGATCTGG CAGAGCTGAA

A   A   L   K   *
                                      BamHI
                                      ~~~~~
801   AGCCGCTTTA AAATAA
801   AGCCGCTTTG AAATAAGCTG AGCGGATCC
```

The top strand is the original sequence (SEQ ID NO: 46) and the bottom strand is the optimised sequence (SEQ ID NO: 47). The amino acid sequence (SEQ ID NO: 6).

CHIMERIC OSPA GENES, PROTEINS, AND METHODS OF USE THEREOF

FIELD OF THE INVENTION

The invention generally relates to chimeric OspA polypeptides, nucleic acids encoding the polypeptides, compositions comprising these molecules, and methods of use thereof.

BACKGROUND OF THE INVENTION

Lyme disease is a tick-borne disease caused by *Borrelia burgdorferi sensu lato* (s.l.). The disease is typically characterized by the development of an expanding red rash at the site of the tick bite that may be followed by systemic complications including meningitis, carditis or arthritis. Almost all cases of Lyme disease are caused by one of three genospecies, *Borrelia afzelii*, *Borrelia garinii* and *Borrelia burgdorferi sensu stricto* (s.s.). In Europe, all three species which infect humans are found. However, in North America only a single species, *Borrelia burgdorferi sensu stricto*, is found. *Borrelia burgdorferi* is a species of Gram negative bacteria of the spirochete class of the genus *Borrelia*. Antibiotic treatment of Lyme disease is usually effective but some patients develop a chronic disabling form of the disease involving joints or nervous system, which does not substantially improve even after parenteral antibiotic therapy, thus highlighting the need for a vaccine for high-risk populations.

Outer surface protein A (OspA) is a 31 kDa antigen, expressed by *Borrelia burgdorferi* s.l. species present in the midgut of *Ixodes* ticks. OspA has proven to be efficacious in preventing Lyme disease in North America (Steere et al., *N. Engl. J. Med.* 339: 209-15, 1998; Sigal et al., *N. Engl. J. Med.* 339:216-22, 1998; erratum in: *N. Engl. J. Med.* 339:571, 1998). The amino terminus of fully processed OspA is a cysteine residue that is post-translationally modified with three fatty-acyl chains that anchor the protein to the outer surface of the bacterial membrane (Bouchon et al., *Anal. Biochem.* 246: 52-61, 1997). Lipidation of OspA is reported to stabilize the molecule (Luft, personal communication) and is essential for protection in the absence of a strong adjuvant (Erdile et al., *Infect. Immun.* 61: 81-90, 1993). A soluble, recombinant form of the protein lacking the amino-terminal lipid membrane anchor was co-crystallized with the Fab fragment of an agglutinating mouse monoclonal antibody to determine the structure of OspA, which was shown to comprise 21 anti-parallel β-strands followed by a single α-helix (Li et al., *Proc. Natl. Acad. Sci. U.S.A.* 94:3584-9, 1997).

A monovalent OspA-based vaccine (LYMErix®) was marketed in the USA for the prevention of Lyme disease. However, in Europe heterogeneity in OspA sequences across the three genospecies precludes broad protection with a vaccine based on OspA from a single strain (Gern et al., *Vaccine* 15:1551-7, 1997). Seven principal OspA serotypes have been recognized among European isolates (designated serotypes 1 to 7, Wilske et al., *J. Clin. Microbiol.* 31:340-50, 1993). OspA serotypes correlate with species; serotype 1 corresponds to *B. burgdorferi* s.s., serotype 2 corresponds to *B. afzelii* and serotypes 3 to 7 correspond to *B. garinii*.

Protective immunity acquired through immunization with OspA is unusual since the interaction between the host's immune response and the pathogen does not take place in the host, but in the mid-gut of the tick vector. In the case of Lyme disease, a tick acts as a vector or carrier for the transmission of Lyme disease from animals to humans. OspA specific antibody acquired during feeding by an infected tick prevents transmission of *B. burgdorferi* s.l. to the immunized mammalian host (de Silva et al., *J. Exp. Med.* 183: 271-5, 1996). Protection is antibody-mediated and is mainly affected through bactericidal antibody although an antibody that blocks attachment of the spirochete to a receptor on the lining of the tick gut epithelium may also be efficacious (Pal et al., *J. Immunol.* 166: 7398-403, 2001).

Rational development of effective OspA vaccines requires identification of the protective epitopes such as that defined by the protective monoclonal antibody LA-2 (Golde et al., *Infect. Immun.* 65: 882-9, 1997). X-ray crystallography and NMR analysis have been used to identify immunologically important hypervariable domains in OspA and have mapped the LA-2 epitope to amino acids 203-257 (Ding et al., *J. Mol. Biol.* 302: 1153-64, 2000; Luft et al. *J Infect Dis.* 185 (Suppl. 1): S46-51, 2002).

There is a need in the art for the development of an OspA vaccine that can provide broad protection against a variety of species of *Borrelia* that are present in the United States, Europe, and elsewhere. The following disclosure describes the specifics of such a vaccine.

SUMMARY OF THE INVENTION

The invention addresses one or more needs in the art relating to the prevention and treatment of Lyme disease or Lyme borreliosis.

The invention includes a chimeric polypeptide comprising a first polypeptide fragment from an outer surface protein A (OspA) serotype 3 protein of *Borrelia garinii* and a second polypeptide fragment from an OspA serotype 5 protein of *Borrelia garinii*, the polypeptide having the property of inducing an immune response against the OspA serotype 3 protein and the OspA serotype 5 protein. In some aspects, the chimeric polypeptide comprises an N-terminal polypeptide fragment from the OspA serotype 5 protein and a C-terminal polypeptide fragment from the OspA serotype 3 protein. In other aspects, the chimeric polypeptide comprises an N-terminal polypeptide fragment from the OspA serotype 3 protein and a C-terminal polypeptide fragment from the OspA serotype 5 protein. In certain aspects, the chimeric polypeptide further comprises an N-terminal outer surface protein B (OspB) polypeptide fragment of *Borrelia*, wherein the OspB polypeptide fragment comprises an OspB leader sequence. In particular aspects, the chimeric polypeptide comprises an amino acid sequence having at least 200 amino acid residues with at least or about 79, 80, 81, 82, 83, 84, 85, 86, 87, 88, 89, 90, 91, 92, 93, 94, 95, 96, 97, 98, or 99 percent sequence identity to the amino acid sequence set forth in SEQ ID NO: 173. In various aspects, the chimeric polypeptide comprises the amino acid sequence set forth in SEQ ID NO: 173. In other aspects, the chimeric polypeptide consists of the amino acid sequence set forth in SEQ ID NO: 173.

The invention includes compositions comprising a chimeric polypeptide of the invention and a pharmaceutically acceptable carrier. In some aspects, such compositions further comprise an additional polypeptide from an outer surface protein A (OspA) protein of *Borrelia*. In some aspects, such compositions further comprise an additional polypeptide from an outer surface protein B (OspB) protein of *Borrelia*. In particular aspects, the additional polypeptide comprises an N-terminal outer surface protein B (OspB) polypeptide fragment of *Borrelia*, wherein the OspB polypeptide fragment comprises an OspB leader sequence. In various aspects, *Borrelia* is *Borrelia burgdorferi*, *Borrelia afzelii*, *Borrelia garinii*, *Borrelia japonica*, *Borrelia andersonii*, *Borrelia bissettii*, *Borrelia sinica*, *Borrelia turdi*, *Borrelia tanukii*, *Borrelia val-*

*aisiana, Borrelia lusitaniae, Borrelia spielmanii, Borrelia miyamotoi* or *Borrelia lonestar.*

In some aspects, the additional polypeptide is a chimeric polypeptide comprising a first polypeptide fragment from an outer surface protein A (OspA) serotype 4 protein of *Borrelia garinii* and a second polypeptide fragment from an OspA serotype 6 protein of *Borrelia garinii*, the polypeptide having the property of inducing an immune response against the OspA serotype 4 protein and the OspA serotype 6 protein. In particular aspects, the additional polypeptide comprises an N-terminal polypeptide fragment of the OspA serotype 6 protein and a C-terminal polypeptide fragment of the OspA serotype 4 protein. In other aspects, the additional polypeptide comprises an N-terminal polypeptide fragment from the OspA serotype 4 protein and a C-terminal polypeptide fragment from the OspA serotype 6 protein. In certain aspects, the additional polypeptide comprises an amino acid sequence having at least 200 amino acid residues with at least or about 79, 80, 81, 82, 83, 84, 85, 86, 87, 88, 89 90, 91, 92, 93, 94, 95, 96, 97, 98, or 99 percent sequence identity to the amino acid sequence set forth in SEQ ID NO: 171. In particular aspects, the additional polypeptide comprises the amino acid sequence set forth in SEQ ID NO: 171. In further aspects, the additional polypeptide consists of the amino acid sequence set forth in SEQ ID NO: 171.

In some aspects, the additional polypeptide is a chimeric polypeptide comprising a first polypeptide fragment from an outer surface protein A (OspA) serotype 1 protein of *Borrelia burgdorferi sensu stricto* and a second polypeptide fragment from an OspA serotype 2 protein of *Borrelia afzelii*, the polypeptide having the property of inducing an immune response against the OspA serotype 1 protein and the OspA serotype 2 protein. In particular aspects, the additional polypeptide comprises an N-terminal polypeptide fragment from the OspA serotype 1 protein and a C-terminal polypeptide fragment from the OspA serotype 2 protein. In other aspects, the additional polypeptide comprises an N-terminal polypeptide fragment from the OspA serotype 2 protein and a C-terminal polypeptide fragment from the OspA serotype 1 protein. In particular aspects, the additional polypeptide further comprises an N-terminal outer surface protein B (OspB) polypeptide fragment of *Borrelia*, wherein the OspB polypeptide fragment comprises an OspB leader sequence. In certain aspects, the additional polypeptide comprises an amino acid sequence having at least 200 amino acid residues with at least or about 79, 80, 81, 82, 83, 84, 85, 86, 87, 88, 89 90, 91, 92, 93, 94, 95, 96, 97, 98, or 99 percent sequence identity to the amino acid sequence set forth in SEQ ID NO: 169. In particular aspects, the additional polypeptide comprises the amino acid sequence set forth in SEQ ID NO: 169. In further aspects, the additional polypeptide consists of the amino acid sequence set forth in SEQ ID NO: 169.

The invention includes compositions comprising at least three chimeric OspA polypeptides, wherein the polypeptides have different sequences. In some aspects, the chimeric OspA polypeptides individually comprise the amino acid sequences set forth in SEQ ID NOS: 169, 171, and 173. In other aspects, the chimeric OspA polypeptides induce an immune response against at least OspA serotype proteins 1, 2, 3, 4, 5, and 6.

The invention includes a chimeric nucleic acid molecule comprising a first nucleotide sequence fragment from an outer surface protein A (OspA) serotype 3 protein coding region of *Borrelia garinii* and a second nucleotide sequence fragment from an OspA serotype 5 protein coding region of *Borrelia garinii*, the nucleic acid molecule encoding a polypeptide having the property of inducing an immune response against the OspA serotype 3 protein and the OspA serotype 5 protein. In some aspects, the chimeric nucleic acid molecule comprises a 5'-terminal nucleotide sequence encoding a fragment of the OspA serotype 5 protein coding region and a 3'-terminal nucleotide sequence encoding a fragment of the OspA serotype 3 protein coding region. In other aspects, the chimeric nucleic acid molecule comprises a 3'-terminal nucleotide sequence encoding a fragment of the OspA serotype 5 protein coding region and a 5'-terminal nucleotide sequence encoding a fragment of the OspA serotype 3 protein coding region. In various aspects, the chimeric nucleic acid molecule further comprises a 5'-terminal outer surface protein B (OspB) nucleotide sequence fragment of *Borrelia*, wherein the OspB nucleotide sequence fragment comprises an OspB leader sequence. In certain aspects, the chimeric nucleic acid molecule comprises a nucleotide sequence selected from the group consisting of: (a) a nucleotide sequence with at least about 79, 80, 81, 82, 83, 84, 85, 86, 87, 88, 89, 90, 91, 92, 93, 94, 95, 96, 97, 98, or 99 percent sequence identity with the nucleic acid sequence set forth in SEQ ID NO: 172; and (b) a nucleotide sequence complementary to (a). In other aspects, the chimeric nucleic acid molecule comprises a nucleotide sequence selected from the group consisting of: (a) a nucleotide sequence encoding a polypeptide with at least about 79, 80, 81, 82, 83, 84, 85, 86, 87, 88, 89, 90, 91, 92, 93, 94, 95, 96, 97, 98, or 99 percent sequence identity with the amino acid sequence set forth in SEQ ID NO: 173; and (b) a nucleotide sequence complementary to (a). In particular aspects of the invention, the chimeric nucleic acid molecule comprises a nucleotide sequence selected from the group consisting of: (a) a nucleotide sequence encoding a polypeptide comprising the amino acid sequence set forth in SEQ ID NO: 173, the polypeptide having a substitution of one to 25 conservative amino acids; (b) a nucleotide sequence encoding a polypeptide comprising the amino acid sequence set forth in SEQ ID NO: 173, the polypeptide having an insertion of one to 25 conservative amino acids; (c) a nucleotide sequence encoding a polypeptide comprising the amino acid sequence set forth in SEQ ID NO: 173, the polypeptide having an internal deletion of one to 25 conservative amino acids; (d) a nucleotide sequence encoding a polypeptide comprising the amino acid sequence set forth in SEQ ID NO: 173, the polypeptide having a C- and/or N-terminal truncation of one to 25 amino acids; (e) a nucleotide sequence encoding a polypeptide comprising the amino acid sequence set forth in SEQ ID NO: 173, the polypeptide having a modification of one to 25 amino acids selected from amino acid substitutions, amino acid insertions, amino acid deletions, a C-terminal truncation, or an N-terminal truncation; and (f) a nucleotide sequence complementary to any of (a)-(e). In various aspects, such substitutions, insertions, deletions, or modifications occur at any of amino acid positions 1-4, 6, 8, 9, 11, 16, 18, 20-28, 47, 49, 50, 81, 82, 83, 100 139, 155, 160, 176, 189, 190, and 250 of SEQ ID NO: 173. In some aspects, the chimeric nucleic acid molecule comprises the nucleotide sequence set forth in SEQ ID NO: 172. In other aspects, the chimeric nucleic acid molecule consists of the nucleotide sequence set forth in SEQ ID NO: 172.

The invention includes vectors, host cells, and processes of producing polypeptides by culturing the host cells discussed herein. In some aspects, the invention includes a vector comprising any of the nucleic acid molecules described herein. In other aspects, the invention includes a host cell that comprises such vectors. In some aspects, the host cell is a eukaryotic cell. In other aspects, the host cell is a prokaryotic cell. In various aspects, the process of producing a polypeptide comprises culturing the host cells described herein under conditions suitable to express the polypeptide, and optionally isolating the polypeptide from the culture. In various aspects, the invention includes compositions comprising any of these chimeric nucleic acid molecules or any vectors comprising such nucleic acid molecules and a pharmaceutically acceptable carrier or carriers.

As set out above, the invention includes a composition comprising a chimeric nucleic acid molecule comprising a first nucleotide sequence fragment from an outer surface protein A (OspA) serotype 3 protein coding region of *Borrelia garinii* and a second nucleotide sequence fragment from an OspA serotype 5 protein coding region of *Borrelia garinii*, the nucleic acid molecule encoding a polypeptide having the property of inducing an immune response against the OspA serotype 3 protein and the OspA serotype 5 protein. In some aspects, the composition further comprises an additional nucleic acid molecule encoding an outer surface protein A (OspA) protein of *Borrelia*. In other aspects, the composition further comprises an additional nucleic acid molecule encoding an outer surface protein B (OspB) protein of *Borrelia*. In particular aspects, the additional nucleic acid molecule further comprises a 5'-terminal outer surface protein B (OspB) fragment nucleotide sequence of *Borrelia*, wherein the OspB nucleotide sequence fragment comprises an OspB leader sequence. In various aspects, the *Borrelia* is *Borrelia burgdorferi, Borrelia afzelii, Borrelia garinii, Borrelia japonica, Borrelia andersonii, Borrelia bissettii, Borrelia sinica, Borrelia turdi, Borrelia tanukii, Borrelia valaisiana, Borrelia lusitaniae, Borrelia spielmanii, Borrelia miyamotoi* or *Borrelia lonestar*.

In some aspects, the additional nucleic acid molecule is a chimeric nucleic acid molecule comprising a first nucleotide sequence fragment from an outer surface protein A (OspA) serotype 6 protein coding region of *Borrelia* garinii and a second nucleotide sequence fragment from an OspA serotype 4 protein coding region of *Borrelia garinii*, the nucleic acid molecule encoding a polypeptide having the property of inducing an immune response against the OspA serotype 6 protein and the OspA serotype 4 protein. In other aspects, the additional nucleic acid molecule comprises a 5'-terminal nucleotide sequence encoding a fragment of the OspA serotype 6 protein coding region and a 3'-terminal nucleotide sequence encoding a fragment of the OspA serotype 4 protein coding region. In various aspects, the additional nucleic acid molecule comprises a 5'-terminal nucleotide sequence encoding a fragment of the OspA serotype 4 protein and a 3'-terminal nucleotide sequence encoding a fragment of the OspA serotype 6 protein. In some aspects, the additional nucleic acid molecule comprises a nucleotide sequence selected from the group consisting of: (a) a nucleotide sequence with at least or about 79, 80, 81, 82, 83, 84, 85, 86, 87, 88, 89, 90, 91, 92, 93, 94, 95, 96, 97, 98, or 99 percent sequence identity with the nucleotide sequence set forth in SEQ ID NO: 170; and (b) a nucleotide sequence complementary to (a). In other aspects, the additional nucleic acid molecule comprises a nucleotide sequence selected from the group consisting of: (a) a nucleotide sequence encoding a polypeptide with at least or about 79, 80, 81, 82, 83, 84, 85, 86, 87, 88, 89, 90, 91, 92, 93, 94, 95, 96, 97, 98, or 99 percent sequence identity with a polypeptide comprising the amino acid sequence set forth in SEQ ID NO: 171; and (b) a nucleotide sequence complementary to (a). In particular aspects, the additional nucleic acid molecule comprises a nucleotide sequence selected from the group consisting of: (a) a nucleotide sequence encoding a polypeptide comprising the amino acid sequence set forth in SEQ ID NO: 171, the polypeptide having a substitution of one to 25 conservative amino acids; (b) a nucleotide sequence encoding a polypeptide comprising the amino acid sequence set forth in SEQ ID NO: 171, the polypeptide having an insertion of one to 25 conservative amino acids; (c) a nucleotide sequence encoding a polypeptide comprising the amino acid sequence set forth in SEQ ID NO: 171, the polypeptide having an internal deletion of one to 25 conservative amino acids; (d) a nucleotide sequence encoding a polypeptide comprising the amino acid sequence set forth in SEQ ID NO: 171, the polypeptide having a C- and/or N-terminal truncation of one to 25 amino acids; (e) a nucleotide sequence encoding a polypeptide comprising the amino acid sequence set forth in SEQ ID NO: 171, the polypeptide having a modification of one to 25 amino acids selected from amino acid substitutions, amino acid insertions, amino acid deletions, a C-terminal truncation, or an N-terminal truncation; and (f) a nucleotide sequence complementary to any of (a)-(e). In various aspects, the substitutions, insertions, deletions, or modifications occur at any of amino acid positions 1-4, 6, 8, 9, 11, 16, 18, 20-28, 47, 49, 50, 81, 82, 83, 100 139, 155, 160, 176, 189, 190, and 250 of SEQ ID NO: 171. In some aspects, the additional nucleic acid molecule comprises a nucleotide sequence set forth in SEQ ID NO: 170. In other aspects, the additional nucleic acid molecule consists of a nucleotide sequence set forth in SEQ ID NO: 170.

In other aspects, the additional nucleic acid molecule is a chimeric nucleic acid molecule comprising a first nucleotide sequence fragment from an outer surface protein A (OspA) serotype 1 protein coding region of *Borrelia burgdorferi sensu stricto* and a second nucleotide sequence fragment from an OspA serotype 2 protein coding region of *Borrelia afzelii*, the nucleic acid molecule encoding a polypeptide having the property of inducing an immune response against the OspA serotype 1 protein and the OspA serotype 2 protein. In certain aspects, the additional nucleic acid molecule comprises a 5'-terminal nucleotide sequence encoding a fragment of the OspA serotype 1 protein coding region and a 3'-terminal nucleotide sequence encoding a fragment of the OspA serotype 2 protein coding region. In other aspects, the additional nucleic acid molecule comprises a 5'-terminal nucleotide sequence encoding a fragment of the OspA serotype 2 protein coding region and a 3'-terminal nucleotide sequence encoding a fragment of the OspA serotype 1 protein coding region. In various aspects, the additional nucleic acid molecule comprises a nucleotide sequence selected from the group consisting of: (a) a nucleotide sequence with at least or about 79, 80, 81, 82, 83, 84, 85, 86, 87, 88, 89, 90, 91, 92, 93, 94, 95, 96, 97, 98, or 99 percent sequence identity with the nucleotide sequence set forth in SEQ ID NO: 168; and (b) a nucleotide sequence complementary to (a). In further aspects, the additional nucleic acid molecule comprises a nucleotide sequence selected from the group consisting of: (a) a nucleotide sequence encoding a polypeptide with at least or about 79, 80, 81, 82, 83, 84, 85, 86, 87, 88, 89, 90, 91, 92, 93, 94, 95, 96, 97, 98, or 99 percent sequence identity with a polypeptide comprising the amino acid sequence set forth in SEQ ID NO: 169; and (b) a nucleotide sequence complementary to (a). In some aspects, the additional nucleic acid molecule comprises a nucleotide sequence selected from the group consisting of: (a) a nucleotide sequence encoding a polypeptide comprising the amino acid sequence set forth in SEQ ID NO: 169, the polypeptide having a substitution of one to 25 conservative amino acids; (b) a nucleotide sequence encoding a polypeptide comprising the amino acid sequence set forth in SEQ ID NO: 169, the polypeptide having an insertion of one to 25 conservative amino acids; (c) a nucleotide sequence encoding a polypeptide comprising the amino acid sequence set forth in SEQ ID NO: 169, the polypeptide having an internal deletion of one to 25 conservative amino acids; (d) a nucleotide sequence encoding a polypeptide comprising the amino acid sequence set forth in SEQ ID NO: 169, the polypeptide having a C- and/or N-terminal truncation of one to 25 amino acids; (e) a nucleotide sequence encoding a polypeptide comprising the amino acid sequence set forth in SEQ ID NO: 169, the polypeptide having a modification of one to 25 amino acids selected from amino acid substitutions, amino acid insertions, amino acid deletions, a C-terminal truncation, or an N-terminal truncation; and (f) a nucleotide sequence complementary to any of (a)-(e). In various aspects, the substitutions, insertions, deletions, or modifications occur at any of amino acid positions 1-4, 6, 8, 9, 11, 16, 18, 20-28, 47, 49, 50, 81, 82, 83, 100 139, 155, 160, 176, 189, 190, and 250 of SEQ ID NO: 169. In some aspects, the additional nucleic acid molecule comprises the nucleotide sequence set forth in SEQ ID NO: 168. In other aspects, the additional nucleic acid molecule consists of the nucleotide sequence set forth in SEQ ID NO: 168.

As set out above, the invention includes a composition comprising a chimeric nucleic acid molecule comprising a first nucleotide sequence fragment from an outer surface protein A (OspA) serotype 3 protein coding region of *Borrelia garinii* and a second nucleotide sequence fragment from an OspA serotype 5 protein coding region of *Borrelia garinii*, the nucleic acid molecule encoding a polypeptide having the property of inducing an immune response against the OspA serotype 3 protein and the OspA serotype 5 protein. In some aspects, the composition further comprises at least two additional nucleic acid molecules encoding an outer surface protein A (OspA) protein of *Borrelia*. In various aspects, such additional nucleic acid molecules have different nucleotide sequences. In certain aspects, a composition of the invention comprises at least three nucleic acid molecules encoding an outer surface protein A (OspA) protein of *Borrelia*, wherein the nucleic acid molecules have different nucleotide sequences. In particular aspects, a composition of the invention comprises nucleic acid molecules, wherein the nucleic acid molecules individually comprise the nucleotide sequences set forth in SEQ ID NOS: 168, 170, and 172. In some aspects, a composition of the invention comprises chimeric nucleic acid molecules, wherein the nucleic acid molecules encode polypeptides that induce an immune response against at least OspA serotype proteins 1, 2, 3, 4, 5, and 6.

The invention also includes immunogenic compositions. In some aspects, an immunogenic composition of the invention comprises any of the compositions discussed herein and a pharmaceutically acceptable carrier. In various aspects, the immunogenic composition has the property of inducing production of an antibody that specifically binds an outer surface protein A (OspA) protein. In certain aspects, the immunogenic composition has the property of inducing production of an antibody that specifically binds *Borrelia*. In particular aspects, the immunogenic composition has the property of inducing production of an antibody that neutralizes *Borrelia*. In some aspects, the antibody is produced by an animal. In further aspects, the animal is a mammal. In even further aspects, the mammal is human.

The invention further includes vaccine compositions. In some aspects, a vaccine composition of the invention comprises any immunogenic composition discussed herein and a pharmaceutically acceptable carrier. In various aspects, the invention includes a combination vaccine. In certain aspects, a combination vaccine of the invention comprises any vaccine composition discussed herein in combination with at least a second vaccine composition. In some aspects, the second vaccine composition protects against a tick-borne disease. In various aspects, the tick-borne disease is Rocky Mountain Spotted Fever, Babesiosis, Relapsing Fever, Colorado tick fever, Human monocytic ehrlichiosis (HME), Human granulocytic ehrlichiosis (HGE), Southern Tick-Associated Rash Illness (STARI), Tularemia, Tick paralysis, Powassan encephalitis, Q fever, Crimean-Congo hemorrhagic fever, Cytauxzoonosis, boutonneuse fever, or tick-borne encephalitis. In other aspects, the second vaccine composition is a vaccine selected from the group consisting of: a tick-borne encephalitis vaccine, a Japanese encephalitis vaccine, and a Rocky Mountain Spotted Fever vaccine. In various aspects, the second vaccine composition has a seasonal immunization schedule compatible with immunization against *Borrelia* infection or Lyme disease.

The invention also includes methods for inducing an immunological response in a subject. In various aspects, such methods comprise the step of administering any of the immunogenic compositions or vaccine compositions discussed herein to the subject in an amount effective to induce an immunological response. In certain aspects, the immunological response comprises production of an anti-OspA antibody.

The invention includes methods for preventing or treating a *Borrelia* infection or Lyme disease in a subject. In various aspects, such methods comprise the step of administering any of the vaccine compositions discussed herein or any of the combination vaccines discussed herein to the subject in an amount effective to prevent or treat the *Borrelia* infection or Lyme disease.

The invention includes uses of compositions of the invention for the preparation of medicaments. Other related aspects are also provided in the instant invention.

The foregoing summary is not intended to define every aspect of the invention, and additional aspects are described in other sections, such as the following detailed description. The entire document is intended to be related as a unified disclosure, and it should be understood that all combinations of features described herein are contemplated, even if the combination of features are not found together in the same sentence, or paragraph, or section of this document. Other features and advantages of the invention will become apparent from the following detailed description. It should be understood, however, that the detailed description and the specific examples, while indicating specific embodiments of the invention, are given by way of illustration only, because various changes and modifications within the spirit and scope of the invention will become apparent to those skilled in the art from this detailed description.

BRIEF DESCRIPTION OF THE DRAWINGS

FIG. 2 is the amino acid sequence of lipB sOspA 1/2$^{251}$ (SEQ ID NO: 2).

FIG. 3 shows nucleotide (SEQ ID NO: 1) and deduced amino acid sequences (SEQ ID NO: 2) of lipB sOspA 1/2$^{251}$.

FIG. 4 is the amino acid sequence of lipB sOspA 6/4 (SEQ ID NO: 4).

FIG. 5 shows nucleotide (SEQ ID NO: 3) and deduced amino acid sequences (SEQ ID NO: 4) of lipB sOspA 6/4.

FIG. 6 is the amino acid sequence of lipB sOspA 5/3 (SEQ ID NO: 6).

FIG. 7 shows nucleotide (SEQ ID NO: 5) and deduced amino acid sequences (SEQ ID NO: 6) of lipB sOspA 5/3.

FIG. 9 shows sequence differences between lipidated and non-lipidated constructs.

FIG. 13 is a map of plasmid pET30a.

FIG. 14 shows the strategy for creation of the lipB sOspA 5/3 Kpn I-Bam HI fragment.

FIG. 15 is an alignment highlighting the amino acid change (SEQ ID NO: 39) in lipB sOspA $1/2^{251}$ and the PCR primer sequences (SEQ ID NOS: 21 and 41) used to introduce the change (lipB OspA 1/2 mod (SEQ ID NO: 38); consensus sequence (SEQ ID NO: 40)).

FIG. 16 is an alignment of OspA sequence of Blip OspA BPBP/A1 with the modified molecule lipB sOspA $1/2^{251}$. The top strand is the original sequence (SEQ ID NO: 42) and the bottom strand is the optimized sequence (SEQ ID NO: 43). Note: Three bases (CAT) at the start of the sequence are not shown; they form part of the Nde I site CATATG.

FIG. 17 is an alignment of OspA sequence of Blip OspA KT with the modified molecule lipB sOspA 6/4. The top strand is the original sequence (SEQ ID NO: 44) and the bottom strand is the optimized sequence (SEQ ID NO: 45). Note: A single base (C) at the start of the sequence is not shown; they form part of the Nde I site CATATG.

FIG. 18 is an alignment of OspA sequence of Blip OspA 5/3 with the modified molecule lipB sOspA 5/3. The top strand is the original sequence (SEQ ID NO: 46) and the bottom strand is the optimized sequence (SEQ ID NO: 47).

DETAILED DESCRIPTION OF THE INVENTION

Figure 1:
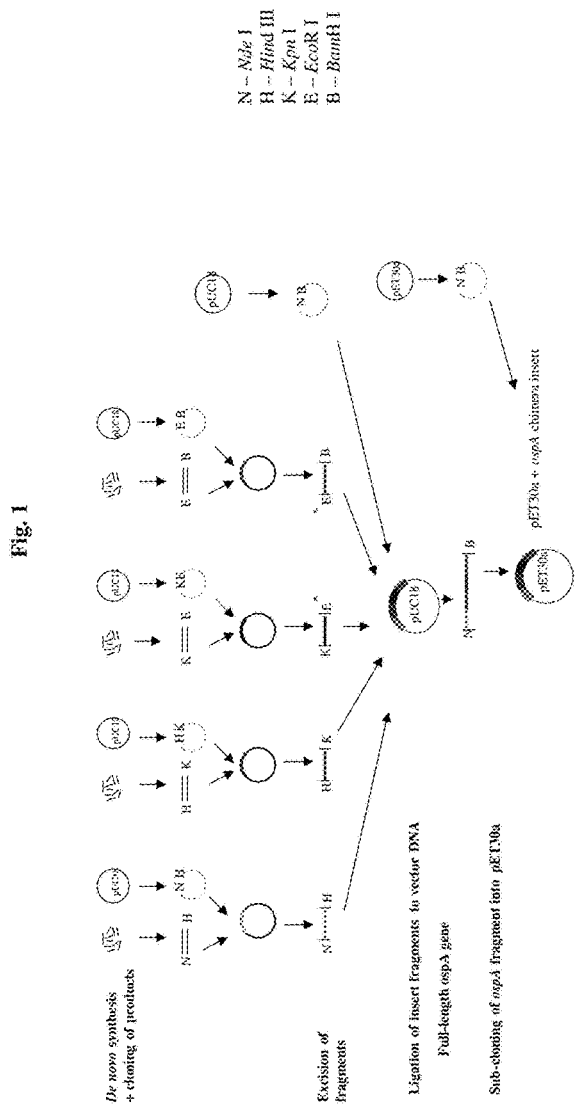
FIG. 1 is a schematic overview for preparation of lipidated OspA chimera constructs.
Figure 8:
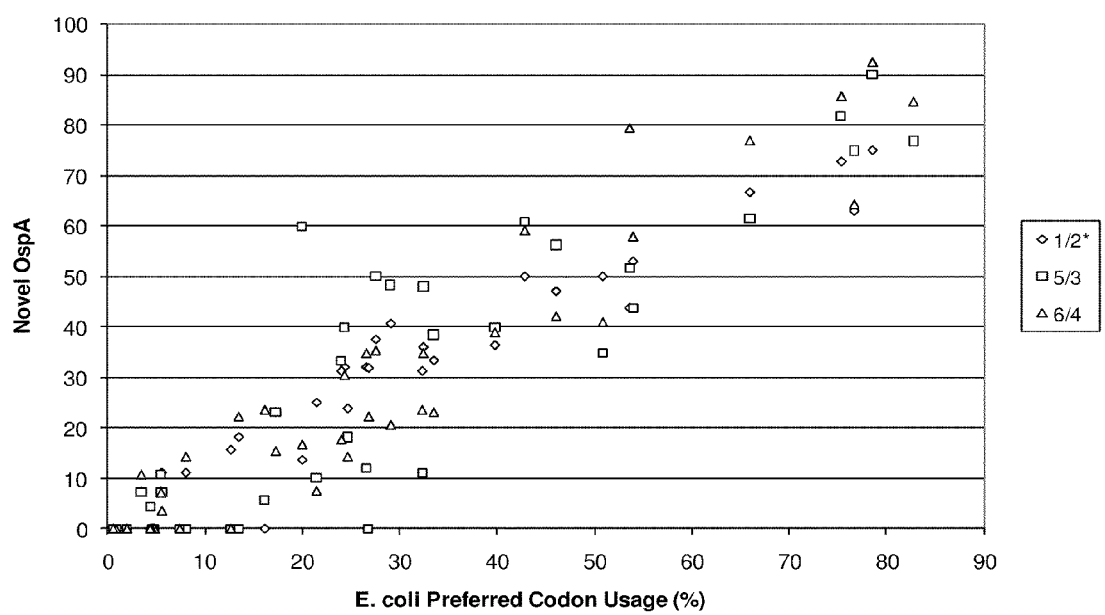
FIG. 8 depicts optimization of codon usage for high level expression.
Figure 10:
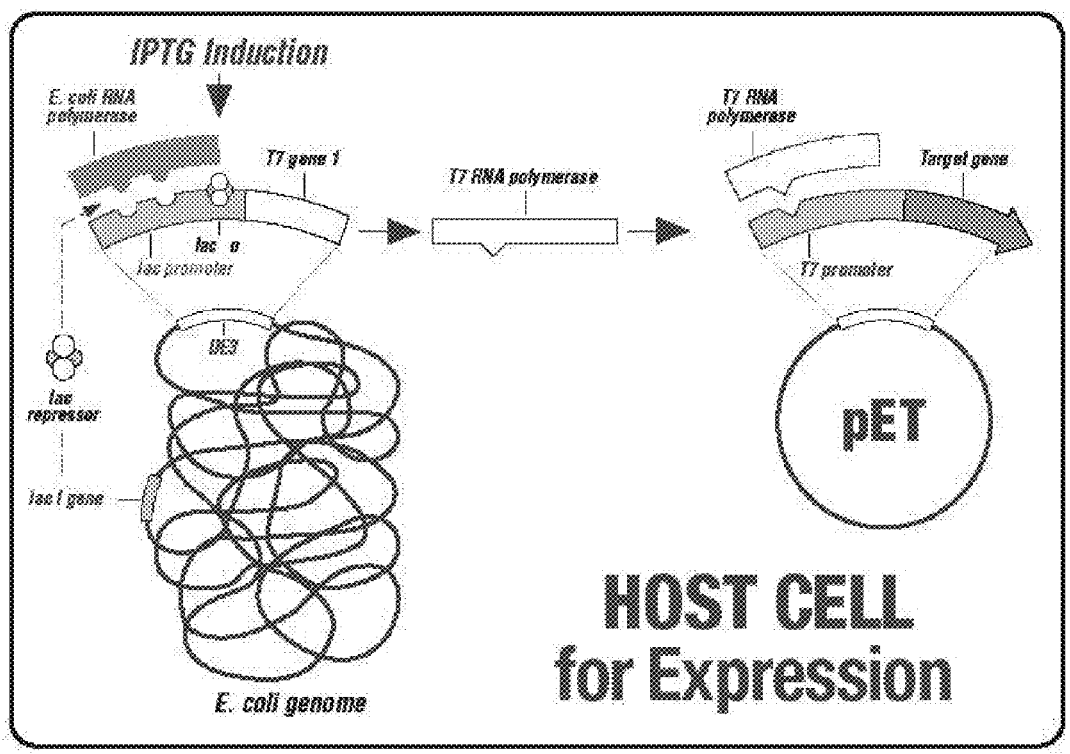
FIG. 10 is a description of the T7 expression system.
Figure 11:
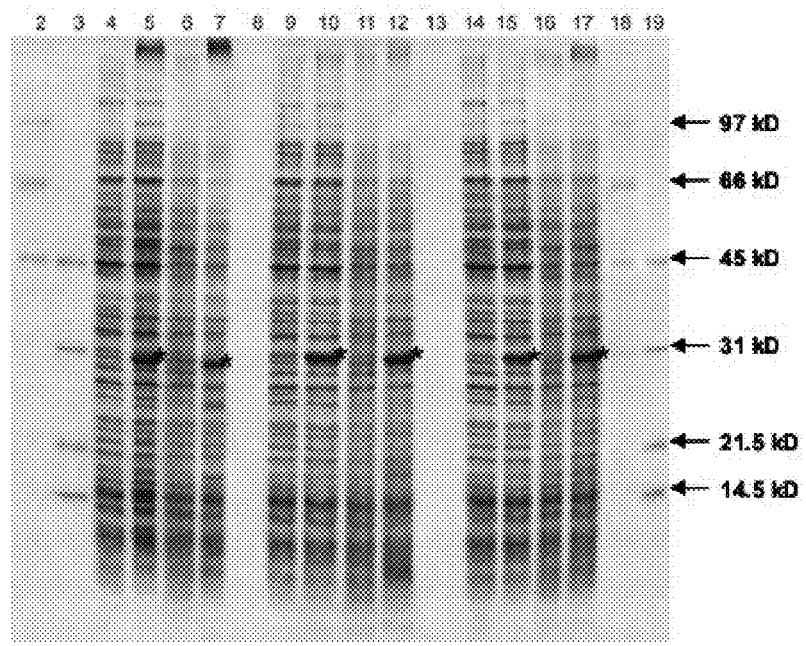
FIG. 11 is an SDS-PAGE showing expression of the novel recombinant OspA proteins from induced and un-induced cultures.

The invention provides chimeric OspA molecules that are useful as antigens that can be delivered as an immunogenic composition or vaccine composition for Lyme disease or a *Borrelia* infection. Before any embodiments of the invention are explained in detail, it is to be understood that the invention is not limited in its application to the details of construction and the arrangement of components set forth in the following description or illustrated in the figures and examples. The section headings used herein are for organizational purposes only and are not to be construed as limiting the subject matter described. All references cited in this application are expressly incorporated by reference herein.

The invention embraces other embodiments and is practiced or carried out in various ways. Also, it is to be understood that the phraseology and terminology used herein is for the purpose of description and should not be regarded as limiting. The terms "including," "comprising," or "having" and variations thereof are meant to encompass the items listed thereafter and equivalents thereof as well as additional items.

Embodiments of the invention are exemplified in the design and synthesis of three chimeric OspA coding sequences that encode three distinct lipidated OspA molecules, all of which share some common features. Each chimeric coding sequence represents two OspA serotypes and the chimeric coding sequences were designed to encode stable chimeric OspA molecules that are safe and highly immunogenic, and afford a subject protection against infection with *B. burgdorferi sensu lato* (s.l.).

In one aspect, the chimeric OspA molecules comprise the proximal portion from one OspA serotype, together with the distal portion from another OspA serotype while retaining the protective properties of both of the parent polypeptides. The chimeric OspA nucleic acid molecules were expressed in *Escherichia coli* (*E. coli*) to provide antigens which could be formulated as a combination vaccine to provide protection against all six prevalent serotypes (serotypes 1-6) associated with Lyme disease or *Borrelia* infection in Europe and against the single OspA serotype associated with Lyme disease or *Borrelia* infection in North America. Because a vaccine comprising serotypes 1-6 provides protection against *B. afzelii*, *B. garinii*, and *B. burgdorferi*, the vaccine is designed for global use.

The invention also includes the preparation of a second set of chimeric OspA coding sequences which is, in one aspect, derived from the first set of three genes, by removing nucleic acid sequences encoding a leader sequence needed to produce a lipidated OspA molecule. The two sets of constructs (giving rise to lipidated and non-lipidated polypeptides) were needed to evaluate their ease of production in the fermentor (biomass, stability, product yields etc.), to assess how readily different types of antigen can be purified and to compare their biological characteristics (safety profile and protective potency).

The invention includes immunogenic compositions comprising the chimeric OspA molecules of the invention. The invention likewise includes vaccines and vaccine kits comprising such OspA molecules, processes for making the immunogenic compositions and vaccines and the use of the immunogenic compositions and vaccines in human and veterinary medical therapy and prevention. The invention further includes methods of immunizing against Lyme disease or

*Borrelia* infection using the OspA compositions described herein and the use of the OspA compositions in the manufacture of a medicament for the prevention of Lyme disease or *Borrelia* infection.

DEFINITIONS

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

The following abbreviations are used throughout.

| | |
|---|---|
| AA | Amino acid |
| Amp | Ampicillin |
| bp | Base pairs |
| *B. afzelii* | *Borrelia afzelii* |
| *B. burdorferi* | *Borrelia burgdorferi* |
| *B. garinii* | *Borrelia garinii* |
| DNA | Deoxyribonucleic acid |
| dNTPs | Deoxynucleotide triphosphate |
| *E. coli* | *Escherichia coli* |
| GC content | Percentage of a sequence containing bases Guanine and Cytosine |
| hLFA-1 | Human leukocyte function-associated antigen-1 |
| HPLC | High Performance Liquid Chromatography |
| IP | Intellectual property |
| IPTG | Isopropyl-beta-D-thiogalactopyranoside |
| Kan | Kanamycin |
| kDa | KiloDaltons |
| LB | Luria Broth |
| Lip B | Leader sequence from Outer surface protein B |
| Mab | Monoclonal antibody |
| OD | Optical density |
| OspA | Outer surface protein A |
| OspB | Outer surface protein B |
| PCR | Polymerase chain reaction |
| RNA | Ribonucleic acid |
| s.l. | *Sensu lato* |
| s.s. | *Sensu stricto* |
| SDS | Sodium dodecyl sulfate |
| SMK | Growth media for *E. coli* (ketoglutarate sorbitol media) |
| tRNA | Transfer ribonucleic acid |
| WCB | Working cell bank |

It is noted here that, as used in this specification and the appended claims, the singular forms "a," "an," and "the" include plural reference unless the context clearly dictates otherwise.

As used herein, the following terms have the meanings ascribed to them unless specified otherwise.

The term "gene" refers to a DNA sequence that encodes a sequence of amino acids which comprise all or part of one or more polypeptides, proteins or enzymes, and may or may not include introns, and regulatory DNA sequences, such as promoter or enhancer sequences, 5'-untranslated region, or 3'-untranslated region which affect, for example, the conditions under which the gene is expressed. In the present disclosure, the OspA gene is bacterial and, therefore, there are no introns. The term "coding sequence" refers to a DNA sequence that encodes a sequence of amino acids, but does not contain introns or regulatory sequences. Likewise, in the present disclosure the OspA coding sequence does not contain regulatory sequences.

"Nucleic acid" or "nucleic acid sequence" or "nucleic acid molecule" refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs). The terms encompass molecules formed from any of the known base analogs of DNA and RNA such as, but not limited to 4-acetylcytosine, 8-hydroxy-N6-methyladenine, aziridinyl-cytosine, pseudoisocytosine, 5-(carboxyhydroxylmethyl) uracil, 5-fluorouracil, 5-bromouracil, 5-carboxymethylaminomethyl-2-thiouracil, 5-carboxy-methylaminomethyluracil, dihydrouracil, inosine, N6-iso-pentenyladenine, 1-methyladenine, 1-methylpseudouracil, 1-methylguanine, 1-methylinosine, 2,2-dimethyl-guanine, 2-methyladenine, 2-methylguanine, 3-methylcytosine, 5-methylcytosine, N6-methyladenine, 7-methylguanine, 5-methylaminomethyluracil, 5-methoxyamino-methyl-2-thiouracil, beta-D-mannosylqueosine, 5'-methoxycarbonyl-methyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions, in some aspects, are achieved by generating sequences in which the third position of one or more selected (or all) codons is substituted with mixed-base and/or deoxyinosine residues (Batzer et al., *Nucleic Acid Res.* 19:5081 (1991); Ohtsuka et al., *J. Biol. Chem.* 260:2605-2608 (1985); Rossolini et al., *Mol. Cell. Probes* 8:91-98 (1994)). The term nucleic acid is used interchangeably with gene, cDNA, mRNA, oligonucleotide, and polynucleotide.

The terms "polypeptide," "peptide" and "protein" are used interchangeably herein to refer to a polymer of amino acid residues linked via peptide bonds. The terms apply to amino acid polymers in which one or more amino acid residue is an artificial chemical mimetic of a corresponding naturally occurring amino acid, as well as to naturally occurring amino acid polymers and non-naturally occurring amino acid polymers. The term "protein" typically refers to large polypeptides. The term "peptide" typically refers to short polypeptides. Synthetic polypeptides can be synthesized, for example, using an automated polypeptide synthesizer.

The term "Osp A molecule" or "chimeric OspA molecule" refers, in one aspect, to an "OspA nucleic acid" comprising the nucleotide sequence of SEQ ID NO: 1 (lipB sOspA $1/2^{251}$), SEQ ID NO: 3 (lipB sOspA 6/4), SEQ ID NO: 5 (lipB sOspA 5/3), SEQ ID NO: 7 (sOspA $1/2^{251}$), SEQ ID NO: 9 (sOspA 6/4), SEQ ID NO: 11 (sOspA 5/3), SEQ ID NO: 168 (orig sOspA 1/2), SEQ ID NO: 170 (orig sOspA 6/4), or SEQ ID NO: 172 (orig sOspA 5/3), or, in another aspect to an "OspA polypeptide" comprising the amino acid sequence of SEQ ID NO: 2 (lipB sOspA $1/2^{251}$), SEQ ID NO: 4 (lipB sOspA 6/4), SEQ ID NO: 6 (lipB sOspA 5/3), SEQ ID NO: 8

(sOspA 1/2^251), SEQ ID NO: 10 (sOspA 6/4), SEQ ID NO: 12 (sOspA 5/3), SEQ ID NO: 169 (orig sOspA 1/2), SEQ ID NO: 171 (orig sOspA 6/4), or SEQ ID NO: 173 (orig sOspA 5/3).

The term "lipB sOspA molecule" refers, in one aspect, to an "OspA nucleic acid" comprising the nucleotide sequence of SEQ ID NO: 1 (lipB sOspA 1/2^251), SEQ ID NO: 3 (lipB sOspA 6/4), or SEQ ID NO: 5 (lipB sOspA 5/3) or, in another aspect to an "OspA polypeptide" comprising the amino acid sequence of SEQ ID NO: 2 (lipB sOspA 1/2^251), SEQ ID NO: 4 (lipB sOspA 6/4), or SEQ ID NO: 6 (lipB sOspA 5/3). The nucleic acid sequences of SEQ ID NOS: 7, 9, and 11 lack the nucleic acid sequence encoding the lipB leader sequence (MRLLIGFALALALIG (SEQ ID NO: 13). In addition, the nucleic acid sequences of SEQ ID NOS: 7, 9, and 11 encode a methionine residue at the amino terminus of SEQ ID NOS: 8, 10, and 12 in place of the cysteine residue present at the carboxy terminus of the lipB leader sequence in SEQ ID NOS: 2, 4, and 6.

The term "orig sOspA molecule" or "original sOspA molecule" refers, in one aspect, to an "OspA nucleic acid" comprising the nucleotide sequence of SEQ ID NO: 168 (orig sOspA 1/2), SEQ ID NO: 170 (orig sOspA 6/4), or SEQ ID NO: 172 (orig sOspA 5/3) or, in another aspect to an "OspA polypeptide" comprising the amino acid sequence of SEQ ID NO: 169 (orig sOspA 1/2), SEQ ID NO: 171 (orig sOspA 6/4), or SEQ ID NO: 173 (orig sOspA 5/3). These "original" molecules are chimeric constructs without mutations and without codon optimization.

The invention includes "lipidated OspA" and "non-lipidated OspA" chimeric molecules. In various aspects, lipidation confers adjuvant properties on OspA. In some aspects of the invention, the lipidated OspA molecules comprise an OspB leader sequence. In some aspects of the invention, the OspB leader sequence comprises amino acids MRLLIGFALALALIG (SEQ ID NO: 13). In other aspects, the OspB leader sequence comprises other amino acids.

The terms "identical" or percent "identity" as known in the art refers to a relationship between the sequences of two or more polypeptide molecules or two or more nucleic acid molecules, as determined by comparing the sequences. In the art, "identity" also means the degree of sequence relatedness between nucleic acid molecules or polypeptides, as the case may be, as determined by the match between strings of two or more nucleotide or two or more amino acid sequences. "Identity" measures the percent of identical matches between the smaller of two or more sequences with gap alignments (if any) addressed by a particular mathematical model or computer program (i.e., "algorithms"). "Substantial identity" refers to sequences with at least about 70%, about 71%, about 72%, about 73%, about 74%, about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, or about 99% sequence identity over a specified sequence. In some aspects, the identity exists over a region that is at least about 50-100 amino acids or nucleotides in length. In other aspects, the identity exists over a region that is at least about 100-200 amino acids or nucleotides in length. In other aspects, the identity exists over a region that is at least about 200-500 amino acids or nucleotides in length. In certain aspects, percent sequence identity is determined using a computer program selected from the group consisting of GAP, BLASTP, BLASTN, FASTA, BLASTA, BLASTX, BestFit and the Smith-Waterman algorithm It also is specifically understood that any numerical value recited herein includes all values from the lower value to the upper value, i.e., all possible combinations of numerical values between the lowest value and the highest value enumerated are to be considered to be expressly stated in this application. For example, if a concentration range is stated as about 1% to 50%, it is intended that values such as 2% to 40%, 10% to 30%, or 1% to 3%, etc., are expressly enumerated in this specification. The values listed above are only examples of what is specifically intended.

Ranges, in various aspects, are expressed herein as from "about" or "approximately" one particular value and/or to "about" or "approximately" another particular value. When values are expressed as approximations, by use of the antecedent "about," it will be understood that some amount of variation is included in the range.

The term "similarity" is a related concept but, in contrast to "identity", refers to a measure of similarity which includes both identical matches and conservative substitution matches. If two polypeptide sequences have, for example, 10/20 identical amino acids, and the remainder are all non-conservative substitutions, then the percent identity and similarity would both be 50%. If, in the same example, there are five more positions where there are conservative substitutions, then the percent identity remains 50%, but the percent similarity would be 75% (15/20). Therefore, in cases where there are conservative substitutions, the degree of percent similarity between two polypeptides will be higher than the percent identity between those two polypeptides.

The term "isolated nucleic acid molecule" refers to a nucleic acid molecule of the invention that (1) has been separated to any degree from proteins, lipids, carbohydrates or other materials with which it is naturally found when total DNA is isolated from the source cells, (2) is not linked to all or a portion of a polynucleotide to which the "isolated nucleic acid molecule" is linked in nature, (3) is operably linked to a polynucleotide which it is not linked to in nature, or (4) does not occur in nature as part of a larger polynucleotide sequence. Substantially free as used herein indicates that the nucleic acid molecule is free from any other contaminating nucleic acid molecule(s) or other contaminants that are found in its natural environment that would interfere with its use in polypeptide production or its therapeutic, diagnostic, prophylactic or research use.

The term "isolated polypeptide" refers to a polypeptide of the present invention that (1) has been separated to any degree from polynucleotides, lipids, carbohydrates or other materials with which it is naturally found when isolated from the source cell, (2) is not linked (by covalent or noncovalent interaction) to all or a portion of a polypeptide to which the "isolated polypeptide" is linked in nature, (3) is operably linked (by covalent or noncovalent interaction) to a polypeptide with which it is not linked in nature, or (4) does not occur in nature. In one aspect, the isolated polypeptide is substantially free from any other contaminating polypeptides or other contaminants that are found in its natural environment that would interfere with its therapeutic, diagnostic, prophylactic or research use.

As used herein a "fragment" of a polypeptide refers to any portion of the polypeptide smaller than the full-length polypeptide or protein expression product. Fragments are typically deletion analogs of the full-length polypeptide wherein one or more amino acid residues have been removed from the amino terminus and/or the carboxy terminus of the full-length polypeptide. Accordingly, "fragments" are a subset of deletion analogs described below.

As used herein an "analog" refers to a polypeptide substantially similar in structure and having the same biological activity, albeit in certain instances to a differing degree, to a naturally-occurring molecule. Analogs differ in the composition of their amino acid sequences compared to the naturally-occurring polypeptide from which the analog is derived, based on one or more mutations involving (i) deletion of one or more amino acid residues at one or more termini of the polypeptide (including fragments as described above) and/or one or more internal regions of the naturally-occurring polypeptide sequence, (ii) insertion or addition of one or more amino acids at one or more termini (typically an "addition" analog) of the polypeptide and/or one or more internal regions (typically an "insertion" analog) of the naturally-occurring polypeptide sequence or (iii) substitution of one or more amino acids for other amino acids in the naturally-occurring polypeptide sequence. Substitutions are conservative or non-conservative based on the physico-chemical or functional relatedness of the amino acid that is being replaced and the amino acid replacing it.

"Conservatively modified analogs" applies to both amino acid and nucleic acid sequences. With respect to particular nucleic acid sequences, conservatively modified nucleic acids refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified analogs. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence.

As to amino acid sequences, one of skill will recognize that individual substitutions, insertions, deletions, additions, or truncations to a nucleic acid, peptide, polypeptide, or protein sequence which alters, adds or deletes a single amino acid or a small percentage of amino acids in the encoded sequence is a "conservatively modified analog" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another:
1) Alanine (A), Glycine (G);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V);
6) Phenylalanine (F), Tyrosine (Y), Tryptophan (W);
7) Serine (S), Threonine (T); and
8) Cysteine (C), Methionine (M) (see, e.g., Creighton, Proteins (1984)).

As used herein a "variant" refers to a polypeptide, protein or analog thereof that comprises at least one amino acid substitution, deletion, insertion, or modification, provided that the variant retains the biological activity of the native polypeptide.

As used herein an "allelic variant" refers to any of two or more polymorphic forms of a gene occupying the same genetic locus. Allelic variations arise naturally through mutation and, in some aspects, result in phenotypic polymorphism within populations. In certain aspects, gene mutations are silent (no change in the encoded polypeptide) or, in other aspects, encode polypeptides having altered amino acid sequences. "Allelic variants" also refer to cDNAs derived from mRNA transcripts of genetic allelic variants, as well as the proteins encoded by them.

The term "derivative" refers to polypeptides that are covalently modified by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. In some aspects, derivatives are modified to comprise additional chemical moieties not normally a part of the molecule. Such moieties, in various aspects, modulate the molecule's solubility, absorption, and/or biological half-life. The moieties, in various other aspects, alternatively decrease the toxicity of the molecule and eliminate or attenuate any undesirable side effect of the molecule, etc. Moieties capable of mediating such effects are disclosed in Remington's Pharmaceutical Sciences (1980). Procedure for coupling such moieties to a molecule are well known in the art. For example, in some aspects, an OspA derivative is an OspA molecule having a chemical modification which confers a longer half-life in vivo to the protein. In one embodiment, the polypeptides are modified by addition of a water soluble polymer known in the art. In a related embodiment, polypeptides are modified by glycosylation, PEGylation, and/or polysialylation.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, underexpressed or not expressed at all.

As used herein "selectable marker" refers to a gene encoding an enzyme or other protein that confers upon the cell or organism in which it is expressed an identifiable phenotypic change such as resistance to a drug, antibiotic or other agent, such that expression or activity of the marker is selected for (for example, but without limitation, a positive marker, such as the neo gene) or against (for example, and without limitation, a negative marker, such as the diphtheria gene). A "heterologous selectable marker" refers to a selectable marker gene that has been inserted into the genome of an animal in which it would not normally be found.

Examples of selectable markers include, but are not limited to, an antibiotic resistance gene such as neomycin (neo), puromycin (Puro), diphtheria toxin, phosphotransferase, hygromycin phosphotransferase, xanthineguanine phosphoribosyl transferase, the Herpes simplex virus type 1 thymidine kinase, adenine phosphoribosyltransferase and hypoxanthine phosphonbosyltransferase. The worker of ordinary skill in the art will understand any selectable marker known in the art is useful in the methods described herein.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

As used herein, the term "homologous" refers to the relationship between proteins that possess a "common evolutionary origin," including proteins from superfamilies (e.g., the immunoglobulin superfamily) and homologous proteins from different species (e.g., myosin light chain, etc.) (Reeck et al., Cell 50:667, 1987). Such proteins (and their encoding genes) have sequence homology, as reflected by their sequence similarity, whether in terms of percent similarity or the presence of specific residues or motifs at conserved positions.

Optimal alignment of sequences for comparison is conducted, for example and without limitation, by the local homology algorithm of Smith et al., Adv. Appl. Math. 2:482, 1981; by the homology alignment algorithm of Needleman et al., J. Mol. Biol. 48:443, 1970; by the search for similarity method of Pearson et al., Proc. Natl. Acad. Sci. USA 85:2444, 1988; by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra). Another example of algorithm that is suitable for determining percent sequence identity and sequence similarity is the BLAST algorithm, which is described in Altschul et al., J. Mol. Biol. 215:403-410, 1990. Software for performing BLAST analyses is publicly available through the National Center for Biotechnology Information. In addition to calculating percent sequence identity, the BLAST algorithm also performs a statistical analysis of the similarity between two sequences (see, e.g., Karlin et al., Proc. Natl. Acad. Sci. USA 90:5873-5787, 1993).

The term "vector" is used to refer to any molecule (e.g., nucleic acid, plasmid or virus) used to transfer coding information to a host cell.

A "cloning vector" is a small piece of DNA into which a foreign DNA fragment can be inserted. The insertion of the fragment into the cloning vector is carried out by treating the vehicle and the foreign DNA with the same restriction enzyme, then ligating the fragments together. There are many types of cloning vectors and all types of cloning vectors are used in the invention. Genetically engineered plasmids and bacteriophages (such as phage λ) are perhaps most commonly used for this purpose. Other types of cloning vectors include bacterial artificial chromosomes (BACs) and yeast artificial chromosomes (YACs).

An "expression vector" is a nucleic acid construct, generated recombinantly or synthetically, with a series of specified nucleic acid elements that permit transcription of a particular nucleic acid in a host cell. The expression vector can be part of a plasmid, virus, or nucleic acid fragment. In certain aspects, the expression vector includes a nucleic acid to be transcribed operably linked to a promoter.

The term "coding sequence" is defined herein as a nucleic acid sequence that is transcribed into mRNA, which is translated into a polypeptide when placed under the control of the appropriate control sequences. The boundaries of the coding sequence are generally determined by the ATG start codon, which is normally the start of the open reading frame at the 5' end of the mRNA and a transcription terminator sequence located just downstream of the open reading frame at the 3' end of the mRNA. A coding sequence can include, but is not limited to, genomic DNA, cDNA, semisynthetic, synthetic, and recombinant nucleic acid sequences. In one aspect, a promoter DNA sequence is defined by being the DNA sequence located upstream of a coding sequence associated thereto and by being capable of controlling the expression of this coding sequence.

A "promoter" is defined as an array of nucleic acid control sequences that direct transcription of a nucleic acid. As used herein, a promoter includes necessary nucleic acid sequences near the start site of transcription, such as, in the case of a polymerase II type promoter, a TATA element. A promoter also optionally includes distal enhancer or repressor elements, which can be located as much as several thousand base pairs from the start site of transcription. A "constitutive" promoter is a promoter that is active under most environmental and developmental conditions. An "inducible" promoter is a promoter that is active under environmental or developmental regulation.

The term "operably linked" refers to a functional linkage between a nucleic acid expression control sequence (such as a promoter, or array of transcription factor binding sites) and a second nucleic acid sequence, wherein the expression control sequence directs transcription of the nucleic acid corresponding to the second sequence.

The term "transduction" is used to refer to the transfer of nucleic acids from one bacterium to another, usually by a phage. "Transduction" also refers to the acquisition and transfer of eukaryotic cellular sequences by retroviruses.

The term "transfection" is used to refer to the uptake of foreign or exogenous DNA by a cell, and a cell has been "transfected" when the exogenous DNA has been introduced inside the cell membrane. A number of transfection techniques are well known in the art and are disclosed herein. See, for example, Graham et al., Virology, 52:456 (1973); Sambrook et al., Molecular Cloning, a Laboratory Manual, Cold Spring Harbor Laboratories, New York, (1989); Davis et al., Basic Methods in Molecular Biology, Elsevier, (1986); and Chu et al., Gene, 13:197 (1981). Such techniques can be used to introduce one or more exogenous DNA moieties into suitable host cells.

The term "transformation" as used herein refers to a change in a cells genetic characteristics, and a cell has been transformed when it has been modified to contain new DNA. For example, a cell is transformed where it is genetically modified from its native state. Following transfection or transduction, the transforming DNA may recombine with that of the cell by physically integrating into a chromosome of the cell. In some instances, the DNA is maintained transiently as an episomal element without being replicated, or it replicates independently as a plasmid. A cell is considered to have been stably transformed when the DNA is replicated with the division of the cell.

The term "endogenous" refers to a polypeptide or polynucleotide or other compound that is expressed naturally in the host organism, or originates within a cell, tissue or organism. "Exogenous" refers to a polypeptide, polynucleotide or other compound that originates outside a cell, tissue or organism.

The term "agent" or "compound" describes any molecule, e.g. protein or pharmaceutical, with the capability of affecting a biological parameter in the invention.

A "control," as used herein, can refer to an active, positive, negative or vehicle control. As will be understood by those of skill in the art, controls are used to establish the relevance of experimental results, and provide a comparison for the condition being tested.

The term "reduces the severity," when referring to a symptom of Lyme or Lyme disease, means that the symptom has delayed onset, reduced severity, or causes less damage to the subject. Generally, severity of a symptom is compared to a control, e.g., that does not receive an active prophylactic or therapeutic composition. In that case, a composition can be said to reduce the severity of a symptom of Lyme if the symptom is reduced by 10%, 25%, 30%, 50%, 80%, or 100% (i.e., essentially eliminated), as compared to the control level of the symptom.

The term "antigen" refers to a molecule or a portion of a molecule capable of being bound by a selective binding agent, such as an antibody, and additionally capable of being used in a subject to produce antibodies capable of binding to an epitope of each antigen. An antigen, in various aspects, has one or more epitopes.

The term "antibody" refers to a molecule or molecules having specificity for an OspA polypeptide. As used herein the terms, "specific," "specificity," and "specifically binds" refer to the ability of the antibody to bind to OspA polypeptides and not to bind to non-OspA polypeptides. In certain aspects, the antibody is a "neutralizing antibody," wherein the antibody reacts with an infectious agent and destroys or inhibits its infectiveness or virulence. The invention includes immunogenic compositions comprising antibodies that "neutralize" Borrelia.

The terms "pharmaceutically acceptable carrier" or "physiologically acceptable carrier" as used herein refer to one or more formulation materials suitable for accomplishing or enhancing the delivery of the OspA polypeptide, OspA nucleic acid molecule or OspA antibody as a pharmaceutical composition.

The term "stabilizer" refers to a substance or vaccine excipient which protects the immunogenic composition of the vaccine from adverse conditions, such as those which occur during heating or freezing, and/or prolongs the stability or shelf-life of the immunogenic composition in a stable and immunogenic condition or state. Examples of stabilizers include, but are not limited to, sugars, such as sucrose, lactose and mannose; sugar alcohols, such as manitol; amino acids, such as glycine or glutamic acid; and proteins, such as human serum albumin or gelatin.

The term "antimicrobial preservative" refers to any substance which is added to the immunogenic composition or vaccine that inhibits the growth of microorganisms that may be introduced upon repeated puncture of multidose vials, should such containers be used. Examples of antimicrobial preservatives include, but are not limited to, substances such as thimerosal, 2-phenoxyethanol, benzethonium chloride, and phenol.

The term "immunogenic composition" refers to a composition comprising an antigen (e.g., chimeric OspA molecules) against which antigen-specific antibodies are raised, an adjuvant that stimulates the subject host's immune response, and a suitable immunologically-inert, pharmaceutically-acceptable carrier. Optionally, an immunogenic composition comprises one or more stabilizers. Optionally, an immunogenic composition comprises one or more antimicrobial preservatives.

The terms "vaccine" or "vaccine composition" refer to a biological preparation that improves immunity to a particular disease (e.g., Lyme disease or Borrelia infection). A vaccine typically contains an agent that resembles a disease-causing microorganism (e.g., chimeric OspA molecules (antigen) of Borrelia). The agent stimulates the body's immune system to recognize the agent as foreign, destroy it, and "remember" it, so that the immune system can more easily recognize and destroy any of these microorganisms that it later encounters. Vaccines, in various aspects, are prophylactic (prevent or ameliorate the effects of a future infection by any natural or "wild" pathogen), or therapeutic (vaccines against present infection). As set forth above, such vaccine compositions include formulations comprising pharmaceutically acceptable carriers. Optionally, a vaccine also comprises one or more stabilizers and/or one or more antimicrobial preservatives.

The terms "effective amount" and "therapeutically effective amount" each refer to the amount of nucleic acid molecule, polypeptide, composition, or antibody used to support an observable level of one or more biological activities of the OspA polypeptides as set forth herein. For example, an effective amount, in some aspects of the invention, would be the amount necessary to prevent, neutralize, or reduce a Borrelia infection.

The term "combination" refers to two or more nucleic acid molecules of the invention, or two or more polypeptides of the invention. In some aspects, combinations of molecules of the invention are administered to provide immunity or fight infection from at least four of the six serotypes (1-6) of Borrelia described herein. In various aspects, combinations of two or three molecules or polypeptides of the invention are used. In certain aspects, combinations of molecules of the invention are administered to a subject to provide immunity from all six serotypes (1-6) of Borrelia described herein. The latter combination has been shown to provide immunity to heterologous strains of Borrelia expressing OspA types not present in the combination of nucleic acid molecules or polypeptides.

The term "combination vaccine" refers to a vaccine formulation containing more than one vaccine composition or more than one protective antigen to one or more diseases. The invention includes a combination vaccine comprising OspA chimeric antigens against Lyme disease or Borrelia in addition to an antigen against one or more other diseases. In various aspects, one or more of the other diseases is a tick-borne disease. In certain aspects, the other tick-borne disease is Rocky Mountain Spotted Fever, Babesiosis, Relapsing Fever, Colorado tick fever, Human monocytic ehrlichiosis (HME), Human granulocytic ehrlichiosis (HGE), Southern Tick-Associated Rash Illness (STARI), Tularemia, Tick paralysis, Powassan encephalitis, Q fever, Crimean-Congo hemorrhagic fever, Cytauxzoonosis, boutonneuse fever, or tick-borne encephalitis. In particular aspects, the invention includes a combination vaccine which comprises one or more vaccines, including a tick-borne encephalitis vaccine, a Japanese encephalitis vaccine, and a Rocky Mountain Spotted Fever vaccine. In some aspects, the combination vaccine comprises vaccine compositions that have a seasonal immunization schedule compatible with immunization against Borrelia infection or Lyme disease. In more particular aspects, combination vaccines are useful in the prevention of multiple diseases for use in geographical locations where these diseases are prevalent.

The term "Borrelia" refers to a species of Gram negative bacteria of the spirochete class of the genus Borrelia. In one aspect, "Borrelia burgdorferi sensu lato (s.l.)" refers to Borrelia burgdorferi in the wider sense. Almost all cases of Lyme disease or Borreliosis are caused by one of three genospecies, Borrelia afzelii, Borrelia garinii and Borrelia burgdorferi sensu stricto (s.s.), which refers to B. burgdorferi in the stricter sense). OspA serotypes of Borrelia correlate with species; serotype 1 corresponds to *B. burgdorferi* s.s., serotype 2 corresponds to *B. afzelii* and serotypes 3 to 7 correspond to *B. garinii*. In various aspects, the immunogenic or vaccine compositions of the invention also provide protection against other species of *Borrelia* including, but not limited to, *Borrelia japonica, Borrelia andersonii, Borrelia bissettii, Borrelia sinica, Borrelia turdi, Borrelia tanukii, Borrelia valaisiana, Borrelia lusitaniae, Borrelia spielmanii, Borrelia miyamotoi* or *Borrelia lonestar*.

A "subject" is given its conventional meaning of a non-plant, non-protist living being. In most aspects, the subject is an animal. In particular aspects, the animal is a mammal. In more particular aspects, the mammal is a human. In other aspects, the mammal is a pet or companion animal, a domesticated farm animal, or a zoo animal. In certain aspects, the mammal is a cat, dog, horse, or cow. In various other aspects, the mammal is a deer, mouse, chipmunk, squirrel, opossum, or raccoon.

Lyme Disease (Borreliosis or Lyme Borreliosis)

In some aspects, the invention includes chimeric OspA molecules and compositions comprising these molecules in the prevention of Lyme disease or *Borrelia* infection. Lyme Disease is also known in the art as Borreliosis or Lyme Borreliosis and, therefore, all of these terms are included in the invention. Likewise, the invention includes methods of preventing or treating Lyme disease comprising administering the chimeric OspA molecules described herein. Lyme disease, or borreliosis, is an infectious disease caused by at least three species of Gram-negative spirochetal bacteria belonging to the genus *Borrelia*. There are at least 13 *Borrelia* species which have been discovered, three of which are known to be Lyme-related. The *Borrelia* species that cause Lyme disease are collectively known as *Borrelia burgdorferi sensu lato*, and show a great deal of genetic diversity. The group *Borrelia burgdorferi sensu lato* is made up of three closely-related species that are probably responsible for the large majority of cases. *Borrelia burgdorferi sensu stricto* is the main cause of Lyme disease in the United States (but it is also present in Europe), whereas *Borrelia afzelii* and *Borrelia garinii* cause most European cases. Some studies have also proposed that *Borrelia* species (e.g. *Borrelia bissettii, Borrelia spielmanii, Borrelia lusitaniae*, and *Borrelia valaisiana*) may sometimes infect humans. Although these species do not seem to be important causes of disease, immunogenic protection against these species is also include in the invention.

Lyme disease is the most common tick-borne disease in the Northern Hemisphere. The disease is named after the village of Lyme, Connecticut where a number of cases were identified in 1975. *Borrelia* is transmitted to humans by the bite of infected ticks belonging to a few species of the genus *Ixodes* ("hard ticks"). Early symptoms, in some instances, include fever, headache, fatigue, depression, and a characteristic circular skin rash called erythema migrans. Left untreated, later symptoms can often involve the joints, heart, and central nervous system. In most cases, the infection and its symptoms are eliminated by antibiotics, especially if the illness is treated early. However, late, delayed, or inadequate treatment can lead to the more serious symptoms, which can be disabling and difficult to treat. Occasionally, symptoms such as arthritis persist after the infection has been eliminated by antibiotics.

Some groups have argued that "chronic" Lyme disease is responsible for a range of medically unexplained symptoms beyond the recognized symptoms of late Lyme disease, and that additional, long-term antibiotic treatments are needed. However, long-term treatment is controversial and the dispute regarding such treatment has led to legal action over treatment guidelines.

Lyme disease is classified as a zoonosis, as it is transmitted to humans from a natural reservoir which includes rodents and birds by ticks that feed on both sets of hosts. Hard-bodied ticks of the genus *Ixodes* are the main vectors of Lyme disease. Most human infections are caused by ticks in the nymphal stage, as the nymphal ticks are very small and may feed for long periods of time undetected. Tick bites often go unnoticed because of the small size of the tick in its nymphal stage, as well as tick secretions that prevent the host from feeling any itch or pain from the bite.

Lyme disease is diagnosed clinically based on symptoms, objective physical findings (such as erythema migrans, facial palsy, or arthritis), a history of possible exposure to infected ticks, as well as serological blood tests. Approximately half of the patients with Lyme disease will develop the characteristic bulls-eye rash, but many may not recall a tick bite. Laboratory testing is not recommended for persons who do not have symptoms of Lyme disease.

Because of the difficulty in culturing *Borrelia* bacteria in the laboratory, diagnosis of Lyme disease is typically based on the clinical exam findings and a history of exposure to endemic Lyme areas. The Erythema migrans (EM) rash, which only occurs in about 50% of all cases, is considered sufficient to establish a diagnosis of Lyme disease even when serologic blood tests are negative. Serological testing can be used to support a clinically suspected case but is not diagnostic by itself. Diagnosis of late-stage Lyme disease is often difficult because of the multi-faceted appearance which can mimic symptoms of many other diseases. For this reason, a reviewer called Lyme the new "great imitator." Lyme disease, in some instances, is misdiagnosed as multiple sclerosis, rheumatoid arthritis, fibromyalgia, chronic fatigue syndrome (CFS), lupus, or other autoimmune and neurodegenerative diseases. Thus, there is a great need in the art for a vaccine to prevent or treat Lyme disease.

Outer Surface Protein A (OspA) of *Borrelia*

In various aspects, the invention includes chimeric OspA molecules of *Borrelia* and compositions comprising these molecules in the prevention and treatment of Lyme disease or *Borrelia* infection. Several *Borrelia* outer surface proteins have been identified over the past decade that are up-regulated by temperature- and/or mammalian host-specific signals as this spirochete is transmitted from ticks to mammals.

The major outer surface protein, OspA, of *Borrelia burgdorferi* is a lipoprotein of particular interest because of its potential as a vaccine candidate. Serotypic and genetic analysis of OspA from both European and North American strains of *Borrelia* have demonstrated antigenic and structural heterogeneities. OspA is described in published PCT patent application WO 92/14488, in Jiang et al. (*Clin. Diagn. Lab. Immunol.* 1: 406-12, 1994) and is known in the art. Osp A has been shown to induce protective immunity in mouse, hamster and dog challenge studies. Clinical trials in humans have shown the formulations of OspA to be safe and immunogenic in humans (Keller et al., JAMA (1994) 271:1764 1768).

While OspA is expressed in the vast majority of clinical isolates of *Borrelia burgdorferi* from North America, a different picture has emerged from examination of the clinical *Borrelia* isolates in Europe. In Europe, Lyme disease is mainly caused by three genospecies of *Borrelia*, namely *B. burgdorferi, B. garinii* and *B. afzelii*. The invention is directed to chimeric OspA molecules that provide protective immunity against all genospecies of *Borrelia*. The invention describes the design and synthesis of three chimeric OspA genes that encode for three distinct lipidated OspA molecules that share common features. Each gene represents two OspA serotypes and the genes were designed to encode stable OspA molecules that are safe and highly immunogenic, and afford a subject protection against infection with *B. burgdorferi sensu*

*lato* (s.l.). The invention also describes three original chimeric OspA genes without mutations and without codon optimization that encode three distinct lipidated OspA molecules that share common features. Each gene represents two OspA serotypes and encode molecules that afford a subject protection against infection with *B. burgdorferi sensu lato* (s.l.).

Seven principal OspA serotypes have been recognized among European isolates (designated serotypes 1 to 7, Wilske et al., *J. Clin. Microbiol.* 31:340-50, 1993). OspA serotypes correlate with species; serotype 1 corresponds to *B. burgdorferi* s.s., serotype 2 corresponds to *B. afzelii* and serotypes 3 to 7 correspond to *B. garinii*. Epidemiological studies of European *Borrelia* isolates indicate that a vaccine based on OspA types 1, 2, 3, 4, 5 and 6 would provide theoretical coverage in Europe of 98.1% of Lyme disease and cover 96.7% of invasive disease isolates. The invention provides six chimeric OspA nucleic acid molecules (SEQ ID NOS: 1, 3, and 5, and SEQ ID NOS: 168, 170, and 172) and six chimeric OspA polypeptide molecules (SEQ ID NOS: 2, 4, and 6, and SEQ ID NOS: 169, 171, and 173) that can provide protective immunity against all six serotypes 1-6. Six synthetic OspA genes were designed to encode OspA molecules with the protective epitopes from OspA serotypes 1 and 2 (lipB sOspA 1/2$^{251}$ (SEQ ID NOS: 1 (nucleic acid) and 2 (amino acid) and orig sOspA 1/2 (SEQ ID NOS: 168 (nucleic acid) and 169 (amino acid)); OspA serotypes 6 and 4 (lipB sOspA 6/4 (SEQ ID NOS: 3 (nucleic acid) and 4 (amino acid) and orig sOspA 6/4 (SEQ ID NOS: 170 (nucleic acid) and 171 (amino acid)); and OspA serotypes 5 and 3 (lipB sOspA 5/3 (SEQ ID NOS: 5 (nucleic acid) and 6 (amino acid) and orig sOspA 5/3 (SEQ ID NOS: 172 (nucleic acid) and 173 (amino acid)). The chimeric OspA genes were made using synthetic overlapping oligonucleotides. These recombinant proteins are, in certain aspects, produced at high yield and purity and, in various aspects, manipulated to maximize desirable activities and minimize undesirable ones.

Chimeric OspA Nucleic Acid Molecules and Polypeptide Molecules

In various aspects, the invention includes chimeric OspA nucleic acid and polypeptide molecules of *Borrelia*. The OspA nucleic acids of the invention include a nucleic acid molecule comprising, consisting essentially of, or consisting of a nucleotide sequence as set forth in SEQ ID NO: 1 (lipB sOspA 1/2$^{251}$), SEQ ID NO: 3 (lipB sOspA 6/4), SEQ ID NO: 5 (lipB sOspA 5/3), SEQ ID NO: 7 (sOspA 1/2$^{251}$), SEQ ID NO: 9 (sOspA 6/4), SEQ ID NO: 11 (sOspA 5/3), SEQ ID NO: 168 (orig sOspA 1/2), SEQ ID NO: 170 (orig sOspA 6/4), or SEQ ID NO: 172 (orig sOspA 5/3), or a nucleotide sequence encoding the polypeptide as set forth in SEQ ID NO: 2 (lipB sOspA 1/2$^{251}$), SEQ ID NO: 4 (lipB sOspA 6/4), SEQ ID NO: 6 (lipB sOspA 5/3), SEQ ID NO: 8 (sOspA 1/2$^{251}$), SEQ ID NO: 10 (sOspA 6/4), SEQ ID NO: 12 (sOspA 5/3), SEQ ID NO: 169 (orig sOspA 1/2), SEQ ID NO: 171 (orig sOspA 6/4), or SEQ ID NO: 173 (orig sOspA 5/3).

The nucleic acid sequences of SEQ ID NOS: 7, 9, and 11 lack the nucleic acid sequence encoding the lipB leader sequence (MRLLIGFALALALIG (SEQ ID NO: 13). In addition, the nucleic acid sequences of SEQ ID NOS: 7, 9, and 11 encode a methionine residue at the amino terminus of SEQ ID NOS: 8, 10, and 12 in place of the cysteine residue present at the carboxy terminus of the lipB leader sequence in SEQ ID NOS: 2, 4, and 6. SEQ ID NOS: 1, 3, and 5 are lipB sOspA polynucleotides, and SEQ ID NOS: 2, 4, and 6 are lipB sOspA polypeptides.

In some aspects, the invention includes original ("orig") chimeric OspA nucleic acid and polypeptide molecules of *Borrelia* without mutations and without codon optimization. The OspA nucleic acids of the invention, therefore, include a nucleic acid molecule comprising, consisting essentially of, or consisting of a nucleotide sequence as set forth in SEQ ID NO: 168 (orig sOspA 1/2), SEQ ID NO: 170 (orig sOspA 6/4), or SEQ ID NO: 172 (orig sOspA 5/3), or a nucleotide sequence encoding the polypeptide as set forth in SEQ ID NO: 169 (orig sOspA 1/2), SEQ ID NO: 171 (orig sOspA 6/4), or SEQ ID NO: 173 (orig sOspA 5/3).

Sequence identification numbers for DNA and amino acid sequences for the chimeric OspA molecules are set out in Table 1 below.

TABLE 1

Chimeric OspA DNA and Amino Acid Sequences

| Sequence | DNA SEQ ID NO: | Amino Acid SEQ ID NO: | Complementary Strand SEQ ID NO: |
| --- | --- | --- | --- |
| lipB sOspA 1/2$^{251}$ | 1 | 2 | 48 |
| lipB sOspA 6/4 | 3 | 4 | 49 |
| lipB sOspA 5/3 | 5 | 6 | 50 |
| sOspA 1/2$^{251}$ | 7 | 8 | 56 |
| sOspA 6/4 | 9 | 10 | 57 |
| sOspA 5/3 | 11 | 12 | 58 |
| Orig sOspA 1/2 | 168 | 169 | |
| Orig sOspA 6/4 | 170 | 171 | |
| Orig sOspA 5/3 | 172 | 173 | | lipB sOspA 1/2$^{251}$ Amino Acid Sequence (SEQ ID NO: 2)
MRLLIGFALALALIGCAQKGAESIGSVSVDLPGEMKVLVSKEKDKNGKYDLIATVDKLELKGTSDKNNGS

GVLEGVKTNKSKVKLTISDDLGQTTLEVFKEDGKTLVSKKVTSKDKSSTEEKFNEKGEVSEKIITMADGT

TABLE 1-continued

Chimeric OspA DNA and Amino Acid Sequences

RLEYTGIKSDGTGKAKYVLKNFTLEGKVANDKTTLEVKEGTVTLSMNISKSGEVSVELNDTDSSAATKKT

AAWNSKTSTLTISVNSKKTTQLVFTKQDTITVQKYDSAGTNLEGTAVEIKTLDELKNALK

DNA Sequence (SEQ ID NO: 1)

catatgcgtctgttgatcggctttgctctggcgctggctctgatcggctgcgcacagaaaggtgctgagt ctattggttccgtttctgtagatctgcccggtgaaatgaaggttctggtgagcaaagaaaaagacaagaa cggcaagtacgatctcatcgcaaccgtcgacaagctggagctgaaaggtacttctgataaaaacaacggc tctggtgtgctggagggcgtcaaaactaacaagagcaaagtaaagcttacgatctctgacgatctcggtc agaccacgctggaagttttcaaagaggatggcaagaccctcgtgtccaaaaaagtaacttccaaagacaa gtcctctacggaagaaaaattcaacgaaaaaggtgaggtgtctgaaaagatcatcaccatggcagacggc acccgtcttgaatacaccggtattaaaagcgatggtaccggtaaagcgaaatatgttctgaaaaacttca ctctggaaggcaaagtggctaatgataaaaccaccttggaagtcaaggaaggcaccgttactctgagcat gaatatctccaaatctggtgaagtttccgttgaactgaacgacactgacagcagcgctgcgactaaaaaa actgcagcgtggaattccaaaacttctactttaaccattagcgttaacagcaaaaaaactacccagctgg tgttcactaaacaagacacgatcactgtgcagaaatacgactccgcaggcaccaacttagaaggcacggc agtcgaaattaaaacccttgatgaactgaaaaacgcgctgaaataagctgagcggatcc Complementary Strand (SEQ ID NO: 48)

catatgcgtctgttgatcggctttgctttggcgctggctttaatcggctgtgcacagaaaggtgctgagt ctattggttccgtttctgtagatctgcccgggggtatgaaagttctggtaagcaaagaaaaagacaaaaa cggtaaatacagcctgatggcaaccgtagaaaagctggagcttaaaggcacttctgataaaaacaacggt tctggcaccctggaaggtgaaaaaactaacaaaagcaaagtaaagcttactattgctgaggatctgagca aaaccacctttgaaatcttcaaagaagatggcaaaactctggtatctaaaaaagtaaccctgaaagacaa gtcttctaccgaagaaaaattcaacgaaaagggtgaaatctctgaaaaaactatcgtaatggcaaatggt acccgtctggaatacaccgacatcaaaagcgataaaaccggcaaagctaaatacgttctgaaagacttta ctctggaaggcactctggctgctgacggcaaaaccactctgaaagttaccgaaggcactgttactctgag catgaacatttctaaatccggcgaaatcaccgttgcactggatgacactgactctagcggcaataaaaaa tccggcacctgggattctgatacttctactttaaccattagcaaaaacagccagaaaactaaacagctgg tattcaccaaagaaaacactatcaccgtacagaactataaccgtgcaggcaatgcgctggaaggcagccc ggctgaaattaaagatctggcagagctgaaagccgctttgaaataagctgagcggatcc lipB sOspA 6/4
Amino Acid Sequence (SEQ ID NO: 4)

MRLLIGFALALALIGCAQKGAESIGSVSVDLPGGMTVLVSKEKDKNGKYSLEATVDKLELKGTSDKNNGS

GTLEGEKTNKSKVKLTIADDLSQTKFEIFKEDAKTLVSKKVTLKDKSSTEEKFNEKGETSEKTIVMANGT

RLEYTDIKSDGSGKAKYVLKDFTLEGTLAADGKTTLKVTEGTVVLSMNILKSGEITVALDDSDTTQATKK

TGKWDSNTSTLTISVNSKKTKNIVETKEDTITVQKYDSAGTNLEGNAVEIKTLDELKNALK

DNA Sequence (SEQ ID NO: 3)

catatgcgtctgttgatcggctttgctctggcgctggctctgatcggctgcgcacagaaaggtgctgagt ctattggttccgtttctgtagatctgcccggtggcatgaccgttctggtcagcaaagaaaaagacaaaaa

TABLE 1-continued

Chimeric OspA DNA and Amino Acid Sequences cggtaaatacagcctcgaggcgaccgtcgacaagcttgagctgaaaggcacctctgataaaaacaacggt tccggcaccctggaaggtgaaaaaactaacaaaagcaaagtgaaactgaccattgctgatgacctcagcc agaccaaattcgaaattttcaaagaagatgccaaaaccttagtatccaaaaaagtgaccctgaaagacaa gtcctctaccgaagaaaaattcaacgaaaagggtgaaacctctgaaaaaaccatcgtaatggcaaatggt acccgtctggaatacaccgacatcaaaagcgatggctccggcaaagccaaatacgttctgaaagacttca ccctggaaggcaccctcgctgccgacggcaaaaccaccttgaaagttaccgaaggcactgttgttttaag catgaacatcttaaaatccggtgaaatcaccgttgcgctggatgactctgacaccactcaggccactaaa aaaaccggcaaatgggattctaacacttccactctgaccatcagcgtgaattccaaaaaaactaaaaaca tcgtgttcaccaaagaagacaccatcaccgtccagaaatacgactctgcgggcaccaacctcgaaggcaa cgcagtcgaaatcaaaaccctggatgaactgaaaaacgctctgaaataagctgagcggatcc Complementary Strand (SEQ ID NO: 49)

ggatccgctcagcttatttcagcgcgtttttcagttcatcaagggttttaatttcgactgccgtgccttc taagttggtgcctgcggagtcgtatttctgcacagtgatcgtgtcttgtttagtgaacaccagctgggta gtttttttgctgttaacgctaatggttaaagtagaagttttggaattccacgctgcagtttttttagtcg cagcgctgctgtcagtgtcgttcagttcaacggaaacttcaccagatttggagatattcatgctcagagt aacggtgccttccttgacttccaaggtggttttatcattagccactttgccttccagagtgaagtttttc agaacatatttcgctttaccggtaccatcgcttttaataccggtgtattcaagacgggtgccgtctgcca tggtgatgatcttttcagacacctcacctttttcgttgaatttttcttccgtagaggacttgtctttgga agttactttttggacacgagggtcttgccatcctctttgaaaacttccagcgtggtctgaccgagatcg tcagagatcgtaagctttactttgctcttgttagttttgacgccctccagcacaccagagccgttgtttt tatcagaagtacctttcagctccagcttgtcgacggttgcgatgagatcgtacttgccgttcttgtcttt ttctttgctcaccagaaccttcatttcaccgggcagatctacagaaacggaaccaatagactcagcacct ttctgtgcgcagccgatcagagccagcgccagagcaaagccgatcaacagacgcatatg lipB sOspA 5/3
Amino Acid Sequence (SEQ ID NO: 6)

MRLLIGFALALALIGCAQKGAESIGSVSVDLPGGMKVLVSKEKDKNGKYSLMATVEKLELKGTSDKNNGS

GTLEGEKTNKSKVKLTIAEDLSKTTFEIFKEDGKTLVSKKVTLKDKSSTEEKFNEKGEISEKTIVMANGT

RLEYTDIKSDKTGKAKYVLKDFTLEGTLAADGKTTLKVTEGTVTLSMNISKSGEITVALDDTDSSGNKKS

GTWDSDTSTLTISKNSQKTKQLVFTKENTITVQNYNRAGNALEGSPAEIKDLAELKAALK

DNA Sequence (SEQ ID NO: 5)

catatgcgtctgttgatcggctttgctttggcgctggctttaatcggctgtgcacagaaaggtgctgagt ctattggttccgtttctgtagatctgcccggggtatgaaagttctggtaagcaaagaaaaagacaaaaa cggtaaatacagcctgatggcaaccgtagaaaagctggagcttaaaggcacttctgataaaaacaacggt tctggcaccctggaaggtgaaaaaactaacaaaagcaaagtaaagcttactattgctgaggatctgagca aaaccacctttgaaatcttcaaagaagatggcaaaactctggtatctaaaaaagtaaccctgaaagacaa gtcttctaccgaagaaaaattcaacgaaaagggtgaaatctctgaaaaaactatcgtaatggcaaatggt acccgtctggaatacaccgacatcaaaagcgataaaaccggcaaagctaaatacgttctgaaagacttta ctctggaaggcactctggctgctgacggcaaaaccactctgaaagttaccgaaggcactgttactctgag TABLE 1-continued Chimeric OspA DNA and Amino Acid Sequences catgaacatttctaaatccggcgaaatcaccgttgcactggatgacactgactctagcggcaataaaaaa tccggcacctgggattctgatacttctactttaaccattagcaaaaacagccagaaaactaaacagctgg tattcaccaaagaaaacactatcaccgtacagaactataaccgtgcaggcaatgcgctggaaggcagccc ggctgaaattaaagatctggcagagctgaaagccgctttgaaataagctgagcggatcc Complementary Strand (SEQ ID NO: 50)
ggatccgctcagcttatttcagagcgttttcagttcatccagggttttgatttcgactgcgttgccttc gaggttggtgcccgcagagtcgtatttctggacggtgatggtgtcttctttggtgaacacgatgttttta gttttttggaattcacgctgatggtcagagtggaagtgttagaatcccatttgccggttttttttagtgg cctgagtggtgtcagagtcatccagcgcaacggtgatttcaccggattttaagatgttcatgcttaaaac aacagtgccttcggtaactttcaaggtggttttgccgtcggcagcgagggtgccttccagggtgaagtct ttcagaacgtatttggctttgccggagccatcgcttttgatgtcggtgtattccagacgggtaccatttg ccattacgatggttttttcagaggtttcacccttttcgttgaattttcttcggtagaggacttgtcttt cagggtcacttttttggatactaaggttttggcatcttctttgaaaatttcgaatttggtctggctgagg tcatcagcaatggtcagtttcactttgcttttgttagttttttccacttccagggtgccggaaccgttgt ttttatcagaggtgcctttcagctcaagcttgtcgacggtcgcctcgaggctgtatttaccgttttgtc tttttctttgctgaccagaacggtcatgccaccgggcagatctacagaaacggaaccaatagactcagca cctttctgtgcgcagccgatcagagccagcgccagagcaaagccgatcaacagacgcatatg sOspA 1/2$^{251}$
Amino Acid Sequence (SEQ ID NO: 8)
MAQKGAESIGSVSVDLPGEMKVLVSKEKDKNGKYDLIATVDKLELKGTSDKNNGSGVLEGVKTNKSKVKL

TISDDLGQTTLEVFKEDGKTLVSKKVTSKDKSSTEEKFNEKGEVSEKIITMADGTRLEYTGIKSDGTGKA

KYVLKNFTLEGKVANDKTTLEVKEGTVTLSMNISKSGEVSVELNDTDSSAATKKTAAWNSKTSTLTISVN

SKKTTQLVFTKQDTITVQKYDSAGTNLEGTAVEIKTLDELKNALK

DNA Sequence (SEQ ID NO: 7)
catatggcacagaaaggtgctgagtctattggttccgtttctgtagatctgcccggtgaaatgaaggttc tggtgagcaaagaaaaagacaagaacggcaagtacgatctcatcgcaaccgtcgacaagctggagctgaa aggtacttctgataaaaacaacggctctggtgtgctggagggcgtcaaaactaacaagagcaaagtaaag cttacgatctctgacgatctcggtcagaccacgctggaagttttcaaagaggatggcaagaccctcgtgt ccaaaaagtaacttccaaagacaagtcctctacggaagaaaaattcaacgaaaaggtgaggtgtctga aaagatcatcaccatggcagacggcacccgtcttgaatacaccggtattaaaagcgatggtaccggtaaa gcgaaatatgttctgaaaaacttcactctggaaggcaaagtggctaatgataaaaccaccttggaagtca aggaaggcaccgttactctgagcatgaatatctccaaatctggtgaagtttccgttgaactgaacgacac tgacagcagcgctgcgactaaaaaaactgcagcgtggaattccaaaacttctactttaaccattagcgtt aacagcaaaaaaactacccagctggtgttcactaaacaagacacgatcactgtgcagaaatacgactcca acggcaccaacttagaaggcacggcagtcgaaattaaaaccccttgatgaactgaaaaacgcgctgaaata agctgagcggatcc TABLE 1-continued Chimeric OspA DNA and Amino Acid Sequences Complementary Strand (SEQ ID NO: 56)
gtataccgtgtctttccacgactcagataaccaaggcaaagacatctagacgggccactttacttccaag accactcgtttcttttttctgttcttgccgttcatgctagagtagcgttggcagctgttcgacctcgactt tccatgaagactattttttgttgccgagaccacacgacctcccgcagttttgattgttctcgtttcatttc gaatgctagagactgctagagccagtctggtgcgaccttcaaaagtttctcctaccgttctgggagcaca ggttttttcattgaaggtttctgttcaggagatgccttcttttaagttgcttttttccactccacagact tttctagtagtggtaccgtctgccgtgggcagaacttatgtggccataattttcgctaccatggccattt cgctttatacaagacttttgaagtgagaccttccgtttcaccgattactatttttggtggaaccttcagt tccttccgtggcaatgagactcgtacttatagaggtttagaccacttcaaaggcaacttgacttgctgtg actgtcgtcgcgacgctgatttttttgacgtcgcaccttaaggttttgaagatgaaattggtaatcgcaa ttgtcgttttttgatgggtcgaccacaagtgatttgttctgtgctagtgacacgtctttatgctgaggt tgccgtggttgaatcttccgtgccgtcagctttaattttgggaactacttgacttttgcgcgactttat tcgactcgcctagg sOspA 6/4
Amino Acid Sequence (SEQ ID NO: 10)

TABLE 1-continued

Chimeric OspA DNA and Amino Acid Sequences tttttggtagcattaccgtttaccatgggcagaccttatgtggctgtagttttcgctaccgaggccgttt cggtttatgcaagactttctgaagtgggaccttccgtgggagcgacggctgccgttttggtggaactttc aatggcttccgtgacaacaaaattcgtacttgtagaattttaggccactttagtggcaacgcgacctact gagactgtggtgagtccggtgattttttttggccgtttaccctaagattgtgaaggtgagactggtagtcg cacttaaggttttttttgattttttgtagcacaagtggtttcttctgtggtagtggcaggtctttatgctga gacgcccgtggttggagcttccgttgcgtcagctttagttttgggacctacttgacttttttgcgagactt tattcgactcgcctagg sOspA 5/3
Amino Acid Sequence (SEQ ID NO: 12)

MAQKGAESIGSVSVDLPGGMKVLVSKEKDKNGKYSLMATVEKLELKGTSDKNNGSGTLEGEKTNKSKVKL

TIAEDLSKTTFEIFKEDGKTLVSKKVTLKDKSSTEEKFNEKGEISEKTIVMANGTRLEYTDIKSDKTGKA

KYVLKDFTLEGTLAADGKTTLKVTEGTVTLSMNISKSGEITVALDDTDSSGNKKSGTWDSDTSTLTISKN

SQKTKQLVFTKENTITVQNYNRAGNALEGSPAEIKDLAELKAALK

DNA Sequence (SEQ ID NO: 11)

catatggcacagaaaggtgctgagtctattggttccgtttctgtagatctgcccgggggtatgaaagttc tggtaagcaaagaaaagacaaaaacggtaaatacagcctgatggcaaccgtagaaaagctggagcttaa aggcacttctgataaaaacaacggttctggcaccctggaaggtgaaaaaactaacaaaagcaaagtaaag cttactattgctgaggatctgagcaaaaccacctttgaaatcttcaaagaagatggcaaaactctggtat ctaaaaaagtaaccctgaaagacaagtcttctaccgaagaaaaattcaacgaaaagggtgaaatctctga aaaaactatcgtaatggcaaatggtacccgtctggaatacaccgacatcaaaagcgataaaaccggcaaa gctaaatacgttctgaaagactttactctggaaggcactctggctgctgacggcaaaaccactctgaaag ttaccgaaggcactgttactctgagcatgaacatttctaaatccggcgaaatcaccgttgcactggatga cactgactctagcggcaataaaaaatccggcacctgggattctgatacttctactttaaccattagcaaa aacagccagaaaactaaacagctggtattcaccaaagaaaacactatcaccgtacagaactataaccgtg caggcaatgcgctggaaggcagcccggctgaaattaaagatctggcagagctgaaagccgctttgaaata agctgagcggatcc Complementary Strand (SEQ ID NO: 58)

gtataccgtgtctttccacgactcagataaccaaggcaaagacatctagacgggccccatactttcaag accattcgtttcttttttctgttttttgccatttatgtcggactaccgttggcatcttttcgacctcgaatt tccgtgaagactattttttgttgccaagaccgtgggaccttccactttttttgattgttttcgtttcatttc gaatgataacgactcctagactcgttttggtggaaactttagaagtttcttctaccgttttgagaccata gatttttttcattgggacttctgttcagaagatggcttcttttttaagttgcttttccccactttagagact ttttttgatagcattaccgtttaccatgggcagaccttatgtggctgtagttttcgctattttggccgttt cgatttatgcaagactttctgaaatgagaccttccgtgagaccgacgactgccgttttggtgagactttc aatggcttccgtgacaatgagactcgtacttgtaaagatttaggccgctttagtggcaacgtgacctact gtgactgagatcgccgttatttttaggccgtggaccctaagactatgaagatgaaattggtaatcgttt

TABLE 1-continued

Chimeric OspA DNA and Amino Acid Sequences ttgtcggtcttttgatttgtcgaccataagtggtttcttttgtgatagtggcatgtcttgatattggcac gtccgttacgcgaccttccgtcgggccgactttaatttctagaccgtctcgactttcggcgaaactttat tcgactcgcctagg

Orig sOspA 1/2
Amino Acid Sequence (SEQ ID NO: 169)

MKKYLLGIGLILALIACKQNVSSLDEKNSVSVDLPGEMKVLVSKEKNKDGKYDLIATVDKLEL

KGTSDKNNGSGVLEGVKADKSKVKLTISDDLGQTTLEVFKEDGKTLVSKKVTSKDKSSTEEKF

NEKGEVSEKIITRADGTRLEYTGIKSDGSGKAKEVLKNFTLEGKVANDKVTLEVKEGTVTLSK

NISKSGEVSVELNDTDSSAATKKTAAWNSKTSTLTISVNSKKTTQLVFTKQDTITVQKYDSAG

TNLEGTAVEIKTLDELKNALK

DNA Sequence (SEQ ID NO: 168)
atgaaaaaatatttattgggaataggtctaatattagccttaatagcatgtaagcaaaatgt tagcagccttgacgagaaaaacagcgtttcagtagatttgcctggtgaaatgaaagttcttg taagcaaagaaaaaaacaaagacggcaagtacgatctaattgcaacagtagacaagcttgag cttaaaggaacttctgataaaaacaatggatctggagtacttgaaggcgtaaaagctgacaa aagtaaagtaaaattaacaatttctgacgatctaggtcaaaccacacttgaagttttcaaag aagatggcaaaacactagtatcaaaaaaagtaacttccaaagacaagtcatcaacagaagaa aaattcaatgaaaaaggtgaagtatctgaaaaaataataacaagagcagacggaaccagact tgaatacacaggaattaaaagcgatggatctggaaaagctaaagaggttttaaaaaacttta ctcttgaaggaaaagtagctaatgataaagtaacattggaagtaaaagaaggaaccgttact ttaagtaaaaatatttcaaaatctggggaagtttcagttgaacttaatgacactgacagtag tgctgctactaaaaaaactgcagcttggaattcaaaaacttctactttaacaattagtgtta acagcaaaaaaactacacaacttgtgtttactaaacaagacacaataactgtacaaaaatac gactccgcaggtaccaatttagaaggcacagcagtcgaaattaaaacacttgatgaacttaa aaacgctttaaaatag Orig sOspA 6/4
Amino Acid Sequence (SEQ ID NO: 171)
MKKYLLGIGLILALIACKQNVSTLDEKNSVSVDLPGGMTVLVSKEKDKDGKYSLEATVDKLE

LKGTSDKNNGSGTLEGEKTDKSKVKLTIADDLSQTKFEIFKEDAKTLVSKKVTLKDKSSTEE

KFNEKGETSEKTIVRANGTRLEYTDIKSDGSGKAKEVLKDFTLEGTLAADGKTTLKVTEGTV

VLSKNILKSGEITVALDDSDTTQATKKTGKWDSNTSTLTISVNSKKTKNIVFTKEDTITVQK

YDSAGTNLEGNAVEIKTLDELKNALK

DNA Sequence (SEQ ID NO: 170)
atgaaaaaatatttattgggaataggtctaatattagccttaatagcatgtaagcaaaatgt tagcacgcttgatgaaaaaaatagcgtttcagtagatttacctggtggaatgacagttcttg taagtaaagaaaaagacaaagacggtaaatacagtctagaggcaacagtagacaagcttgag cttaaaggaacttctgataaaaacaacggttctggaacacttgaaggtgaaaaaactgacaa aagtaaagtaaaattaacaattgctgatgacctaagtcaaactaaatttgaaattttcaaag

TABLE 1-continued

Chimeric OspA DNA and Amino Acid Sequences aagatgccaaaacattagtatcaaaaaaagtaaccct taaagacaagtcatcaacagaagaa aaattcaacgaaaagggtgaaacatctgaaaaaacaatagtaagagcaaatggaaccagact tgaatacacagacataaaaagcgatggatccggaaaagctaaagaagttttaaaagactttta ctcttgaaggaactctagctgctgacggcaaaacaacattgaaagttacagaaggcactgtt gttttaagcaagaacatttttaaaatccggagaaataacagttgcacttgatgactctgacac tactcaggctactaaaaaaactggaaaatgggattcaaatacttccactttaacaattagtg tgaatagcaaaaaaactaaaaacattgtatttacaaaagaagacacaataacagtacaaaaa tacgactcagcaggcaccaatctagaaggcaacgcagtcgaaattaaaacacttgatgaact taaaaacgctttaaaataa Orig sOspA 5/3
Amino Acid Sequence (SEQ ID NO: 173)

MKKYLLGIGLILALIACKQNVSSLDEKNSVSVDLPGGMKVLVSKEKDKDGKYSLMATVEKLE

LKGTSDKNNGSGTLEGEKTDKSKVKLTIAEDLSKTTFEIFKEDGKTLVSKKVTLKDKSSTEE

KFNEKGEISEKTIVRANGTRLEYTDIKSDKTGKAKEVLKDFTLEGTLAADGKTTLKVTEGTV

TLSKNISKSGEITVALDDTDSSGNKKSGTWDSDTSTLTISKNSQKTKQLVFTKENTITVQNY

NRAGNALEGSPAEIKDLAELKAALK

DNA Sequence (SEQ ID NO: 172)

atgaaaaaatatttattgggaataggtctaatattagccttaatagcatgtaagcaaaatgt tagcagccttgatgaaaaaatagcgtttcagtagatttacctggtggaatgaaagttcttg taagtaaagaaaagacaaagatggtaaatacagtctaatggcaacagtagaaaagcttgag cttaaaggaacttctgataaaaacaacggttctggaacacttgaaggtgaaaaaactgacaa aagtaaagtaaaattaacaattgctgaggatctaagtaaaaccacatttgaaatcttcaaag aagatggcaaaacattagtatcaaaaaaagtaacccttaaagacaagtcatcaacagaagaa aaattcaacgaaaagggtgaaatatctgaaaaaacaatagtaagagcaaatggaaccagact tgaatacacagacataaaaagcgataaaaccggaaaagctaaagaagttttaaaagactttta ctcttgaaggaactctagctgctgacggcaaaacaacattgaaagttacagaaggcactgtt actttaagcaagaacatttcaaatccggagaaataacagttgcacttgatgacactgactc tagcggcaataaaaaatccggaacatgggattcagatacttctactttaacaattagtaaaa acagtcaaaaaactaaacaacttgtattcacaaaagaaacacaataacagtacaaaactat aacagagcaggcaatgcgcttgaaggcagcccagctgaaattaaagatcttgcagagcttaa agccgctttaaaataa

---

The OspA polypeptides of the invention include a polypeptide comprising, consisting essentially of, or consisting of the amino acid sequence of SEQ ID NO: 2 (lipB sOspA 1/2$^{251}$), SEQ ID NO: 4 (lipB sOspA 6/4), SEQ ID NO: 6 (lipB sOspA 5/3), SEQ ID NO: 8 (sOspA 1/2$^{251}$), SEQ ID NO: 10 (sOspA 6/4), SEQ ID NO: 12 (sOspA 5/3), SEQ ID NO: 169 (orig sOspA 1/2), SEQ ID NO: 171 (orig sOspA 6/4), or SEQ ID NO: 173 (orig sOspA 5/3) and related polypeptides. Related polypeptides include OspA polypeptide analogs, OspA polypeptide variants and OspA polypeptide derivatives. In some aspects, an OspA polypeptide has an amino terminal methionine residue, depending on the method by which they are prepared. In related aspects, the OspA polypeptide of the invention comprises OspA activity.

In one embodiment, related nucleic acid molecules comprise or consist of a nucleotide sequence that is about 70 percent (70%) identical or similar to the nucleotide sequence as shown in SEQ ID NO: 1 (lipB sOspA 1/2$^{251}$), SEQ ID NO: 3 (lipB sOspA 6/4), SEQ ID NO: 5 (lipB sOspA 5/3), SEQ ID NO: 7 (sOspA 1/2$^{251}$), SEQ ID NO: 9 (sOspA 6/4), SEQ ID NO: 11 (sOspA 5/3), SEQ ID NO: 168 (orig sOspA 1/2), SEQ ID NO: 170 (orig sOspA 6/4), or SEQ ID NO: 172 (orig sOspA 5/3), in certain aspects, comprise, consist essentially of, or consist of a nucleotide sequence encoding a polypeptide that is about 70 percent (70%) identical to the polypeptide as set forth in SEQ ID NO: 2 (lipB sOspA 1/2$^{251}$), SEQ ID NO: 4 (lipB sOspA 6/4), SEQ ID NO: 6 (lipB sOspA 5/3), SEQ ID NO: 8 (sOspA 1/2$^{251}$), SEQ ID NO: 10 (sOspA 6/4), SEQ ID NO: 12 (sOspA 5/3), SEQ ID NO: 169 (orig sOspA 1/2), SEQ ID NO: 171 (orig sOspA 6/4), or SEQ ID NO: 173 (orig sOspA 5/3). In various embodiments, the nucleotide sequences are about 70 percent, or about 71, 72, 73, 74, 75, 76, 77, 78, or 79 percent, or about 80 percent, or about 81, 82, 83, 84, 85, 86, 87, 88, or 89 percent, or about 90 percent, or about 91, 92, 93, 94, 95, 96, 97, 98, or 99 percent identical to the nucleotide sequence as shown in SEQ ID NO: 1 (lipB sOspA 1/2$^{251}$), SEQ ID NO: 3 (lipB sOspA 6/4), SEQ ID NO: 5 (lipB sOspA 5/3), SEQ ID NO: 7 (sOspA 1/2$^{251}$), SEQ ID NO: 9 (sOspA 6/4), SEQ ID NO: 11 (sOspA 5/3), SEQ ID NO: 168 (orig sOspA 1/2), SEQ ID NO: 170 (orig sOspA 6/4), or SEQ ID NO: 172 (orig sOspA 5/3), or the nucleotide sequences encode a polypeptide that is about 70 percent, or about 71, 72, 73, 74, 75, 76, 77, 78, or 79 percent, or about 80 percent, or about 81, 82, 83, 84, 85, 86, 87, 88, or 89 percent, or about 90 percent, or about 91, 92, 93, 94, 95, 96, 97, 98, or 99 percent identical to the polypeptide sequence as set forth in SEQ ID NO: 2 (lipB sOspA 1/2$^{251}$), SEQ ID NO: 4 (lipB sOspA 6/4), SEQ ID NO: 6 (lipB sOspA 5/3), SEQ ID NO: 8 (sOspA 1/2$^{251}$), SEQ ID NO: 10 (sOspA 6/4), SEQ ID NO: 12 (sOspA 5/3), SEQ ID NO: 169 (orig sOspA 1/2), SEQ ID NO: 171 (orig sOspA 6/4), or SEQ ID NO: 173 (orig sOspA 5/3).

In some embodiments, methods to determine sequence identity and/or similarity are designed to give the largest match between the sequences tested. Methods to determine identity and similarity are described in publicly available computer programs. In some aspects, computer program methods to determine identity and similarity between two sequences include, but are not limited to, the GCG program package, including GAP (Devereux et al., *Nucl. Acid. Res.*, 12:387 (1984); Genetics Computer Group, University of Wisconsin, Madison, Wis., BLASTP, BLASTN, and FASTA (Altschul et al., *J. Mol. Biol.*, 215:403-410 (1990)). The BLASTX program is publicly available from the National Center for Biotechnology Information (NCBI) and other sources (BLAST Manual, Altschul et al. NCB/NLM/NIH Bethesda, Md. 20894; Altschul et al., supra (1990)). The well-known Smith Waterman algorithm is also used to determine identity.

Certain alignment schemes for aligning two amino acid sequences, in some aspects, result in the matching of only a short region of the two sequences, and this small aligned region may have very high sequence identity even though there is no significant relationship between the two full-length sequences. Accordingly, in one embodiment the selected alignment method (GAP program) will result in an alignment that spans at least 50 contiguous amino acids of the target polypeptide. For example, using the computer algorithm GAP (Genetics Computer Group, University of Wisconsin, Madison, Wis.), two polypeptides for which the percent sequence identity is to be determined are aligned for optimal matching of their respective amino acids (the "matched span", as determined by the algorithm). A gap opening penalty (which is calculated as 3× the average diagonal; the "average diagonal" is the average of the diagonal of the comparison matrix being used; the "diagonal" is the score or number assigned to each perfect amino acid match by the particular comparison matrix) and a gap extension penalty (which is usually 1/10 times the gap opening penalty), as well as a comparison matrix such as PAM 250 or BLOSUM 62 are used in conjunction with the algorithm. A standard comparison matrix (see Dayhoff et al., Atlas of Protein Sequence and Structure, 5(3)(1978) for the PAM 250 comparison matrix; Henikoff et al., *Proc. Natl. Acad. Sci USA*, 89:10915-10919 (1992) for the BLOSUM 62 comparison matrix) is also used by the algorithm.

In various aspects, parameters for a polypeptide sequence comparison include the following:
Algorithm: Needleman et al., J. Mol. Biol., 48:443-453 (1970);
Comparison matrix: BLOSUM 62 from Henikoff et al., supra (1992);
Gap Penalty: 12
Gap Length Penalty: 4
Threshold of Similarity: 0
The GAP program is useful with the above parameters. The aforementioned parameters are the default parameters for polypeptide comparisons (along with no penalty for end gaps) using the GAP algorithm.

In some aspects, parameters for nucleic acid molecule sequence comparisons include the following:
Algorithm: Needleman et al., supra (1970);
Comparison matrix: matches=+10, mismatch=0
Gap Penalty: 50
Gap Length Penalty: 3
The GAP program is also useful with the above parameters. The aforementioned parameters are the default parameters for nucleic acid molecule comparisons. Other exemplary algorithms, gap opening penalties, gap extension penalties, comparison matrices, thresholds of similarity, and the like, are used by those of skill in the art, including those set forth in the Program Manual, Wisconsin Package, Version 9, September, 1997. The particular choices to be made will be apparent to those of skill in the art and will depend on the specific comparison to be made, such as DNA-to-DNA, protein-to-protein, protein-to-DNA; and additionally, whether the comparison is between given pairs of sequences (in which case GAP or BestFit are generally preferred) or between one sequence and a large database of sequences (in which case FASTA or BLASTA are preferred).

Differences in the nucleic acid sequence, in some aspects, result in conservative and/or non-conservative modifications of the amino acid sequence relative to the amino acid sequence of SEQ ID NO: 2 (lipB sOspA 1/2$^{251}$), SEQ ID NO: 4 (lipB sOspA 6/4), SEQ ID NO: 6 (lipB sOspA 5/3), SEQ ID NO: 8 (sOspA 1/2$^{251}$), SEQ ID NO: 10 (sOspA 6/4), SEQ ID NO: 12 (sOspA 5/3), SEQ ID NO: 169 (orig sOspA 1/2), SEQ ID NO: 171 (orig sOspA 6/4), or SEQ ID NO: 173 (orig sOspA 5/3).

Conservative modifications to the amino acid sequence of SEQ ID NO: 2 (lipB sOspA 1/2$^{251}$), SEQ ID NO: 4 (lipB sOspA 6/4), SEQ ID NO: 6 (lipB sOspA 5/3), SEQ ID NO: 8 (sOspA 1/2$^{251}$), SEQ ID NO: 10 (sOspA 6/4), SEQ ID NO: 12 (sOspA 5/3), SEQ ID NO: 169 (orig sOspA 1/2), SEQ ID NO: 171 (orig sOspA 6/4), or SEQ ID NO: 173 (orig sOspA 5/3) (and corresponding modifications to the encoding nucleotides) will produce OspA polypeptides having functional and chemical characteristics similar to those of a naturally occurring OspA polypeptide. In contrast, substantial modifications in the functional and/or chemical characteristics of OspA polypeptides are accomplished by selecting substitutions in the amino acid sequence of SEQ ID NO: 2 (lipB sOspA 1/2$^{251}$), SEQ ID NO: 4 (lipB sOspA 6/4), SEQ ID NO: 6 (lipB sOspA 5/3), SEQ ID NO: 8 (sOspA 1/2$^{251}$), SEQ ID NO: 10 (sOspA 6/4), SEQ ID NO: 12 (sOspA 5/3), SEQ ID NO: 169 (orig sOspA 1/2), SEQ ID NO: 171 (orig sOspA 6/4), or SEQ ID NO: 173 (orig sOspA 5/3) that differ significantly in their effect on maintaining (a) the structure of the molecular backbone in the area of the substitution, for example, as a sheet or helical conformation, (b) the charge or hydrophobicity of the molecule at the target site, or (c) the bulk of the side chain.

For example, a "conservative amino acid substitution," in some aspects, involves a substitution of a native amino acid residue with a normative residue such that there is little or no effect on the polarity or charge of the amino acid residue at that position. Furthermore, any native residue in the polypeptide, in certain aspects, is also substituted with alanine, as has been previously described for "alanine scanning mutagenesis."

Conservative amino acid substitutions also encompass non-naturally occurring amino acid residues which are typically incorporated by chemical peptide synthesis rather than by synthesis in biological systems. These include peptidomimetics and other reversed or inverted forms of amino acid moieties.

Naturally occurring residues, in various aspects, are divided into classes based on common side chain properties:
1) hydrophobic: norleucine, Met, Ala, Val, Leu, Ile;
2) neutral hydrophilic: Cys, Ser, Thr, Asn, Gln;
3) acidic: Asp, Glu;
4) basic: His, Lys, Arg;
5) residues that influence chain orientation: Gly, Pro; and
6) aromatic: Trp, Tyr, Phe.

For example, non-conservative substitutions, in some aspects, involve the exchange of a member of one of these classes for a member from another class. Such substituted residues, in various aspects, are introduced into regions of the OspA polypeptide that are homologous, or similar, with OspA polypeptide orthologs, or into the non-homologous regions of the molecule.

In making such changes, the hydropathic index of amino acids is often considered. Each amino acid has been assigned a hydropathic index on the basis of its hydrophobicity and charge characteristics. They are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is understood in the art. Kyte et al., *J. Mol. Biol.,* 157:105-131 (1982). It is known that certain amino acids may be substituted for other amino acids having a similar hydropathic index or score and still retain a similar biological activity. In making changes based upon the hydropathic index, the substitution of amino acids whose hydropathic indices are within ±2 is, in certain aspects, preferred, those which are within ±1 are, in other aspects, particularly preferred, and those within ±0.5 are, in various aspects, more particularly preferred.

It is also understood in the art that the substitution of like amino acids can be made effectively on the basis of hydrophilicity, particularly where the biologically functional equivalent protein or peptide thereby created is intended, in part, for use in immunological embodiments, as in the present case. The greatest local average hydrophilicity of a protein, as governed by the hydrophilicity of its adjacent amino acids, correlates with its immunogenicity and antigenicity, i.e., with a biological property of the protein.

The following hydrophilicity values have been assigned to these amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5) and tryptophan (−3.4). In making changes based upon similar hydrophilicity values, the substitution of amino acids whose hydrophilicity values are within ±2 is, in certain aspects, preferred, those which are within ±1 are in other aspects, particularly preferred, and those within ±0.5 are, in various aspects, more particularly preferred. One of skill also identifies epitopes from primary amino acid sequences on the basis of hydrophilicity. These regions are also referred to as "epitopic core regions."

Desired amino acid substitutions (whether conservative or non-conservative) can be determined by those skilled in the art at the time such substitutions are desired. For example, amino acid substitutions can be used to identify important residues of the OspA polypeptide, or to increase or decrease the affinity of the OspA polypeptides for their substrates, described herein.

In some aspects, substitutions of nucleotides in nucleotide sequences and amino acids in amino acid sequences are included in the invention. The substitutions include one to 5, one to 10, one to 15, one to 20, one to 25, one to 30, one to 35, one to 40, one to 45, one to 50, one to 55, one to 60, one to 65, one to 70, one to 75, one to 80, one to 85, one to 90, one to 95, one to 100, one to 150, and one to 200 nucleotides. Likewise, substitutions include one to 5, one to 10, one to 15, one to 20, one to 25, one to 30, one to 35, one to 40, one to 45, one to 50, one to 55, one to 60, one to 65, one to 70, one to 75, one to 80, one to 85, one to 90, one to 95, and one to 100 amino acids. The substitutions, in various aspects, are conservative or non-conservative.

Exemplary Amino Acid Substitutions are Set Forth in Table 2.

TABLE 2

Amino Acid Substitutions

| Original Residues | Exemplary Substitutions | Preferred Substitutions |
|---|---|---|
| Ala | Val, Leu, Ile | Val |
| Arg | Lys, Gln, Asn | Lys |
| Asn | Gln | Gln |
| Asp | Glu | Glu |
| Cys | Ser, Ala | Ser |
| Gln | Asn | Asn |
| Glu | Asp | Asp |
| Gly | Pro, Ala | Ala |
| His | Asn, Gln, Lys, Arg | Arg |
| Ile | Leu, Val, Met, Ala, Phe, Norleucine | Leu |
| Leu | Norleucine, Ile, Val, Met, Ala, Phe | Ile |
| Lys | Arg, 1,4 Diamino-butyric Acid, Gln, Asn | Arg |
| Met | Leu, Phe, Ile | Leu |
| Phe | Leu, Val, Ile, Ala, Tyr | Leu |
| Pro | Ala | Gly |
| Ser | Thr, Ala, Cys | Thr |
| Thr | Ser | Ser |
| Trp | Tyr, Phe | Tyr |
| Tyr | Trp, Phe, Thr, Ser | Phe |
| Val | Ile, Met, Leu, Phe, Ala, Norleucine | Leu |

A skilled artisan can determine suitable analogs or variants of the polypeptide as set forth in SEQ ID NO: 2, 4, 6, 8, 10, 12, 169, 171, or 173 using well-known techniques. For identifying suitable areas of the molecule that may be changed without destroying activity, one skilled in the art may target areas not believed to be important for activity. For example, when similar polypeptides with similar activities from the same species or from other species are known, one skilled in the art may compare the amino acid sequence of an OspA polypeptide to such similar polypeptides. With such a comparison, one can identify residues and portions of the molecules that are conserved among similar polypeptides. It will be appreciated that changes in areas of an OspA polypeptide that are not conserved relative to such similar polypeptides would be less likely to adversely affect the biological activity and/or structure of the OspA polypeptide. One skilled in the art would also know that, even in relatively conserved regions, one may substitute chemically similar amino acids for the naturally occurring residues while retaining activity (conservative amino acid residue substitutions).

In some embodiments, OspA polypeptide variants include glycosylation variants wherein the number and/or type of glycosylation sites has been altered compared to the amino acid sequence set forth in SEQ ID NO: 2, 4, 6, 8, 10, 12, 169, 171, or 173. In one embodiment, OspA polypeptide variants comprise a greater or a lesser number of N-linked glycosylation sites than the amino acid sequence set forth in SEQ ID NO: 2, 4, 6, 8, 10, 12, 169, 171, or 173. An N-linked glycosylation site is characterized by the sequence: Asn-X-Ser or Asn-X-Thr, wherein the amino acid residue designated as X may be any amino acid residue except proline. The substitution of amino acid residues to create this sequence provides a potential new site for the addition of an N-linked carbohydrate chain. Alternatively, substitutions which eliminate this sequence will remove an existing N-linked carbohydrate chain. Also provided is a rearrangement of N-linked carbohydrate chains wherein one or more N-linked glycosylation sites (typically those that are naturally occurring) are eliminated and one or more new N-linked sites are created. Additional OspA variants include cysteine variants wherein one or more cysteine residues are deleted from or substituted for another amino acid (e.g., serine) as compared to the amino acid sequence set forth in SEQ ID NO: 2, 4, 6, 8, 10, 12, 169, 171, or 173. Cysteine variants are useful when OspA polypeptides must be refolded into a biologically active conformation such as after the isolation of insoluble inclusion bodies. Cysteine variants generally have fewer cysteine residues than the native protein, and typically have an even number to minimize interactions resulting from unpaired cysteines.

The invention further provides polypeptides that comprise an epitope-bearing portion of a protein as shown in SEQ ID NO: 2, 4, 6, 8, 10, 12, 169, 171, or 173. The term, "epitope" refers to a region of a protein to which an antibody can bind. See e.g., Geysen et al., *Proc. Natl. Acad. Sci. USA* 81:3998-4002 (1984). Epitopes can be linear or conformational, the latter being composed of discontinuous regions of the protein that form an epitope upon folding of the protein. Linear epitopes are generally at least 6 amino acid residues in length. Relatively short synthetic peptides that mimic part of a protein sequence are routinely capable of eliciting an antiserum that reacts with the partially mimicked protein. See, Sutcliffe et al., Science 219:660-666 (1983). Antibodies that recognize short, linear epitopes are particularly useful in analytic and diagnostic applications that employ denatured protein, such as Western blotting. See Tobin, Proc. Natl. Acad. Sci. USA, 76:4350-4356 (1979). Antibodies to short peptides, in certain instances, also recognize proteins in native conformation and will thus be useful for monitoring protein expression and protein isolation, and in detecting OspA proteins in solution, such as by ELISA or in immunoprecipitation studies.

Synthesis of Chimeric OspA Nucleic Acid Molecules and Polypeptide Molecules

The nucleic acid molecules encode a polypeptide comprising the amino acid sequence of an OspA polypeptide and can readily be obtained in a variety of ways including, without limitation, recombinant DNA methods and chemical synthesis.

Recombinant DNA methods are generally those set forth in Sambrook et al., Molecular Cloning: A Laboratory Manual, Cold Spring Harbor Laboratory Press, Cold Spring Harbor, N.Y. (1989), and/or Ausubel et al., eds., Current Protocols in Molecular Biology, Green Publishers Inc. and Wiley and Sons, NY (1994). Recombinant expression techniques conducted in accordance with the descriptions set forth below, in various aspects, are followed to produce these polynucleotides and to express the encoded polypeptides. For example, by inserting a nucleic acid sequence which encodes the amino acid sequence of an OspA polypeptide into an appropriate vector, one skilled in the art can readily produce large quantities of the desired nucleotide sequence. The sequences can then be used to generate detection probes or amplification primers. Alternatively, a polynucleotide encoding the amino acid sequence of an OspA polypeptide can be inserted into an expression vector. By introducing the expression vector into an appropriate host, the encoded OspA polypeptide or OspA polypeptides are, in some aspects, produced in large amounts.

Likewise, chemical synthesis of nucleic acids and polypeptides are well known in the art, such as those described by Engels et al., Angew. Chem. Intl. Ed., 28:716-734 (1989). These methods include, inter alia, the phosphotriester, phosphoramidite and H-phosphonate methods for nucleic acid synthesis. In one aspect, a method for such chemical synthesis is polymer-supported synthesis using standard phosphoramidite chemistry. Typically, the DNA encoding the amino acid sequence of an OspA polypeptide will be several hundred nucleotides in length. Nucleic acids larger than about 100 nucleotides are synthesized as several fragments using these methods. The fragments are then ligated together to form the full-length nucleotide sequences of the invention. In particular aspects, the DNA fragment encoding the amino terminus of the polypeptide has an ATG, which encodes a methionine residue.

In a particular aspect of the invention, chimeric OspA coding sequences are made using synthetic overlapping oligonucleotides. Because DNA from *Borrelia* cells is not used, a further benefit of the synthetic approach is the avoidance of contamination with adventitious agents contained in material of animal origin (i.e. serum or serum albumin) present in *Borrelia* culture medium. This strategy also substantially reduces the number of manipulations required to make the chimeric genes, since it allows sequence alterations to be made in a single step, such as modifications to optimize expression (OspB leader sequence), to introduce restriction sites to facilitate cloning, or to avoid potential intellectual property issues. It also enables codon usage to be optimized for an *E. coli* host, since the presence of codons that are rarely used in *E. coli* is known to present a potential impediment to high-level expression of foreign genes (Makoff et al., *Nucleic Acids Res.* 17:10191-202, 1989; Lakey et al., *Infect. Immun.* 68:233-8, 2000). Other methods known to the skilled artisan are used as well.

In certain embodiments, nucleic acid variants contain codons which have been altered for the optimal expression of an OspA polypeptide in a given host cell. Particular codon alterations depend upon the OspA polypeptide(s) and host cell(s) selected for expression. Such "codon optimization" can be carried out by a variety of methods, for example, by selecting codons which are preferred for use in highly expressed genes in a given host cell. Computer algorithms which incorporate codon frequency tables such as "Ecohigh.cod" for codon preference of highly expressed bacterial genes are used, in some instances, and are provided by the University of Wisconsin Package Version 9.0, Genetics Computer Group, Madison, Wis. Other useful codon frequency tables include "Celegans_high.cod", "Celegans_low.cod", "Drosophila_high.cod", "Human_high.cod", "Maize_high.cod", and "Yeast_high.cod."

A nucleic acid molecule encoding the amino acid sequence of an OspA polypeptide, in certain aspects, is inserted into an appropriate expression vector using standard ligation techniques. The vector is typically selected to be functional in the particular host cell employed (i.e., the vector is compatible with the host cell machinery such that amplification of the gene and/or expression of the gene can occur). A nucleic acid molecule encoding the amino acid sequence of an OspA polypeptide, in various aspects, is amplified/expressed in prokaryotic, yeast, insect (baculovirus systems), and/or eukaryotic host cells. Selection of the host cell depends in part on whether an OspA polypeptide is to be post-translationally modified (e.g., glycosylated and/or phosphorylated). If so, yeast, insect, or mammalian host cells are preferable. For a review of expression vectors, see Meth. Enz., vol. 185, D. V. Goeddel, ed., Academic Press Inc., San Diego, Calif. (1990).

Figure 12:
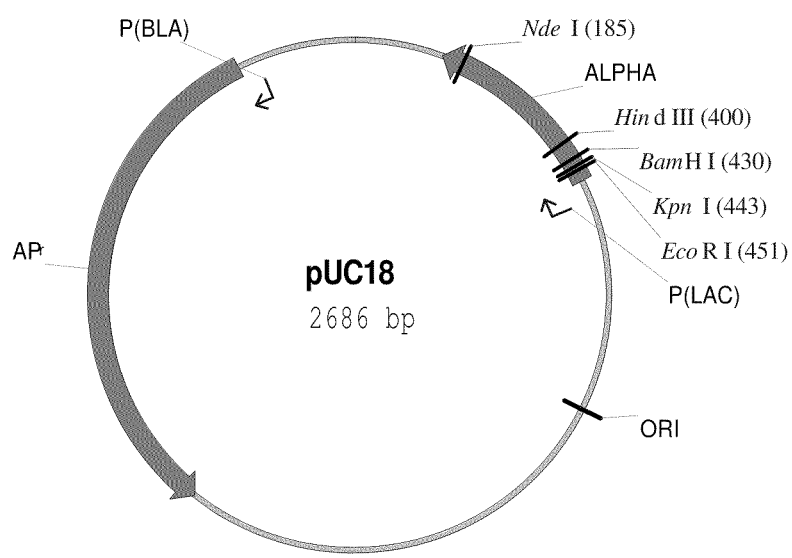
FIG. 12 is a map of plasmid pUC18.

Cloning vectors include all those known in the art. See, e.g., Sambrook, Fritsch & Maniatis, Molecular Cloning: A Laboratory Manual, Second Edition. Cold Spring Harbor, N.Y.: Cold Spring Harbor Laboratory Press, 1989. In one aspect, pUC18 is used as the cloning vector for all intermediate steps, because genetic manipulations and sequencing are easier with this plasmid than with the vector pET30a. The principal features are notably, the lacZ gene fragment coding for LacZ alpha peptide from base pairs 149 to 469 (lac promoter at base pairs 507), the bla gene encoding the ampicillin resistance determinant from base pairs 1629 to 2486 (bla promoter at base pairs 2521), the origin of replication at base pairs 867 and multiple cloning sites from base pairs 185 to 451 (FIG. 12).

Figure 13:
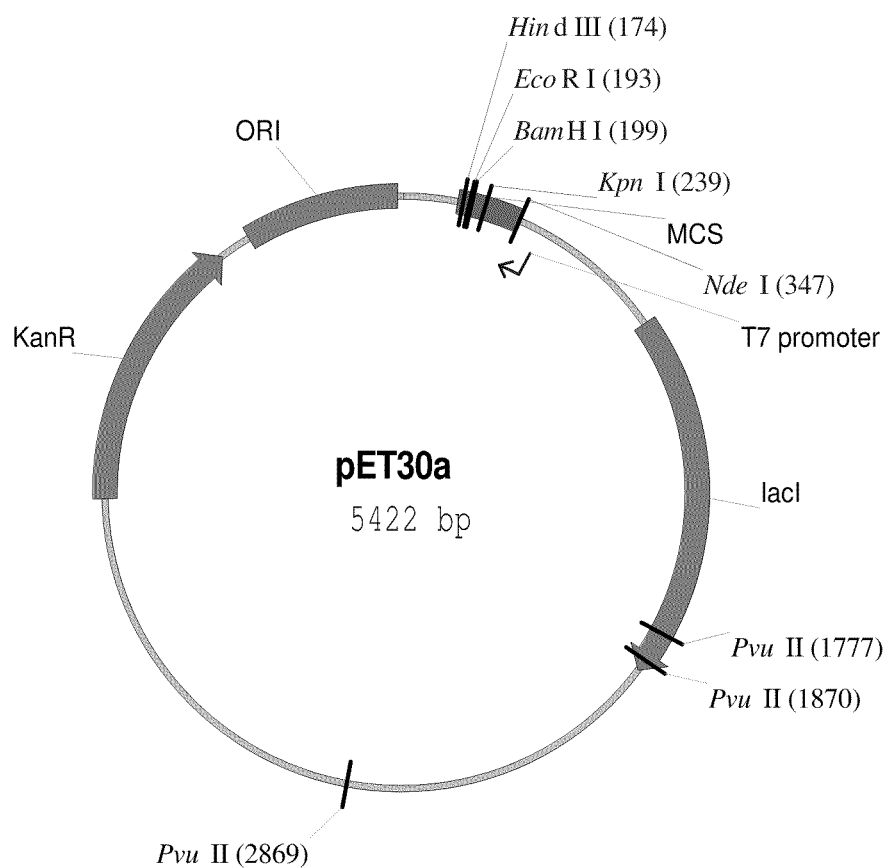

Expression vectors include all those known in the art, including without limitation cosmids, plasmids (e.g., naked or contained in liposomes) and viruses that incorporate the recombinant polynucleotide. The expression vector is inserted (e.g., via transformation or transduction) into an appropriate host cell for expression of the polynucleotide and polypeptide via transformation or transfection using techniques known in the art. See, e.g., Sambrook, Fritsch & Maniatis, Molecular Cloning: A Laboratory Manual, Second Edition. Cold Spring Harbor, N.Y.: Cold Spring Harbor Laboratory Press, 1989. In one aspect, pET30a (Novagen) is used as the expression vector for the final complete OspA gene insert. In pET vectors, genes are cloned under the control of a T7 promoter and expression is induced by providing a source of T7 RNA polymerase in the host cell (no expression occurs until a source of T7 RNA polymerase is provided). The principal features are the gene encoding kanamycin resistance (kan) at base pairs 4048 to 4860, the lacI gene base pairs 826-1905, the F1 origin of replication at base pairs 4956-5411 and multiple cloning sites from base pairs 158 to 346 (FIG. 13).

After the vector has been constructed and a nucleic acid molecule encoding an OspA polypeptide has been inserted into the proper site of the vector, the completed vector is inserted into a suitable host cell for amplification and/or polypeptide expression. The transformation of an expression vector for an OspA polypeptide into a selected host cell is, in various aspects, accomplished by well-known methods such as transfection, infection, calcium chloride-mediated transformation, electroporation, microinjection, lipofection or the DEAE-dextran method or other known techniques. The method selected will in part be a function of the type of host cell to be used. These methods and other suitable methods are well known to the skilled artisan and are set forth, for example, in Sambrook et al., supra.

Host cells, in some aspects, are prokaryotic host cells (such as *E. coli*) or eukaryotic host cells (such as yeast, insect or vertebrate cells). The host cell, when cultured under appropriate conditions, synthesizes an OspA polypeptide which can subsequently be collected from the culture medium (if the host cell secretes it into the medium) or directly from the host cell producing it (if it is not secreted). The selection of an appropriate host cell depends upon various factors, such as desired expression levels, polypeptide modifications that are desirable or necessary for activity (such as glycosylation or phosphorylation), and ease of folding into a biologically active molecule. Such host cells include, but are not limited to, host cells of bacterial, yeast, fungal, viral, invertebrate, and mammalian sources. For examples of such host cells, see Maniatis et al., Molecular Cloning: A Laboratory Manual, Cold Spring Harbor Laboratory, Cold Spring Harbor, N.Y. (1989). In additional aspects, host cells used in the art since the publication of the Maniatis (supra) manual are also used in the invention.

In one aspect, the host cell is an *E. coli* cell. Suitable strains of *E. coli* include, but are not limited to, BL21, DH5α, HMS174(DE3), DH10B, or E. CLONI 10G (Lucigen, Middleton, Wis.). In some embodiments, host cells are engineered to enhance transformation efficiency and/or maintenance of the vector.

In one aspect, the *E. coli* strain DH5α [genotype: end A1 hsdR17 (rK-mK+) supE44 thi-1 recA1 gyrA (NaIr) relA1 D(IacZYA-argF)U169 deoR (F80dlacD(lacZ)M15] (Gibco BRL) is used for all intermediate cloning steps. This strain is derived from *E. coli* strain K12, one of the most widely used hosts in genetic engineering. The strain is amp- to allow selection of transformants with vectors containing the ampicillin resistance gene (amp).

In another aspect, the *E. coli* strain HMS174(DE3) is used as the host for expression. *E. coli* HMS174(DE3) host cells [genotype: F-recA1 hsdR (rk12-mk12+) RifR (DE3)] (Novagen) are used in various examples described herein for the final cloning steps. The strain is kan- to allow selection of transformants with vectors containing the kanamycin resistance gene (kan).

Host cells comprising an OspA polypeptide expression vector are cultured using standard media well known to the skilled artisan. The media will usually contain all nutrients necessary for the growth and survival of the cells. Suitable media for culturing *E. coli* cells include, for example, Luria Broth (LB) and/or Terrific Broth (TB). Suitable media for culturing eukaryotic cells include Roswell Park Memorial Institute medium 1640 (RPMI 1640), Minimal Essential Medium (MEM) and/or Dulbecco's Modified Eagle Medium (DMEM), all of which, in some instances, are supplemented with serum and/or growth factors as indicated by the particular cell line being cultured. A suitable medium for insect cultures is Grace's medium supplemented with yeastolate, lactalbumin hydrolysate and/or fetal calf serum, as necessary.

Typically, an antibiotic or other compound useful for selective growth of transformed cells is added as a supplement to the media. The compound to be used will be dictated by the selectable marker element present on the plasmid with which the host cell was transformed. For example, where the selectable marker element is kanamycin resistance, the compound added to the culture medium will be kanamycin. Other compounds for selective growth include ampicillin, tetracycline and neomycin.

The amount of an OspA polypeptide produced by a host cell can be evaluated using standard methods known in the art. Such methods include, without limitation, Western blot analysis, SDS-polyacrylamide gel electrophoresis, non-denaturing gel electrophoresis, chromatographic separation such as Hgh Performance Liquid Chromatography (HPLC), immunodetection such as immunoprecipitation, and/or activity assays such as DNA binding gel shift assays.

In some cases, an OspA polypeptide is not biologically active upon isolation. Various methods for "refolding" or converting the polypeptide to its tertiary structure and generating disulfide linkages are used to restore biological activity. Such methods include exposing the solubilized polypeptide to a pH usually above 7 and in the presence of a particular concentration of a chaotrope. The selection of chaotrope is very similar to the choices used for inclusion body solubilization, but usually the chaotrope is used at a lower concentration and is not necessarily the same as chaotropes used for the solubilization. In some instances, the refolding/oxidation solution also contains a reducing agent or the reducing agent plus its oxidized form in a specific ratio to generate a particular redox potential allowing for disulfide shuffling to occur in the formation of the protein's cysteine bridge(s). Some of the commonly used redox couples include cysteine/cystamine, glutathione (GSH)/dithiobis GSH, cuprous chloride, dithiothreitol(DTT)/dithiane DTT, and 2-2mercaptoethanol(bME)/dithio-b(ME). A cosolvent is often used to increase the efficiency of the refolding, and the more common reagents used for this purpose include glycerol, polyethylene glycol of various molecular weights, arginine and the like.

If inclusion bodies are not formed to a significant degree upon expression of an OspA polypeptide, then the polypeptide will be found primarily in the supernatant after centrifugation of the cell homogenate. The polypeptide is further isolated from the supernatant using methods such as those described herein or otherwise known in the art.

The purification of an OspA polypeptide from solution can be accomplished using a variety of techniques known in the art. If the polypeptide has been synthesized such that it contains a tag such as Hexahistidine (OspA polypeptide/hexa-His) or other small peptide such as FLAG (Eastman Kodak Co., New Haven, Conn.) or myc (Invitrogen, Carlsbad, Calif.) at either its carboxyl or amino terminus, the polypeptide is often purified in a one-step process by passing the solution through an affinity column where the column matrix has a high affinity for the tag. For example, polyhistidine binds with great affinity and specificity to nickel; thus an affinity column of nickel (such as the Qiagen® nickel columns) can be used for purification of OspA polypeptide/polyHis. See for example, Ausubel et al., eds., Current Protocols in Molecular Biology, Section 10.11.8, John Wiley & Sons, New York (1993).

Additionally, the OspA polypeptide may be purified through use of a monoclonal antibody which is capable of specifically recognizing and binding to the OspA polypeptide. Suitable procedures for purification thus include, without limitation, affinity chromatography, immunoaffinity chromatography, ion exchange chromatography, molecular sieve chromatography, High Performance Liquid Chromatography (HPLC), electrophoresis (including native gel electrophoresis) followed by gel elution, and preparative isoelectric focusing ("Isoprime" machine/technique, Hoefer Scientific, San Francisco, Calif.). In some cases, two or more purification techniques are combined to achieve increased purity.

OspA polypeptides are also prepared by chemical synthesis methods (such as solid phase peptide synthesis) using techniques known in the art, such as those set forth by Merrifield et al., J. Am. Chem. Soc., 85:2149 (1963), Houghten et al., Proc. Natl. Acad. Sci. USA, 82:5132 (1985), and Stewart and Young, "Solid Phase Peptide Synthesis", Pierce Chemical Co., Rockford, Ill. (1984). Such polypeptides are synthesized with or without a methionine on the amino terminus. Chemically synthesized OspA polypeptides, in some aspects, are oxidized using methods set forth in these references to form disulfide bridges. Chemically synthesized OspA polypeptides are expected to have comparable biological activity to the corresponding OspA polypeptides produced recombinantly or purified from natural sources, and thus are often used interchangeably with a recombinant OspA polypeptide. It is appreciated that a number of additional methods for producing nucleic acids and polypeptides are known in the art, and the methods can be used to produce OspA polypeptides.

Chemical Derivatives of OspA Polypeptide Molecules

Chemically modified derivatives of the OspA polypeptides are prepared by one skilled in the art, given the disclosures set forth herein below. OspA polypeptide derivatives are modified in a manner that is different either in the type or location of the molecules naturally attached to the polypeptide. Derivatives, in some aspects, include molecules formed by the deletion of one or more naturally-attached chemical groups. The polypeptide comprising the amino acid sequence of SEQ ID NO: 2, 4, 6, 8, 10, 12, 169, 171, or 173, or an OspA polypeptide variant, in one aspect, is modified by the covalent attachment of one or more polymers. For example, the polymer selected is typically water soluble so that the protein to which it is attached does not precipitate in an aqueous environment, such as a physiological environment. Included within the scope of suitable polymers is a mixture of polymers. In certain aspects, for therapeutic use of the end-product preparation, the polymer will be pharmaceutically acceptable.

The polymers each are, in various aspects, of any molecular weight and are branched or unbranched. The polymers each typically have an average molecular weight of between about 2 kDa to about 100 kDa (the term "about" indicating that in preparations of a water-soluble polymer, some molecules will weigh more, some less, than the stated molecular weight). The average molecular weight of each polymer is, in various aspects, between about 5 kDa to about 50 kDa, between about 12 kDa to about 40 kDa, and between about 20 kDa to about 35 kDa.

Suitable water-soluble polymers or mixtures thereof include, but are not limited to, N-linked or O-linked carbohydrates; sugars; phosphates; polyethylene glycol (PEG) (including the forms of PEG that have been used to derivatize proteins, including mono-(C1-C10) alkoxy- or aryloxy-polyethylene glycol); monomethoxy-polyethylene glycol; dextran (such as low molecular weight dextran of, for example, about 6 kDa); cellulose; or other carbohydrate-based polymers, poly-(N-vinyl pyrrolidone) polyethylene glycol, propylene glycol homopolymers, a polypropylene oxide/ethylene oxide co-polymer, polyoxyethylated polyols (e.g., glycerol) and polyvinyl alcohol. Also encompassed by the present invention are bifunctional crosslinking molecules which are sometimes used to prepare covalently attached multimers of the polypeptide comprising the amino acid sequence of SEQ ID NO: 2, 4, 6, 8, 10, 12, 169, 171, or 173, or an OspA polypeptide variant.

In some aspects, chemical derivatization is performed under any suitable condition used to react a protein with an activated polymer molecule. Methods for preparing chemical derivatives of polypeptides generally comprise the steps of (a) reacting the polypeptide with the activated polymer molecule (such as a reactive ester or aldehyde derivative of the polymer molecule) under conditions whereby the polypeptide comprising the amino acid sequence of SEQ ID NO: 2, 4, 6, 8, 10, 12, 169, 171, or 173, or an OspA polypeptide variant becomes attached to one or more polymer molecules, and (b) obtaining the reaction product(s). The optimal reaction conditions are determined based on known parameters and the desired result. For example, the larger the ratio of polymer molecules:protein, the greater the percentage of attached polymer molecule. In one embodiment, the OspA polypeptide derivative has a single polymer molecule moiety at the amino terminus (see, for example, U.S. Pat. No. 5,234,784).

The pegylation of the polypeptide, in certain aspects, is specifically carried out by any of the pegylation reactions known in the art, as described for example in the following references: Francis et al., Focus on Growth Factors, 3:4-10 (1992); EP 0154316; EP 0401384 and U.S. Pat. No. 4,179,337. For example, pegylation is carried out via an acylation reaction or an alkylation reaction with a reactive polyethylene glycol molecule (or an analogous reactive water-soluble polymer) as described herein. For the acylation reactions, the polymer(s) selected should have a single reactive ester group. For reductive alkylation, the polymer(s) selected should have a single reactive aldehyde group. A reactive aldehyde is, for example, polyethylene glycol propionaldehyde, which is water stable, or mono C1-C10 alkoxy or aryloxy derivatives thereof (see U.S. Pat. No. 5,252,714).

In another embodiment, OspA polypeptides are chemically coupled to biotin, and the biotin/OspA polypeptide molecules which are conjugated are then allowed to bind to avidin, resulting in tetravalent avidin/biotin/OspA polypeptide molecules. OspA polypeptides are also covalently coupled to dinitrophenol (DNP) or trinitrophenol (TNP) and the resulting conjugates precipitated with anti-DNP or anti-TNP-IgM to form decameric conjugates with a valency of 10. The OspA polypeptide derivatives disclosed herein, in certain aspects, have additional activities, enhanced or reduced biological activity, or other characteristics, such as increased or decreased half-life, as compared to the non-derivatized molecules.

Immunogenic Compositions, Vaccines, and Antibodies

Some aspects of the invention include immunogenic compositions and vaccines. Immuogenic chimeric OspA molecules of the invention are used in combination as antigen(s) to elicit an anti-OspA immune response in a subject (i.e., act as a vaccine). Exemplary immunogenic OspA polypeptides (SEQ ID NOS: 2, 4, 6, 169, 171, and 173) are delivered in combination to elicit an immune response to any one or more of serotypes 1-6 of Borrelia, and more generally to many other species of Borrelia as discussed herein. An immune response can also be raised by delivery of plasmid vectors encoding the OspA polypeptides of the invention (i.e., administration of "naked DNA"). In some aspects, OspA nucleic acid molecules (SEQ ID NOS: 1, 3, 5, 168, 170, and 172) are delivered by injection, via liposomes, or by other means of administration described herein. Once immunized, the subject elicits a heightened immune response against the OspA protein of serotypes 1-6 of Borrelia and against other species of Borrelia.

As set out above, therefore, both OspA polypeptides and OspA nucleic acid molecules are included as antigens for use in the immunogenic and/or vaccine compositions of the invention. In certain aspects, both the nucleic acid and protein are delivered to the subject. In particular aspects, the immune response to a nucleic acid vaccine is proposed to be enhanced by simultaneous administration of a cognate protein (see WO 99/30733). The nucleic acid and protein do not need to be administered in the same composition. Both must merely be administered during the induction phase of the immune response with the protein, in some aspects, being masked or held back until after the nucleic acid has primed the immune system. In a particular aspect, vaccines are intended to deliver nucleic acid and protein antigen into antigen presenting cells (see WO 97/28818). In various aspects, the nucleic acid and protein are complexed, e.g., by covalent conjugation. In further aspects, liposomal formulations are also included to enhance the immunogenicity of vaccine antigens.

In certain aspects, an immunogenic composition of the invention includes any one or more of the OspA molecules described herein in combination with a pharmaceutical carrier, wherein the composition induces production of an antibody that specifically binds an Outer surface protein A (OspA) protein. In some aspects, the immunogenic composition also comprises a stabilizer or antimicrobial preservative. In particular aspects, the immunogenic composition induces production of an antibody that specifically binds Borrelia. In other aspects, the composition induces production of an antibody that neutralizes Borrelia.

In some aspects, the invention includes the use of adjuvants in the immunogenic compositions comprising the chimeric OspA molecules (antigens) described herein. In certain aspects, immunogenicity is significantly improved if an antigen is co-administered with an adjuvant. In some aspects, an adjuvant is used as 0.001% to 50% solution in phosphate buffered saline (PBS). Adjuvants enhance the immunogenicity of an antigen but are not necessarily immunogenic themselves.

Adjuvants, in various aspects, have a number of positive effects on vaccination. In some instances, adjuvants accelerate the generation of a robust immune response in subjects. Adjuvants, in other instances, increase the level of immune response, prolong its duration and improve immune memory. Adjuvants are often used to overcome weakened immunity of particular subject groups (e.g., the elderly or immune-suppressed patients) or to improve the immunogenicity of particular "at risk group" (such as, but not limited to, the very young or elderly). The immune enhancing effects of an adjuvant, in various instances, leads to a reduction of the amount of antigen required in the final formulation to give a protective response (i.e. dose-sparing).

In general, adjuvants are classified, based on their dominant mechanism of action, into two main groups: The first group are the agonists of innate immunity system receptors or sensors, such as Toll-like-receptor (TLR) agonists, C-type lectin receptor agonists, retinoic acid inducible gene 1 (RIG-1) like receptor (RLR) agonists, and nucleotide-binding domain and leucine rich repeat-containing receptor (NLR) agonists. The second group are the substances which act as delivery systems, also known as TLR-independent adjuvants. Examples of TLR agonist adjuvants are ASO4 (Glaxo Smith Kline), a TLR-4 agonist, used as an adjuvant in commercial Hepatitis B and papilloma virus vaccines; Vaxinate, a flagellin-fusion protein TLR-5 agonist; and numerous TLR-9 agonist adjuvants, such as those that use double-stranded DNA (dsDNA) and oligonucleotides CpG or ODN1a. Other TLR-agonists falling into this category of adjuvants include glycolipids (TLR-1), lipoteichoic acid and lipoprotein (TLR-1/TLR-2 and TLR-2/TLR-6) lipopolysaccharide, lipooligocaccharides and monophosphoryt lipid A (MPL) (TLR-4), double-stranded RNA (TLR-3); peptidoglycan (TLR-6), single stranded RNA (TLR-7). Examples of two C-type lectin receptor agonist adjuvants include β-glucans (Dectin-1) and mannans (Dectin-2), both derived from fungal cell walls. RLR receptor agonist adjuvants include single-stranded viral RNA and double-stranded viral DNA, while NLR agonist adjuvants include peptidoglycan degradation products, microbial products, and non-infectious crystal particles. In all cases, the agonists act by directly activating the innate immune system receptor to trigger an immune enhancing inflammatory response. The second group of adjuvants, the TLR independent adjuvants, mostly act as delivery systems and enhance antigen uptake and presentation by an antigen presenting cell. In some instances, these adjuvants can also act by retaining the antigen locally near the site of administration to produce a depot effect facilitating a slow, sustained release of antigen to cells of the immune system. Adjuvants also attract cells of the immune system to an antigen depot and stimulate such cells to elicit immune responses. Examples of TLR independent adjuvants include mineral salts, such as aluminum hydroxide and aluminum phosphate (collectively referred to as alum) and calcium phosphate; oil-in-water emulsion (e.g., MF59, AS03 and ProVax); water in oil emulsion (Montanide, TiterMax); biopolymers (Advax); plant derivatives, especially fractions of saponin, a triterpenoid extract from the bark of the South American Molina soap tree *Quillaja saponaria* (SFA-1, QS21, Quil A); immune stimulating complexes (ISCOM and ISCOM matrix) composed of saponin fractions, sterol and, optionally, phospholipids (ISCOMATRIX and Matrix-M); liposomes, which are phospholipid spheres of various sizes and charge (Vaxfectin and Vaxisome); virus-like particles and virosomes, which are liposomes containing viral surface antigens, such as Influenza haemagglutinin and neuraminidase; nanoparticles of various composition; chitosan, peptides such as polyarginine and a peptide known as the KLK peptide.

The adjuvants listed herein above are used singly or in combination. Combinations of TLR-dependent and a TLR-independent adjuvants are often preferred as the antigen and the TLR-dependent adjuvant are believed to be trafficked to antigen presenting cells by the TLR-independent adjuvant, which would also stimulate uptake and stability, while the TLR-dependent adjuvant would directly enhance immunity through the activation of TLR signaling.

Examples of TLR-dependent and TLR-independent adjuvant combinations include AS01: a mixture of MPL (a TLR-4 agonist), liposomes and QS-21 (both TLR-independent adjuvant); AS04: MPL (a TLR-4 agonist) and aluminum hydroxide/phosphate; IC31: ODN1a (a TLR-9 agonist) and KLK peptide (a TLR-independent adjuvant); and Freunds complete adjuvant, a membrane extract of *Mycobacterium tuberculosis* (TLR-4 agonist) and a oil-in-water emulsion (a TLR-independent adjuvant).

Combinations consisting of multiple TLR-dependent adjuvants are also used to maximize the immune enhancing effect of adjuvanted vaccine formulations. Agonists of TLRs, which use different adaptor proteins, are often combined (e.g., a combination of an agonist for the plasma membrane-bound TLR-3 or TLR-4 receptor which utilizes the TRIF (Toll/interleukin 1 receptor domain-containing adaptor protein inducing INF-β) adaptor pathway with an agonist of the TLRs (TLR-7, TLR-8 and TLR-9), which are expressed in endosomal or lysosomal organelles and utilize the MyD88 (myeloid differentiating primary response protein) adaptor protein pathway).

These immunostimulatory agents or adjuvants improve the host immune response in vaccines as well. In some cases, substances such as lipopolysaccarides can act as intrinsic adjuvants since they normally are the components of the killed or attenuated bacteria used as vaccines. Extrinsic adjuvants, such as those listed herein above, are immunomodulators which are typically non-covalently linked to antigens and are formulated to enhance the host immune response.

A wide range of extrinsic adjuvants can provoke potent immune responses to antigens. These include saponins complexed to membrane protein antigens (immune stimulating complexes), pluronic polymers with mineral oil, killed mycobacteria in mineral oil, Freund's complete adjuvant, bacterial products, such as muramyl dipeptide (MDP) and lipopolysaccharide (LPS), as well as lipid A, and liposomes. To efficiently induce humoral immune response (HIR) and cell-mediated immunity (CMI), immunogens are, in certain aspects, emulsified in adjuvants.

Desirable characteristics of ideal adjuvants include any or all of: lack of toxicity; ability to stimulate a long-lasting immune response; simplicity of manufacture and stability in long-term storage; ability to elicit both CMI and HIR to antigens administered by various routes; synergy with other adjuvants; capability of selectively interacting with populations of antigen presenting cells (APC); ability to specifically elicit appropriate $T_{H1}$ or $T_{H2}$ cell-specific immune responses; and ability to selectively increase appropriate antibody isotype levels (for example IgA) against antigens.

U.S. Pat. No. 4,855,283, incorporated herein by reference, thereto teaches glycolipid analogs including N-glycosylamides, N-glycosylureas and N-glycosylcarbamates, each of which is substituted in the sugar residue by an amino acid, as immune-modulators or adjuvants. U.S. Pat. No. 4,855,283 reported that N-glycolipids analogs displaying structural similarities to the naturally occurring glycolipids, such as glycosphingolipids and glycoglycerolipids, are capable of eliciting strong immune responses in both herpes simplex virus vaccine and pseudorabies virus vaccine. Some glycolipids have been synthesized from long chain alkylamines and fatty acids that are linked directly with the sugar through the anomeric carbon atom, to mimic the functions of the naturally occurring lipid residues.

In some aspects, the immunogenic composition contains an amount of an adjuvant sufficient to enhance the immune response to the immunogen. Suitable adjuvants include, but are not limited to, aluminium salts (aluminium phosphate or aluminium hydroxide), squalene mixtures (SAF-1), muramyl peptide, saponin derivatives, mycobacterium cell wall preparations, monophosphoryl lipid A, mycolic acid derivatives, non-ionic block copolymer surfactants, Quil A, cholera toxin B subunit, polphosphazene and derivatives, and immuno-stimulating complexes (ISCOMs) such as those described by Takahashi et al. (*Nature* 344:873-875, 1990). In some aspects, the adjuvant is a synthetic adjuvant. In a particular aspect, the synthetic adjuvant is glucopyranosyl lipid adjuvant (GLA).

A further aspect of the invention is a vaccine comprising the immunogenic composition of the invention and a pharmaceutically acceptable carrier. As discussed herein above, the vaccine, in certain aspects, includes one or more stabilizers and/or one or more preservatives.

In one aspect, there is provided a vaccine comprising at least one recombinant expression construct which comprises a promoter operably linked to a nucleic acid sequence encoding an antigen (chimeric OspA polypeptide described herein) and an adjuvant. In one embodiment the recombinant expression construct (expression vector comprising the OspA polynucleotide) is present in a viral vector, which in certain further embodiments is present in a virus that is selected from an adenovirus, an adeno-associated virus, a herpesvirus, a lentivirus, a poxvirus, and a retrovirus.

Further aspects of the invention include antibodies to the chimeric OspA molecules described herein. In various aspects, the invention includes the chimeric OspA molecules to make anti-OspA antibodies and to provide immunity from Borrelia infection. In some aspects, these anti-OspA antibodies, e.g., murine, human, or humanized monoclonal antibodies or single chain antibodies, are administered to a subject (e.g., passive immunization) to effect an immune response against the OspA protein of any one or more of serotypes 1-6 of Borrelia. As used herein, the term "antibodies" refers to a molecule which has specificity for one or more OspA polypeptides. Suitable antibodies are prepared using methods known in the art. In certain aspects, an OspA antibody is capable of binding a certain portion of the OspA polypeptide thereby inhibiting the binding of the polypeptide to the OspA polypeptide receptor(s). Antibodies and antibody fragments that bind the chimeric OspA polypeptides of the invention are within the scope of the present invention.

In some aspects, antibodies of the invention include an antibody or fragment thereof that specifically binds one or more OspA polypeptides produced by immunizing an animal with a polypeptide comprising the amino acid sequence selected from the group consisting of SEQ ID NOS: 2, 4, 6, 8, 10, 12, 169, 171, and 173. In other aspects, the invention includes an antibody or fragment thereof that specifically binds to a polypeptide encoded by a nucleic acid sequence selected from the group consisting of SEQ ID NOS: 1, 3, 5, 7, 9, 11, 168, 170, and 172. In various aspects, the antibody or fragment thereof is human, humanized, polyclonal, or monoclonal. In further aspects, the antibody is an Fab or an Fab' antibody. In particular aspects, the antibody comprises a detectable label. In some aspects, the antibody is a chemically modified derivative of the antibody.

The administration of the chimeric OspA molecules in accordance with the invention stimulates an immune or antibody response in humans or animals. In some aspects, three chimeric OspA molecules (e.g., lipidated OspA $1/2^{251}$, lipidated OspA 6/4 OspA, and lipidated OspA 5/3; or original OspA 1/2, original OspA 6/4, and original OspA 5/3) are administered together to elicit antibody response against all six serotypes (1-6) discussed herein. This antibody response means that the inventive methods are, in various aspects, used for merely stimulating an immune response (as opposed to also being a protective response) because the resultant antibodies (without protection) are nonetheless useful. From eliciting antibodies, by techniques well-known in the art, monoclonal antibodies are prepared; and, those monoclonal antibodies are employed in well known antibody binding assays, diagnostic kits or tests to determine the presence or absence of *Borrelia burgdorferi* s.l. or to determine whether an immune response to the spirochete has simply been stimulated. The monoclonal antibodies, in certain aspects, are employed in immunoadsorption chromatography to recover or isolate *Borrelia* antigens such as OspA.

The OspA antibodies of the invention, in various aspects, are polyclonal, including monospecific polyclonal, monoclonal (MAbs), recombinant, chimeric, humanized such as CDR-grafted, human, single chain, and/or bispecific, as well as fragments, variants or derivatives thereof. Antibody fragments include those portions of the antibody which bind to an epitope on the OspA polypeptide. Examples of such fragments include Fab and F(ab') fragments generated by enzymatic cleavage of full-length antibodies. Other binding fragments include those generated by recombinant DNA techniques, such as the expression of recombinant plasmids containing nucleic acid sequences encoding antibody variable regions.

Polyclonal antibodies directed toward an OspA polypeptide generally are produced in a subject (including rabbits, mice, or other animal or mammal) by means of multiple subcutaneous, intramuscular or intraperitoneal injections of OspA polypeptide and an adjuvant. It is useful, in certain aspects, to conjugate an OspA polypeptide of the invention to a carrier protein that is immunogenic in the species to be immunized, such as keyhole limpet hemocyanin, serum, albumin, bovine thyroglobulin, or soybean trypsin inhibitor. Also, adjuvants, such as alum, are used to enhance the immune response. After immunization, blood samples are drawn from the subject immunized and the serum is assayed for anti-OspA polypeptide antibody titer.

Monoclonal antibodies directed toward an OspA polypeptide are produced using any method which provides for the production of antibody molecules by continuous cell lines in culture. Examples of suitable methods for preparing monoclonal antibodies include the hybridoma methods of Kohler et al., Nature, 256:495-497 (1975) and the human B-cell hybridoma method, Kozbor, J. Immunol., 133:3001 (1984) and Brodeur et al., Monoclonal Antibody Production Techniques and Applications, pp. 51-63 (Marcel Dekker, Inc., New York, 1987). Also provided by the invention are hybridoma cell lines which produce monoclonal antibodies reactive with OspA polypeptides.

Monoclonal antibodies of the invention, in some instances, are modified for use as therapeutics. One embodiment is a "chimeric" antibody in which a portion of the heavy and/or light chain is identical with or homologous to a corresponding sequence in antibodies derived from a particular species or belonging to a particular antibody class or subclass, while the remainder of the chain(s) is/are identical with or homologous to a corresponding sequence in antibodies derived from another species or belonging to another antibody class or subclass. Also included are fragments of such antibodies, so long as they exhibit the desired biological activity. See, U.S. Pat. No. 4,816,567 and Morrison et al., Proc. Natl. Acad. Sci. USA, 81:6851-6855 (1985).

In another embodiment, a monoclonal antibody of the invention is a "humanized" antibody. Methods for humanizing non-human antibodies are well known in the art (see U.S. Pat. Nos. 5,585,089, and 5,693,762). Generally, a humanized antibody has one or more amino acid residues introduced into it from a source which is non-human. Humanization can be performed, for example, using methods described in the art (Jones et al., *Nature* 321:522-525 (1986); Riechmann et al., *Nature* 332:323-327 (1988); Verhoeyen et al., *Science* 239: 1534-1536 (1988)), by substituting at least a portion of a rodent complementarity-determining region (CDR) for the corresponding regions of a human antibody.

In an alternative embodiment, human antibodies are produced from phage-display libraries (Hoogenboom et al., *J. Mol. Biol.* 227:381 (1991) and Marks et al., J. Mol. Biol. 222:581 (1991)). These processes mimic immune identification through the display of antibody repertoires on the surface of filamentous bacteriophage, and subsequent selection of phage by their binding to an antigen of choice. One such technique is described in PCT Application No. PCT/US98/17364 (Adams et al.), which describes the isolation of high affinity and functionally agonistic antibodies for MPL- and msk-receptors using such an approach.

Chimeric, CDR grafted, and humanized antibodies are typically produced by recombinant methods. Nucleic acids encoding the antibodies are introduced into host cells and expressed using materials and procedures described herein or known in the art. In one embodiment, the antibodies are produced in mammalian host cells, such as CHO cells. Monoclonal (e.g., human) antibodies are, in various aspects, produced by the expression of recombinant DNA in host cells or by expression in hybridoma cells as described herein. In some aspects, the monoclonal antibody or fragment thereof is humanized. In a particular aspect, the monoclonal antibody is F237/BK2 as described herein.

In certain aspects, the invention includes methods for preventing or treating a *Borrelia* infection or Lyme disease in a subject, the method comprising the step of administering an antibody or fragment thereof as described herein to the subject in an amount effective to prevent or treat the *Borrelia* infection or Lyme disease. In particular aspects, the antibody or fragment thereof is a hyperimmune serum, a hyperimmune plasma, or a purified immunoglobulin fraction thereof. In other aspects, the antibody or fragment thereof is a purified immunoglobulin preparation or an immunoglobulin fragment preparation.

The anti-OspA antibodies of the invention, in various aspects, are employed in any known assay method, such as competitive binding assays, direct and indirect sandwich assays, and immunoprecipitation assays (Sola, Monoclonal Antibodies: A Manual of Techniques, pp. 147-158 (CRC Press, Inc., 1987)) for the detection and quantitation of OspA polypeptides. The antibodies will bind OspA polypeptides with an affinity which is appropriate for the assay method being employed.

For diagnostic or clinical applications, in certain embodiments, anti-OspA antibodies are labeled with a detectable moiety. The detectable moiety can be any one which is capable of producing, either directly or indirectly, a detectable signal. For example, in certain aspects, the detectable moiety is a radioisotope, such as 3H, 14C, 32P, 35S, or 125I; a fluorescent or chemiluminescent compound, such as fluorescein isothiocyanate, rhodamine, or luciferin; or an enzyme, such as alkaline phosphatase, β-galactosidase, or horseradish peroxidase (Bayer et al., Meth. Enzym. 184:138-163 (1990)).

Competitive binding assays rely on the ability of a labeled standard (e.g., an OspA polypeptide, or an immunologically reactive portion thereof) to compete with the test sample analyte (an OspA polypeptide) for binding with a limited amount of anti-OspA antibody. The amount of an OspA polypeptide in the test sample is inversely proportional to the amount of standard that becomes bound to the antibodies. To facilitate determining the amount of standard that becomes bound, the antibodies typically are insolubilized before or after the competition, so that the standard and analyte that are bound to the antibodies are conveniently separated from the standard and analyte which remain unbound.

Sandwich assays typically involve the use of two antibodies, each capable of binding to a different immunogenic portion, or epitope, of the protein to be detected and/or quantitated. In a sandwich assay, the test sample analyte is typically bound by a first antibody which is immobilized on a solid support, and thereafter a second antibody binds to the analyte, thus forming an insoluble three-part complex. See, e.g., U.S. Pat. No. 4,376,110. The second antibody itself, in some instances, is labeled with a detectable moiety (direct sandwich assays) or is measured using an anti-immunoglobulin antibody that is labeled with a detectable moiety (indirect sandwich assays). For example, one type of sandwich assay is an enzyme-linked immunosorbent assay (ELISA), in which case the detectable moiety is an enzyme.

The anti-OspA antibodies are also useful for in vivo imaging. An antibody labeled with a detectable moiety, in certain aspects, is administered to an animal into the bloodstream, and the presence and location of the labeled antibody in the host is assayed. The antibody, in various aspects, is labeled with any moiety that is detectable in an animal, whether by nuclear magnetic resonance, radiology, or other detection means known in the art. In some aspects of the invention, OspA antibodies are used as therapeutics.

Chimeric OspA Compositions and Administration

To administer OspA chimeric polypeptides described herein to subjects, OspA polypeptides are formulated in a composition comprising one or more pharmaceutically acceptable carriers. The phrase "pharmaceutically or pharmacologically acceptable" refers to molecular entities and compositions that do not produce allergic, or other adverse reactions when administered using routes well-known in the art, as described below. "Pharmaceutically acceptable carriers" include any and all clinically useful solvents, dispersion media, coatings, antibacterial and antifungal agents, isotonic and absorption delaying agents and the like. In some aspects, the composition forms solvates with water or common organic solvents. Such solvates are included as well.

The immunogenic composition or vaccine composition of the invention is, in various aspects, administered orally, topically, transdermally, parenterally, by inhalation spray, vaginally, rectally, or by intracranial injection. The term parenteral as used herein includes subcutaneous injections, intravenous, intramuscular, intracisternal injection, or infusion techniques. Administration by intravenous, intradermal, intramusclar, intramammary, intraperitoneal, intrathecal, retrobulbar, intrapulmonary injection and or surgical implantation at a particular site is contemplated as well. Generally, compositions are essentially free of pyrogens, as well as other impurities that could be harmful to the recipient.

Formulation of the pharmaceutical composition will vary according to the route of administration selected (e.g., solution, emulsion). An appropriate composition comprising the composition to be administered is prepared in a physiologically acceptable vehicle or carrier. For solutions or emulsions, suitable carriers include, for example, aqueous or alcoholic/aqueous solutions, emulsions or suspensions, including saline and buffered media. Parenteral vehicles, in some aspects, include sodium chloride solution, Ringer's dextrose, dextrose and sodium chloride, lactated Ringer's or fixed oils. Intravenous vehicles, in certain aspects, include various additives, preservatives, or fluid, nutrient or electrolyte replenishers.

Pharmaceutical compositions useful in the compounds and methods of the present invention containing OspA polypeptides as an active ingredient contain, in various aspects, pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention.

A variety of aqueous carriers, e.g., water, buffered water, 0.4% saline, 0.3% glycine, or aqueous suspensions contain, in various aspects, the active compound in admixture with excipients suitable for the manufacture of aqueous suspensions. Such excipients are suspending agents, for example sodium carboxymethylcellulose, methylcellulose, hydroxypropylmethylcellulose, sodium alginate, polyvinylpyrrolidone, gum tragacanth and gum acacia; dispersing or wetting agents, in some instances, are a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions, in some aspects, contain one or more preservatives, for example ethyl, or n-propyl, p-hydroxybenzoate.

In some aspects, OspA compositions are lyophilized for storage and reconstituted in a suitable carrier prior to use. This technique has been shown to be effective with conventional immunoglobulins. Any suitable lyophilization and reconstitution techniques known in the art are employed. It is appreciated by those skilled in the art that lyophilization and reconstitution leads to varying degrees of antibody activity loss and that use levels are often adjusted to compensate.

Dispersible powders and granules suitable for preparation of an aqueous suspension by the addition of water provide the active compound in admixture with a dispersing or wetting agent, suspending agent and one or more preservatives. Suitable dispersing or wetting agents and suspending agents are exemplified by those already mentioned above.

In certain aspects, the concentration of OspA in these formulations varies widely, for example from less than about 0.5%, usually at or at least about 1% to as much as 15 or 20% by weight and will be selected primarily based on fluid volumes, viscosities, etc., in accordance with the particular mode of administration selected. Thus, for example, and without limitation, a typical pharmaceutical composition for parenteral injection is made up to contain 1 ml sterile buffered water, and 50 mg of blood clotting factor. A typical composition for intravenous infusion could be made up to contain 250 ml of sterile Ringer's solution, and 150 mg of blood clotting factor. Actual methods for preparing parenterally administrable compositions are known or are apparent to those skilled in the art and are described in more detail in, for example, Remington's Pharmaceutical Science, 15th ed., Mack Publishing Company, Easton, Pa. (1980). An effective dosage is usually within the range of 0.01 mg to 1000 mg per kg of body weight per administration.

In various aspects, the pharmaceutical compositions are in the form of a sterile injectable aqueous, oleaginous suspension, dispersions or sterile powders for the extemporaneous preparation of sterile injectable solutions or dispersions. The suspension, in some aspects, is formulated according to the known art using those suitable dispersing or wetting agents and suspending agents which have been mentioned above. The sterile injectable preparation, in certain aspects, is a sterile injectable solution or suspension in a non-toxic parenterally-acceptable diluent or solvent, for example as a solution in 1,3-butane diol. In some embodiments, the carrier is a solvent or dispersion medium containing, for example, water, ethanol, polyol (for example, glycerol, propylene glycol, and liquid polyethylene glycol, and the like), suitable mixtures thereof, vegetable oils, Ringer's solution and isotonic sodium chloride solution. In addition, sterile, fixed oils are conventionally employed as a solvent or suspending medium. For this purpose any bland fixed oil is employed, in various aspects, including synthetic mono- or diglycerides. In addition, fatty acids such as oleic acid find use in the preparation of injectables.

In all cases the form must be sterile and must be fluid to the extent that easy syringability exists. The proper fluidity is maintained, for example, by the use of a coating, such as lecithin, by the maintenance of the required particle size in the case of dispersion and by the use of surfactants. It must be stable under the conditions of manufacture and storage and must be preserved against the contaminating action of microorganisms, such as bacteria and fungi. The prevention of the action of microorganisms is brought about by various antibacterial and antifungal agents, for example, parabens, chlorobutanol, phenol, sorbic acid, thimerosal, and the like. In many cases, it will be desirable to include isotonic agents, for example, sugars or sodium chloride. In certain aspects, prolonged absorption of the injectable compositions is brought about by the use in the compositions of agents delaying absorption, for example, aluminum monostearate and gelatin.

Compositions useful for administration, in certain aspects, are formulated with uptake or absorption enhancers to increase their efficacy. Such enhancers, include, for example, salicylate, glycocholate/linoleate, glycholate, aprotinin, bacitracin, SDS, caprate and the like. See, e.g., Fix (*J. Pharm. Sci.*, 85:1282-1285, 1996) and Oliyai et al. (*Ann. Rev. Pharmacol. Toxicol.*, 32:521-544, 1993).

In addition, the properties of hydrophilicity and hydrophobicity of the compositions used in the compounds and methods of the invention are well balanced, thereby enhancing their utility for both in vitro and especially in vivo uses, while other compositions lacking such balance are of substantially less utility. Specifically, compositions in the invention have an appropriate degree of solubility in aqueous media which permits absorption and bioavailability in the body, while also having a degree of solubility in lipids which permits the compounds to traverse the cell membrane to a putative site of action.

In particular aspects, the OspA polypeptides described herein are formulated in a vaccine composition comprising adjuvant. Any adjuvant known in the art is used in various aspects of the vaccine composition, including oil-based adjuvants such as Freund's Complete Adjuvant and Freund's Incomplete Adjuvant, mycolate-based adjuvants (e.g., trehalose dimycolate), bacterial lipopolysaccharide (LPS), peptidoglycans (i.e., mureins, mucopeptides, or glycoproteins such as N-Opaca, muramyl dipeptide [MDP], or MDP analogs), proteoglycans (e.g., extracted from *Klebsiella pneumoniae*), streptococcal preparations (e.g., OK432), Biostim™ (e.g., 01K2), the "Iscoms" of EP 109 942, EP 180 564 and EP 231 039, aluminum hydroxide, saponin, DEAE-dextran, neutral oils (such as miglyol), vegetable oils (such as arachis oil), liposomes, Pluronic® polyols, the Ribi adjuvant system (see, for example GB-A-2 189 141), or interleukins, particularly those that stimulate cell mediated immunity. An alternative adjuvant consisting of extracts of *Amycolata*, a bacterial genus in the order Actinomycetales, has been described in U.S. Pat. No. 4,877,612. Additionally, proprietary adjuvant mixtures are commercially available. The adjuvant used depends, in part, on the recipient subject. The amount of adjuvant to administer depends on the type and size of the subject. Optimal dosages are readily determined by routine methods.

The vaccine composition optionally includes vaccine-compatible pharmaceutically acceptable (i.e., sterile and non-toxic) liquid, semisolid, or solid diluents that serve as pharmaceutical vehicles, excipients, or media. Any diluent known in the art is used. Exemplary diluents include, but are not limited to, polyoxyethylene sorbitan monolaurate, magnesium stearate, methyl- and propylhydroxybenzoate, talc, alginates, starches, lactose, sucrose, dextrose, sorbitol, mannitol, gum acacia, calcium phosphate, mineral oil, cocoa butter, and oil of *theobroma*.

The vaccine composition is packaged in forms convenient for delivery. The compositions are enclosed within a capsule, caplet, sachet, cachet, gelatin, paper, or other container. These delivery forms are preferred when compatible with entry of the immunogenic composition into the recipient organism and, particularly, when the immunogenic composition is being delivered in unit dose form. The dosage units are packaged, e.g., in tablets, capsules, suppositories, vials, or cachets.

The invention includes methods for inducing an immunological response in a subject, including OspA antibodies in a mammalian host comprising administering an effective amount of the Osp A compositions described herein. Likewise, the invention includes methods for preventing or treating a *Borrelia* infection or Lyme disease in a subject, the method comprising the step of administering an effective amount of the vaccine compositions described herein to the subject.

The vaccine composition is introduced into the subject to be immunized by any conventional method as described herein in detail above. In certain aspects, the composition is administered in a single dose or a plurality of doses over a period of time (as described in more detail below).

Dosing of a Chimeric OspA Composition/Methods for Inducing an Immunological Response The useful dosage of immunogenic composition or vaccine composition to be administered will vary depending on various factors which modify the action of drugs, e.g. the age, condition, body weight, sex and diet of the subject, the severity of any infection, time of administration, mode of administration, and other clinical factors.

In some aspects, formulations or compositions of the invention are administered by an initial bolus followed by booster delivery after a period of time has elapsed. In certain aspects, formulations of the invention are administered by an initial bolus followed by a continuous infusion to maintain therapeutic circulating levels of drug product. In particular aspects, immunogenic compositions or vaccine compositions of the invention are administered in a vaccination scheme after various periods of time. In some aspects, the vaccination is delivered in a rapid immunization scheme for travelers to regions that are prone to *Borrelia* infection. As another example, the composition or formulation of the invention is administered as a one-time dose. Those of ordinary skill in the art readily optimize effective dosages and administration regimens as determined by good medical practice and the clinical condition of the individual subject. The frequency of dosing depends on the pharmacokinetic parameters of the agents and the route of administration.

The pharmaceutical formulation is determined by one skilled in the art depending upon the route of administration and desired dosage. See for example, Remington's Pharmaceutical Sciences, 18th Ed. (1990, Mack Publishing Co., Easton, Pa. 18042) pages 1435-1712, the disclosure of which is hereby incorporated by reference. Such formulations, in some instances, influence the physical state, stability, rate of in vivo release, and rate of in vivo clearance of the administered composition. Depending on the route of administration, a suitable dose is calculated, in particular aspects, according to body weight, body surface area or organ size. In some aspects, appropriate dosages are ascertained through use of established assays for determining blood level dosages in conjunction with appropriate dose-response data. In certain aspects, the antibody titer of an individual is measured to determine optimal dosage and administration regimens. The final dosage regimen will be determined by the attending doctor or physician, considering various factors which modify the action of the pharmaceutical compositions, e.g. the composition's specific activity, the responsiveness of the subject, the age, condition, body weight, sex and diet of the subject, the severity of any infection or malignant condition, time of administration and other clinical factors. As studies are conducted, further information will emerge regarding the appropriate dosage levels and duration of treatment for the prevention and/or treatment of relevant conditions.

In certain aspects, the OspA immunogenic or vaccine composition comprises any dose of OspA nucleic acid molecule(s) or polypeptide(s) sufficient to evoke an immune response in the subject. The effective amount of an OspA immunogenic or vaccine composition to be employed therapeutically will depend, for example, upon the therapeutic context and objectives. One skilled in the art will appreciate that the appropriate dosage levels for vaccination or treatment will thus vary depending, in part, upon the molecule delivered, the indication for which the OspA molecule(s) are being used, the route of administration, and the size (body weight, body surface or organ size) and condition (the age and general health) of the patient. Accordingly, the clinician, in some instances, titers the dosage and modifies the route of administration to obtain the optimal therapeutic effect.

A typical dosage, in various aspects, ranges from about 0.1 μg/kg to up to about 100 mg/kg or more, depending on the factors mentioned above. In other embodiments, the dosage may range from 0.1 μg/kg up to about 100 mg/kg; or 1 μg/kg up to about 100 mg/kg; or 5 μg/kg up to about 100 mg/kg. By way of example, a dose of a OspA polypeptide useful in the present invention is approximately 10 μg/ml, 20 μg/ml, 30 μg/ml, 40 μg/ml, 50 μg/ml, 60 μg/ml, 70 μg/ml, 80 μg/ml, 90 μg/ml, 100 μg/ml, 110 μg/ml, 120 μg/ml, 130 μg/ml, 140 μg/ml, 150 μg/ml, 160 μg/ml, 170 μg/ml, 180 μg/ml, 190 μg/ml, 200 μg/ml, 210 μg/ml, 220 μg/ml, 230 μg/ml, 240 μg/ml, 250 μg/ml, 260 μg/ml, 270 μg/ml, 280 μg/ml, 290 μg/ml, 300 μg/ml, 320 μg/ml, 340 μg/ml, 360 μg/ml, 380 μg/ml, 400 μg/ml, 420 μg/ml, 440 μg/ml, 460 μg/ml, 480 μg/ml, 500 μg/ml, 520 μg/ml, 540 μg/ml, 560 μg/ml, 580 μg/ml, 600 μg/ml, 620 μg/ml, 640 μg/ml, In particular aspects, a typical dose comprises 0.1 to 5.0 ml per subject. In more particular aspects, a typical dose comprises 0.2 to 2.0 ml per subject. In certain aspects, a dose comprises 0.5 to 1.0 ml per subject.

The frequency of dosing will depend upon the pharmacokinetic parameters of the OspA molecule in the formulation used. Typically, a clinician will administer the composition until a dosage is reached that achieves the desired effect. The composition, in various aspects, is therefore administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages are often ascertained through use of appropriate dose-response data which is routinely obtained.

Kits

As an additional aspect, the invention includes kits which comprise one or more pharmaceutical formulations for administration of OspA polypeptide(s) to a subject packaged in a manner which facilitates their use for administration to subjects.

In a specific embodiment, the invention includes kits for producing a single dose administration unit. The kits, in various aspects, each contain both a first container having a dried protein and a second container having an aqueous formulation. Also included within the scope of this invention are kits containing single and multi-chambered pre-filled syringes (e.g., liquid syringes and lyosyringes).

In another embodiment, such a kit includes pharmaceutical formulation described herein (e.g., a composition comprising a therapeutic protein or peptide), packaged in a container such as a sealed bottle or vessel, with a label affixed to the container or included in the package that describes use of the compound or composition in practicing the method. In one embodiment, the pharmaceutical formulation is packaged in the container such that the amount of headspace in the container (e.g., the amount of air between the liquid formulation and the top of the container) is very small. Preferably, the amount of headspace is negligible (i.e., almost none).

In one aspect, the kit contains a first container having a therapeutic protein or peptide composition and a second container having a physiologically acceptable reconstitution solution for the composition. In one aspect, the pharmaceutical formulation is packaged in a unit dosage form. The kit optionally further includes a device suitable for administering the pharmaceutical formulation according to a specific route of administration. In some aspects, the kit contains a label that describes use of the pharmaceutical formulations.

Each publication, patent application, patent, and other reference cited herein is incorporated by reference in its entirety to the extent that it is not inconsistent with the present disclosure.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

EXAMPLES

Additional aspects and details of the invention will be apparent from the following examples, which are intended to be illustrative rather than limiting.

Example 1

Analysis of the Sequence of OspA from European *Borrelia burgdorferi sensu lato* Strains (Molecular Epidemiology) for the Determination of an OspA Vaccine Formulation The objective of the study was to determine a suitable formulation for a Lyme disease OspA vaccine for Europe. The study was based on sequence analysis of the OspA gene (molecular epidemiology) from a large and diverse strain collection of *B. burgdorferi sensu lato*, which adequately represents a broad geographic coverage of Europe, the various clinical syndromes associated with disease, and each of the three pathogenic genospecies (*B. afzelii, B. garinii* and *B. burgdorferi* ss) associated with Lyme disease. Lyme disease is caused by *Borrelia burgdorferi sensu lato*, which comprises 13 genospecies in total, three of which (*B. afzelii, B. garinii* and *B. burgdorferi* ss) are recognized as being pathogenic in humans.

At the outset, a large scale epidemiological study (see Table 3 below) was carried out which evaluated *Borrelia burgdorferi sensu lato* strains from patients with Lyme disease (and from ticks) from 21 countries in Europe. A total of 553 European *Borrelia* isolates collected from 16 European countries were studied. Each species was determined by PCR using primer sets specific for the 16s rRNA genes of each species.

Isolates from each of the three *Borrelia* species known to cause human Lyme disease in Europe were well represented: *B. afzelii* (n=309, 55.9%), *B. burgdorferi sensu stricto* (n=67, 12.1%), and *B. garinii* (n=173, 31.3%). Of the 359 human isolates, 56.8% were *B. afzelii* and *B. afzelii* was the predominant species determined from human isolates in most locations. Similarly, *B. afzelii* was isolated from 54.1% of tick isolates. *B. burgdorferi* s.s. was isolated from 11.7% of human strains and 12.9% of tick isolates. *B. burgdorferi* s.s. was isolated from human isolates from South Eastern Europe, notably Italy, Hungary, Slovenia and Austria. *B. garinii* strains were isolated from 30.4% of human isolates and accounted for 33% of tick isolates. *B. garinii* strains isolated from humans and ticks were obtained from most of the geographic regions throughout Europe. The data from this study correlated well with the data presented from other European studies and suggests that the collection of isolates studied represents an accurate picture of Lyme disease in Europe.

OspA sequencing was carried out to determine an optimal vaccine formulation for Europe. Based on this data, a vaccine including OspA types 1 to 6 would cover 98.1% of the strains and 96.7% of invasive disease cases. Epidemiological study results of European *Borrelia* isolates indicate that a vaccine based on OspA types 1, 2, 3, 4, 5 and 6 would provide theoretical coverage in Europe of 98% of Lyme disease and 96.7% of invasive neuroborreliosis isolates.

TABLE 3

Epidemiological Study Results

| OspA type | Human isolates | Isolates from invasive disease cases | Vaccine coverage total[1] | Vaccine coverage of invasive disease[2] |
|---|---|---|---|---|
| *B. afzelii* type 2 | 56.8% (204) | 3% (7) | 56.8% | 11.7% |
| B. b s.s. type 1 | 11.7% (42) | 17% (7) | 68.5% | 23.3% |
| *B. garinii* type 6 | 15.9% (57) | 40% (23) | 84.4% | 61.7% |
| *B. garinii* type 5 | 7.2% (26) | 35% (9) | 91.6% | 76.7% |
| *B. garinii* type 4 | 4.5% (16) | 44% (7) | 96.1% | 88.3% |
| *B. garinii* type 3 | 2.0% (7) | 71% (5) | 98.1% | 96.7% |
| *B. garinii* type 7 | 0.8% (3) | 67% (2) | 98.9% | 100% |
| *B. spielmanii* | 1.1% (4) | 0% | 100% | |

[1]Predicted vaccine coverage based on numbers of isolates; totals are cumulative.
[2]Predicted vaccine coverage of isolates from cases of neuroborreliosis; totals are cumulative.

Hence a vaccine comprising three novel recombinant OspAs (1/2, 6/4, and 5/3), each representing 2 OspA serotypes, would retain key structural elements necessary for protection against all 6 prevalent OspA serotypes (1-6) associated with Lyme borreliosis in Europe and against the single OspA serotype associated with Lyme borreliosis in the USA.

Inclusion of an OspA 5/3 construct, representing *B. garinii* OspA serotypes 5 and 3, (together with OspA serotypes 1/2 and 6/4), should protect against 98.1% of disease and 96.7% of invasive isolates. A vaccine without OspA 5/3 would be expected to protect against only about 88.9% of disease, and only about 73.4% of invasive disease. Thus, a vaccine comprising all six serotypes is more effective in the prevention of Lyme disease than a vaccine with only four serotypes.

Example 2

Strategy for the Construction of Synthetic OspA Genes Encoding Lipidated OspA

The aim of the study was to prepare lipidated OspA chimeric constructs from several strains of *Borrelia* in order to make a vaccine that would protect the recipient from Lyme disease caused by any of these several strains of *Borrelia*. The general strategy is summarized in FIG. 1 and is described below.

For each novel OspA gene, four sets of oligonucleotides of between 30-60 bases were synthesized. Each oligonucleotide set consisted of between 8-12 complementary overlapping oligonucleotides. The oligonucleotides from each set were annealed together, in separate experiments, to generate double-stranded DNA fragments with specific restriction enzyme recognition sites at either end, i.e. fragments N-H (Nde I-Hind III), H-K (Hind III-Kpn I), K-E (Kpn I-EcoR I) and E-B (EcoR I-BamH I). Each of the four fragments was cloned independently into pUC18, cut with the corresponding restriction enzymes and transformed into the *E. coli* host DH5α, after which the sequence of the cloned fragment was verified.

*E. coli* strain DH5α [genotype: end A1 hsdR17 ($r_K^-m_K^+$) supE44 thi-1 recA1 gyrA (Nal$^r$) relA1 Δ(lacZYA-argF)U169 deoR (Φ80dlacΔ(lacZ)M15] (Gibco BRL) was used for all intermediate cloning steps. This strain is derived from *E. coli* strain K12, one of the most widely used hosts in genetic engineering. The strain is amp$^-$ to allow selection of transformants with vectors containing the ampicillin resistance gene (amp). *E. coli* HMS174(DE3) was selected as the host for expression. *E. coli* HMS174(DE3) host cells [genotype: F-recA1 hsdR ($r_{k12}^-m_{k12}^+$) Rif$^R$ (DE3)] (Novagen) were used for the final cloning steps. The strain is kan$^-$ to allow selection of transformants with vectors containing the kanamycin resistance gene (kan).

pUC18 (Gibco BRL, Basel, Switzerland) was used as the cloning vector for all intermediate steps, because genetic manipulations and sequencing were easier with this plasmid than with pET30a. The principal features are notably, the lacZ gene fragment coding for LacZ alpha peptide from base pairs 149 to 469 (lac promoter at base pairs 507), the bla gene encoding the ampicillin resistance determinant from base pairs 1629 to 2486 (bla promoter at base pairs 2521), the origin of replication at base pairs 867 and multiple cloning sites from base pairs 185 to 451 (FIG. 12).

pET30a (Novagen) was used as the expression vector for the final complete OspA gene insert. In pET vectors genes are cloned under the control of a T7 promoter and expression is induced by providing a source of T7 RNA polymerase in the host cell (no expression occurs until a source of T7 RNA polymerase is provided). The principal features are the gene encoding kanamycin resistance (kan) at base pairs 4048 to 4860, the lacI gene base pairs 826-1905, the F1 origin of replication at base pairs 4956-5411 and multiple cloning sites from base pairs 158 to 346 (FIG. 13).

The four fragments needed to make a full-length OspA gene were excised from a DNA miniprep. DNA was isolated from each of the four clones using the same restriction enzymes used for the original cloning step. The DNA fragments were purified and ligated together with pUC18 DNA cut with Nde I and BamH I and were transformed into *E. coli* DH5α competent cells. The full-length OspA gene cloned in pUC18 was sequenced to confirm that no errors had been introduced in this step.

The OspA gene was then sub-cloned into a pET-30a expression vector using the restriction enzymes Nde I and BamH I and transformed into the *E. coli* host HMS 174(DE3). In the pET30a vector, the OspA gene is controlled by the bacteriophage T7 promoter.

Three synthetic OspA genes were designed to encode OspA molecules with the protective epitopes from serotype 1 and 2 OspAs (lipB sOspA 1/2$^{251}$), serotype 6 and 4 OspAs (lipB sOspA 6/4) and serotype 5 and 3 OspAs (lipB sOspA 5/3) of *Borrelia*. The primary amino acid sequences of these molecules (SEQ ID NOS: 2, 4, and 6, respectively) are shown in FIGS. 2-8 and described herein with a full description of the main features incorporated into their design.

The oligonucleotides for the lipB sOspA 1/2 construct were synthesized in-house on an ABI 394 DNA/RNA synthesizer. The oligonucleotides for the lipB sOspA 5/3 and lipB sOspA 6/4 constructs were purchased from GenXpress (Wiener Neudorf, Austria) and were HPLC purified.

TABLE 4

| Oligonucleotides for lipB sOspA 1/2* gene fragments | | | | |
|---|---|---|---|---|
| Name | Sequence (5'-3') | L | S | SEQ ID NO |
| HindIII- Kpn I fragment | | | | |
| NH1 | TATGCGTCTGTTGATCGGCTTTGCTCTGGCGCTGGCTCTGATCGG | 45 | C | 59 |
| NH2 | CTGCGCACAGAAAGGTGCTGAGTCTATTGGTTCCGTTTCTGTAGATCTGC | 50 | C | 60 |
| NH3 | CCGGTGAAATGAAGGTTCTGGTGAGCAAAGAAAAAGACAAGAACGGCAAG | 50 | C | 61 |
| NH4 | TACGATCTCATCGCAACCGTCGACAAGCTGGAGCTGAAAGGTACTTCTGA | 50 | C | 62 |
| NH5 | TAAAAACAACGGCTCTGGTGTGCTGGAGGGCGTCAAAACTAACAAGAGCAAAGTAA | 56 | C | 63 |
| NH6 | AGCTTTACTTTGCTCTTGTTAGTTTTGACGCCCTCCAGCA | 40 | C' | 64 |
| NH7 | CACCAGAGCCGTTGTTTTTATCAGAAGTACCTTTCAGCTCCAGCTTGTCG | 50 | C' | 65 |

TABLE 4-continued

Oligonucleotides for lipB sOspA 1/2* gene fragments

| Name | Sequence (5'-3') | L | S | SEQ ID NO |
|---|---|---|---|---|
| NH8 | ACGGTTGCGATGAGATCGTACTTGCCGTTCTTGTCTTTTTCTTTGCTCAC | 50 | C' | 66 |
| NH9 | CAGAACCTTCATTTCACCGGGCAGATCTACAGAAACGGAACCAATAGACT | 50 | C' | 67 |
| NH10 | CAGCACCTTTCTGTGCGCAGCCGATCAGAGCCAGCGCCAGAGCAAAGCCGATCAACAGACGCA | 63 | C' | 68 |
| HindIII- Kpn I fragment | | | | |
| HK1 | AGCTTACGATCTCTGACGATCTCGGTCAGACCAC | 34 | C | 69 |
| HK2 | GCTGGAAGTTTTCAAAGAGGATGGCAAGACCCTCGTGTCCAAAAAAGTAA | 50 | C | 70 |
| HK3 | CTTCCAAAGACAAGTCCTCTACGGAAGAAAAATTCAACGAAAAAGGTGAG | 50 | C | 71 |
| HK4 | GTGTCTGAAAAGATCATCACCATGGCAGACGGCACCCGTC | 40 | C | 72 |
| HK5 | TTGAATACACCGGTATTAAAAGCGATGGTAC | 31 | C | 73 |
| HK6 | CATCGCTTTTAATACCGGTGTATTCAAGACGGGTGCCGTCTGCCATG | 47 | C' | 74 |
| HK7 | GTGATGATCTTTTCAGACACCTCACCTTTTTCGTTGAATTTTTCTTCCGT | 50 | C' | 75 |
| HK8 | AGAGGACTTGTCTTTGGAAGTTACTTTTTTGGACACGAGGGTCTTGCCAT | 50 | C' | 76 |
| HK9 | CCTCTTTGAAAACTTCCAGCGTGGTCTGACCGAGATCGTCAGAGATCGTA | 40 | C' | 77 |
| Kpn I- EcoR I fragment | | | | |
| KE1 | CGGTAAAGCGAAATATGTTCTGAAAAACTTCACTCTGGA | 39 | C | 78 |
| KE2 | AGGCAAAGTGGCTAATGATAAAACCACCTTGGAAGTCAAGGAAGGCACCG | 50 | C | 79 |
| KE3 | TTACTCTGAGCATGAATATCTCCAAATCTGGTGAAGTTTCCGTTGAACTG | 50 | C | 80 |
| KE4 | AACGACACTGACAGCAGCGCTGCGACTAAAAAAACTGCAGCGTGG | 45 | C | 81 |
| KE5 | AATTCCACGCTGCAGTTTTTTTAGTCGCA | 29 | C' | 82 |
| KE6 | GCGCTGCTGTCAGTGTCGTTCAGTTCAACGGAAACTTCACCAGATTTGGA | 50 | C' | 83 |
| KE7 | GATATTCATGCTCAGAGTAACGGTGCCTTCCTTGACTTCCAAGGTGGTTT | 50 | C' | 84 |
| KE8 | TATCATTAGCCACTTTGCCTTCCAGAGTGAAGTTTTTCAGAACATATTTCGCTTTACCGGTAC | 63 | C' | 85 |
| EcoR I- BamH I fragment | | | | |
| EB1 | AATTCCAAAACTTCTACTTTAACCATTAGCGTTAACAGCAAAAAA | 45 | C | 86 |
| EB2 | ACTACCCAGCTGGTGTTCACTAAACAAGACACGATCACTGTGCAGAAATA | 50 | C | 87 |
| EB3 | CGACTCCAACGGCACCAACTTAGAAGGCACGGCAGTCGAAATTAAAACCC | 50 | C | 88 |
| EB4 | TTGATGAACTGAAAAACGCGCTGAAATAAGCTGAGCG | 40 | C | 89 |
| EB5 | GATCCGCTCAGCTTATTTCAGCGCGTTTTTCAGTTCATCAAGGGTTTTAATTTCGACTGCC | 60 | C' | 90 |
| EB6 | GTGCCTTCTAAGTTGGTGCCGTTGGAGTCGTATTTCTGCACAGTGATCGT | 50 | C' | 91 |
| EB7 | GTCTTGTTTAGTGAACACCAGCTGGGTAGTTTTTTTGCTGTTAACGCTAA | 50 | C' | 92 |
| EB8 | TGGTTAAAGTAGAAGTTTTGG | 21 | C' | 93 |

*A single amino acid change was introduced by PCR, lipB sOspA 1/2 was the name of the construct before the introduced change and lipB sOspA 1/2* was the name after the introduced change.
L Length of oligonucleotide in bases
S Strand, C (coding) or complementary (C')

TABLE 5

Oligonucleotides for lipB sOspA 5/3 gene fragments

| Name | Sequence (5'-3') | L | S | SEQ ID NO |
|---|---|---|---|---|
| Nde I- HindIII fragment | | | | |
| N51 | TATGCGTCTGTTGATCGGCTTTGCTTTGGCGCTGGCTTTAATCGGCTG | 48 | C | 94 |
| N52 | TGCACAGAAAGGTGCTGAGTCTATTGGTTCCGTTTCTGTAGATCTGCCCG | 50 | C | 95 |
| N53 | GGGGTATGAAAGTTCTGGTAAGCAAAGAAAAAGACAAAAACGGTAAATAC | 50 | C | 96 |
| N54 | AGCCTGATGGCAACCGTAGAAAAGCTGGAGCTTAAAGGCACTTCTGATAA | 50 | C | 97 |
| N55 | AAACAACGGTTCTGGCACCCTGGAAGGTGAAAAAACTAACAAAAGCAAGTAA | 53 | C | 98 |
| N56 | AGCTTTACTTTGCTTTTGTTAGTTTTTTCACCTTCCA | 37 | C' | 99 |
| N57 | GGGTGCCAGAACCGTTGTTTTTATCAGAAGTGCCTTTAAGCTCCAGCTTT | 50 | C' | 100 |
| N58 | TCTACGGTTGCCATCAGGCTGTATTTACCGTTTTTGTCTTTTTCTTTGCT | 50 | C' | 101 |
| N59 | TACCAGAACTTTCATACCCCCGGGCAGATCTACAGAAACGGAACCAATAG | 50 | C' | 102 |
| N510 | ACTCAGCACCTTTCTGTGCACAGCCGATTA | 30 | C' | 103 |
| N511 | AAGCCAGCGCCAAAGCAAAGCCGATCAACAGACGCA | 36 | C' | 104 |
| HindIII- Kpn I fragment | | | | |
| H51 | AGCTTACTATTGCTGAGGATCTGAGCAAAACCACCTTTGAAATCTTC | 47 | C | 105 |
| H52 | AAAGAAGATGGCAAAACTCTGGTATCTAAAAAAGTAACCCTGAAAGACAA | 50 | C | 106 |
| H53 | GTCTTCTACCGAAGAAAAATTCAACGAAAGGGTGAAATC | 40 | C | 107 |
| H54 | TCTGAAAAAACTATCGTAATGGCAAATGGTAC | 32 | C | 108 |
| H55 | AAGGTGGTTTTGCTCAGATCCTCAGCAATAGTA | 33 | C' | 109 |
| H56 | AGAGTTTTGCCATCTTCTTTGAAGATTTCA | 30 | C' | 110 |
| H57 | ATTTTTCTTCGGTAGAAGACTTGTCTTTCAGGGTTACTTTTTTAGATACC | 50 | C' | 111 |
| H58 | CATTTGCCATTACGATAGTTTTTTCAGAGATTTCACCCTTTTCGTTGA | 48 | C' | 112 |
| Kpn I- EcoR I fragment | | | | |
| K51 | CCGTCTGGAATACACCGACATCAAAAGCGATAAAACCGGCAAAGCTAA | 48 | C | 113 |
| K52 | ATACGTTCTGAAAGACTTTACTCTGGAAGGCACTCTGGCTGCTGACGGCA | 50 | C | 114 |
| K53 | AAACCACTCTGAAAGTTACCGAAGGCACTGTTACTCTGAGCATGAACATT | 50 | C | 115 |
| K54 | TCTAAATCCGGCGAAATCACCGTTGCACTGGATGACACTGACTCTAGCGG | 50 | C | 116 |
| K55 | CAATAAAAAATCCGGCACCTGGGATTCTGATACTTCTACTTTAACCATTA | 50 | C | 117 |
| K56 | GCAAAAACAGCCAGAAAACTAAACAGCTGGG | 31 | C | 118 |
| K57 | GCTTTTGATGTCGGTGTATTCCAGACGGGTAc | 31 | C' | 119 |
| K58 | CCTTCCAGAGTAAAGTCTTTCAGAACGTATTTAGCTTTGCCGGTTTTATC | 50 | C' | 120 |
| K59 | CAGTGCCTTCGGTAACTTTCAGAGTGGTTTTGCCGTCAGCAGCCAGAGTG | 50 | C' | 121 |
| K510 | CAGTGCAACGGTGATTTCGCCGGATTTAGAAATGTTCATGCTCAGAGTAA | 50 | C' | 122 |
| K511 | TCAGAATCCCAGGTGCCGGATTTTTTATTGCCGCTAGAGTCAGTGTCATC | 50 | C' | 123 |
| K512 | AATTcCCAGCTGTTTAGTTTTCTGGCTGTTTTTGCTAATGGTTAAAGTAGAAGTA | 55 | C' | 124 |
| EcoR I- BamH I fragment | | | | |
| E51 | AATTCAAACAGCTGGTATTCACCAAAGAAAACACTATCACCGTAC | | | 125 |
| E52 | AGAACTATAACCGTGCAGGCAATGCGCTGGAAGGCAGCCC | 45 | C | 126 |
| E53 | GGCTGAAATTAAAGATCTGGCAGAGCTGAAAGCCGCTTTGAAATAAGCTGAGCG | 40 | C | 127 |

TABLE 5-continued

Oligonucleotides for lipB sOspA 5/3 gene fragments

| Name | Sequence (5'-3') | L | S | SEQ ID NO |
|---|---|---|---|---|
| E54 | GATCCGCTCAGCTTATTTCAAAGCGGCT | 54 | C | 128 |
| E55 | TTCAGCTCTGCCAGATCTTTAATTTCAGCCGGGCTGCCTTCCAGCGCATT | 28 | C' | 129 |
| E56 | GCCTGCACGGTTATAGTTCTGTACGGTGATAGTGTTTTCTTTGGTGAATACCAGCTGTTTG | 50 | C' | 130 |

L Length of oligonucleotide in bases
S Strand, C (coding) or complementary (C')

TABLE 6

Oligonucleotides for lipB sOspA 6/4 gene fragments

| Name | Sequence (5'-3') | L | S | SEQ ID NO |
|---|---|---|---|---|
| Nde I- HindIII fragment | | | | |
| KNH1 | TATGCGTCTGTTGATCGGCTTTGCTCTGGCGCTGGCTCTGATCGGCTG | | | 131 |
| KNH2 | CGCACAGAAAGGTGCTGAGTCTATTGGTTCCGTTTCTGTAGATCTGCCCG | 48 | C | 132 |
| KNH3 | GTGGCATGACCGTTCTGGTCAGCAAAGAAAAAGACAAAAACG | 50 | C | 133 |
| KNH4 | GTAAATACAGCCTCGAGGCGACCGTCGACA | 42 | C | 134 |
| KNH5 | AGCTTGTCGACGGTCGCCTCGAGGCTGTATTTACCGTTTTTGTCTTTTTCTTTGCT | 30 | C | 135 |
| KNH6 | GACCAGAACGGTCATGCCACCGGGCAGATCTACAGAAACG | 56 | C' | 136 |
| KNH7 | GAACCAATAGACTCAGCACCTTTCTGTGCGCAGCCGATCAGAGCCAGCGC | 40 | C' | 137 |
| KNH8 | CAGAGCAAAGCCGATCAACAGACGCA | 50 | C' | 138 |
| HindIII- Kpn I fragment | | | | |
| KHK1 | AGCTTGAGCTGAAAGGCACCTCTGATAAAAACAACGGTTCCGGCACCCTG | 50 | C | 139 |
| KHK2 | GAAGGTGAAAAAACTAACAAAAGCAAAGTGAAACTGACCATTGCTGAT | 48 | C | 140 |
| KHK3 | GACCTCAGCCAGACCAAATTCGAAATTTTCAAAGAAGATGCCAAAACCTT | 50 | C | 141 |
| KHK4 | AGTATCCAAAAAGTGACCCTGAAAGACAAGTCCTCTACCGAAGAAAAT | 50 | C | 142 |
| KHK5 | TCAACGAAAAGGGTGAAACCTCTGAAAAAACCATCGTAATGGCAAATGGTAC | 52 | C | 143 |
| KHK7 | CATTTGCCATTACGATGGTTTTTTCAGA | 28 | C' | 144 |
| KHK8 | GGTTTCACCCTTTTCGTTGAATTTTTCTTCGGTAGAGGAC | 40 | C' | 145 |
| KHK9 | TTGTCTTTCAGGGTCACTTTTTTGGATACTAAGGTTTTGGCATCTTCTTT | 50 | C' | 146 |
| KHK10 | GAAAATTTCGAATTTGGTCTGGCTGAGGTCATCAGCAATGGTCAGTTTCA | 50 | C' | 147 |
| KHK11 | CTTTGCTTTTGTTAGTTTTTTCACCTTCCAGGGTGCCGGA | 40 | C' | 148 |
| KHK12 | ACCGTTGTTTTTATCAGAGGTGCCTTTCAGCTCA | 34 | C' | 149 |
| Kpn I- EcoR I fragment | | | | |
| KKE1 | CCGTCTGGAATACACCGACATCAAAAGCGATGGCTCCGGCAAAGCCAA | 48 | C | 150 |
| KKE2 | ATACGTTCTGAAAGACTTCACCCTGGAAGGCACCCTCGCTGCCGACGG | 48 | C | 151 |
| KKE3 | CAAAACCACCTTGAAAGTTACCGAAGGCACTGTTGTTTTAAG | 42 | C | 152 |
| KKE4 | CATGAACATCTTAAAATCCGGTGAAATCACCGTTGCGCTG | 40 | C | 153 |
| KKE5 | GATGACTCTGACACCACTCAGGCCACTAAAAAAACCGGCAAATGGGATTC | 50 | C | 154 |
| KKE6 | TAACACTTCCACTCTGACCATCAGCGTG | 28 | C | 155 |

TABLE 6-continued

Oligonucleotides for lipB sOspA 6/4 gene fragments

| Name | Sequence (5'-3') | L | S | SEQ ID NO |
|---|---|---|---|---|
| KKE7 | AATTCACGCTGATGGTCAGAGTGGAAGTGTTAGAATCCCATTTGCCG | 47 | C' | 156 |
| KKE8 | GTTTTTTTAGTGGCCTGAGTGGTGTCAGAGTCATCCAGCGCAACGGTGATTTCAC | 55 | C' | 157 |
| KKE9 | CGGATTTTAAGATGTTCATGCTTAAAACAACAGTGCCTTCGGTAACTTTC | 50 | C' | 158 |
| KKE10 | AAGGTGGTTTTGCCGTCGGCAGCGAGGGTGCCTTCCAGGG | 40 | C' | 159 |
| KKE11 | TGAAGTCTTTCAGAACGTATTTGGCTTTGCCGGAGCCATC | 40 | C' | 160 |
| KKE12 | GCTTTTGATGTCGGTGTATTCCAGACGGGTAC | 32 | C' | 161 |
| EcoR I - BamH I fragment | | | | |
| KEB1 | AATTCCAAAAAAACTAAAAACATCGTGTTCACCAAAGAAGACACCATCACCG | | | 162 |
| KEB2 | TCCAGAAATACGACTCTGCGGGCACCAACCTCGAAGGCAACGCAGTCGAA | 52 | C | 163 |
| KEB3 | ATCAAAACCCTGGATGAACTGAAAAACGCTCTGAAATAAGCTGAGCG | 50 | C | 164 |
| KEB4 | GATCCGCTCAGCTTATTTCAGAGCGTTTTTCAGTTCATCCAGGGTTTTGATTTCGACTGCGTTGCCTTCGA | 47 | C | 165 |
| KEB5 | GGTTGGTGCCCGCAGAGTCGTATTTCTGGACGGTGATGGTGTCTTCTTTG | 71 | C' | 166 |
| KEB6 | GTGAACACGATGTTTTTAGTTTTTTTGG | 50 | C' | 167 |

L Length of oligonucleotide in bases
S Strand, C (coding) or complementary (C')

Preparation of *E. Coli* Competent Cells.

A single colony was used to inoculate 5 ml modified LB broth (5.5 g NaCl, 5 g yeast extract, 10 g soya peptone, which was not obtained from an animal or genetically modified plant source—per liter of water). The culture was incubated until it became turbid, after which the culture was diluted to a volume of 25 ml with pre-warmed modified LB broth. The culture was incubated further until it had reached an OD600 nm of 0.2 to 0.6 (40-60 min) and was diluted to a volume of 125 ml, transferred to a 500 ml flask and incubated until an OD600 nm of 0.6 was reached. The culture was chilled quickly by gentle shaking for 5 min in an ice bath and the cells were pelleted directly (Beckman centrifuge, 4000 rpm for 10 min.), washed carefully with TfBI buffer (Teknova Hollister, Calif.) (30 mM K-acetate, 50 mM $MnCl_2$, 100 mM KCL, 10 mM $CaCl_2$ 15% glycerol), resuspended in 5 ml of TfBII (10 mM Na-MOPS, 75 mM $CaCl_2$, 10 mM KCL, 15% glycerol) and held on ice for 15 min. The cells were then pipetted into 100 µl aliquots and were snap frozen directly in dry ice.

Annealing of Oligonucleotide Mixtures to Form OspA Gene Fragments (De Novo Synthesis).

Three synthetic OspA genes were designed to encode OspA molecules with the protective epitopes from serotype 1 and 2 OspAs (lipB sOspA 1/2), serotype 6 and 4 OspAs (lipB sOspA 6/4) and serotype 5 and 3 OspAs (lipB sOspA 5/3). For each novel OspA gene (lipidated), four sets of oligonucleotides of between 30-60 base pairs were synthesized (see Tables 4-6). FIGS. 16-18 show the codon optimized sequences for each of the constructs aligned with the nucleotide sequences predicted from published sequences). Each oligonucleotide set consisted of between 8-12 complementary overlapping oligonucleotides. The oligonucleotides from each set were annealed together, in separate experiments, to generate double-stranded DNA fragments with specific restriction enzyme recognition sites at either end i.e. fragments N-H (Nde I-Hind III), H-K (Hind III-Kpn I), K-E (Kpn I-EcoR I) and E-B (EcoR I-BamH I).

The lyophilized oligonucleotides were reconstituted with distilled water, the OD260 nm was measured and the concentration was adjusted to 10 µM. For each OspA fragment, 2 µl of each of the oligonucleotides were mixed together with 1 µl of T4 polynucleotide kinase and T4 DNA ligase buffer (10×) and the mixture was incubated at room temperature for 30 minutes to enable phosphorylation of the oligos (for the lipB sOspA 6/4 construct this step was omitted as the oligos were already phosphorylated). The mixture was heated to 95° C. for 1 minute (denaturing step) and then the oligos were allowed to anneal by leaving the mix to cool slowly to room temperature. The annealed mix was used directly in ligations, or was stored at −20° C. until further needed.

Cloning of OspA Gene Fragments.

Each of the four fragments required for constructing an individual synthetic OspA gene was cloned independently into pUC18 and transformed into the *E. coli* host DH5α (see FIG. 1).

For each novel OspA gene, four sets of oligonucleotides of between 30-60 bases were synthesized. Each oligonucleotide set consisted of between 8-12 complementary overlapping oligonucleotides. The oligonucleotides from each set were annealed together, in separate experiments, to generate double-stranded DNA fragments with specific restriction enzyme recognition sites at either end, i.e. fragments N-H (Nde I-Hind III), H-K (Hind III-Kpn I), K-E (Kpn I-EcoR I) and E-B (EcoR I-BamH I). Each of the four (4) fragments was cloned independently into pUC18 cut with the corresponding restriction enzymes and transformed into the *E. coli* host DH5α, after which the sequence of the cloned fragment was verified.

Plasmid DNA (pUC18) was purified from an overnight *E. coli* culture (LB broth) with a QIAGEN plasmid purification system according to the manufacturer's protocol. Vector DNA was then digested with pairs of restriction enzymes; Nde I & Hind III, Hind III & Kpn I, Kpn I & EcoR I, EcoR I & BamH I in accordance with the manufacturers' protocols. The digested samples were applied to a 0.8% agarose gel and electrophoretically separated. The linearized vector DNA was excised and eluted using a commercial gel elution kit (QIAquick Gel Extraction Kit, Qiagen) according to the manufacturer's protocol and ligated, using T4 DNA ligase, to the annealed oligonucleotide mixture. The ligation products were transformed into competent cells of *E. coli* DH5α and transformants containing the plasmid were selected on LB agar containing ampicillin (100 µg/ml).

The presence of the insert of the expected size in the cloning vector, pUC18, was confirmed by purifying plasmid DNA, digesting the DNA with the enzymes used for cloning and analyzing the DNA fragments by agarose gel electrophoresis using the procedures previously described. The cloned DNA fragment was sequenced using purified plasmid DNA as the DNA template and the sequencing primers 5'-TCGGGGCTGGCTTAACTATG-3 (SEQ ID NO: 14) and 5'-GCTTCCGGCTCGTAT (SEQ ID NO:15) (which are in the pUC18 vector outside the multiple cloning sites, by 130-150 and by 530-515, respectively). Sequence reactions were run on an automatic sequencer (ABI 310). Sequences were edited using SequenceEditor and the sequences were imported into VectorNTI for analysis. Only clones with the correct sequences were used as building blocks for constructing full-length OspA genes.

For the lipB sOspA 5/3 gene a different strategy was employed, since no suitable unique internal site could be found within the Kpn I-BamH I fragment and the amino acid sequence did not permit the use of an internal EcoR I site (see FIG. 14). A Pvu II site exists within the Kpn I-BamH I fragment, however there are two Pvu II sites in the pUC18 vector which mean direct cloning of the fragments in pUC18 is not possible. Hence, the oligos for the constructs were designed to have an EcoR I site inserted outside and adjacent to the Pvu II site, to permit cloning of the Kpn I-EcoR I and the EcoR I-BamH I fragments into pUC18. Subsequent digestion of the inserted fragments with Kpn I, EcoR I and BamH I generated fragments, which were subsequently digested with Pvu II. The Pvu II-digested fragments (Kpn I-Pvu II and Pvu II-BamH I) were then used in a triple ligation with pUC18 vector DNA cut with Kpn I and BamH I to generate the Kpn I-BamH I fragment.

Constructing Full-Length OspA Genes.

In the next step, each of the four fragments required for constructing an individual synthetic OspA gene was excised from the pUC18 vector and re-cloned, in a single step, into pUC18 vector to generate a full-length OspA gene (see FIG. 1).

The four fragments needed to make full-length genes were excised from miniprep. DNA isolated using the same restriction enzymes used for the original cloning step. The digested samples were applied to an agarose gel and electrophoretically separated. The DNA for each of the respective 4 insert fragments was excised and eluted using a commercial gel elution kit (QiaQuick Gel Extraction Kit) according to the manufacturer's protocol and ligated, using T4 DNA ligase, to linearized vector DNA digested with Nde I and BamH I and purified using a QIAquick Gel Extraction Kit. The ligated DNA was transformed into competent cells of *E. coli* DH5α and clones containing the plasmid were selected on LB agar containing ampicillin (100 μg/ml). Colonies were screened by PCR for the presence of inserts of the expected size (approx 830 bp).

Single colonies were used as template DNA in PCR reactions comprising 10× buffer (15 mM Tris-HCl (pH 8.0), 50 mM KCl, 1.5 mM $MgCl_2$), 200 μM dNTPs, 1.25 U Amplitaq DNA polymerase, 400 nM forward primer 5'-TCGGGGCTGGCTTAACTATG-3 (SEQ ID NO: 14) and 400 nM reverse primer 5'-GCTTCCGGCTCGTAT (SEQ ID NO: 15). PCR reaction conditions were as follows; 94° C. for 5 min., 35×(94° C. for 30 s, 48° C. for 30 s, 72° C. for 1 min 30s) followed by a soak at 72° C. for 5 minutes and a hold at 4° C. PCR products were used directly or stored at ≦15° C. until further use. PCR products were analyzed by agarose gel electrophoresis for the presence of inserts of the correct size (approx. 980 bp). Inserts of the correct size were sequenced to confirm that no errors had been introduced i.e. sequence reactions were set up using plasmid DNA isolated (QIAGEN Plasmid Purification kit) from overnight cultures (LB amp broth) and using sequencing primers that flank the cloning sites (5'-TCGGGGCTGGCTTAACTATG-3'(SEQ ID NO: 14) and 5'-GCTTCCGGCTCGTATGTTGT-3' (SEQ ID NO: 16), by 130-150 and 530-510, respectively). Sequence reactions were run on an automatic sequencer (ABI 310). Sequences were edited using SequenceEditor and the sequences were imported into VectorNTI for analysis.

Sub-Cloning of Novel OspA Genes into the pET30a Expression Vector.

Once the full length OspA gene was verified in pUC18, the OspA genes were then sub-cloned into the pET-30a expression vector using the restriction enzymes NdeI and BamH I and transformed into the *E. coli* host HMS 174(DE3).

Miniprep DNA from pUC18 clones with the correct sequence was digested with Nde I and BamH I. Similarly pET30a vector DNA was digested with Nde I and BamH I. The digested DNAs were run on an agarose gel and electrophoretically separated. The insert fragment of approximately 830 bp and the linearized vector DNA were excised and purified as described previously. The vector and insert DNA were ligated, using T4 DNA ligase and the ligation products were transformed into competent cells of *E. coli* HMS174 (DE3) (Novagen). The transformants were plated onto LB plates containing kanamycin (30 μg/ml). Single colonies were screened by PCR using the primers 5'-TTATGCTAGTTATTGCTCAGCG-3' (SEQ ID NO:17) and 5'-TTCCCCTCTAGAAATAATTTTGT-3' (SEQ ID NO: 18). PCR products were applied to an agarose gel and were electrophoretically separated. Colonies that yielded a product of the correct size (approx. 1 kb) were subsequently used to set up overnight cultures, from which miniprep DNA was isolated using a QIAGEN Plasmid Purification kit according to the manufacturer's protocol. The sequence was again confirmed (using primers 5'-TTATGCTAGTTATTGCTCAGCG-3' (SEQ ID NO: 17) and 5'-TTCCCCTCTAGAAATAATTTTGT-3' (SEQ ID NO:18), by 65-86 and 395-373, respectively) and colonies were selected for expression testing.

Generating lipB sOspA $1/2^{251}$ from lipB sOspA 1/2.

A single amino acid was changed in the lipB sOspA 1/2 construct, namely amino acid alanine at position 251 was changed to an asparagine residue, to enhance immunogenicity. The amino acid change was introduced by PCR. First, PCR was set up with the external forward primer and the internal reverse primer yielding a product of about 730 bp with the introduced amino acid change (see FIG. 15). Second, PCR was set up with the internal forward primer and the external reverse primer to yield a product of 100 bp containing the introduced amino acid change. The two PCR products, which overlapped in sequence, were then used as template DNA in a final PCR reaction with the external forward and external reverse primers to yield the final full-length OspA product containing the introduced amino acid change.

The pET30a construct was used as the source of template DNA. PCR reactions were set up comprising 10× buffer [15 mM Tris-HCl (pH 8.0), 50 mM KCl, 1.5 mM MgCl2], 200 μm dNTPs, 1.25 U Amplitaq DNA polymerase, and 400 nM of each primer pair (primer pair 5'-GGA ATT CCA TAT GCG TCT GTT GAT CGG CT (SEQ ID NO: 19) & 5'-TTG GTG CCT GCG GAG TCG (SEQ ID NO:20) and primer pair 5'-AAT ACG ACT CCG CAG GCA CC (SEQ ID NO: 21) & 5'-CTG-GGA TCC GCT CAG CTT ATT TCA (SEQ ID NO: 22)). PCR reactions were set up with the following conditions; 94° C. for 5 min., 35×(94° C. for 30 s, 48° C. for 30 s, 72° C. for 1 min 30 s) followed by a soak at 72° C. for 5 minutes and a hold at 4° C. The reactions yielded 2 separate overlapping products and the 2 products were used as the template DNA in a third PCR reaction using the external primers 5'-GGA ATT CCA TAT GCG TCT GTT GAT CGG CT (SEQ ID NO:19) and 5'-CTG-GGA TCC GCT CAG CTT ATT TCA (SEQ ID NO: 22) which incorporated restriction sites for Nde I and BamH I. The reaction conditions were 94° C. for 60 sec followed by 35 cycles of (30 sec 94° C., 60 sec 49° C., 90 sec 72° C.) followed by 72° C. for 5 min. The amplified product was purified with a QiaQuick purification kit (Qiagen) in accordance with the manufacturer's specifications and the product was digested with Nde I and BamH I and ligated to pET30a vector DNA cut Nde I and BamH I. The ligation products were transformed into competent cells of E. coli DH5α. The transformants were plated onto LB plates containing kanamycin (30 μg/ml). Single colonies were screened by PCR using the primers 5'-TTATGCTAGTTAT-TGCTCAGCG-3' (SEQ ID NO:17) and 5'-TTCCCCTCTA-GAAATAATTTTGT-3' (SEQ ID NO: 18). PCR products were applied to an agarose gel and were electrophoretically separated. Colonies which yielded a product of the correct size (approx. 1 kb) were subsequently used to set up overnight cultures, from which miniprep DNA was isolated using a QIAGEN Plasmid Purification System according to the manufacturer's protocol. The sequence was confirmed (using primers 5'-TTATGCTAGTTATTGCTCAGCG-3' (SEQ ID NO: 17) and 5-TTCCCCTCTAGAAATAATTTTGT-3' (SEQ ID NO: 18)) and the resulting construct was transformed into E. coli HMS174(DE3) competent cells and the resulting positive transformants were given the name lipB sOspA $1/2^{251}$.

Generation of Constructs without Leader Sequence.

Constructs were prepared with a lipB leader sequence, to which a lipid moiety is typically attached at the amino terminal cysteine residue. Experimental testing of the recombinant lipidated OspAs verified the presence of a lipid moiety. However, constructs which did not contain the lipB leader sequence were also prepared. Constructs which did not contain the lipB leader sequence were made by PCR amplification from each of the three lipB constructs (in pET30a) using primers selected to generate a final product of 769-771 bp without the nucleic acid sequence coding for the leader sequence and with the codon for the cysteine residue replaced with a codon for a methionine residue.

PCR reactions comprised 10× buffer [15 mM Tris-HCl (pH 8.0), 50 mM KCl, 1.5 mM MgCl2], 200 μm dNTPs, 1.25 U Amplitaq DNA polymerase, 400 nM forward primer 5'-CGT-GCGTACCATATGGCACAGAAAGGTGCTGAGTCT-3' (SEQ ID NO: 23) and 400 nM reverse primer 5'-CTGG-GATCCGCTCAGCTTATTTCA-3' (SEQ ID NO: 22) and template DNA. PCR conditions were; 94° C. for 5 min, 35× (94° C. for 30 s, 48° C. for 30 s, 72° C. for 1 min 30 s) followed by a soak at 72° C. for 5 min and a hold at 4° C. PCR reactions were used directly or stored at ≦15° C. until further use.

The PCR products were purified using a QiaQuick PCR purification kit (Qiagen), were digested with Nde I and BamH I and were ligated to pET30a vector DNA digested with Nde I and BamH I. The ligation mixes were used to transform E. coli HMS174(DE3) and colonies containing recombinant plasmids were selected by their resistance to kanamycin and the sequence was verified from PCR products.

Evaluation of Expression in E. Coli HMS 174(DE3).

Selected colonies were tested for their ability to express the respective novel OspA protein. In each case, single colonies were used to inoculate LB broth containing kanamycin (30 μg/ml) and were incubated at 37° C. for 1 to 5 hours until an OD (600 nm) value greater than 0.6 and less than 1 was reached. At this point, a sample of the culture was retained (representing the un-induced sample) and the remainder of the culture was induced by the addition of IPTG to a final concentration of 1 mM. The un-induced sample (1 ml) was centrifuged and the pellet retained and stored at −20° C. The induced culture was allowed to grow for a further three hours, after which a 1 ml sample was taken, the OD (600 nm) was measured, the sample centrifuged and the pellet retained and stored at −20° C.

Preparation of Primary Cells.

Primary Cells were Prepared for Each of the three lipidated constructs and for each of the three non-lipidated constructs. The primary cells comprised E. coli cells (HMS174(DE3)) carrying a pET30a plasmid expressing the respective OspA. For preparation of primary cells, a single colony from the respective stock was picked from a plate containing kanamycin (30 μg/ml) and rifampicin (200 μg/ml) and was used to inoculate 500 μl of SMK medium (SOP 8114) and incubated overnight. One hundred microliters of this culture was then used to inoculate 100 ml of SMK medium (in duplicate) and the culture was incubated for 17 to 20 hours at 37° C. shaking. Sterile glycerol was then added to the culture at a final concentration of 15% and the material was pipetted in aliquots in 500 μl amounts into 60 ampoules, thus yielding 60 ampoules of primary cells which were directly stored at −80° C.

Three synthetic OspA genes were designed to encode OspA molecules with the protective epitopes from serotype 1 and 2 OspAs (lipB sOspA 1/2251), serotype 6 and 4 OspAs (lipB sOspA 6/4) and serotype 5 and 3 OspAs (lipB sOspA 5/3). The primary amino acid sequences of these molecules and a description of the main features incorporated into their design are set out in the following Examples.

Example 3

Description of Lipidated $1/2^{251}$ OspA (lipB sOspA$1/2^{251}$)

The aim of the study was to design a novel OspA antigen, lipidated $1/2^{251}$ OspA (lipB sOspA $1/2^{251}$), comprising serotypes 1 and 2. LipB sOspA $1/2^{251}$, comprises the proximal portion of a serotype 1 OspA sequence (Strain B31, GenBank Accession No. X14407) fused to the distal portion of a serotype 2 sequence (Strain Pko, GenBank Accession No. S48322). The start of the sequence unique to the type 2 serotype is the lysine (K) residue at position 216. The construct was originally designed to encode the amino acid alanine (A) at position 251. However, the construct was subsequently altered by PCR to encode an asparagine (N) residue (the actual residue in the published sequence from Pko) to enhance immunogenicity, hence the nomenclature lipB sOspA $1/2^{251}$.

Secondary features of lipB sOspA 1/2$^{251}$ are shown in the annotated amino acid sequence of lipB sOspA 1/2$^{251}$ in FIG. 2 and include:

the replacement of the putative arthritogenic epitope (Gross et al., 1998), hLFA-1 (YVLEGTLTA) (SEQ ID NO:24), in the proximal portion of the molecule (amino acids 161 to 185) with an equivalent sequence (shown in italics and a flanking sequence) from a serotype 2 OspA sequence (Strain Pko; GenBank Accession No. S48322): a sequence that is distinct from the hLFA-1 epitope;

an OspB leader sequence (amino acids 1 to 15 of FIG. 2) and various substitutions to avoid prior art. The asparagine (N) and aspartic acid (D) residues at positions 44 and 46 were replaced with an aspartic acid (D) and an asparagine (N), respectively, to produce the sequence KEKDKN (SEQ ID NO: 25). The alanine (A) and aspartic acid (D) residues at positions 78 and 79 were replaced with a threonine (T) and an asparagine (N), respectively, to produce the sequence KTNKSK (SEQ ID NO: 26);

stabilizing mutations as described in international patent publication number WO 02/16421 A2 (Luft & Dunn). For example, methionine (M) replaced arginine (R) at amino acid 136 (R139M); tyrosine (Y) replaced glutamic acid (E) at amino acid 157 (E160Y); and methionine (M) replaced lysine (K) at amino acid 186 (K189M); and additional stabilizing mutations. For example, threonine (T) replaced valine (V) at amino acid 173 (aa 176 of the disclosure). The removal of the putative arthritogenic epitope (position 161-185), by replacing a B. burgdorferi sequence with a B. afzelii sequence, disrupted the hydrogen bonding between amino acids 173 and 174 (aa 176 and 177 of the disclosure). This led to decreased binding to protective monoclonal antibodies (105.5 and LA-2 (Jiang et al., *J. Immunol.* 144: 284-9, 1990; Golde et al., *Infect. Immun.* 65: 882-9, 1997; and Ding et al., *J. Mol. Biol.* 302: 1153-64, 2000). A threonine (T) was introduced at position 173, instead of a valine (V), to restore the hydrogen bond and increase reactivity to protective monoclonal antibodies 105.5 and LA2.

In addition, amino acids 16-25 (start of the mature protein) are identical to the OspB sequence (GenBank Accession No. X74810).

The nucleotide and deduced amino acid sequences of lipB sOspA 1/2$^{251}$ are shown in FIG. 3. The leader sequence (green) is cleaved off during protein secretion. The sequence of the mature OspA protein starts with a cysteine residue (underlined), which forms the attachment site for the protein's lipid anchor.

Example 4

Description of Lipidated 6/4 OspA (LipB sOspA 6/4)

The aim of the study was to design a novel OspA antigen, lipidated sOspA 6/4 OspA (lipB sOspA 6/4), comprising serotypes 4 and 6. LipB sOspA 6/4 comprises the proximal portion of a serotype 6 OspA sequence (Strain K48, GenBank Accession No. I40098) fused to the distal portion of a serotype 4 sequence (Strain pTroB; GenBank Accession No. I40089). The start of the sequence unique to the type 4 serotype is the asparagine (N) residue at position 217. Secondary features are shown in the annotated amino acid sequence of lipB sOspA 6/4 in FIG. 4 and include:

stabilizing mutations described in International Patent Application No. WO 02/16421A2 (Luft and Dunn): methionine (M) instead of an arginine (R) at amino acid 136, tyrosine (Y) instead of a glutamic acid (E) at amino acid 157, and methionine (M) instead of a lysine (K) at amino acid 187; and like lipB sOspA 1/2$^{251}$, described above, an OspB leader sequence was used (amino acids 1 to 15 in FIG. 4) and amino acids 16-25 are identical to sequence from OspB (GenBank Accession No. X74810).

Although the peptide sequence KEKNKD (SEQ ID NO: 27) was absent from the parent OspA type 6 sequence (KEKDKD) (SEQ ID NO: 28), the aspartic acid (D) residue at position 46 was replaced with an asparagine residue (N) in conformity with an equivalent change made in the lipB sOspA 1/2$^{251}$ construct to produce the sequence KEKDKN (SEQ ID NO:25).

Although the peptide sequence KADKSK (SEQ ID NO:29) was absent from the parent OspA type 6 sequence (KTDKSK) (SEQ ID NO: 30), the aspartic acid (D) residue at position 79 was replaced with an asparagine residue (N) in conformity with an equivalent change made in the lipB sOspA 1/2$^{251}$ construct to produce the sequence KTNKSK (SEQ ID NO:26).

Amino acid 37 was changed from the glutamine acid (E), as present in the parent sequence (Strain K48; GenBank Accession No. I40098), to a valine (V), because almost all type 6 sequences have a valine in this position.

The nucleotide and deduced amino acid sequences of lipB sOspA 6/4 are shown in FIG. 5. The leader sequence (green) is cleaved off during protein secretion. The sequence of the mature OspA protein starts with a cysteine residue (underlined, see FIG. 5), which forms the attachment site for the protein's lipid anchor.

Example 5

Description of Lipidated 5/3 OspA (lipB sOspA 5/3)

The aim of the study was to design a novel OspA antigen, lipidated sOspA 5/3 OspA (lipB sOspA 5/3), comprising serotypes 3 and 5. LipB sOspA 5/3 comprises the proximal portion of a serotype 5 OspA sequence [Database Accession No. embIX85441IBGWABOSPA, B. garinii OspA gene (WABSou substrain)] fused to the distal portion of a serotype 3 sequence (Strain PBr; Genbank Accession No. X80256, *B. garinii* OspA gene) with modifications as shown in SEQ ID NOS: 5 and 6. The start of the sequence unique to the type 3 serotype is the aspartic acid (D) residue at position 216. Secondary features are shown in the annotated amino acid sequence of lipB sOspA 5/3 in FIG. 6 and include:

stabilizing mutations described in International Patent Application No. WO 02/16421A2 (Luft and Dunn): methionine (M) instead of an arginine (R) at amino acid 136; tyrosine (Y) instead of a glutamic acid (E) at amino acid 157; and methionine (M) instead of a lysine (K) at amino acid 187; and like lipB sOspA 1/2$^{251}$ and lipB sOspA 6/4, described above, an OspB leader sequence was used (amino acids 1 to 15 in FIG. 6) and amino acids 16-25 are identical to sequence from OspB (GenBank Accession No. X74810).

Although the peptide sequence KEKNKD (SEQ ID NO:27) was absent from the parent OspA type 5 sequence (KEKDKD) (SEQ ID NO: 28), the aspartic acid (D) residue at position 46 was replaced with an asparagine residue (N) in conformity with an equivalent change made in the lipB sOspA 1/2$^{251}$ construct giving the sequence KEKDKN (SEQ ID NO:25).

Although the peptide sequence KADKSK (SEQ ID NO:29) was absent from the parent OspA type 5 sequence (KTDKSK) (SEQ ID NO: 30), the aspartic acid (D) residue at position 79 was replaced with an asparagine residue (N) in conformity with an equivalent change made in the lipB sOspA 1/2251 construct giving the sequence KTNKSK (SEQ ID NO: 26).

The nucleotide and deduced amino acid sequences of lipB sOspA 5/3 are shown in FIG. 7. The leader sequence (green) is cleaved off during protein secretion. The sequence of the mature OspA protein starts with a cysteine codon (underlined, see FIG. 7), which forms the attachment site for the protein's lipid anchor.

Example 6

Optimization of Codon Usage for High Level Expression in *E. Coli*

Because the presence of codons that are rarely used in *E. coli* is known to present a potential impediment to high-level expression of foreign genes, low-usage codons were replaced with codons which are used by highly expressed genes in *E. coli*. The nucleotide sequences of the novel OspA genes were designed to utilize the codons found most frequently (preferred codons) among the highly expressed class II, *E. coli* genes (Guerdoux-Jamet et. al., *DNA Research* 4:257-65, 1997). The data for codon usage among the novel OspA genes and for the highly expressed class II *E. coli* genes are summarized in Tables 7 and 8. The data for the less frequent amino acids for which tRNA molecules are less likely to be rate limiting is presented separately (Table 7) from the data for the amino acids which occur most often (Table 8).

TABLE 7

Codon usage in novel OspA genes (less common amino acids*)

| Amino Acid | Codon | OspA 1/2 AA Counts Total | OspA 1/2 AA Counts Codon | OspA 1/2 AA Counts % | OspA 5/3 AA Counts Total | OspA 5/3 AA Counts Codon | OspA 5/3 AA Counts % | OspA 6/4 AA Counts Total | OspA 6/4 AA Counts Codon | OspA 6/4 AA Counts % | Class II Counts (%) |
|---|---|---|---|---|---|---|---|---|---|---|---|
| Gln | CAA | 5 | 1 | 20.0 | 4 | 0 | 0.0 | 4 | 0 | 0.0 | 18.7 |
| | CAG | | 4 | 80.0 | | 4 | 100.0 | | 4 | 100.0 | 81.4 |
| Phe | TTT | 5 | 1 | 20.0 | 6 | 3 | 50.0 | 6 | 1 | 16.7 | 29.1 |
| | TTC | | 4 | 80.0 | | 3 | 50.0 | | 5 | 83.3 | 70.9 |
| Met | ATG | 4 | 4 | 100.0 | 5 | 5 | 100.0 | 4 | 4 | 100.0 | 100.0 |
| Tyr | TAT | 4 | 1 | 25.0 | 4 | 1 | 25.0 | 4 | 0 | 0.0 | 35.2 |
| | TAC | | 3 | 75.0 | | 3 | 75.0 | | 4 | 100.0 | 64.8 |
| Arg | CGT | 2 | 2 | 100.0 | 3 | 3 | 100.0 | 2 | 2 | 100.0 | 64.3 |
| | CGC | | 0 | 0.0 | | 0 | 0.0 | | 0 | 0.0 | 33.0 |
| | CGA | | 0 | 0.0 | | 0 | 0.0 | | 0 | 0.0 | 1.1 |
| | CGG | | 0 | 0.0 | | 0 | 0.0 | | 0 | 0.0 | 0.8 |
| | AGA | | 0 | 0.0 | | 0 | 0.0 | | 0 | 0.0 | 0.6 |
| | AGG | | 0 | 0.0 | | 0 | 0.0 | | 0 | 0.0 | 0.3 |
| Cys | TGT | 1 | 0 | 0.0 | 1 | 1 | 100.0 | 1 | 0 | 0.0 | 38.9 |
| | TGC | | 1 | 100.0 | | 0 | 0.0 | | 1 | 100.0 | 61.2 |
| Pro | CCT | 1 | 0 | 0.0 | 2 | 0 | 0.0 | 1 | 0 | 0.0 | 11.2 |
| | CCC | | 1 | 100.0 | | 1 | 50.0 | | 1 | 100.0 | 1.6 |
| | CCA | | 0 | 0.0 | | 0 | 0.0 | | 0 | 0.0 | 15.3 |
| | CCG | | 0 | 0.0 | | 1 | 50.0 | | 0 | 0.0 | 71.9 |
| Trp | TGG | 1 | 1 | 100.0 | 1 | 1 | 100.0 | 1 | 1 | 100.0 | 100.0 |

*i.e. Amino acids that, individually, make up <2.5% of the total amino acids by number.

TABLE 8

Codon usage in novel OspA genes (more prevalent amino acids)

| Amino Acid | Codon | OspA 1/2 AA Counts Total | Codon | % | OspA 5/3 AA Counts Total | Codon | % | OspA 6/4 AA Counts Total | Codon | % | Class II Counts (%) |
|---|---|---|---|---|---|---|---|---|---|---|---|
| Lys | AAA | 40 | 30 | 75.0 | 40 |

TABLE 8-continued

Codon usage in novel OspA genes (more prevalent amino acids)

| Amino Acid | Codon | OspA 1/2 AA Counts | | | OspA 5/3 AA Counts | | | OspA 6/4 AA Counts | | | Class II Counts (%) |
|---|---|---|---|---|---|---|---|---|---|---|---|
| | | Total | Codon | % | Total | Codon | % | Total | Codon | % | |
| Ile | ATT | 12 | 4 | 33.3 | 13 | 5 | 38.5 | 13 | 3 | 23.1 | 33.5 |
| | ATC | | 8 | 66.7 | | 8 | 61.5 | | 10 | 76.9 | 65.9 |
| | ATA | | 0 | 0.0 | | 0 | 0.0 | | 0 | 0.0 | 0.6 |

The high degree of concordance between codon usage chosen for the novel OspA genes (common amino acids only) and among *E. coli* class II genes is apparent (i.e. plot of percentage figures from Table 8 for class II genes against individual novel OspA genes; see FIG. 8). For the three lipidated constructs, the original sequences had a GC content ranging from 32.8% to 33.8%, while the codon-optimized sequences had a GC content ranging from 43.8% to 46.8%, which is similar to the 50% GC content of *E. coli.*

Example 7

Construction of Synthetic Non-Lipidated OspA Genes

Constructs were also prepared which did not contain the lipB leader sequence. The two sets of constructs (lipidated and non-lipidated) are needed to evaluate their ease of production in the fermentor (biomass, stability, product yield, and the like), to assess how readily the different types of antigen can be purified and to compare their biological characteristics (safety profile and protective potency).

The constructs (SEQ ID NOS: 7, 9, and 11) were generated by PCR amplification from each of the three lipB OspA constructs (SEQ ID NOS: 1, 3, and 5) using PCR primers with incorporated restriction sites. The PCR products were purified, digested with Nde I and BamH I and ligated to digested pET30a vector DNA. The ligation mixes were used to transform *E. coli* DH5α and the OspA sequences were verified. Miniprep DNA was prepared, isolated, and used to transform HMS 174(DE3) host cells. The sequences of the non-lipidated derivatives are identical to the lipidated versions, except they lack the first 45 base pairs coding for the leader sequence and contain an Nde I site which contains a methionine codon which replaces the cysteine codon in the lipidated versions (see FIG. 9).

Example 8

Expression of Novel Recombinant OspA Antigens

To express/produce the novel recombinant OspA genes for antigenic purposes, an *E. coli* expression system controlled by the bacteriophage T7 RNA polymerase (Studier et al., *J. Mol. Biol.* 189:113-30, 1986) was used. In this expression system, the novel OspA genes were cloned into the multiple cloning site in one of the pET series of plasmids (e.g., pET30a). Because expression of the foreign gene is under the control of a bacteriophage T7 promoter, which is not recognized by *E. coli* RNA polymerase, expression is dependent on a source of T7 RNA polymerase. This enzyme is provided when the recombinant plasmids are transferred into an appropriate expression host, such as *E. coli* HMS174(DE3), which contains a chromosomal copy of the T7 RNA polymerase gene. Expression of the chromosomally integrated T7 RNA polymerase gene is under control of a lacUV5 promoter, which can be switched on (i.e. induced) by the addition of isopropyl β-D-1-thiogalactopyranoside (IPTG) or lactose (see FIG. 10). Consequently, expression of the foreign gene is also regulated by the addition of the inducer molecule.

The cells were induced at late log-phase and harvested 3-4 hours after induction. In induced cells, the chimeric OspA antigen was the most highly expressed protein as determined by SDS-PAGE of cell lysates. Most of the OspA chimeras were found in the supernatant. Contaminating *E. coli* proteins were removed by anion-exchange chromatography and the chimeric OspA proteins eluted in the void volume were concentrated by ultrafiltration.

The expression of the novel recombinant OspA proteins from each of the constructs was tested, and samples from induced and un-induced cultures were run on an SDS polyacrylamide gel (FIG. 11). For the lipidated (SEQ ID NOS: 2, 4, and 6) and non-lipidated (SEQ ID NOS: 8, 10, and 12) antigens, a band of approximately 31 kDa was observed in each case (see FIG. 11). The proteins were characterized and the molecular weights determined correlated (+/−0.5 daltons) with the theoretical molecular weights assuming the terminal methionine is cleaved off. FIG. 11 shows that the expressed recombinant lipidated OspA proteins comprise at least 10% of the total protein yield, verifying that the constructs are useful for their intended purpose.

Example 9

A Single Recombinant OspA Antigen (R OspA 1/2) Protects Against Infection with *B. burgdorferi* s.s. and *B. Afzelii*

The purpose of this study was to determine if a single recombinant antigen (rOspA 1/2; the polypeptide comprising SEQ ID NO: 2 (lipB sOspA $1/2^{251}$)), designed to retain the protective properties of OspA serotypes 1 and 2, is able to induce antibody responses which protect mice against infection with either *B. burgdorferi* s.s. (OspA serotype 1) or *B. afzelii* (OspA serotype 2). Evidence is provided to show that the inclusion of additional rOspA antigens did not have an antagonistic effect on the protective immunity afforded by the rOspA 1/2 antigen.

Design and Construction of rOspA 1/2.

To eliminate the risk of introducing adventitious agents, complementary overlapping synthetic oligonucleotides were used to generate DNA fragments that were ligated together and cloned into vector pET30a and the sequence was verified. This approach also enabled codon usage to be optimized for the *E. coli* host HMS174 (DE3) used to express the OspA gene. The novel gene is based on the proximal portion of a serotype-1 OspA sequence (amino acids 29 to 218, Strain B31; GenBank Accession Number X14407) fused to the distal portion of a serotype-2 sequence (amino acids 219 to 273, Strain PKo; Accession Number S48322). The 25 amino acid fragment from B. burgdorferi strain B31 (aa 164 to 188) was replaced with sequence from B. afzelii strain PKo (aa 164 to 188) because this region of the B31 OspA (aa 165-173) is highly related to the region encompassing the hLFA-1 epitope (aa 332-340). The N-terminal sequence including the leader sequence and the first 11 amino acids were derived from OspB (Strain B31; GenBank Accession Number X74810) in order to optimize lipidated protein expression. Other specific amino acid changes were made to improve the immunogenicity and conformational stability of the rOspA 1/2 molecule and the sequence of rOspA 1/2 (lipB sOspA $1/2^{251}$) is set out in SEQ ID NO: 2.

Animal Testing.

The ability of a single recombinant OspA antigen (rOspA 1/2) to prevent infection with two species of Borrelia, which express different OspA antigens, was assessed in C3H/HeJ mice immunized subcutaneously (days 0 and 28) with purified OspA antigen (0.1 μg or 0.03 μg doses) formulated with 0.2% (w/v) aluminum hydroxide as adjuvant. Mice were challenged 2 weeks after the booster immunization, either by intradermal injection (needle challenge; $7 \times 10^4$ cells) or by the natural route of infection (tick challenge). For the latter experiments, 8 nymphal ticks were applied per mouse and allowed to feed for up to 5 days. The nymphs were collected in the vicinity of Budweis (Czech Republic), an area endemic for Lyme disease. The majority of these ticks were infected with B. afzelii as determined by testing unfed ticks by PCR. The infectious status of the mice was determined four weeks later. In the tick challenge experiments, the presence of Borrelia was confirmed by culture (urinary bladder) and by detection of Borrelia DNA by real-time PCR (heart). Animal experiments were conducted in accordance with Austrian laws on animal experimentation and international guidelines (AAALAC and OLAW) and were reviewed by the Institutional Animal Care and Use Committee and approved by the Austrian regulatory authorities. Immunogenicity. The antibody response (μg IgG/ml) to rOspA 1/2 antigen was determined by ELISA using rOspA 1/2 as the coating antigen and an OspA specific monoclonal antibody (prepared in house) with a defined IgG content as a standard.

Diagnostic Procedures.

For the needle challenge experiments, the presence of antibodies to a conserved epitope in the surface-exposed lipoprotein VlsE protein (C6 ELISA; coated plates from Immunetics® C6 Lyme ELISA™) or to Borrelia antigens other than the OspA immunogen (Western blotting) was used to diagnose infection. Western blotting used a cell lysate prepared from B. burgdorferi s.s. strain ZS7 as this was the challenge organism. Animals were deemed infected if they were positive in both assays.

For the tick challenge experiments, the C6 ELISA and Western blotting were also done. However, Western blotting used lysates from B. burgdorferi s.s. ZS7, B. afzelii ACA1 and B. garinii KL11, because the identity of the infecting organism was unknown. Animals were considered to have undergone seroconversion only if both assays were positive. In addition, Borrelia infection was assessed by culture from the urinary bladder and by detection of B. burgdorferi s.l. nucleic acids in genomic DNA extracted from heart tissue using a real-time PCR assay targeting the 5'-region of OspA and a 16S rRNA gene-based assay. Animals were scored as PCR-positive only if a PCR product was detected with both assays. Overall, to judge an animal as infected, mice needed to be positive either by culture, PCR or serology.

Characterization of Infecting Borrelia.

Where possible, the infecting organism was cultured and the OspA sequence and deduced amino acid sequence determined for OspA residues 38-262 (B. afzelii VS461, GenBank Accession Number Z29087). This information was compared to OspA reference sequences so that the OspA type and Borrelia species could be inferred. For species which express a single OspA serotype, the OspA sequence for the type strain for the species was chosen as a reference, e.g., B. afzelii VS461 or B. valaisiana VS116 (GenBank Accession Number Z29087; AF095940). As B. garinii has multiple OspA types, OspA sequences for OspA genotypes 3-7 were used (i.e. strains PBr, PTrob, WABSou, TlsI and T25; GenBank Accession Numbers X80256, X80186, X85441, X85440 and X80254, respectively). For real-time PCR-based typing, sequence alignments of the OspA gene of 124 B. burgdorferi s.l. species deposited in GenBank were inspected for serotype-specific sequences and suitable primer-probe combinations were designed using Primer Express 3.0 (Applied Biosystems). All assays were run on an ABI Prism® 7900HT sequence detection unit using universal cycling conditions.

Prevention of B. Burgdorferi s.s (OspA Serotype-1) Infection by Immunization with rOspA 1/2.

All of the mice immunized with low doses of two different lots of the rOspA 1/2 antigen developed IgG antibodies specific for the immunogen as determined by ELISA. No antibodies were detected in the control mice which had been treated with vaccine formulation buffer containing aluminum hydroxide. To assess the ability of this immune response to prevent infection with B. burgdorferi s.s., a species that encodes a serotype-1 OspA, the mice were injected intradermally with $7 \times 10^4$ cells of B. burgdorferi s.s. strain ZS7. All of the control mice treated with buffer containing adjuvant showed serological evidence of infection as demonstrated by C6 ELISA and by Western blotting. None of the mice immunized with the rOspA 1/2 antigen became infected and the sera from these mice were negative by both assays. As little as 0.03 μg of the rOspA 1/2 antigen, when formulated with aluminum hydroxide as adjuvant and administered in a two dose immunization regimen, conferred 100% protection ($P<0.0001$, Fisher exact two tailed test) against a needle challenge with the virulent B. burgdorferi s.s. strain ZS7.

Prevention of B. Afzelii (OspA Serotype-2) Infection by Immunization with rOspA 1/2.

To assess the ability of immunization with the rOspA 1/2 antigen to prevent infection with B. afzelii, a species that encodes a serotype-2 OspA, mice were immunized, in two separate experiments, with the same antigen lots and study design as used in the needle challenge experiment described above. However, in this case, the immunized mice were challenged with feral ticks (nymphs) known to be infected mainly with B. afzelii. The ability of these feral ticks to transmit B. burgdorferi s.l. to mice was confirmed by challenging non-immunized control animals.

Most of the control mice (total 11/14, 79%) became infected. All infected control animals were positive for Borrelia DNA by two independent real-time PCR assays (16S rRNA and OspA genes). In 10/11 cases, it was possible to isolate Borrelia by culture of the urinary bladder. The remaining mouse was positive by serology and PCR. For 9 of the 10 culture isolates, OspA sequences were retrieved and all were typed as B. afzelii (>99% OspA sequence identity). Furthermore, all infecting organisms were typed as B. afzelii by PCR analysis of the DNA extracted from the heart using a real-time PCR assay specifically targeting serotype 2 OspA genes.

These data confirm that *B. afzelii* was the principal *Borrelia* species being transmitted from the infected feral ticks to their mouse host.

Few of the mice immunized with rOspA 1/2 (total 3/32, 9%) became infected. Of these three mice, one was infected as determined by all three diagnostic criteria (serology, PCR and culture) and sequence analysis revealed that the infecting organism was *B. garinii* serotype-6 (>99% OspA sequence identity). The remaining two animals deemed infected were positive by only two of the three criteria. One mouse was positive by serology and PCR. However, the infecting organism could not be retrieved in culture. Nevertheless, this organism could be typed as *B. garinii* serotype-7 by PCR analysis of the DNA extracted from the heart using PCR specific for the serotype-7 OspA gene. The third mouse was PCR and culture positive but serologically negative. The isolate cultured from this mouse was *B. valaisiana* as determined by sequencing (OspA sequence identity with *B. valaisiana* strain VS116). Importantly, none of the immunized mice (0/32) became infected with *B. afzelii*. As little as 0.03 μg of the rOspA 1/2 antigen, when formulated with aluminum hydroxide as adjuvant and administered in a two dose immunization regimen, conferred full protection against *B. afzelii* transmitted by feral ticks.

Conclusion.

A single recombinant outer surface protein A (OspA) antigen designed to contain protective elements from two different OspA serotypes (1 and 2) was able to induce antibody responses which protect mice against infection with either *B. burgdorferi sensu stricto* (OspA serotype-1) or *B. afzelii* (OspA serotype-2). Protection against infection with *B. burgdorferi* s.s. strain ZS7 was demonstrated in a needle challenge model. Protection against *B. afzelii* species was shown in a tick challenge model using feral ticks. In both models, as little as 0.03 μg of antigen, when administered in a two dose immunization schedule with aluminum hydroxide as adjuvant, was sufficient to provide complete protection against the species targeted. As anticipated, the protection afforded by this novel antigen did not extend to other *Borrelia* species as demonstrated by the antigen's inability to provide protection against infection with *B. garinii* and *B. valaisiana* strains. This proof of principle study proves that knowledge of protective epitopes can be used for the rational design of effective, genetically-modified vaccines requiring fewer OspA antigens and suggests that this approach may facilitate the development of an OspA vaccine for global use.

Example 10

Efficiency of Mouse Anti-OspA Antibodies to Bind to the Surface of Live *Borrelia* or to Inhibit Growth Thereof Correlates with Protection Against Needle Challenge Using A *B. Burgdorferi* s.s. Type 1 Strain The purpose of this study was to establish correlates of protection for mice immunized with the rOspA 1/2 antigen in a needle challenge model using a *Borrelia burgdorferi sensu stricto* OspA type 1 strain. Parameters analyzed were the potency of anti-OspA antibodies to bind to the surface of live Borreliae or to inhibit growth of Borreliae.

98 mice were deliberately immunized with a sub-optimal 3 ng dose of the rOspA 1/2 antigen adjuvanted with 0.2% Al(OH)3, which was 10-fold lower than the lower dose used in Example 9, in a prime-booster regimen so that, upon challenge, both protected and infected animals would be observed. Vaccination was carried out subcutaneously using a dose volume of 100 μl on days 0, 14 and 28. On day 38, pre-challenge sera samples were taken from 96 mice, and animals were challenged 10 days later with $19.4 \times ID_{50}$ of culture grown *B. burgdorferi* s.s. ZS7, and infection status was determined after four weeks. 71 of the 96 mice (72%) were found to be protected after immunizing with this low dose of antigen.

Four weeks post-challenge blood was taken to identify infected mice by Western blotting their sera against a membrane fraction of *B. burgdorferi* s.s. strain ZS7. At the challenge doses used, only infected mice had an antibody response to membrane antigens of strain ZS7 other than OspA (the response to OspA, induced by vaccine, was not scored).

Quantitation of OspA Antibody Binding to the Surface of Live Borreliae.

In this assay, *B. burgdorferi* s.s. strain B31 expressing OspA types 1 were incubated at a fixed dilution (1:100) with the pre-challenge mouse sera at room temperature in the presence of EDTA to prevent complement activation. After washing to remove unbound antibody, antibodies that were specifically bound to the cell surface were labeled by incubating the treated cells with an r-Phycoerythrin-conjugated anti-mouse Ig polyclonal antibody. Subsequently, a DNA stain (LDS-751) that emits red fluorescence, thereby enhancing detection, was used, and bacteria were then analyzed by flow cytometry (FACSCalibur, Beckton-Dickinson). The fluorescence intensity, which correlates with the number of antibody molecules attached to the cell surface, was recorded for at least 2,000 individual Borreliae, and the mean of the fluorescence intensities (MFI) was calculated. Normal mouse serum served as the negative control to evaluate the extent of non-specific surface binding of antibodies, while an OspA serotype 1-specific mAb served as a positive control to confirm the identity of the OspA type and to verify the level of OspA expression of the cells in the bacterial culture.

A Bacterial Growth Inhibition Assay.

To measure the potency of the pre-challenge sera to inhibit growth of the Borreliae, *B. burgdorferi* s.s. strain B31 expressing OspA type 1 was cultured at 33° C. in the presence of serial dilutions of heat-inactivated pre-challenge or non-immune mouse serum (negative control) in the presence of complement (normal guinea pig serum). When the bacteria in the control cultures incubated with non-immune sera had grown sufficiently, as determined microscopically, accurate cell counts were made by flow cytometric analysis. Cell cultures were mixed with a solution containing a defined number of fluorescence-labeled beads and a DNA-dye was added to fluorescently label the *Borrelia* cells. Samples were processed using a FACSCalibur Flow cytometer until 100 beads were counted, and the absolute cell concentrations were calculated (cells/ml) by comparing the numbers of events in the gate defining the beads and in the gate defining the Borreliae. The serum dilution that inhibited bacterial growth by 50% was calculated in comparison to the NMS control and reported as GI-50 titer. A standard serum preparation was used to normalize titers between different assays. Distribution of the measured serum parameters were compared among infected and protected animals by the non-parametric Mann-Whitney U test (Graphpad Prism Vers. 5.0).

Figure 19:
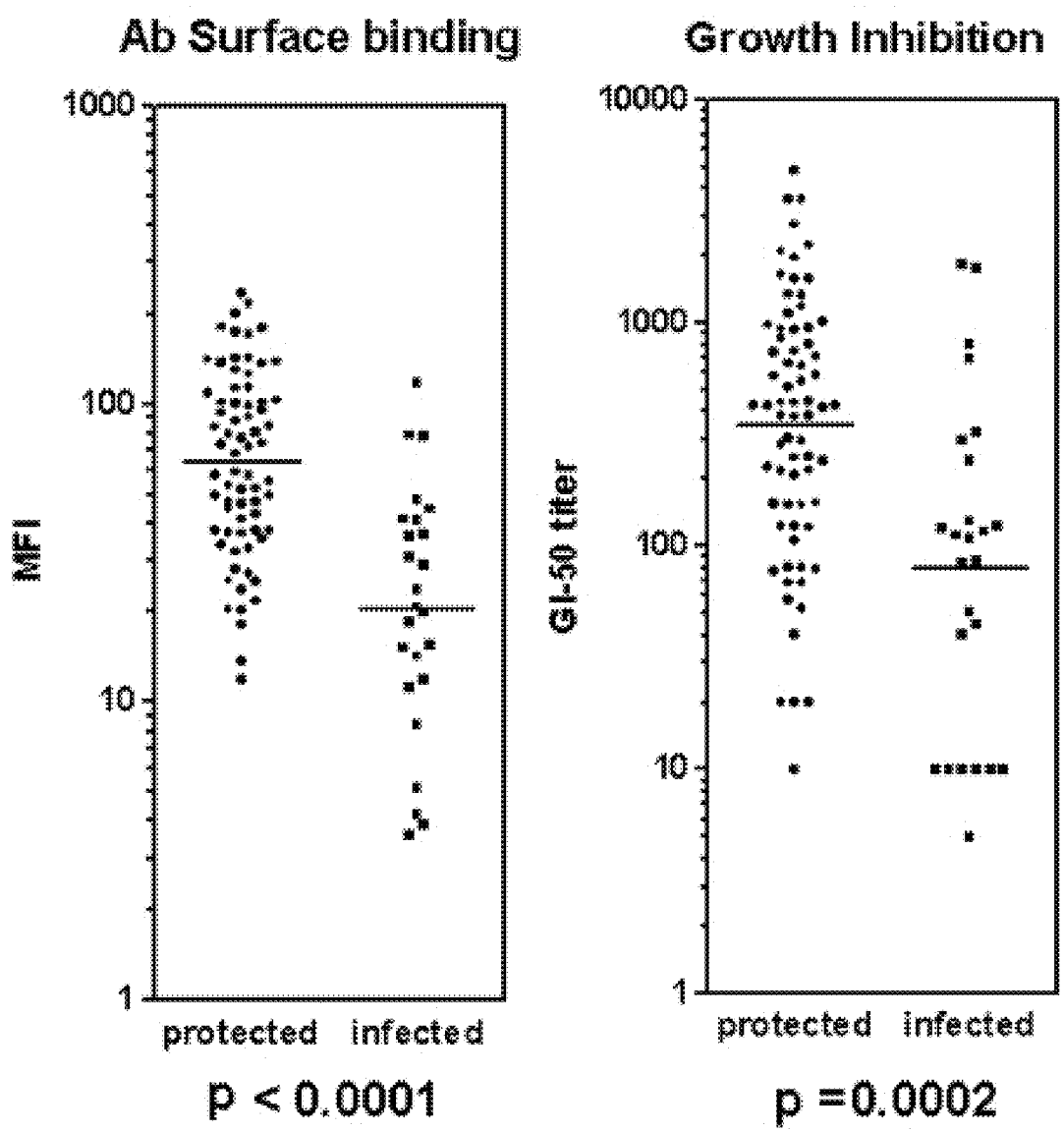
FIG. 19 shows the distribution of functional anti-OspA responses in antibody surface binding and growth inhibition assays among protected and infected animals immunized with 3 ng of OspA 1/2 before challenge with *B. burgdorferi* s.s. B31 strain. Mann-Whitney p values demonstrated a highly significant difference in functional antibody content between protected and infected animals.

Results of this study (see FIG. 19) clearly demonstrate that a highly significant correlation exists between the functional antibody content of the immune serum at the time of challenge and protection against infection with a high dose ($19.4 \times ID_{50}$) needle challenge of *B. burgdorferi* s.s. (ZS7). FACS-based fluorescence intensity measurements of live Borreliae expressing OspA type 1, which reflects the number of anti-OspA antibody molecules attached to the cell surface, carried out after incubation of the bacteria with the pre-challenge sera at a fixed dilution, correlated best with protection (p<0.0001 Mann-Whitney U test). However, growth inhibition titers also correlated highly significantly with protection (p=0.0002 Mann-Whitney U test, FIG. 19).

Example 11

Efficiency of Mouse Anti-OspA Antibodies to Bind to the Surface of Live Borrelia or to Inhibit Growth Correlates with Protection Against Tick Challenge Using a *B. Afzelii* Type 2 Strain The purpose of this study was to establish correlates of protection of mice immunized with the chimeric OspA 1/2 antigen in a tick challenge model, which utilizes the natural infection route by using feral ticks collected from Budweis in the Czech Republic to infect the mice. Since nymphal ticks from this endemic area are so predominantly infected with *B. afzelii*, they are considered to provide a *B. afzelii* OspA type 2 strain challenge. As set out in Example 10, the parameters analyzed were the potency of anti-OspA antibodies to bind to the surface of live Borreliae or to inhibit growth of Borreliae, both of which had been shown to correlate well against needle challenge with *Borrelia burgdorferi* s.s. Thus, this study serves to extend the applicability of using these two parameters as correlates of protection against natural infection of *B. afzelii*, the most prominent human disease associated genospecies in Europe.

Forty mice were immunized with a sub-optimal 3 ng dose of the rOspA 1/2 antigen adjuvanted with 0.2% Al(OH)3), which was 10-fold lower than the lower dose used in Example 9, in a prime-booster regimen. As in Example 10, this sub-optimal dose was chosen in order to ensure that both protected and infected animals would be observed after challenge. Vaccination was carried out subcutaneously using an injection volume of 100 µl on days 0, 14 and 28. On day 40, individual blood samples were taken from the mice to generate pre-challenge sera. Because the limited number of ticks available did not allow the challenge of all 40 mice, 20 mice were selected based on surface binding and anti-type 2 IgG concentrations to cover a broad range of responses. Eight ticks were applied to each mouse and were allowed to feed on the mice for 5 days. Four weeks after the challenge, the mice were sacrificed and the infectious status of the immunized and control mice was determined by Western blotting of sera against membrane antigens from *B. burgdorferi* s.s., *B. afzelii* and *B. garinii*; culture of *Borrelia* organisms from the bladder; and real time PCR detection of *Borrelia* from DNA extracted from the bladder.

Quantitation of OspA Antibody Binding to the Surface of Live Borreliae.

In this assay, *B. afzelii* strain Arcon expressing OspA type 2 was incubated at a fixed dilution (1:100) with the pre-challenge mouse sera at room temperature in the presence of EDTA to prevent complement activation. After washing to remove unbound antibody, antibodies specifically bound to the cell surface were labeled by incubating the treated cells with an r-Phycoerythrin-conjugated anti-mouse Ig polyclonal antibody. All subsequent steps in the assay where similar to those described in Example 10. Normal mouse serum served as the negative control for non-specific antibody binding. A high titer mouse serum raised against the tri-component rOspA vaccine formulation, together with OspA serotype 2-specific mAbs served as positive controls to confirm OspA serotype specificity and the OspA expression level of cells in the bacterial culture.

Bacterial Growth Inhibition Assay.

To measure the potency of the pre-challenge sera to inhibit growth of Borreliae, the *B. afzelii* strain Arcon expressing OspA type 2 was cultured at 33° C. in the presence of serial dilutions of heat-inactivated pre-challenge or non-immune mouse serum (negative control) without complement. When the bacteria in the control cultures, which were incubated with non-immune sera, had grown sufficiently, as determined microscopically, accurate cell counts were made by flow cytometric analysis. The procedure used to count the bacteria was similar to that previously described for the growth inhibition assay in Example 10. The serum dilution which inhibited bacterial growth by 50% was calculated in comparison to the NMS control and reported as GI-50 titer. A standard serum preparation was used to normalize titers between different assays.

Statistical Analysis.

Distribution of the measured serum parameters were compared in infected and protected animals by the non-parametric Mann-Whitney U test (Graphpad Prism Version 5.0).

Results.

Of the 20 animals immunized three times with 0.003 pg of rOspA 1/2 and challenged with 8 feral ticks, 7/20 (35%) were found to be infected. Due to limited tick availability, it was not possible to determine the exact infection rate of the challenge by challenging a control group of non-immunized mice. However, this challenge was not required for the purpose of the present study, and typically a rate of infection of 70-80% is achieved in challenge experiments with feral ticks from Budweis.

Figure 20:
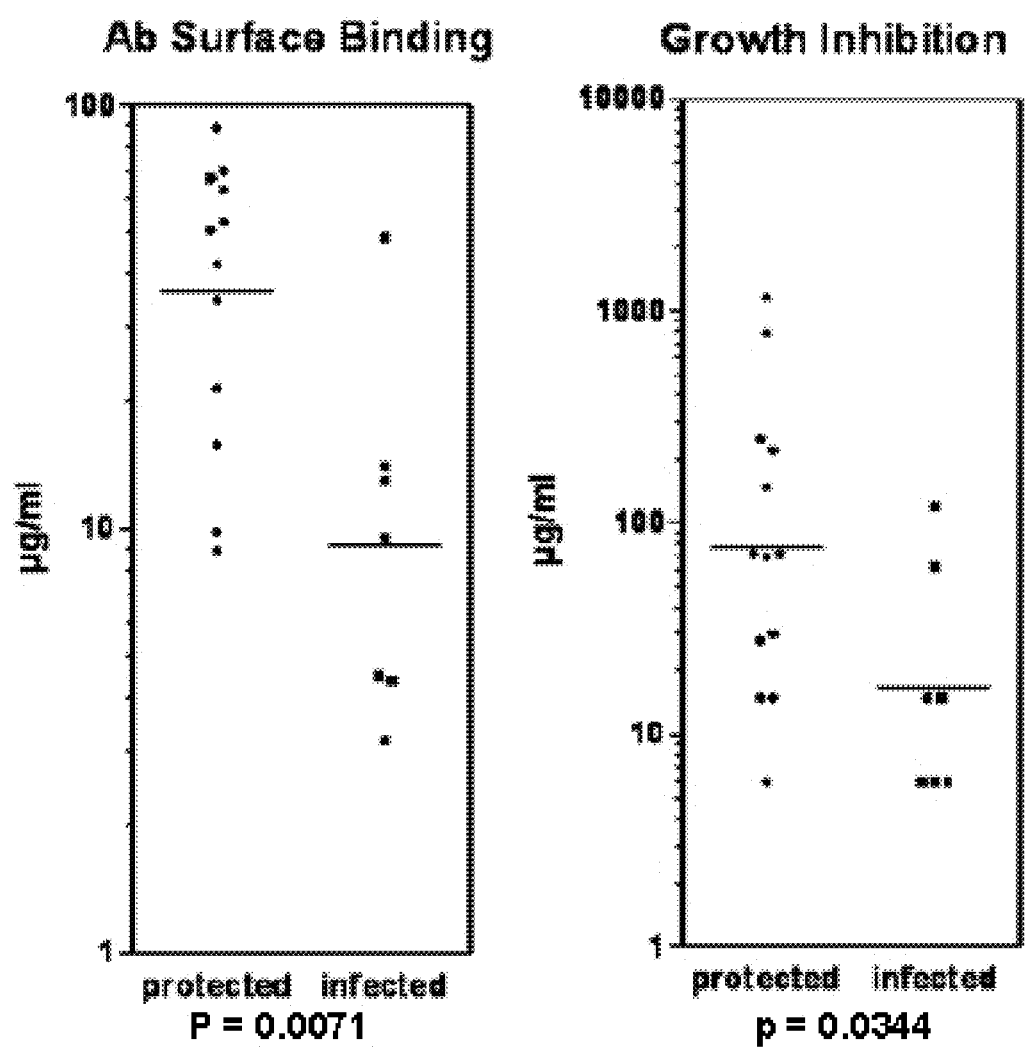
FIG. 20 shows the distribution of functional anti-OspA responses in antibody surface binding and growth inhibition assays among protected and infected animals immunized with 3 ng of OspA 1/2 before challenge with feral ticks. Mann-Whitney p values demonstrated a highly significant difference in functional antibody content between protected and infected animals.

Significant differences were detected between the protected and infected groups for the results of the surface binding (p=0.007) and growth inhibition (p=0.03) assays (FIG. 20).

Conclusion.

In this study it has been shown that a statistically significant correlation exists between the functional antibody content in mouse serum at the time of challenge and the protection against infection with a feral tick challenge applying 8 ticks per mouse. FACS-based fluorescence intensity measurements of live Borreliae expressing OspA type 2, which reflects the number of anti-OspA antibody molecules attached to the cell surface performed after incubation of the bacteria with the pre-challenge sera at a fixed dilution, correlated best with protection. Growth inhibition titers also correlated well with protection. In contrast to *Borrelia burgdorferi* s.s. strains, where complement is required for efficient killing, rOspA1/2 antigen induced antibodies that effectively inhibit *Borrelia* growth even in the absence of complement.

The results of the studies presented in Example 10 and 11, when taken together, establish the in vitro parameters of the mean fluorescent intensity (MFI) of surface bound antibody to live Borreliae and the GI-50 titer of immune mouse sera as "correlates of protection" in both examples where active mouse protection models are currently available (e.g., namely, a needle challenge model for *B. burgdorferi* s.s. OspA Type 1 strains and a tick challenge model for *B. afzelii* OspA Type 2 strains. Moreover, in the absence of reliable active protection models for evaluating protection against homologous *B. garinii* strains expressing OspA types 3-6, by inference, the aforementioned models can be used as in vitro "surrogate markers of protection" to evaluate the protective potential and cross strain coverage of various vaccine formulations for strains expressing all the vaccine homologous OspA types and even for those expressing heterologous OspA types. Indeed, when studies using these functional immune response assays were carried out on immune sera from mice immunized with the 3-component chimeric rOspA vaccine formulation, then comparable MFI and GI-50 titers were obtained for *B. garinii* (OspA types 3, 4, 5, 6) (see Examples 13), thus indicating, through these surrogate markers of protection, that protective responses were also achieved against strains for which currently no active mouse protection model exists. Furthermore, by comparing the immune responses of mice immunized with either (a), individual chimeric rOspA antigens; (b), or any one of the possible 2-component chimeric rOspA antigen vaccine formulation combinations; or (c), the 3-component chimeric rOspA antigen formulation, it was possible to show that the latter 3-component vaccine was required to optimally cover strains expressing OspA types 1-6 (Example 14). Moreover, through the use of these in vitro surrogate marker assays, it was possible to show that immune responses produced after immunizing mice with the 3-component chimeric rOspA vaccine formulation (rOspA 1/2, rOspA 6/4 and rOspA 5/3) do induce functional immune responses to all intra type variants (or subtypes) of types 1, 2, 3, 5, and 6 tested to date (see Example 15) and even to heterologous OspA types, other than the homologous OspA types 1-6 present within the vaccine (see Example 16).

Example 12

Multivalent Recombinant OspA Formulation Comprising 3 Antigens (1/2, 6/4, and 5/3) is Highly Immunogenic in Mice A multivalent OspA vaccine (rOspA 1/2, rOspA 5/3, and rOspA 6/4) was evaluated in a tick challenge model. Three recombinant OspA antigens containing the protective epitopes from OspA serotype 1 and 2 (SEQ ID NO: 2), OspA serotype 6 and 4 (SEQ ID NO: 4), and OspA serotype 5 and 3 (SEQ ID NO: 6) were combined in a vaccine.

Groups of ten female C3H/HeJ mice (age at immunization: 11 weeks) were immunized subcutaneously on days 0 and 28 with a fixed dose of 0.3 µg of the multivalent vaccine (0.1 µg of each, rOspA 1/2, rOspA 5/3, and rOspA 6/4). The tick challenge was done as described herein above with ticks from Budweis, Czech Republic. The ability of the feral ticks to transmit *B. burgdorferi* s.l. to mice was confirmed by challenging un-immunized control animals. The infection status of the challenged mice was determined by Western blotting, real-time PCR, and by culture.

Interim blood samples were taken on day 41 by orbital puncture. Final blood samples (day 70/71) were collected by heart puncture. Individual sera were prepared from whole blood by centrifugation (10 minutes; 1000-2000×G; RT). Sera were stored at ≤−20° C. until use.

In this experiment unfed ticks, taken from the same batch used to challenge the mice, were characterized to determine the overall infection rate and to confirm the species of the infecting organisms. When 80 nymphal ticks were tested for the presence of *B. burgdorferi* s.l. DNA by 16S rRNA real-time PCR, 32.5% (26/80) were found to be infected. The OspA-serotype could be determined by PCR-ELISA for 22 of the 26 infected nymphs; 86% (19/22) were typed as *B. afzelii* and 14% (3/22) as *B. burgdorferi* s.s.

All of the non-immunized control mice (100%; 10/10) became infected, whereas only one of the mice immunized with the multivalent rOspA vaccine became infected (10%; 1/10). There was 100% agreement between the different methods used to identify infected mice. The multivalent rOspA vaccine resulted in a statistically highly significant protection (p=0.00012; Fisher's exact two tailed test) when compared to the control group.

These data show that immunization with a multivalent rOspA vaccine, which contains the rOspA 1/2 antigen, is able to prevent infection with *B. afzelii*, a *Borrelia* species which expresses a serotype 2 OspA. Further, there is no evidence that the inclusion of additional rOspA antigens has an antagonistic effect on the protective immunity afforded by the rOspA 1/2 antigen.

This vaccine provided protection against tick-transmitted infection with *B. afzelii* which was equivalent to that seen with the OspA 1/2 antigen; 0.3 µg of the vaccine (0.1 µg of each antigen) formulated with 0.2% Al(OH)3 and administered in a two dose schedule provided 90% protection as determined by Western blot, culture of *Borrelia* and detection of *Borrelia* DNA by PCR.

Example 13

A Vaccine Comprising the Three-Component Vaccine (OspA 1/2, OspA 6/4, and OspA 5/3) Induces High Levels of Functional Anti-OspA Antibodies which Bind to and Inhibit Growth of *Borrelia* Strains Expressing OspA Types 1-6

Since both surface binding (MFI) and growth inhibition (GI-50 titers) were shown to be good correlates of protection in a needle challenge (*B. burgdorferi* s.s.) model (Example 10) and in a tick challenge (*B. afzelii*) mouse model (Example 11), the present study was undertaken to determine if equivalent functional immune responses are induced by the 3-component chimeric rOspA antigen vaccine formulation against *B. garinii* OspA serotypes 3-6, for which no in vivo protection model is available to investigate the efficacy of a vaccine.

Mouse Immunization.

Groups of 10 female C3H/HeJ mice were immunized subcutaneously three times (day 0, day 14, day 28) with a 1:1:1 mixture of rOspA-1/2, rOspA-6/4 and rOspA-5/3) at three different doses (1, 0.1, 0.03 µg protein per dose) combined with 0.2% Al(OH)3 as an adjuvant. Serum was generated from blood samples taken on day 40.

Quantitation of OspA antibody binding to the surface of live Borreliae. In this assay, in vitro grown cultures of six representative *Borrelia* strains expressing OspA types 1-6 (*B. burgdorferi sensu stricto* B31/OspA-1; *B. afzelii* Arcon/OspA-2; *B. garinii* PBr/OspA-3; *B. garinii* DK6/OspA-4; *B. garinii* W/OspA-5; and *B. garinii* KL11/0spA-6) were incubated at a fixed dilution (1:100) with pools of the peak titer mouse sera at room temperature in the presence of EDTA to prevent complement activation. The subsequent washing, labeling, detection and analysis procedures were similar to those described in Example 10. Normal mouse serum served as the negative control for non-specific binding of antibodies.

Bacterial Growth Inhibition Assay.

To measure the potency of the pre-challenge sera to inhibit growth of Borreliae, six representative strains expressing OspA types 1-6 (B31, Arcon, PBr, DK6, W, and KL11) were cultured at 33° C. in the presence of serial dilutions of heat-inactivated peak titer serum pools or non-immune mouse serum (negative control). B31 was cultured in the presence of complement (guinea pig serum), while the other five strains were tested in the absence of complement. Once again, growth inhibition assays were carried out as described in Example 10. A standard serum preparation was used to normalize titers between different assays.

Surface Binding and Growth Inhibiting Efficiency of Anti-OspA Antibody Responses.

Figure 21:
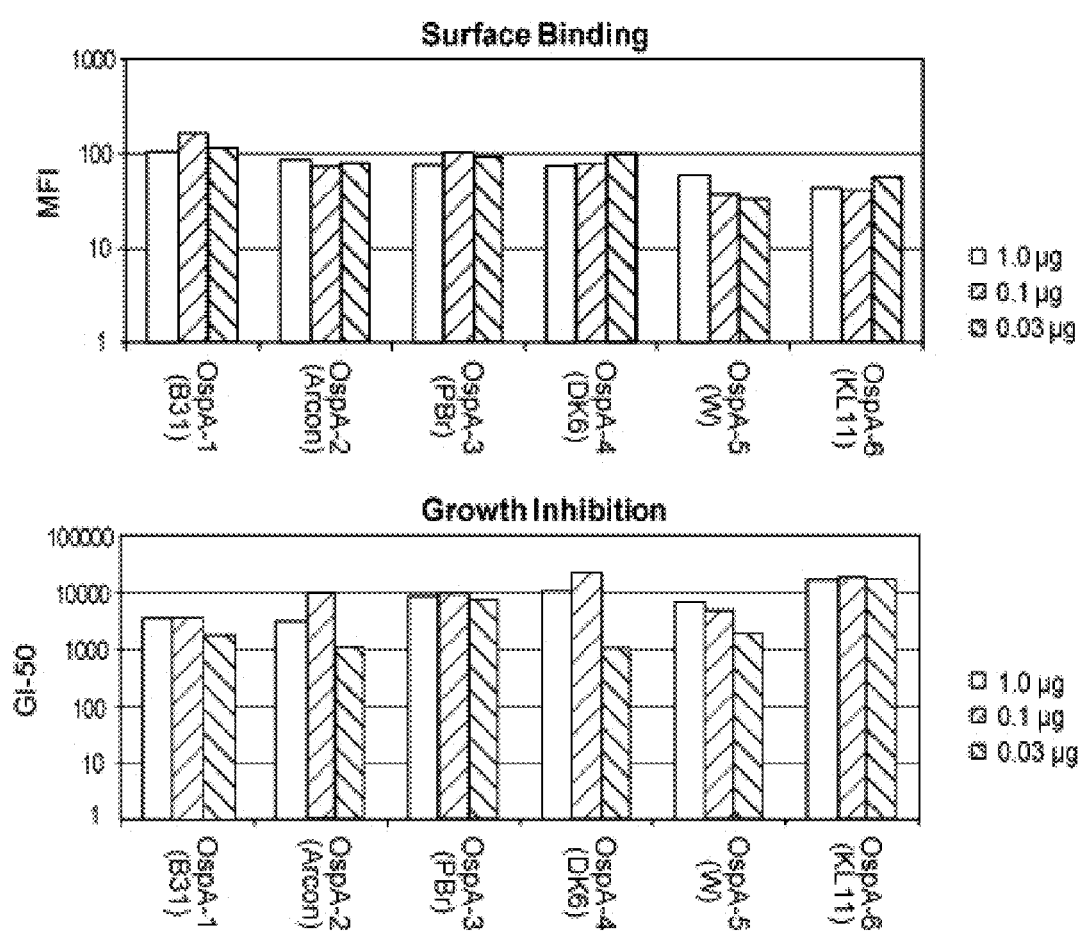
FIG. 21 shows surface binding (mean fluorescence intensities (MFI)) and growth inhibition (GI-50 titers) in pooled mouse sera after immunization with three doses of the 3-component chimeric OspA vaccine. Efficient surface binding and growth inhibition were detected against all six *Borrelia* strains expressing OspA types homologous to the OspA types in the vaccine (types 1-6).

Intense fluorescence staining with MFI values, ranging from 50 to 200, was observed for all six *Borrelia* strains when tested with the three serum pools derived from the different immunization dose groups (1.0, 0.1 and 0.03 µg protein per dose) of the 3-component vaccine at a dilution of 1:100 (FIG. 21). When the serum pools from the 3 dose groups were tested for their capacity to inhibit bacterial growth, the 3-component vaccine was also found to have induced strong GI-50 titers to all six OspA type strains, ranging from 1000 (type 4 strain, 0.03 µg dose) to 20,000 (type 6 strain).

Conclusion.

Taken together, these results demonstrate that the rOspA antigens are highly immunogenic and induce large quantities of functional antibodies which can bind to the surface of live Borreliae and inhibit growth of Borreliae. Coverage among the six strains tested was complete, as high fluorescence intensities and high growth inhibition titers were detected, comparable to the levels observed for the OspA types 1 and 2. In summary, the results presented in this study indicate that antibody responses induced by the tri-component rOspA vaccine (1/2+5/3+6/4), when formulated with Al(OH)3, prevent infections by strains expressing OspA types 1-6, which, as epidemiological studies have shown, theoretically covers over 99% of isolates causing human disease in Europe and North America and, thus, is highly effective in preventing Lyme Borreliosis.

Example 14

A vaccine comprising the three component vaccine (OspA 1/2, OspA 6/4, and OspA 5/3) is Required to Optimally Cover *Borrelia* Expressing OspA Types 1-6

The purpose of this study was to investigate and compare the immunogenicity and the cross strain coverage of functional surface binding and/or growth inhibiting antibodies induced by single and multi-component formulations of rOspA Lyme Borreliosis vaccine, again using the efficiency of anti-OspA antibodies to bind to the surface of live Borreliae and to inhibit growth of Borreliae in vitro as correlates of protection Immunization of Mice.

Ten female mice (C3H) per group were immunized with 0.1 µg of a single component vaccine comprising rOspA 1/2 antigen, rOspA 6/4 antigen, or rOspA 5/3 antigen; a two-component vaccine comprising 0.1 µg of both 1/2+5/3 antigens, 1/2+6/4 antigens, or 5/3+6/4 antigens; or a three-component vaccine comprising a combination 0.1 µg of all three 1/2+5/3+6/4 antigens adjuvanted with 0.2% Al(OH)3 in a prime-booster regimen. Vaccination was carried out subcutaneously using a dose volume of 200 µl on days 0, 14 and 28. On day 42, individual blood samples were taken from mice to generate sera.

Antibody Surface Binding and Growth Inhibition Assays.

A slightly modified version of the surface binding assay was used to determine the efficiency of anti-OspA IgG to bind to the surface of live Borreliae. Serial dilutions of a serum pool with defined MFI titers were included in the analyses to create a standard curve from which relative titers of test sera were read off after interpolation with a non-linear regression curve. The MFI titer of standard serum for the individual strains expressing OspA types 1-6 was defined as the highest dilution at which the fluorescence intensity of the Borreliae was determined to be at least 3-fold over the fluorescence intensity observed with normal mouse serum. All determinations were carried out in duplicate.

Figure 22:
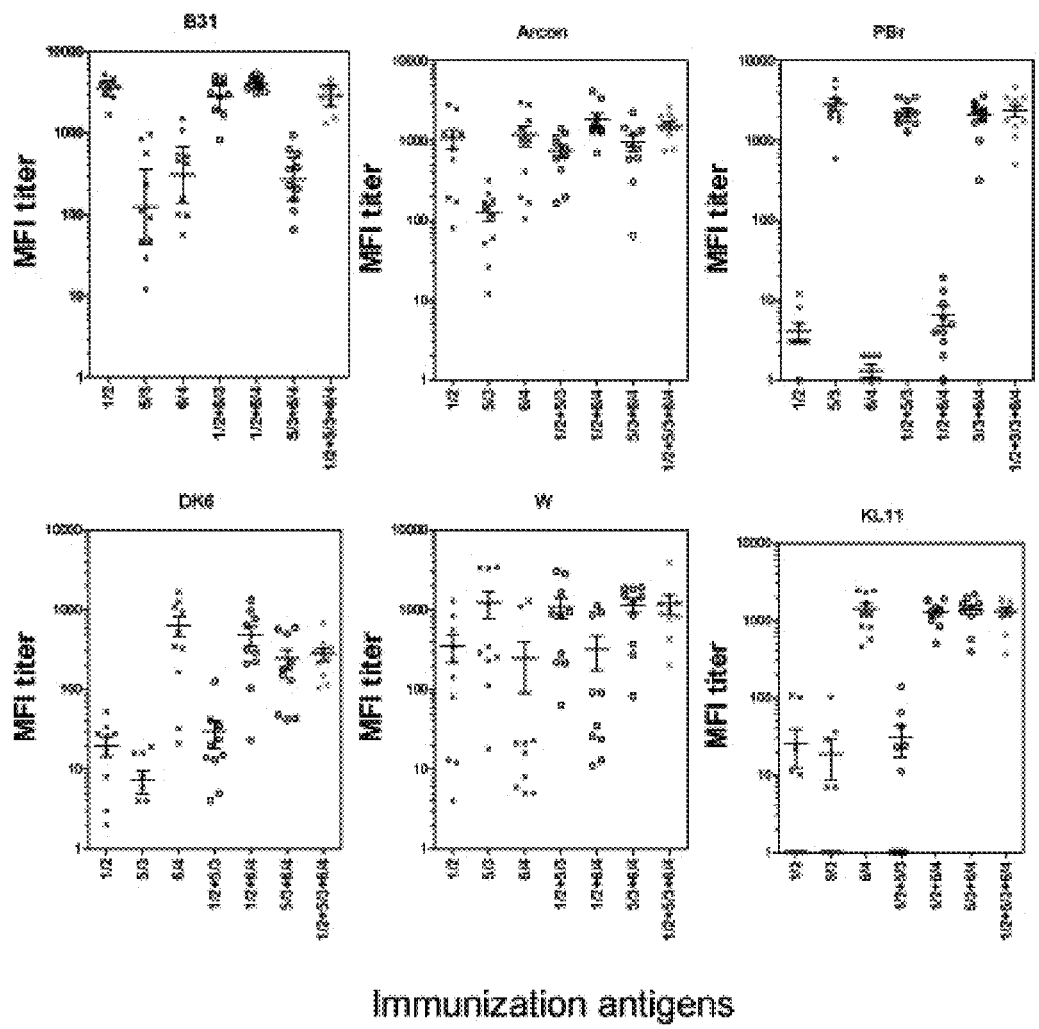
FIG. 22 shows mean fluorescence intensity (MFI) titers that were obtained using day 42 sera from individual mice immunized with combinations of rOspA vaccines in a surface binding assay (SBA). Results showed that all three rOspA components (1/2, 6/4, and 5/3) are required in a multivalent vaccine to induce high titers of surface binding IgG antibodies against all 6 strains in C3H mice. Two-component vaccines did not fully cover the 2 missing strains.

The scatter plots presented in FIG. 22 compare the MFI titers to the six strain expressing homologous OspA types observed for the immune sera of individual C3H mice after immunization with either single rOspA antigens or rOspA antigen combinations. Results showed that a formulation containing all three rOspA antigens (1/2, 5/3 and 6/4) was necessary to induce high MFI titers against all six *Borrelia* strains expressing OspA types 1-6, and that formulations composed of two rOspA antigens (i.e. covering four strains) did not fully cover the strains expressing the two OspA types not present in the formulation.

Figure 23:
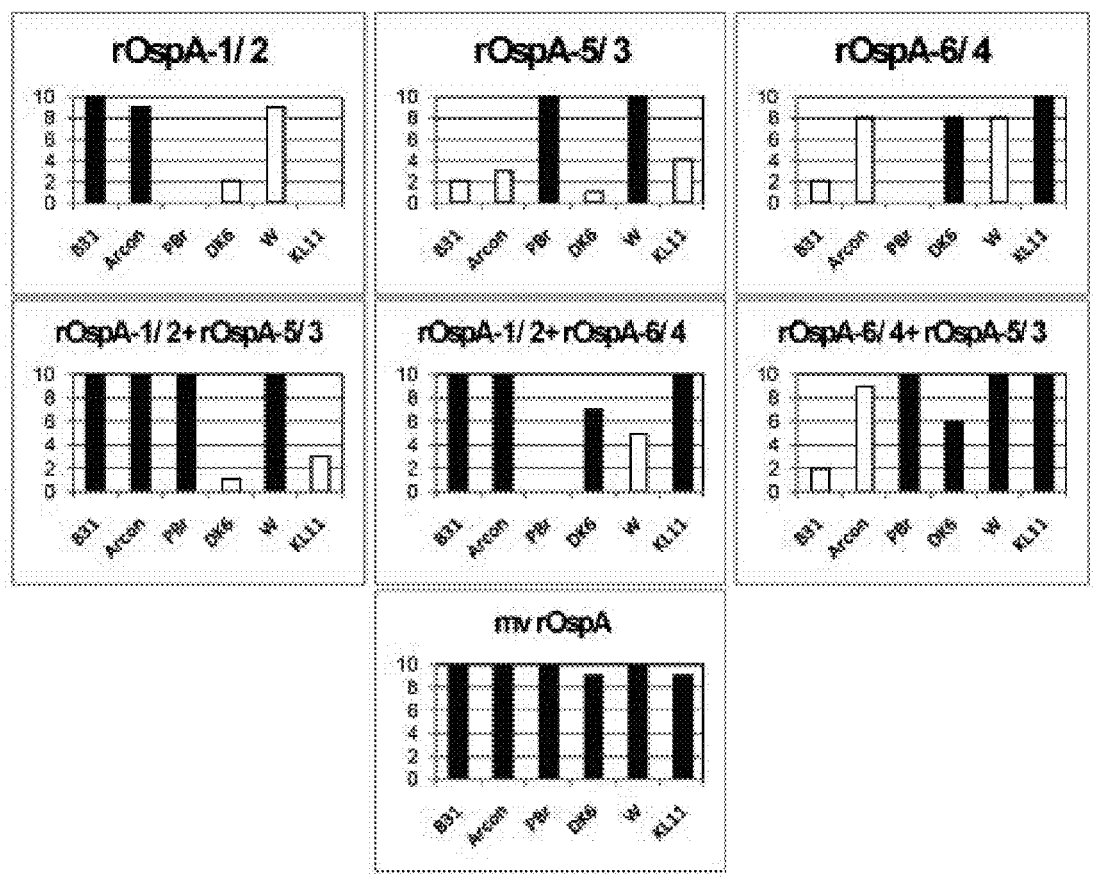
FIG. 23 shows the growth inhibition of Borreliae using day 42 sera from individual mice (in groups of 10) immunized with combinations of rOspA vaccines. Only the multivalent vaccine (the vaccine comprising all three strains) gave >50% growth inhibition in >90% of the animals (n=10). Bars in black (solid bars) indicate the strains homologous to the vaccine used.

To determine the potency of the various vaccine combinations to induce growth inhibiting antibodies, six representative Borreliae strains (B31, Arcon, PBr, DK6, W, KL11), expressing OspA types 1-6 respectively, were cultured at 33° C. in the presence of heat-inactivated immune or non-immune mouse serum pools. All sera were tested at a single dilution. The following dilutions were used: B31, PBr and KL11 1:200, Arcon, DK6 and W 1:100. PBr was cultured in the absence of 20% complement, while the other 5 strains were tested in the presence of complement. Baby rabbit complement was used for DK6, W and KL11, while guinea pig serum was used for B31 and Arcon. When the bacteria in the control cultures incubated with non-immune sera had grown sufficiently, as determined microscopically, accurate cell counts were made as described previously (see Example 10). The percentage of bacterial growth inhibition was calculated from the cell count observed with test serum relative to the normal mouse serum control. The overall growth inhibition observed for the different formulations tested was then presented (FIG. 23) as the number of animals among the different groups of ten C3H mice that showed more than 50% growth inhibition. Results demonstrated that the 3-component formulation was the only formulation capable of inducing high titers of growth-inhibiting antibodies against all six representative strains expressing OspA types 1-6 (FIG. 23). In all cases, the 3-component vaccine formulation provided >50% growth inhibition in >90% of the immunized animals. The 2-component vaccine formulations did not fully cover the two strains expressing the OspA types not present in the vaccine. The formulation comprising rOspA 1/2+6/4 did not cover the type 3 strain; the formulation comprising rOspA 1/2+5/3 formulation did not cover types 4 or 6; and the formulation comprising rOspA 5/3+6/4 did not cover type 1.

Example 15

The Multivalent OspA Vaccine Formulation Covers *Borrelia* Expressing Intra-Type Variants or Subtypes of OspA Types 1-6

Although *Borrelia* OspA types 1-6 were selected as the basis for the design and construction of the multivalent rOspA vaccine, Borreliae which express OspA protein variants of types 1, 2, 3, 5, and 6 have also been isolated. These variants, while being classified as being within the same type, have slightly altered nucleotide gene sequences and amino acid protein sequences. Thus, intra-type variants or subtypes exist among OspA types 1, 2, 3, 5, and 6 (see FIG. 24). No intra-type variant or subtype has yet been observed for OspA type 4.

The purpose of this study was to confirm that immune serum generated by immunizing mice with the 3-component multivalent rOspA vaccine contains functional antibodies which can bind to the surface of live Borreliae expressing these intra-type variants or subtypes.

For this study, a pooled mouse immune serum was generated by immunizing 70 female C3H mice three times with 0.3 µg of the 3-component multivalent rOspA vaccine on days 0, 14 and 28. On day 42, mice were bled and serum was obtained and pooled. The pooled immune serum was then used to test for binding of antibodies to the surface of live Borreliae. *Borrelia* cultures were incubated with the immune serum pool or control normal mouse serum at 1:100 in duplicate, and fluorescence intensities of Borreliae measuring binding of anti-OspA antibodies to the bacteria was monitored by FACS analyses as described herein above.

Figure 24:
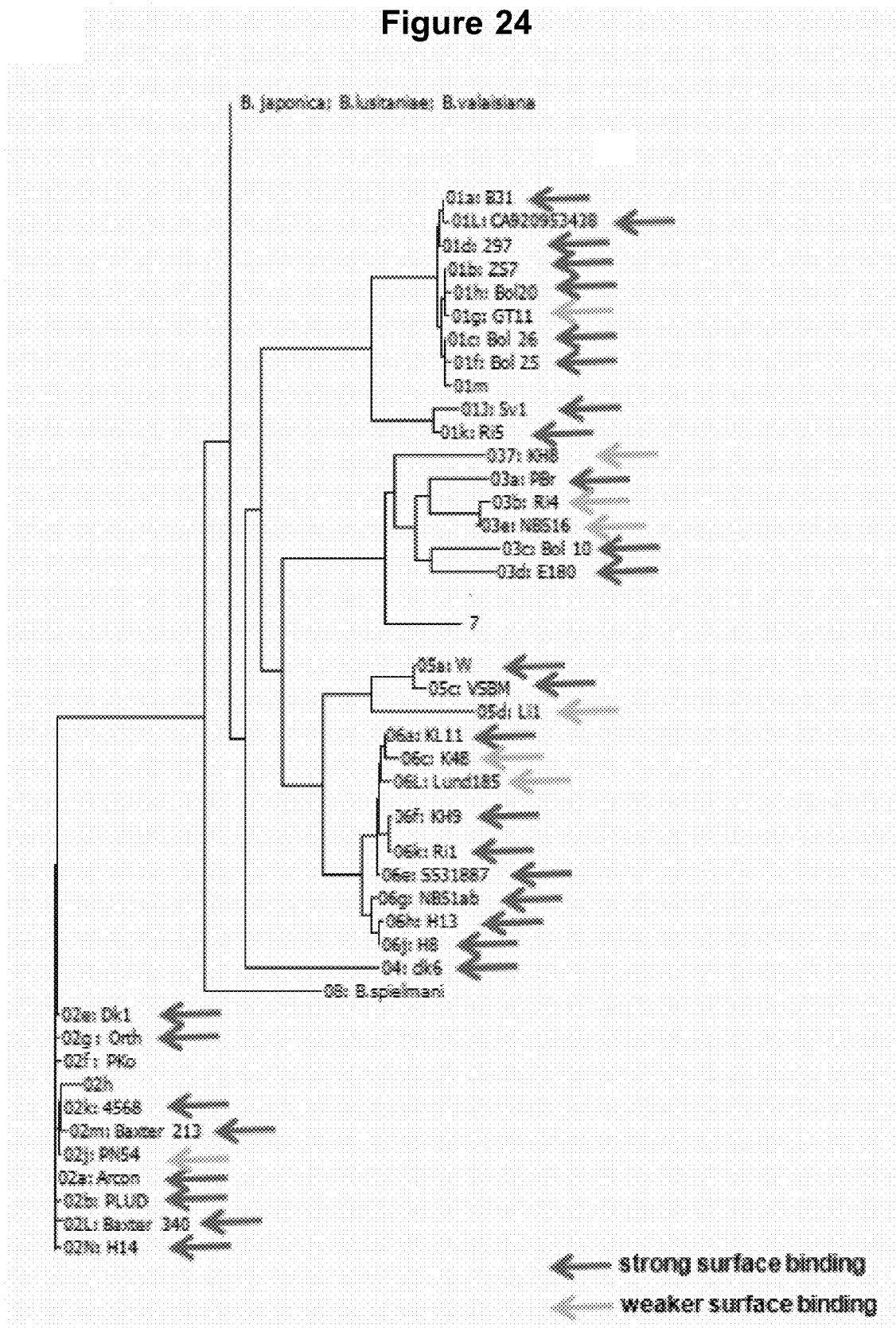
FIG. 24 shows the coverage of Borreliae expressing intratype variants of OspA. Surface binding was categorized into strong (fluorescence increased >10-fold) or weaker (fluorescence increased 2-10-fold).

High levels of surface binding antibodies (defined as a fluorescence intensity of over 10 times that observed for a non-immunized mouse control serum) at a serum dilution of 1:100 were detected for most of the strains expressing OspA subtypes 1-6. In particular, high levels of antibody binding were detected with Borreliae strains expressing OspA subtypes 1a, 1b, 1c, 1d, 1f, 1 h, 1 J, 1 k, and 1l; 2a, 2b, 2e, 2g, 2k, 2l, and 2n; 3a, 3c, 3d, and 3e; 5a and 5c; and 6a, 6e, 6f, 6g, and 6k (FIG. 24). Weaker binding (defined as a fluorescence intensity of between 2-10 times that observed for a non-immunized mouse control serum) was observed with Borreliae strains expressing OspA subtypes 1g, 2j, 2m, 3b, 5d, and 6l (FIG. 24), but this weaker binding was primarily due to the low expression of the OspA protein under the growth conditions used.

Conclusion.

The 3-component chimeric rOspA vaccine induces functional, surface-binding antibodies against all intra-type variants or subtypes of OspA types 1, 2, 3, 5, and 6 in C3H mice.

Example 16

The Multivalent OspA Vaccine Formulation Provides Protection Against Other Types of *Borrelia* in Addition to Those Expressing OspA Types 1-6

The purpose of this study was to determine if the 3-component chimeric rOspA antigen vaccine formulation (comprising all 3 chimeric antigens—1/2, 6/4, and 3/5) could also provide protection against *Borrelia* expressing OspA types other than the homologous OspA types 1-6. 40 C3H mice were immunized three times with 0.3 µg of the 3-component vaccine on days 0, 14 and 28. On day 42, the mice were bled, and a serum pool was made and used to evaluate the efficiency of surface binding and growth inhibition against strains expressing heterologous OspA types.

The results of this study showed that the 3-component chimeric rOspA vaccine does induce antibodies which bind to the surface of Borreliae and inhibit growth of other types of Borreliae, including strains of *B. spielmanii, B. valaisiania, B. lusitaniae* and *B. japonica* (see Table 9). In the case of *B. garinii* expressing OspA type 7, only weak surface binding and little or no growth inhibition was observed; however, this weak binding and small amount of growth inhibition may be due to low expression levels of OspA under the in vitro culture conditions used rather than to the lack of binding of immune serum antibodies.

TABLE 9

Surface Binding and Growth Inhibition against other types of *Borreliae*

| | Genotype | | | | |
|---|---|---|---|---|---|
| | *B. g.* OspA-7 | *B. spielmanii* | *B. valaisiana* | *B. lusitaniae* | *B. japonica* |
| Surface Binding | (+) | + | + | + | + |

TABLE 9-continued

Surface Binding and Growth Inhibition against other types of *Borreliae*

| | Genotype | | | | |
|---|---|---|---|---|---|
| | *B. g.* OspA-7 | *B. spielmanii* | *B. valaisiana* | *B. lusitaniae* | *B. japonica* |
| Growth Inhibition | − | + | + | + | + |

+: significant surface binding and/or growth inhibition
−: no significant binding/growth inhibition
(+−): low intensity surface binding

Example 17

Multivalent OspA Vaccine Formulations Induces Antibodies to a Common Epitope at the N-Terminus of the OspA Molecule which can Contribute to Protection Against any OspA Expressing *Borrelia* Strain During the course of investigating the protective efficacy of multivalent chimeric rOspA formulations, a monoclonal antibody (F237/BK2) was generated against a 2-component rOspA vaccine comprising rOspA-1/2 and rOspA-6/4. F237/BK2 was shown by anti-OspA ELISA to bind to all OspA types investigated thus far (OspA types 1-7), as well as to the 3 chimeric rOspA antigens (rOspA-1/2, rOspA-5/3 and rOspA-6/4) Such result indicate that F237/BK2 recognizes a common epitope found on all OspA molecules. Moreover, preliminary epitope mapping studies indicate that this common epitope is located on the less variable N-terminal half of the molecule (i.e. at the N-terminus of amino acid 130), where OspA sequence homologies are most commonly observed.

Interestingly, F237/BK2 was also shown to bind to the surface of Borreliae expressing homologous OspA types 1-6 and heterologous OspA types, including those expressed by *B. spielmanii, B. valaisiania* and *B. japonica*, albeit less efficiently than monoclonal antibodies directed against C-terminal type-specific epitopes. Using methods similar to those described in previous examples, F237/BK2 was also found to inhibit the growth of representative strains expressing OspA types 1, 2, 4, 5 and 6.

When F237/BK2 was tested in an in vivo passive protection model in mice, F237/BK2 was observed to confer protection against feral tick challenge, corresponding to a *B. afzelii* Type 2 challenge. Ticks were collected in Wundschuh (Styria, Austria), which are known to be predominantly infected with *B. afzelii*. Ten female C3H mice were injected intraperitoneally with 500 µg of affinity-purified mAb F237/BK2. Two hours later, 8 ticks were applied per animal to 10 passively immunized mice as well as to 10 sham-immunized animals. Four days later, the fed ticks were removed. On day 90, mice were sacrificed and analyzed for infection by serological testing, PCR analysis and *Borrelia* culture, as described herein above. No animal was infected in the group treated with F237/BK2, whereas 5 animals (50%) were infected with *B. afzelii* in the control group. Thus, monoclonal antibody F237/BK2 provided statistically significant (p=0.0325) passive protection against a tick challenge when compared with the sham-immunized control mice. This is the first time that a monoclonal antibody which binds to a common epitope on the N-terminal half of the molecule has been reported to be involved in protection. Moreover, if a vaccine could induce antibodies recognizing this common epitope, such an antibody would certainly contribute to the vaccine's cross protective efficacy.

To test whether such antibodies were indeed induced by the 3-component chimeric rOspA vaccine formulation, a monoclonal antibody inhibition ELISA was carried out employing peroxidase-labeled F237/BK2. In these experiments, a GST-OspA type 3 protein was used as coating antigen, and either normal mouse serum or a serum pool from C3H mice immunized three times with the 3-component chimeric rOspA vaccine was added to the wells at a dilution of 1:100. Sixty minutes later, peroxidase-labeled F237/BK2 was added at a pre-optimized concentration to eventually give an Optical Density (OD) value of around 1 for the non-inhibiting normal mouse serum control, and incubation was continued for an additional 60 min. Finally, ELISA plates were washed and developed with TMB substrate.

Using this monoclonal antibody inhibition ELISA assay, it could be demonstrated that the 3-component chimeric rOspA formulation does indeed induce antibodies which bind to an epitope identical to or in close proximity to the epitope recognized by mAb F237/BK2. OD values were significantly reduced (e.g., typically by 20-30%) by the anti-OspA immune sera compared to the non-inhibiting normal mouse serum control.

Conclusion.

This study shows that the 3-component chimeric rOspA vaccine is able to induce both a type-specific and a broad cross-protective immune response.

Example 18

Additional Synthetic OspA Nucleic Acid and Polypeptide Molecules

The aim of the study was to design additional novel OspA antigens comprising serotypes 1 and 2, 6 and 4, and 5 and 3, respectively. Three synthetic OspA genes (SEQ ID NOS: 168 (orig sOspA 1/2), 170 (orig sOspA 6/4), and 172 (orig sOspA 5/3)) were designed to encode OspA polypeptide molecules with protective epitopes from OspA serotypes 1 and 2 (orig sOspA 1/2), OspA serotypes 6 and 4 (orig sOspA 6/4) and OspA serotypes 5 and 3 (orig sOspA 5/3) of *Borrelia*. The primary amino acid sequences of these molecules (SEQ ID NOS: 169, 171, and 173, respectively) are provided in Table 1. These sequences comprise original chimeric constructs, i.e. without mutations and without codon optimization.

Example 19

Multivalent Recombinant OspA Formulation Comprising 3 Antigens (1/2, 6/4, and 5/3) is Immunogenic in Mice A multivalent OspA vaccine comprising original construct formulations without codon optimization and without mutations (orig OspA 1/2, orig OspA 5/3, and orig OspA 6/4) is evaluated in a tick challenge model. Three recombinant OspA antigens containing the protective epitopes from OspA serotypes 1 and 2 (SEQ ID NO: 169), OspA serotypes 6 and 4 (SEQ ID NO: 171), and OspA serotypes 5 and 3 (SEQ ID NO: 173) are combined in a vaccine.

Groups of ten female C3H/HeJ mice (age at immunization: 11 weeks) are immunized subcutaneously on days 0 and 28 with a fixed dose of 0.3 µg of the multivalent vaccine (0.1 µg of each, orig OspA 1/2, orig OspA 5/3, orig OspA 6/4). The tick challenge is done as described herein above with ticks from Budweis, Czech Republic. The ability of the feral ticks to transmit *B. burgdorferi* s.l. to mice is confirmed by challenging un-immunized control animals. The infection status of the challenged mice is determined by Western blotting, real-time PCR, and by culture.

Interim blood samples are taken on day 41 by orbital puncture. Final blood samples (day 70/71) are collected by heart puncture. Individual sera are prepared from whole blood by centrifugation (10 minutes; 1000-2000×G; RT). Sera are stored at ≤−20° C. until use.

In this experiment unfed ticks, taken from the same batch used to challenge the mice, are characterized to determine the overall infection rate and to confirm the species of the infecting organisms.

Example 20

A Vaccine Comprising a Three-Component Vaccine (Orig OspA 1/2, Orig OspA 6/4, and Orig OspA 5/3) Induces High Levels of Functional Anti-OspA Antibodies which Bind to and Inhibit Growth of *Borrelia* Strains Expressing OspA Types 1-6

The results presented in Example 13 indicate that antibody responses induced by the tri-component rOspA vaccine (lipB sOspA1/2+lipB sOspA 5/3+lipB sOspA 6/4), when formulated with Al(OH)3, prevent infections by strains expressing OspA types 1-6 and, therefore, are effective in preventing Lyme Borreliosis. Thus, the present study is being carried out to determine if equivalent functional immune responses are induced by the tri-component OspA vaccine comprising chimeric original (orig) OspA antigens (Orig sOspA1/2+Orig sOspA 5/3+Orig sOspA 6/4).

Mouse Immunization.

Groups of 10 female C3H/HeJ mice are immunized subcutaneously three times (day 0, day 14, day 28) with a 1:1:1 mixture of Orig sOspA1/2+Orig sOspA 5/3+Orig sOspA 6/4) at three different doses (1, 0.1, 0.03 µg protein per dose) combined with 0.2% Al(OH)3 as an adjuvant. Serum is generated from blood samples taken on day 40.

Quantitation of OspA Antibody Binding to the Surface of Live Borreliae.

In this assay, in vitro grown cultures of six representative *Borrelia* strains expressing OspA types 1-6 (*B. burgdorferi sensu stricto* B31/OspA-1; *B. afzelii* Arcon/OspA-2; *B. garinii* PBr/OspA-3; *B. garinii* DK6/OspA-4; *B. garinii* W/OspA-5; and *B. garinii* KL11/0spA-6) are incubated at a fixed dilution (1:100) with pools of the peak titer mouse sera at room temperature in the presence of EDTA to prevent complement activation. The subsequent washing, labeling, detection and analysis procedures are similar to those described in Examples 10 and 13. Normal mouse serum serves as a negative control for non-specific binding of antibodies.

Bacterial Growth Inhibition Assay.

To measure the potency of the pre-challenge sera to inhibit growth of Borreliae, six representative strains expressing OspA types 1-6 (B31, Arcon, PBr, DK6, W, and KL11) are cultured at 33° C. in the presence of serial dilutions of heat-inactivated peak titer serum pools or non-immune mouse serum (negative control). B31 is cultured in the presence of complement (guinea pig serum), while the other five strains are tested in the absence of complement. Growth inhibition assays are carried out as described in Examples 10 and 13. A standard serum preparation is used to normalize titers between different assays.

Surface Binding and Growth Inhibiting Efficiency of Anti-OspA Antibody Responses.

Fluorescence staining is measured in all six *Borrelia* strains when tested with the three serum pools derived from the different immunization dose groups (1.0, 0.1 and 0.03 μg protein per dose) of the 3-component vaccine at a dilution of 1:100.

Example 21

A Vaccine Comprising the Three Component Vaccine (OspA 1/2, OspA 6/4, and OspA 5/3) is Required to Optimally Cover *Borrelia* Expressing OspA Types 1-6

The purpose of this study is to investigate and compare the immunogenicity and the cross strain coverage of functional surface binding and/or growth inhibiting antibodies induced by single and multi-component formulations of Orig sOspA Lyme Borreliosis vaccine using the efficiency of anti-OspA antibodies to bind to the surface of live Borreliae and to inhibit growth of Borreliae in vitro as correlates of protection Immunization of Mice.

Ten female mice (C3H) per group are immunized with 0.1 μg of a single component vaccine comprising Orig sOspA1/2 antigen, Orig sOspA 5/3 antigen, or Orig sOspA 6/4 antigen; a two-component vaccine comprising 0.1 μg of both 1/2+5/3 antigens, 1/2+6/4 antigens, or 5/3+6/4 antigens; or a three-component vaccine comprising a combination 0.1 μg of all three 1/2+5/3+6/4 antigens adjuvanted with 0.2% Al(OH)3 in a prime-booster regimen. Vaccination is carried out subcutaneously using a dose volume of 200 μl on days 0, 14 and 28. On day 42, individual blood samples are taken from mice to generate sera.

Antibody Surface Binding and Growth Inhibition Assays.

A slightly modified version of the surface binding assay described above is used to determine the efficiency of anti-OspA IgG to bind to the surface of live Borreliae. Serial dilutions of a serum pool with defined MFI titers are included in the analyses to create a standard curve from which relative titers of test sera are read off after interpolation with a non-linear regression curve. The MFI titer of standard serum for the individual strains expressing OspA types 1-6 is defined as the highest dilution at which the fluorescence intensity of the Borreliae is determined to be at least 3-fold over the fluorescence intensity observed with normal mouse serum. All determinations are carried out in duplicate.

To determine the potency of the various vaccine combinations to induce growth inhibiting antibodies, six representative Borreliae strains (B31, Arcon, PBr, DK6, W, KL11), expressing OspA types 1-6 respectively, are cultured at 33° C. in the presence of heat-inactivated immune or non-immune mouse serum pools. All sera are tested at a single dilution. The following dilutions are used: B31, PBr and KL11 1:200, Arcon, DK6 and W 1:100. PBr is cultured in the absence of 20% complement, while the other 5 strains are tested in the presence of complement. Baby rabbit complement is used for DK6, W and KL11, while guinea pig serum is used for B31 and Arcon. When the bacteria in the control cultures incubated with non-immune sera has grown sufficiently, as determined microscopically, accurate cell counts are made as described previously (see Example 10). The percentage of bacterial growth inhibition is calculated from the cell count observed with test serum relative to the normal mouse serum control. The overall growth inhibition observed for the different formulations tested is then presented as the number of animals among the different groups of ten C3H mice that showed more than 50% growth inhibition.

Example 22

The Multivalent OspA Vaccine Formulation Covers *Borrelia* Expressing Intra-Type Variants or Subtypes of OspA Types 1-6

The purpose of this study was to confirm that immune serum generated by immunizing mice with the 3-component multivalent orig OspA vaccine (orig sOspA 1/2, orig sOspA 6/4, and orig sOspA 5/3) contains functional antibodies which can bind to the surface of live Borreliae expressing these intra-type variants or subtypes.

For this study, a pooled mouse immune serum is generated by immunizing 70 female C3H mice three times with 0.3 μg of the 3-component multivalent orig OspA vaccine on days 0, 14 and 28. On day 42, mice are bled and serum is obtained and pooled. The pooled immune serum is then used to test for binding of antibodies to the surface of live Borreliae. *Borrelia* cultures are incubated with the immune serum pool or control normal mouse serum at 1:100 in duplicate, and fluorescence intensities of Borreliae measuring binding of anti-OspA antibodies to the bacteria are monitored by FACS analyses as described herein above.

The invention has been described in terms of particular embodiments found or proposed to comprise specific modes for the practice of then invention. Various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A polypeptide selected from the group consisting of:
   (a) a polypeptide comprising an amino acid sequence having at least 95 percent sequence identity to the amino acid sequence set forth in SEQ ID NO: 173;
   (b) a polypeptide comprising the amino acid sequence set forth in SEQ ID NO: 173; and
   (c) a polypeptide consisting of the amino acid sequence set forth in SEQ ID NO: 173.

2. The polypeptide of claim 1 further comprising an N-terminal outer surface protein B (OspB) polypeptide fragment of Borrelia, wherein the OspB polypeptide fragment comprises an OspB leader sequence.

3. A composition comprising the polypeptide of claim 1 and a pharmaceutically acceptable carrier.

4. The composition of claim 3 further comprising an additional polypeptide from an outer surface protein A (OspA) protein of Borrelia.

5. The composition of claim 4, wherein Borrelia is Borrelia burgdorferi, Borrelia afzelii, Borrelia garinii, Borrelia japonica, Borrelia andersonii, Borrelia bissettii, Borrelia sinica, Borrelia turdi, Borrelia tanukii, Borrelia valaisiana, Borrelia lusitaniae, Borrelia spielmanii, Borrelia miyamotoi or Borrelia lonestar.

6. The composition of claim 4, wherein the additional polypeptide is a chimeric polypeptide selected from the group consisting of:
   (a) a polypeptide comprising an amino acid sequence having at least 79, 80, 81, 82, 83, 84, 85, 86, 87, 88, 89 90, 91, 92, 93, 94, 95, 96, 97, 98, or 99 percent sequence identity to the amino acid sequence of SEQ ID NO: 171;
   (b) a polypeptide comprising the amino acid sequence of SEQ ID NO: 171;
   (c) a polypeptide consisting of the amino acid sequence of SEQ ID NO: 171;
   (d) a polypeptide comprising an amino acid sequence having at least 79, 80, 81, 82, 83, 84, 85, 86, 87, 88, 89 90, 91, 92, 93, 94, 95, 96, 97, 98, or 99 percent sequence identity to the amino acid sequence of SEQ ID NO: 169;
   (e) a polypeptide comprising the amino acid sequence of SEQ ID NO: 169; and
   (f) a polypeptide consisting of the amino acid sequence of SEQ ID NO: 169.

7. The composition of claim 6, wherein the additional polypeptide is a chimeric polypeptide having at least 85% sequence identity to SEQ ID NO:171.

8. The composition of claim 7, wherein the additional polypeptide is a chimeric polypeptide having at least 90% sequence identity to SEQ ID NO:171.

9. The composition of claim 8, wherein the additional polypeptide is a chimeric polypeptide having at least 95% sequence identity to SEQ ID NO:171.

10. The composition of claim 6, wherein the additional polypeptide is a chimeric polypeptide having at least 85% sequence identity to SEQ ID NO:169.

11. The composition of claim 10, wherein the additional polypeptide is a chimeric polypeptide having at least 90% sequence identity to SEQ ID NO:169.

12. The composition of claim 11, wherein the additional polypeptide is a chimeric polypeptide having at least 95% sequence identity to SEQ ID NO:169.

13. The composition of claim 4, wherein the additional polypeptide further comprises an N-terminal outer surface protein B (OspB) polypeptide fragment of Borrelia, wherein the OspB polypeptide fragment comprises an OspB leader sequence.

14. The composition of claim 4 comprising at least three polypeptides, wherein the polypeptides have different sequences.

15. The composition of claim 14, wherein the polypeptides individually comprise the amino acid sequences set forth in SEQ ID NOS: 169, 171, and 173.

16. The polypeptide of claim 1 comprising an amino acid sequence having at least 96 percent sequence identity to the amino acid sequence set forth in SEQ ID NO: 173.

17. The polypeptide of claim 1 comprising an amino acid sequence having at least 97 percent sequence identity to the amino acid sequence set forth in SEQ ID NO: 173.

18. The polypeptide of claim 1 comprising an amino acid sequence having at least 98 percent sequence identity to the amino acid sequence set forth in SEQ ID NO: 173.

19. The polypeptide of claim 1 comprising an amino acid sequence having at least 99 percent sequence identity to the amino acid sequence set forth in SEQ ID NO: 173.

20. The polypeptide of claim 1 comprising an amino acid sequence having at least 95 percent sequence identity to the amino acid sequence set forth in SEQ ID NO: 173.

21. The polypeptide of claim 1 comprising the amino acid sequence set forth in SEQ ID NO: 173.

22. The polypeptide of claim 1 consisting of the amino acid sequence set forth in SEQ ID NO: 173.

23. The polypeptide of any one of claims 16-22 further comprising an N-terminal outer surface protein B (OspB) polypeptide fragment of *Borrelia*, wherein the OspB polypeptide fragment comprises an OspB leader sequence.

24. A composition comprising the polypeptide of any one of claims 16-22 and a pharmaceutically acceptable carrier.

25. The composition of claim 24 further comprising an additional polypeptide from an outer surface protein A (OspA) protein of *Borrelia*.

26. The composition of claim 25, wherein *Borrelia* is *Borrelia burgdorferi, Borrelia afzelii, Borrelia garinii, Borrelia japonica, Borrelia andersonii, Borrelia bissettii, Borrelia sinica, Borrelia turdi, Borrelia tanukii, Borrelia valaisiana, Borrelia lusitaniae, Borrelia spielmanii, Borrelia miyamotoi* or *Borrelia lonestar*.

27. The composition of claim 25, wherein the additional polypeptide is a chimeric polypeptide selected from the group consisting of:
  (a) a polypeptide comprising an amino acid sequence having at least 79, 80, 81, 82, 83, 84, 85, 86, 87, 88, 89 90, 91, 92, 93, 94, 95, 96, 97, 98, or 99 percent sequence identity to the amino acid sequence of SEQ ID NO: 171;
  (b) a polypeptide comprising the amino acid sequence of SEQ ID NO: 171;
  (c) a polypeptide consisting of the amino acid sequence of SEQ ID NO: 171;
  (d) a polypeptide comprising an amino acid sequence having at least 79, 80, 81, 82, 83, 84, 85, 86, 87, 88, 89 90, 91, 92, 93, 94, 95, 96, 97, 98, or 99 percent sequence identity to the amino acid sequence of SEQ ID NO: 169;
  (e) a polypeptide comprising the amino acid sequence of SEQ ID NO: 169; and
  (f) a polypeptide consisting of the amino acid sequence of SEQ ID NO: 169.

28. The composition of claim 27, wherein the additional polypeptide is a chimeric polypeptide having at least 85% sequence identity to SEQ ID NO:171.

29. The composition of claim 28, wherein the additional polypeptide is a chimeric polypeptide having at least 90% sequence identity to SEQ ID NO:171.

30. The composition of claim 29, wherein the additional polypeptide is a chimeric polypeptide having at least 95% sequence identity to SEQ ID NO:171.

31. The composition of claim 27, wherein the additional polypeptide is a chimeric polypeptide having at least 85% sequence identity to SEQ ID NO:169.

32. The composition of claim 31, wherein the additional polypeptide is a chimeric polypeptide having at least 90% sequence identity to SEQ ID NO:169.

33. The composition of claim 32, wherein the additional polypeptide is a chimeric polypeptide having at least 95% sequence identity to SEQ ID NO:169.

34. The composition of claim 25 comprising at least three polypeptides, wherein the polypeptides have different sequences.

35. The composition of claim 34, wherein the polypeptides individually comprise the amino acid sequences set forth in SEQ ID NOS: 169, 171, and 173.

* * * * *

SEQUENCE LISTING

```
<160> NUMBER OF SEQ ID NOS: 173

<210> SEQ ID NO 1
<211> LENGTH: 829
<212> TYPE: DNA
<213> ORGANISM: Artificial Sequence
<220> FEATURE:
<223> OTHER INFORMATION: Synthetic oligonucleotide

<400> SEQUENCE: 1
```

```
catatgcgtc tgttgatcgg ctttgctctg gcgctggctc tgatcggctg cgcacagaaa    60
ggtgctgagt ctattggttc cgtttctgta gatctgcccg gtgaaatgaa ggttctggtg   120
agcaaagaaa aagacaagaa cggcaagtac gatctcatcg caaccgtcga caagctggag   180
ctgaaaggta cttctgataa aaacaacggc tctggtgtgc tggagggcgt caaaactaac   240
aagagcaaag taaagcttac gatctctgac gatctcggtc agaccacgct ggaagttttc   300
aaagaggatg gcaagaccct cgtgtccaaa aagtaacttc caaagacaa gtcctctacg   360 gaagaaaaat tcaacgaaaa aggtgaggtg tctgaaaaga tcatcaccat ggcagacggc   420
acccgtcttg aataccacgg tattaaaagc gatggtaccg gtaaagcgaa atatgttctg   480
aaaaacttca ctctggaagg caaagtggct aatgataaaa ccaccttgga agtcaaggaa   540
ggcaccgtta ctctgagcat gaatatctcc aaatctggtg aagtttccgt tgaactgaac   600
gacactgaca gcagcgctgc gactaaaaaa actgcagcgt ggaattccaa aacttctact   660
ttaaccatta gcgttaacag caaaaaaact acccagctgg tgttcactaa acaagacacg   720
atcactgtgc agaaatacga ctccgcaggc accaacttag aaggcacggc agtcgaaatt   780
aaaacccttg atgaactgaa aaacgcgctg aaataagctg agcggatcc               829
```

<210> SEQ ID NO 2
<211> LENGTH: 270
<212> TYPE: PRT
<213> ORGANISM: Artificial Sequence
<220> FEATURE:
<223> OTHER INFORMATION: Synthetic peptide

<400> SEQUENCE: 2

```
Met Arg Leu Leu Ile Gly Phe Ala Leu Ala Leu Ala Leu Ile Gly Cys
1               5                   10                  15

Ala Gln Lys Gly Ala Glu Ser Ile Gly Ser Val Ser Val Asp Leu Pro
            20                  25                  30

Gly Glu Met Lys Val Leu Val Ser Lys Glu Lys Asp Lys Asn Gly Lys
        35                  40                  45

Tyr Asp Leu Ile Ala Thr Val Asp Lys Leu Glu Leu Lys Gly Thr Ser
    50                  55                  60

Asp Lys Asn Asn Gly Ser Gly Val Leu Glu Gly Val Lys Thr Asn Lys
65                  70                  75                  80

Ser Lys Val Lys Leu Thr Ile Ser Asp Asp Leu Gly Gln Thr Thr Leu
                85                  90                  95

Glu Val Phe Lys Glu Asp Gly Lys Thr Leu Val Ser Lys Val Thr
            100                 105                 110

Ser Lys Asp Lys Ser Ser Thr Glu Glu Lys Phe Asn Glu Lys Gly Glu
        115                 120                 125

Val Ser Glu Lys Ile Ile Thr Met Ala Asp Gly Thr Arg Leu Glu Tyr
    130                 135                 140

Thr Gly Ile Lys Ser Asp Gly Thr Gly Lys Ala Lys Tyr Val Leu Lys
145                 150                 155                 160

Asn Phe Thr Leu Glu Gly Lys Val Ala Asn Asp Lys Thr Thr Leu Glu
                165                 170                 175

Val Lys Glu Gly Thr Val Thr Leu Ser Met Asn Ile Ser Lys Ser Gly
            180                 185                 190

Glu Val Ser Val Glu Leu Asn Asp Thr Asp Ser Ser Ala Ala Thr Lys
        195                 200                 205

Lys Thr Ala Ala Trp Asn Ser Lys Thr Ser Thr Leu Thr Ile Ser Val
    210                 215                 220
```

```
Asn Ser Lys Lys Thr Thr Gln Leu Val Phe Thr Lys Gln Asp Thr Ile
225                 230                 235                 240

Thr Val Gln Lys Tyr Asp Ser Ala Gly Thr Asn Leu Glu Gly Thr Ala
            245                 250                 255

Val Glu Ile Lys Thr Leu Asp Glu Leu Lys Asn Ala Leu Lys
        260                 265                 270

<210> SEQ ID NO 3
<211> LENGTH: 832
<212> TYPE: DNA
<213> ORGANISM: Artificial Sequence
<220> FEATURE:
<223> OTHER INFORMATION: Synthetic oligonucleotide

<400> SEQUENCE: 3
catatgcgtc tgttgatcgg ctttgctctg gcgctggctc tgatcggctg cgcacagaaa      60
ggtgctgagt ctattggttc cgtttctgta gatctgcccg gtggcatgac cgttctggtc    120
agcaaagaaa aagacaaaaa cggtaaatac agcctcgagg cgaccgtcga caagcttgag    180
ctgaaaggca cctctgataa aaacaacggt tccggcaccc tggaaggtga aaaactaac    240 aaaagcaaag tgaaactgac cattgctgat gacctcagcc agaccaaatt cgaaattttc    300
aaagaagatg ccaaaacctt agtatccaaa aagtgaccc tgaaagacaa gtcctctacc    360
gaagaaaaat tcaacgaaaa gggtgaaacc tctgaaaaaa ccatcgtaat ggcaaatggt    420
acccgtctgg aatacaccga catcaaaagc gatggctccg gcaaagccaa atacgttctg    480
aaagacttca ccctggaagg caccctcgct gccgacggca aaaccacctt gaaagttacc    540
gaaggcactg ttgtttttaag catgaacatc ttaaaatccg gtgaaatcac cgttgcgctg    600
gatgactctg acaccactca ggccactaaa aaaccggca atgggattc taacacttcc    660 actctgacca tcagcgtgaa ttccaaaaaa actaaaaaca tcgtgttcac caagaagac    720 accatcaccg tccagaaata cgactctgcg ggcaccaacc tcgaaggcaa cgcagtcgaa    780
atcaaaaccc tggatgaact gaaaaacgct ctgaataag ctgagcggat cc              832

<210> SEQ ID NO 4
<211> LENGTH: 271
<212> TYPE: PRT
<213> ORGANISM: Artificial Sequence
<220> FEATURE:
<223> OTHER INFORMATION: Synthetic peptide

<400> SEQUENCE: 4

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Val Ser Val Asp Leu Pro
            20                  25                  30

Gly Gly Met Thr Val Leu Val Ser Lys Glu Lys Asp Lys Asn Gly Lys
        35                  40                  45

Tyr Ser Leu Glu Ala Thr Val Asp Lys Leu Glu Leu Lys Gly Thr Ser
    50                  55                  60

Asp Lys Asn Asn Gly Ser Gly Thr Leu Glu Gly Glu Lys Thr Asn Lys
65                  70                  75                  80

Ser Lys Val Lys Leu Thr Ile Ala Asp Asp Leu Ser Gln Thr Lys Phe
                85                  90                  95

Glu Ile Phe Lys Glu Asp Ala Lys Thr Leu Val Ser Lys Val Thr
            100                 105                 110

Leu Lys Asp Lys Ser Ser Thr Glu Glu Lys Phe Asn Glu Lys Gly Glu
        115                 120                 125
```

Thr Ser Glu Lys Thr Ile Val Met Ala Asn Gly Thr Arg Leu Glu Tyr
    130                 135                 140

Thr Asp Ile Lys Ser Asp Gly Ser Gly Lys Ala Lys Tyr Val Leu Lys
145                 150                 155                 160

Asp Phe Thr Leu Glu Gly Thr Leu Ala Ala Asp Gly Lys Thr Thr Leu
                165                 170                 175

Lys Val Thr Glu Gly Thr Val Val Leu Ser Met Asn Ile Leu Lys Ser
            180                 185                 190

Gly Glu Ile Thr Val Ala Leu Asp Asp Ser Asp Thr Thr Gln Ala Thr
        195                 200                 205

Lys Lys Thr Gly Lys Trp Asp Ser Asn Thr Ser Thr Leu Thr Ile Ser
    210                 215                 220

Val Asn Ser Lys Lys Thr Lys Asn Ile Val Phe Thr Lys Glu Asp Thr
225                 230                 235                 240

Ile Thr Val Gln Lys Tyr Asp Ser Ala Gly Thr Asn Leu Glu Gly Asn
                245                 250                 255

Ala Val Glu Ile Lys Thr Leu Asp Glu Leu Lys Asn Ala Leu Lys
            260                 265                 270

<210> SEQ ID NO 5
<211> LENGTH: 829
<212> TYPE: DNA
<213> ORGANISM: Artificial Sequence
<220> FEATURE:
<223> OTHER INFORMATION: Synthetic oligonucleotide

<400> SEQUENCE: 5
catatgcgtc tgttgatcgg ctttgctttg gcgctggctt taatcggctg tgcacagaaa     60
ggtgctgagt ctattggttc cgtttctgta gatctgcccg ggggtatgaa agttctggta    120
agcaaagaaa aagacaaaaa cggtaaatac agcctgatgg caaccgtaga aaagctggag    180
cttaaaggca cttctgataa aaacaacggt tctggcaccc tggaaggtga aaaaactaac    240
aaaagcaaag taaagcttac tattgctgag gatctgagca aaaccacctt tgaaatcttc    300
aaagaagatg gcaaaactct ggtatctaaa aaagtaaccc tgaaagacaa gtcttctacc    360
gaagaaaaat tcaacgaaaa gggtgaaatc tctgaaaaaa ctatcgtaat ggcaaatggt    420
acccgtctgg aatacaccga catcaaaagc gataaaaccg gcaaagctaa atacgttctg    480
aaagacttta ctctggaagg cactctggct gctgacggca aaaccactct gaaagttacc    540
gaaggcactg ttactctgag catgaacatt tctaaatccg gcgaaatcac cgttgcactg    600
gatgacactg actctagcgg caataaaaaa tccggcacct gggattctga tacttctact    660
ttaaccatta gcaaaacag ccagaaaact aaacagctgg tattcaccaa agaaaacact    720
atcaccgtac agaactataa ccgtgcaggc aatgcgctgg aaggcagccc ggctgaaatt    780
aaagatctgg cagagctgaa agccgctttg aaataagctg agcggatcc                829

<210> SEQ ID NO 6
<211> LENGTH: 270
<212> TYPE: PRT
<213> ORGANISM: Artificial Sequence
<220> FEATURE:
<223> OTHER INFORMATION: Synthetic peptide

<400> SEQUENCE: 6

Met Arg Leu Leu Ile Gly Phe Ala Leu Ala Leu Ala Leu Ile Gly Cys
1               5                   10                  15

Ala Gln Lys Gly Ala Glu Ser Ile Gly Ser Val Ser Val Asp Leu Pro

```
                        20                  25                  30
Gly Gly Met Lys Val Leu Val Ser Lys Glu Lys Asp Lys Asn Gly Lys
            35                  40                  45

Tyr Ser Leu Met Ala Thr Val Glu Lys Leu Glu Leu Lys Gly Thr Ser
 50                  55                  60

Asp Lys Asn Asn Gly Ser Gly Thr Leu Glu Gly Lys Thr Asn Lys
 65                  70                  75                  80

Ser Lys Val Lys Leu Thr Ile Ala Glu Asp Leu Ser Lys Thr Thr Phe
                85                  90                  95

Glu Ile Phe Lys Glu Asp Gly Lys Thr Leu Val Ser Lys Val Thr
                100                 105                 110

Leu Lys Asp Lys Ser Ser Thr Glu Glu Lys Phe Asn Glu Lys Gly Glu
            115                 120                 125

Ile Ser Glu Lys Thr Ile Val Met Ala Asn Gly Thr Arg Leu Glu Tyr
            130                 135                 140

Thr Asp Ile Lys Ser Asp Lys Thr Gly Lys Ala Lys Tyr Val Leu Lys
145                 150                 155                 160

Asp Phe Thr Leu Glu Gly Thr Leu Ala Ala Asp Gly Lys Thr Thr Leu
                165                 170                 175

Lys Val Thr Glu Gly Thr Val Thr Leu Ser Met Asn Ile Ser Lys Ser
            180                 185                 190

Gly Glu Ile Thr Val Ala Leu Asp Asp Thr Asp Ser Ser Gly Asn Lys
            195                 200                 205

Lys Ser Gly Thr Trp Asp Ser Asp Thr Ser Thr Leu Thr Ile Ser Lys
            210                 215                 220

Asn Ser Gln Lys Thr Lys Gln Leu Val Phe Thr Lys Glu Asn Thr Ile
225                 230                 235                 240

Thr Val Gln Asn Tyr Asn Arg Ala Gly Asn Ala Leu Glu Gly Ser Pro
                245                 250                 255

Ala Glu Ile Lys Asp Leu Ala Glu Leu Lys Ala Ala Leu Lys
            260                 265                 270

<210> SEQ ID NO 7
<211> LENGTH: 784
<212> TYPE: DNA
<213> ORGANISM: Artificial Sequence
<220> FEATURE:
<223> OTHER INFORMATION: Synthetic oligonucleotide

<400> SEQUENCE: 7
catatggcac agaaaggtgc tgagtctatt ggttccgttt ctgtagatct gcccggtgaa      60
atgaaggttc tggtgagcaa agaaaaagac aagaacggca agtacgatct catcgcaacc     120
gtcgacaagc tggagctgaa aggtacttct gataaaaaca acggctctgg tgtgctggag     180
ggcgtcaaaa ctaacaagag caaagtaaag cttacgatct ctgacgatct cggtcagacc     240
acgctggaag ttttcaaaga ggatggcaag accctcgtgt ccaaaaaagt aacttccaaa     300
gacaagtcct ctacggaaga aaaattcaac gaaaaaggtg aggtgtctga aagatcatc      360 accatggcag acggcacccg tcttgaatac accggtatta aaagcgatgg taccggtaaa     420
gcgaaatatg ttctgaaaaa cttcactctg gaaggcaaag tggctaatga taaaaccacc     480
ttggaagtca aggaaggcac cgttactctg agcatgaata tctccaaatc tggtgaagtt     540
tccgttgaac tgaacgacac tgacagcagc gctgcgacta aaaaaactgc agcgtggaat     600
tccaaaactt ctactttaac cattagcgtt aacagcaaaa aaactaccca gctggtgttc     660
actaaacaag acacgatcac tgtgcagaaa tacgactcca acggcaccaa cttagaaggc     720
```

```
acggcagtcg aaattaaaac ccttgatgaa ctgaaaaacg cgctgaaata agctgagcgg    780
atcc                                                                784
```

<210> SEQ ID NO 8
<211> LENGTH: 255
<212> TYPE: PRT
<213> ORGANISM: Artificial Sequence
<220> FEATURE:
<223> OTHER INFORMATION: Synthetic peptide

<400> SEQUENCE: 8

```
Met Ala Gln Lys Gly Ala Glu Ser Ile Gly Ser Val Ser Val Asp Leu
1               5                   10                  15

Pro Gly Glu Met Lys Val Leu Val Ser Lys Glu Lys Asp Lys Asn Gly
            20                  25                  30

Lys Tyr Asp Leu Ile Ala Thr Val Asp Lys Leu Glu Leu Lys Gly Thr
        35                  40                  45

Ser Asp Lys Asn Asn Gly Ser Gly Val Leu Glu Gly Val Lys Thr Asn
    50                  55                  60

Lys Ser Lys Val Lys Leu Thr Ile Ser Asp Asp Leu Gly Gln Thr Thr
65                  70                  75                  80

Leu Glu Val Phe Lys Glu Asp Gly Lys Thr Leu Val Ser Lys Lys Val
                85                  90                  95

Thr Ser Lys Asp Lys Ser Ser Thr Glu Glu Lys Phe Asn Glu Lys Gly
            100                 105                 110

Glu Val Ser Glu Lys Ile Ile Thr Met Ala Asp Gly Thr Arg Leu Glu
        115                 120                 125

Tyr Thr Gly Ile Lys Ser Asp Gly Thr Gly Lys Ala Lys Tyr Val Leu
    130                 135                 140

Lys Asn Phe Thr Leu Glu Gly Lys Val Ala Asn Asp Lys Thr Thr Leu
145                 150                 155                 160

Glu Val Lys Glu Gly Thr Val Thr Leu Ser Met Asn Ile Ser Lys Ser
                165                 170                 175

Gly Glu Val Ser Val Glu Leu Asn Asp Thr Asp Ser Ser Ala Ala Thr
            180                 185                 190

Lys Lys Thr Ala Ala Trp Asn Ser Lys Thr Ser Thr Leu Thr Ile Ser
        195                 200                 205

Val Asn Ser Lys Lys Thr Thr Gln Leu Val Phe Thr Lys Gln Asp Thr
    210                 215                 220

Ile Thr Val Gln Lys Tyr Asp Ser Ala Gly Thr Asn Leu Glu Gly Thr
225                 230                 235                 240

Ala Val Glu Ile Lys Thr Leu Asp Glu Leu Lys Asn Ala Leu Lys
                245                 250                 255
```

<210> SEQ ID NO 9
<211> LENGTH: 787
<212> TYPE: DNA
<213> ORGANISM: Artificial Sequence
<220> FEATURE:
<223> OTHER INFORMATION: Synthetic oligonucleotide

<400> SEQUENCE: 9

```
catatggcac agaaaggtgc tgagtctatt ggttccgttt ctgtagatct gcccggtggc    60
atgaccgttc tggtcagcaa agaaaaagac aaaaacggta atacagcct cgaggcgacc    120 gtcgacaagc ttgagctgaa aggcacctct gataaaaaca acggttccgg caccctggaa    180
ggtgaaaaaa ctaacaaaag caaagtgaaa ctgaccattg ctgatgacct cagccagacc    240
```

```
aaattcgaaa ttttcaaaga agatgccaaa accttagtat ccaaaaaagt gaccctgaaa      300
gacaagtcct ctaccgaaga aaaattcaac gaaaagggtg aaacctctga aaaaaccatc      360
gtaatggcaa atggtacccg tctggaatac accgacatca aaagcgatgg ctccggcaaa      420
gccaaatacg ttctgaaaga cttcaccctg gaaggcaccc tcgctgccga cggcaaaacc      480
accttgaaag ttaccgaagg cactgttgtt ttaagcatga acatcttaaa atccggtgaa      540
atcaccgttg cgctggatga ctctgacacc actcaggcca ctaaaaaaac cggcaaatgg      600
gattctaaca cttccactct gaccatcagc gtgaattcca aaaaaactaa aaacatcgtg      660
ttcaccaaag aagacaccat caccgtccag aaatacgact ctgcgggcac caacctcgaa      720
ggcaacgcag tcgaaatcaa aaccctggat gaactgaaaa acgctctgaa ataagctgag      780
cggatcc                                                               787
```

<210> SEQ ID NO 10
<211> LENGTH: 256
<212> TYPE: PRT
<213> ORGANISM: Artificial Sequence
<220> FEATURE:
<223> OTHER INFORMATION: Synthetic peptide

<400> SEQUENCE: 10

```
Met Ala Gln Lys Gly Ala Glu Ser Ile Gly Ser Val Ser Val Asp Leu
1               5                   10                  15

Pro Gly Gly Met Thr Val Leu Val Ser Lys Glu Lys Asp Lys Asn Gly
            20                  25                  30

Lys Tyr Ser Leu Glu Ala Thr Val Asp Lys Leu Glu Leu Lys Gly Thr
        35                  40                  45

Ser Asp Lys Asn Asn Gly Ser Gly Thr Leu Glu Gly Glu Lys Thr Asn
    50                  55                  60

Lys Ser Lys Val Lys Leu Thr Ile Ala Asp Asp Leu Ser Gln Thr Lys
65                  70                  75                  80

Phe Glu Ile Phe Lys Glu Asp Ala Lys Thr Leu Val Ser Lys Val
                85                  90                  95

Thr Leu Lys Asp Lys Ser Ser Thr Glu Glu Lys Phe Asn Glu Lys Gly
                100                 105                 110

Glu Thr Ser Glu Lys Thr Ile Val Met Ala Asn Gly Thr Arg Leu Glu
                115                 120                 125

Tyr Thr Asp Ile Lys Ser Asp Gly Ser Gly Lys Ala Lys Tyr Val Leu
            130                 135                 140

Lys Asp Phe Thr Leu Glu Gly Thr Leu Ala Ala Asp Gly Lys Thr Thr
145                 150                 155                 160

Leu Lys Val Thr Glu Gly Thr Val Val Leu Ser Met Asn Ile Leu Lys
                165                 170                 175

Ser Gly Glu Ile Thr Val Ala Leu Asp Asp Ser Asp Thr Thr Gln Ala
            180                 185                 190

Thr Lys Lys Thr Gly Lys Trp Asp Ser Asn Thr Ser Thr Leu Thr Ile
        195                 200                 205

Ser Val Asn Ser Lys Lys Thr Lys Asn Ile Val Phe Thr Lys Glu Asp
    210                 215                 220

Thr Ile Thr Val Gln Lys Tyr Asp Ser Ala Gly Thr Asn Leu Glu Gly
225                 230                 235                 240

Asn Ala Val Glu Ile Lys Thr Leu Asp Glu Leu Lys Asn Ala Leu Lys
                245                 250                 255
```

```
<210> SEQ ID NO 11
<211> LENGTH: 784
<212> TYPE: DNA
<213> ORGANISM: Artificial Sequence
<220> FEATURE:
<223> OTHER INFORMATION: Synthetic oligonucleotide

<400> SEQUENCE: 11
catatggcac agaaaggtgc tgagtctatt ggttccgttt ctgtagatct gcccgggggt    60
atgaaagttc tggtaagcaa agaaaaagac aaaaacggta atacagcct gatggcaacc   120 gtagaaaagc tggagcttaa aggcacttct gataaaaaca acggttctgg caccctggaa   180
ggtgaaaaaa ctaacaaaag caaagtaaag cttactattg ctgaggatct gagcaaaacc   240
acctttgaaa tcttcaaaga gatggcaaa actctggtat ctaaaaaagt aaccctgaaa   300
gacaagtctt ctaccgaaga aaaattcaac gaaaagggtg aaatctctga aaaaactatc   360
gtaatggcaa atggtacccg tctggaatac accgacatca aaagcgataa accggcaaa   420 gctaaatacg ttctgaaaga ctttactctg gaaggcactc tggctgctga cggcaaaacc   480
actctgaaag ttaccgaagg cactgttact ctgagcatga acatttctaa atccggcgaa   540
atcaccgttg cactggatga cactgactct agcggcaata aaaaatccgg cacctgggat   600
tctgatactt ctactttaac cattagcaaa acagccaga aaactaaaca gctggtattc   660
accaaagaaa acactatcac cgtacagaac tataaccgtg caggcaatgc gctggaaggc   720
agcccggctg aaattaaaga tctggcagag ctgaaagccg ctttgaaata agctgagcgg   780
atcc                                                                784

<210> SEQ ID NO 12
<211> LENGTH: 255
<212> TYPE: PRT
<213> ORGANISM: Artificial Sequence
<220> FEATURE:
<223> OTHER INFORMATION: Synthetic peptide

<400> SEQUENCE: 12

Met Ala Gln Lys Gly Ala Glu Ser Ile Gly Ser Val Ser Val Asp Leu
1               5                   10                  15

Pro Gly Gly Met Lys Val Leu Val Ser Lys Glu Lys Asp Lys Asn Gly
            20                  25                  30

Lys Tyr Ser Leu Met Ala Thr Val Glu Lys Leu Glu Leu Lys Gly Thr
        35                  40                  45

Ser Asp Lys Asn Asn Gly Ser Gly Thr Leu Glu Gly Glu Lys Thr Asn
    50                  55                  60

Lys Ser Lys Val Lys Leu Thr Ile Ala Glu Asp Leu Ser Lys Thr Thr
65                  70                  75                  80

Phe Glu Ile Phe Lys Glu Asp Gly Lys Thr Leu Val Ser Lys Val
                85                  90                  95

Thr Leu Lys Asp Lys Ser Ser Thr Glu Glu Lys Phe Asn Glu Lys Gly
            100                 105                 110

Glu Ile Ser Glu Lys Thr Ile Val Met Ala Asn Gly Thr Arg Leu Glu
        115                 120                 125

Tyr Thr Asp Ile Lys Ser Asp Lys Thr Gly Lys Ala Lys Tyr Val Leu
    130                 135                 140

Lys Asp Phe Thr Leu Glu Gly Thr Leu Ala Ala Asp Gly Lys Thr Thr
145                 150                 155                 160

Leu Lys Val Thr Glu Gly Thr Val Thr Leu Ser Met Asn Ile Ser Lys
                165                 170                 175
```

```
Ser Gly Glu Ile Thr Val Ala Leu Asp Asp Thr Asp Ser Ser Gly Asn
        180                 185                 190

Lys Lys Ser Gly Thr Trp Asp Ser Asp Thr Ser Thr Leu Thr Ile Ser
        195                 200                 205

Lys Asn Ser Gln Lys Thr Lys Gln Leu Val Phe Thr Lys Glu Asn Thr
    210                 215                 220

Ile Thr Val Gln Asn Tyr Asn Arg Ala Gly Asn Ala Leu Glu Gly Ser
225                 230                 235                 240

Pro Ala Glu Ile Lys Asp Leu Ala Glu Leu Lys Ala Ala Leu Lys
                245                 250                 255

<210> SEQ ID NO 13
<211> LENGTH: 15
<212> TYPE: PRT
<213> ORGANISM: Artificial Sequence
<220> FEATURE:
<223> OTHER INFORMATION: Synthetic peptide

<400> SEQUENCE: 13

Met Arg Leu Leu Ile Gly Phe Ala Leu Ala Leu Ala Leu Ile Gly
1               5                   10                  15

<210> SEQ ID NO 14
<211> LENGTH: 20
<212> TYPE: DNA
<213> ORGANISM: Artificial Sequence
<220> FEATURE:
<223> OTHER INFORMATION: Synthetic primer

<400> SEQUENCE: 14
tcggggctgg cttaactatg                                         20

<210> SEQ ID NO 15
<211> LENGTH: 15
<212> TYPE: DNA
<213> ORGANISM: Artificial Sequence
<220> FEATURE:
<223> OTHER INFORMATION: Synthetic primer

<400> SEQUENCE: 15
gcttccggct cgtat                                              15

<210> SEQ ID NO 16
<211> LENGTH: 20
<212> TYPE: DNA
<213> ORGANISM: Artificial Sequence
<220> FEATURE:
<223> OTHER INFORMATION: Synthetic primer

<400> SEQUENCE: 16
gcttccggct cgtatgttgt                                         20

<210> SEQ ID NO 17
<211> LENGTH: 22
<212> TYPE: DNA
<213> ORGANISM: Artificial Sequence
<220> FEATURE:
<223> OTHER INFORMATION: Synthetic primer

<400> SEQUENCE: 17
ttatgctagt tattgctcag cg                                      22

<210> SEQ ID NO 18
<211> LENGTH: 23
<212> TYPE: DNA
```

-continued

<213> ORGANISM: Artificial Sequence
<220> FEATURE:
<223> OTHER INFORMATION: Synthetic primer

<400> SEQUENCE: 18
ttcccctcta gaaataattt tgt                                          23

<210> SEQ ID NO 19
<211> LENGTH: 29
<212> TYPE: DNA
<213> ORGANISM: Artificial Sequence
<220> FEATURE:
<223> OTHER INFORMATION: Synthetic primer

<400> SEQUENCE: 19
ggaattccat atgcgtctgt tgatcggct                                    29

<210> SEQ ID NO 20
<211> LENGTH: 18
<212> TYPE: DNA
<213> ORGANISM: Artificial Sequence
<220> FEATURE:
<223> OTHER INFORMATION: Synthetic primer

<400> SEQUENCE: 20
ttggtgcctg cggagtcg                                                18

<210> SEQ ID NO 21
<211> LENGTH: 20
<212> TYPE: DNA
<213> ORGANISM: Artificial Sequence
<220> FEATURE:
<223> OTHER INFORMATION: Synthetic primer

<400> SEQUENCE: 21
aatacgactc cgcaggcacc                                              20

<210> SEQ ID NO 22
<211> LENGTH: 24
<212> TYPE: DNA
<213> ORGANISM: Artificial Sequence
<220> FEATURE:
<223> OTHER INFORMATION: Synthetic primer

<400> SEQUENCE: 22
ctgggatccg ctcagcttat ttca                                         24

<210> SEQ ID NO 23
<211> LENGTH: 36
<212> TYPE: DNA
<213> ORGANISM: Artificial Sequence
<220> FEATURE:
<223> OTHER INFORMATION: Synthetic primer

<400> SEQUENCE: 23
cgtgcgtacc atatggcaca gaaaggtgct gagtct                            36

<210> SEQ ID NO 24
<211> LENGTH: 9
<212> TYPE: PRT
<213> ORGANISM: Artificial Sequence
<220> FEATURE:
<223> OTHER INFORMATION: Synthetic peptide

<400> SEQUENCE: 24

Tyr Val Leu Glu Gly Thr Leu Thr Ala
1               5

```
<210> SEQ ID NO 25
<211> LENGTH: 6
<212> TYPE: PRT
<213> ORGANISM: Artificial Sequence
<220> FEATURE:
<223> OTHER INFORMATION: Synthetic peptide

<400> SEQUENCE: 25

Lys Glu Lys Asp Lys Asn
1               5

<210> SEQ ID NO 26
<211> LENGTH: 6
<212> TYPE: PRT
<213> ORGANISM: Artificial Sequence
<220> FEATURE:
<223> OTHER INFORMATION: Synthetic peptide

<400> SEQUENCE: 26

Lys Thr Asn Lys Ser Lys
1               5

<210> SEQ ID NO 27
<211> LENGTH: 6
<212> TYPE: PRT
<213> ORGANISM: Artificial Sequence
<220> FEATURE:
<223> OTHER INFORMATION: Synthetic peptide

<400> SEQUENCE: 27

Lys Glu Lys Asn Lys Asp
1               5

<210> SEQ ID NO 28
<211> LENGTH: 6
<212> TYPE: PRT
<213> ORGANISM: Artificial Sequence
<220> FEATURE:
<223> OTHER INFORMATION: Synthetic peptide

<400> SEQUENCE: 28

Lys Glu Lys Asp Lys Asp
1               5

<210> SEQ ID NO 29
<211> LENGTH: 6
<212> TYPE: PRT
<213> ORGANISM: Artificial Sequence
<220> FEATURE:
<223> OTHER INFORMATION: Synthetic peptide

<400> SEQUENCE: 29

Lys Ala Asp Lys Ser Lys
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic peptide

<400> SEQUENCE: 30

Lys Thr Asp Lys Ser Lys
1               5
```

```
<210> SEQ ID NO 31
<211> LENGTH: 60
<212> TYPE: DNA
<213> ORGANISM: Artificial Sequence
<220> FEATURE:
<223> OTHER INFORMATION: Synthetic oligonucleotide

<400> SEQUENCE: 31
catatgcgtc tgttgatcgg ctttgctctg gcgctggctc tgatcggctg cgcacagaaa    60

<210> SEQ ID NO 32
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 32
catatggcac agaaa                                                     15

<210> SEQ ID NO 33
<211> LENGTH: 19
<212> TYPE: PRT
<213> ORGANISM: Artificial Sequence
<220> FEATURE:
<223> OTHER INFORMATION: Synthetic peptide

<400> SEQUENCE: 33

Met Arg Leu Leu Ile Gly Phe Ala Leu Ala Leu Ala Leu Ile Gly Cys
1               5                   10                  15

Ala Gln Lys

<210> SEQ ID NO 34
<211> LENGTH: 4
<212> TYPE: PRT
<213> ORGANISM: Artificial Sequence
<220> FEATURE:
<223> OTHER INFORMATION: Synthetic peptide

<400> SEQUENCE: 34

Met Ala Gln Lys
1

<210> SEQ ID NO 35
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 35
gcaaaaacag ccagaaaact aaacagctgg tattcaccaa agaaaacact               50

<210> SEQ ID NO 36
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 36
gcaaaaacag ccagaaaact aaacagctgg g                                   31

<210> SEQ ID NO 37
<211> LENGTH: 35
<212> TYPE: DNA
<213> ORGANISM: Artificial Sequence
```

```
<220> FEATURE:
<223> OTHER INFORMATION: Synthetic oligonucleotide

<400> SEQUENCE: 37
aattcaaaca gctggtattc accaaagaaa acact                              35

<210> SEQ ID NO 38
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 38
gatcactgtg cagaaatacg actccaacgg caccaactta gaaggcacgg cagtc        55

<210> SEQ ID NO 39
<211> LENGTH: 55
<212> TYPE: DNA
<213> ORGANISM: Artificial Sequence
<220> FEATURE:
<223> OTHER INFORMATION: Synthetic oligonucleotide

<400> SEQUENCE: 39
gatcactgtg cagaaatacg actccgcagg caccaactta gaaggcacgg cagtc        55

<210> SEQ ID NO 40
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 40
gatcactgtg cagaaatacg actccggcac caacttagaa ggcacggcag tc           52

<210> SEQ ID NO 41
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 41
cgactccgca ggcaccaa                                                 18

<210> SEQ ID NO 42
<211> LENGTH: 813
<212> TYPE: DNA
<213> ORGANISM: Artificial Sequence
<220> FEATURE:
<223> OTHER INFORMATION: Synthetic oligonucleotide

<400> SEQUENCE: 42
atgagattat taataggatt tgctttagcg ttagctttaa taggatgtgc acaaaaaggt    60
gctgagtcaa ttggatccgt ttcagtagat ttgcctggtg aaatgaaagt tcttgtaagc   120
aaagaaaaag acaaaacgg caagtacgat ctaattgcaa cagtagacaa gcttgagctt   180
aaaggaactt ctgataaaaa caatggatct ggagtacttg aaggcgtaaa aactaacaaa   240
agtaaagtaa aattaacaat ttctgacgat ctaggtcaaa ccacacttga agttttcaaa   300
gaagatggca aaacactagt atcaaaaaaa gtaacttcca agacaagtc atcaacagaa    360 gaaaattca atgaaaaagg tgaagtatct gaaaaaataa taacaatggc agacggaacc    420
agacttgaat acacaggaat taaagcgat ggaactggaa aagctaaata tgttttaaaa   480
```

```
aattttactc ttgaaggaaa agtagctaat gataaaacaa cattggaagt aaaagaagga      540
accgttactt taagtatgaa tatttcaaaa tctggggaag tttcagttga acttaatgac      600
actgacagta gtgctgctac taaaaaaact gcagcttgga attcaaaaac ttctacttta      660
acaattagtg ttaacagcaa aaaaactaca caacttgtgt ttactaaaca agacacaata      720
actgtacaaa aatacgactc caacggtacc aatttagaag gcacagcagt cgaaattaaa      780
acacttgatg aacttaaaaa cgcttttaaa taa                                  813
```

<210> SEQ ID NO 43
<211> LENGTH: 826
<212> TYPE: DNA
<213> ORGANISM: Artificial Sequence
<220> FEATURE:
<223> OTHER INFORMATION: Synthetic oligonucleotide

<400> SEQUENCE: 43

```
atgcgtctgt tgatcggctt tgctctggcg ctggctctga tcggctgcgc acagaaaggt       60
gctgagtcta ttggttccgt ttctgtagat ctgcccggtg aaatgaaggt tctggtgagc      120
aaagaaaaag acaagaacgg caagtacgat ctcatcgcaa ccgtcgacaa gctggagctg      180
aaaggtactt ctgataaaaa caacggctct ggtgtgctgg agggcgtcaa aactaacaag      240
agcaaagtaa agcttacgat ctctgacgat ctcggtcaga ccacgctgga agttttcaaa      300
gaggatggca agaccctcgt gtccaaaaaa gtaacttcca agacaagtc ctctacggaa       360 gaaaaattca cgaaaaagg tgaggtgtct gaaaagatca tcaccatggc agacggcacc       420
cgtcttgaat acaccggtat taaaagcgat ggtaccggta agcgaaata tgttctgaaa       480 aacttcactc tggaaggcaa agtggctaat gataaaacca ccttggaagt caaggaaggc      540
accgttactc tgagcatgaa tatctccaaa tctggtgaag tttccgttga actgaacgac      600
actgacagca gcgctgcgac taaaaaaact gcagcgtgga attccaaaac ttctacttta      660
accattagcg ttaacagcaa aaaaactacc cagctggtgt tcactaaaca agacacgatc      720
actgtgcaga aatacgactc cgcaggcacc aacttagaag gcacggcagt cgaaattaaa      780
acccttgatg aactgaaaaa cgcgctgaaa taagctgagc ggatcc                    826
```

<210> SEQ ID NO 44
<211> LENGTH: 818
<212> TYPE: DNA
<213> ORGANISM: Artificial Sequence
<220> FEATURE:
<223> OTHER INFORMATION: Synthetic oligonucleotide

<400> SEQUENCE: 44

```
atatgagatt attaatagga tttgctttag cgttagcttt aataggatgt gcacaaaaag       60
gtgctgagtc aattggatcc gtttcagtag atttacctgg tggaatgaca gttcttgtaa      120
gtaaagaaaa agacaaagac ggtaaataca gtctagaggc aacagtagac aagcttgagc      180
ttaaaggaac ttctgataaa acaacggtt ctggaacact tgaaggtgaa aaaactgaca       240
aaagtaaagt aaaattaaca attgctgatg acctaagtca aactaaattt gaaattttca      300
aagaagatgc caaaacatta gtatcaaaaa agtaaccct aaagacaag tcatcaacag       360 aagaaaaatt caacgaaaag ggtgaaacat ctgaaaaac aatagtaaga gcaaatggaa      420
ccagacttga atacacagac ataaaaagcg atggatccgg aaaagctaaa gaagttttaa      480
aagactttac tcttgaagga actctagctg ctgacggcaa acaacattg aaagttacag       540 aaggcactgt tgttttaagc aagaacattt taaaatccgg agaaataaca gttgcacttg      600
```

```
atgactctga cactactcag gctactaaaa aaactggaaa atgggattca aatacttcca    660
ctttaacaat tagtgtgaat agcaaaaaaa ctaaaaacat tgtatttaca aaagaagaca    720
caataacagt acaaaaatac gactcagcag gcaccaatct agaaggcaac gcagtcgaaa    780
ttaaaacact tgatgaactt aaaaacgctt taaaataa                           818

<210> SEQ ID NO 45
<211> LENGTH: 831
<212> TYPE: DNA
<213> ORGANISM: Artificial Sequence
<220> FEATURE:
<223> OTHER INFORMATION: Synthetic oligonucleotide

<400> SEQUENCE: 45
atatgcgtct gttgatcggc tttgctctgg cgctggctct gatcggctgc gcacagaaag     60
gtgctgagtc tattggttcc gtttctgtag atctgcccgg tggcatgacc gttctggtca    120
gcaaagaaaa agacaaaaac ggtaaataca gcctcgaggc gaccgtcgac aagcttgagc    180
tgaaaggcac ctctgataaa aacaacggtt ccggcaccct ggaaggtgaa aaaactaaca    240
aaagcaaagt gaaactgacc attgctgatg acctcagcca gaccaaattc gaattttca    300 agaagatgc caaaacctta gtatccaaaa agtgaccct gaaagacaag tcctctaccg    360
aagaaaaatt caacgaaaag ggtgaaacct ctgaaaaaac catcgtaatg gcaaatggta    420
cccgtctgga atacaccgac atcaaaagcg atggctccgg caaagccaaa tacgttctga    480 agacttcac cctggaaggc accctcgctg ccgacggcaa aaccaccttg aaagttaccg    540
aaggcactgt tgttttaagc atgaacatct aaaatccgg tgaaatcacc gttgcgctgg    600
atgactctga caccactcag gccactaaaa aaaccggcaa atgggattct aacacttcca    660
ctctgaccat cagcgtgaat tccaaaaaaa ctaaaaacat cgtgttcacc aaagaagaca    720
ccatcaccgt ccagaaatac gactctgcgg gcaccaacct cgaaggcaac gcagtcgaaa    780 tcaaaacccct ggatgaactg aaaaacgctc tgaaataagc tgagcggatc c            831

<210> SEQ ID NO 46
<211> LENGTH: 816
<212> TYPE: DNA
<213> ORGANISM: Artificial Sequence
<220> FEATURE:
<223> OTHER INFORMATION: Synthetic oligonucleotide

<400> SEQUENCE: 46
catatgagat tattaatagg atttgcttta gcgttagctt aataggatg tgcacaaaaa     60 ggtgctgagt caattggatc cgtttcagta gatttacctg gtggaatgaa agttcttgta    120
agtaaagaaa aagacaaaga tggtaaatac agtctaatgg caacagtaga aaagcttgag    180
cttaaaggaa cttctgataa aaacaacggt tctggaacac ttgaaggtga aaaaactgac    240
aaaagtaaag taaaattaac aattgctgag gatctaagta aaaccacatt tgaaatcttc    300
aaagaagatg caaaacatt agtatcaaaa aagtaaccc ttaaagacaa gtcatcaaca    360
gaagaaaaat tcaacgaaaa gggtgaaata tctgaaaaaa caatagtaag agcaaatgga    420
accagacttg aatacacaga cataaaaagc gataaaaccg aaaagctaa agaagtttta    480 aaagacttta ctcttgaagg aactctagct gctgacggca aaacaacatt gaaagttaca    540
gaaggcactg ttacttttaag caagaacatt tcaaaatccg gagaaataac agttgcactt    600
gatgacactg actctagcgg caataaaaaa tccggaacat gggattcaga tacttctact    660
ttaacaatta gtaaaaacag tcaaaaaact aaacaacttg tattcacaaa agaaaacaca    720
```

| | |
|---|---:|
| ataacagtac aaaactataa cagagcaggc aatgcgcttg aaggcagccc agctgaaatt | 780 |
| aaagatcttg cagagcttaa agccgcttta aaataa | 816 |

<210> SEQ ID NO 47
<211> LENGTH: 829
<212> TYPE: DNA
<213> ORGANISM: Artificial Sequence
<220> FEATURE:
<223> OTHER INFORMATION: Synthetic oligonucleotide

<400> SEQUENCE: 47

| | |
|---|---:|
| catatgcgtc tgttgatcgg ctttgctttg gcgctggctt taatcggctg tgcacagaaa | 60 |
| ggtgctgagt ctattggttc cgtttctgta gatctgcccg ggggtatgaa agttctggta | 120 |
| agcaaagaaa aagacaaaaa cggtaaatac agcctgatgg caaccgtaga aaagctggag | 180 |
| cttaaaggca cttctgataa aaacaacggt tctggcaccc tggaaggtga aaaaactaac | 240 |
| aaaagcaaag taaagcttac tattgctgag gatctgagca aaaccacctt tgaaatcttc | 300 |
| aaagaagatg gcaaaactct ggtatctaaa aaagtaaccc tgaaagacaa gtcttctacc | 360 |
| gaagaaaaat tcaacgaaaa gggtgaaatc tctgaaaaaa ctatcgtaat ggcaaatggt | 420 |
| acccgtctgg aatacaccga catcaaaagc gataaaaccg gcaaagctaa atacgttctg | 480 |
| aaagacttta ctctggaagg cactctggct gctgacggca aaaccactct gaaagttacc | 540 |
| gaaggcactg ttactctgag catgaacatt tctaaatccg gcgaaatcac cgttgcactg | 600 |
| gatgacactg actctagcgg caataaaaaa tccggcaccct gggattctga tacttctact | 660 |
| ttaaccatta gcaaaaacag ccagaaaact aaacagctgg tattcaccaa agaaaacact | 720 |
| atcaccgtac agaactataa ccgtgcaggc aatgcgctgg aaggcagccc ggctgaaatt | 780 |
| aaagatctgg cagagctgaa agccgctttg aaataagctg agcggatcc | 829 |

<210> SEQ ID NO 48
<211> LENGTH: 829
<212> TYPE: DNA
<213> ORGANISM: Artificial Sequence
<220> FEATURE:
<223> OTHER INFORMATION: Synthetic oligonucleotide

<400> SEQUENCE: 48

| | |
|---|---:|
| ggatccgctc agcttatttc agcgcgtttt tcagttcatc aagggtttta atttcgactg | 60 |
| ccgtgccttc taagttggtg cctgcggagt cgtatttctg cacagtgatc gtgtcttgtt | 120 |
| tagtgaacac cagctgggta gttttttttgc tgttaacgct aatggttaaa gtagaagttt | 180 |
| tggaattcca cgctgcagtt ttttagtcg cagcgctgct gtcagtgtcg ttcagttcaa | 240 |
| cggaaacttc accagatttg gagatattca tgctcagagt aacggtgcct tccttgactt | 300 |
| ccaaggtggt tttatcatta gccactttgc cttccagagt gaagtttttc agaacatatt | 360 |
| tcgctttacc ggtaccatcg cttttaatac cggtgtattc aagacgggtg ccgtctgcca | 420 |
| tggtgatgat cttttcagac acctcacctt ttttcgttgaa tttttcttcc gtagaggact | 480 |
| tgtctttgga agttactttt ttggacacga gggtcttgcc atcctctttg aaaacttcca | 540 |
| gcgtggtctg accgagatcg tcagagatcg taagctttac tttgctcttg ttagttttga | 600 |
| cgccctccag cacaccagag ccgttgtttt tatcagaagt acctttcagc tccagctttgt | 660 |
| cgacggttgc gatgagatcg tacttgccgt tcttgtcttt ttctttgctc accagaacct | 720 |
| tcatttcacc gggcagatct acagaaacgg aaccaatag ctcagcacct ttctgtgcgc | 780 |
| agccgatcag agccagcgcc agagcaaagc cgatcaacag acgcatatg | 829 |

<210> SEQ ID NO 49
<211> LENGTH: 832
<212> TYPE: DNA
<213> ORGANISM: Artificial Sequence
<220> FEATURE:
<223> OTHER INFORMATION: Synthetic oligonucleotide

<400> SEQUENCE: 49

```
ggatccgctc agcttatttc agagcgtttt tcagttcatc cagggttttg atttcgactg      60
cgttgccttc gaggttggtg cccgcagagt cgtatttctg gacggtgatg gtgtcttctt     120
tggtgaacac gatgttttta gttttttttgg aattcacgct gatggtcaga gtggaagtgt    180
tagaatccca tttgccggtt ttttagtgg cctgagtggt gtcagagtca tccagcgcaa      240
cggtgatttc accggatttt aagatgttca tgcttaaaac aacagtgcct tcggtaactt     300
tcaaggtggt tttgccgtcg gcagcgaggg tgccttccag ggtgaagtct ttcagaacgt     360
atttggcttt gccggagcca tcgcttttga tgtcggtgta ttccagacgg gtaccatttg     420
ccattacgat ggttttttca gaggtttcac ccttttcgtt gaattttttct tcggtagagg    480
acttgtcttt cagggtcact tttttggata ctaaggtttt ggcatcttct ttgaaaattt     540
cgaatttggt ctggctgagg tcatcagcaa tggtcagttt cactttgctt ttgttagttt     600
tttcaccttc cagggtgccg gaaccgttgt tttatcaga ggtgcctttc agctcaagct      660
tgtcgacggt cgcctcgagg ctgtatttac cgttttttgtc tttttctttg ctgaccagaa    720
cggtcatgcc accgggcaga tctacagaaa cggaaccaat agactcagca cctttctgtg    780
cgcagccgat cagagccagc gccagagcaa agccgatcaa cagacgcata tg             832
```

<210> SEQ ID NO 50
<211> LENGTH: 829
<212> TYPE: DNA
<213> ORGANISM: Artificial Sequence
<220> FEATURE:
<223> OTHER INFORMATION: Synthetic oligonucleotide

<400> SEQUENCE: 50

```
ggatccgctc agcttatttc aaagcggctt tcagctctgc cagatcttta atttcagccg      60
ggctgccttc cagcgcattg cctgcacggt tatagttctg tacggtgata gtgttttctt     120
tggtgaatac cagctgttta gttttctggc tgttttttgct aatggttaaa gtagaagtat    180
cagaatccca ggtgccggat ttttattgc cgctagagtc agtgtcatcc agtgcaacgg      240
tgatttcgcc ggatttagaa atgttcatgc tcagagtaac agtgccttcg gtaactttca     300
gagtggtttt gccgtcagca gccagagtgc cttccagagt aaagtctttc agaacgtatt     360
tagctttgcc ggttttatcg cttttgatgt cggtgtattc cagacgggta ccatttgcca     420
ttacgatagt ttttcagag atttcaccct tttcgttgaa ttttttcttcg gtagaagact    480
tgtctttcag ggttactttt ttagatacca gagttttgcc atcttctttg aagatttcaa     540
aggtggtttt gctcagatcc tcagcaatag taagctttac tttgctttg ttagttttttt    600
caccttccag ggtgccagaa ccgttgtttt tatcagaagt gcctttaagc tccagctttt    660
ctacggttgc catcaggctg tatttaccgt ttttgtcttt tctttgctt accagaactt      720
tcatacccc gggcagatct acagaaacgg aaccaataga ctcagcacct ttctgtgcac     780
agccgattaa agccagcgcc aaagcaaagc cgatcaacag acgcatatg                829
```

<210> SEQ ID NO 51
<211> LENGTH: 60

```
<212> TYPE: DNA
<213> ORGANISM: Artificial Sequence
<220> FEATURE:
<223> OTHER INFORMATION: Synthetic oligonucleotide

<400> SEQUENCE: 51
tttctgtgcg cagccgatca gagccagcgc cagagcaaag ccgatcaaca gacgcatatg    60

<210> SEQ ID NO 52
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 52
tttctgtgcc atatg                                                    15

<210> SEQ ID NO 53
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 53
agtgttttct tggtgaata ccagctgttt agttttctgg ctgttttgc                 50

<210> SEQ ID NO 54
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 54
aattcccagc tgtttagttt tctggctgtt tttgc                              35

<210> SEQ ID NO 55
<211> LENGTH: 784
<212> TYPE: DNA
<213> ORGANISM: Artificial Sequence
<220> FEATURE:
<223> OTHER INFORMATION: Synthetic oligonucleotide

<400> SEQUENCE: 55
gtataccgtg tctttccacg actcagataa ccaaggcaaa gacatctaga cgggccactt    60
tacttccaag accactcgtt tctttttctg ttcttgccgt tcatgctaga gtagcgttgg   120
cagctgttcg acctcgactt tccatgaaga ctattttgt tgccgagacc acacgacctc    180
ccgcagtttt gattgttctc gtttcatttc gaatgctaga gactgctaga gccagtctgg   240
tgcgaccttc aaaagtttct cctaccgttc tgggagcaca ggttttttca ttgaaggttt   300
ctgttcagga gatgccttct ttttaagttg cttttttccac tccacagact tttctagtag   360
tggtaccgtc tgccgtgggc agaacttatg tggccataat tttcgctacc atggccattt   420
cgctttatac aagactttt gaagtgagac cttccgtttc accgattact attttggtgg   480
aaccttcagt tccttccgtg gcaatgagac tcgtacttat agaggtttag accacttcaa   540
aggcaacttg acttgctgtg actgtcgtcg cgacgctgat tttttgacg tcgcaccatt   600 aggttttgaa gatgaaattg gtaatcgcaa ttgtcgtttt tttgatgggt cgaccacaag   660
tgatttgttc tgtgctagtg acacgtcttt atgctgaggt tgccgtggtt gaatcttccg   720
tgccgtcagc tttaatttg ggaactactt gactttttgc gcgactttat tcgactcgcc    780
```

```
<210> SEQ ID NO 56
<211> LENGTH: 787
<212> TYPE: DNA
<213> ORGANISM: Artificial Sequence
<220> FEATURE:
<223> OTHER INFORMATION: Sythetic nucleotide

<400> SEQUENCE: 56
gtataccgtg tctttccacg actcagataa ccaaggcaaa gacatctaga cgggccaccg    60
tactggcaag accagtcgtt tcttttttctg tttttgccat ttatgtcgga gctccgctgg   120
cagctgttcg aactcgactt tccgtggaga ctattttgt tgccaaggcc gtgggacctt    180
ccactttttt gattgttttc gtttcacttt gactggtaac gactactgga gtcggtctgg   240
tttaagcttt aaaagtttct ctacggtttt tggaatcata ggttttttca ctgggacttt    300
ctgttcagga gatggcttct ttttaagttg cttttcccac tttggagact tttttggtag    360
cattaccgtt taccatgggc agaccttatg tggctgtagt tttcgctacc gaggccgttt    420
cggtttatgc aagactttct gaagtgggac cttccgtggg agcgacggct gccgttttgg    480
tggaactttc aatggcttcc gtgacaacaa aattcgtact tgtagaattt taggccactt    540
tagtggcaac gcgacctact gagactgtgg tgagtccggt gattttttg gccgtttacc    600
ctaagattgt gaaggtgaga ctggtagtcg cacttaaggt tttttttgatt tttgtagcac   660
aagtggtttc ttctgtggta gtggcaggtc tttatgctga gacgcccgtg gttggagctt    720
ccgttgcgtc agctttagtt ttgggaccta cttgactttt tgcgagactt tattcgactc    780
gcctagg                                                              787

<210> SEQ ID NO 57
<211> LENGTH: 784
<212> TYPE: DNA
<213> ORGANISM: Artificial Sequence
<220> FEATURE:
<223> OTHER INFORMATION: Synthetic oligonucleotide

<400> SEQUENCE: 57
gtataccgtg tctttccacg actcagataa ccaaggcaaa gacatctaga cgggcccca    60
tactttcaag accattcgtt tcttttttctg tttttgccat ttatgtcgga ctaccgttgg   120
catcttttcg acctcgaatt tccgtgaaga ctattttgt tgccaagacc gtgggacctt    180
ccactttttt gattgttttc gtttcatttc gaatgataac gactcctaga ctcgttttgg   240
tggaaacttt agaagtttct ctacggtttt tgagaccata gatttttca ttgggacttt     300
ctgttcagaa gatggcttct ttttaagttg cttttcccac tttagagact tttttgatag    360
cattaccgtt taccatgggc agaccttatg tggctgtagt tttcgctatt ttggccgttt    420
cgatttatgc aagactttct gaaatgagac cttccgtgag accgacgact gccgttttgg    480
tgagactttc aatggcttcc gtgacaatga gactcgtact tgtaaagatt taggccgctt    540
tagtggcaac gtgacctact gtgactgaga tcgccgttat ttttaggcc gtggaccta     600
agactatgaa gatgaaattg gtaatcgttt ttgtcggtct tttgatttgt cgaccataag   660
tggtttcttt tgtgatagtg gcatgtcttg atattggcac gtccgttacg cgaccttccg   720
tcgggccgac tttaatttct agaccgtctc gactttcggc gaaactttat tcgactcgcc    780
tagg                                                                 784
```

```
<210> SEQ ID NO 58
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 58
agtgttttct ttggtgaata ccagctgttt g                              31

<210> SEQ ID NO 59
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 59
tatgcgtctg ttgatcggct tgctctggc gctggctctg atcgg                45

<210> SEQ ID NO 60
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 60
ctgcgcacag aaaggtgctg agtctattgg ttccgtttct gtagatctgc          50

<210> SEQ ID NO 61
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 61
ccggtgaaat gaaggttctg gtgagcaaag aaaaagacaa gaacggcaag          50

<210> SEQ ID NO 62
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 62
tacgatctca tcgcaaccgt cgacaagctg gagctgaaag gtacttctga          50

<210> SEQ ID NO 63
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 63
taaaaacaac ggctctggtg tgctggaggg cgtcaaaact aacaagagca aagtaa   56

<210> SEQ ID NO 64
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 64
```

```
agctttactt tgctcttgtt agttttgacg ccctccagca                          40

<210> SEQ ID NO 65
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 65
caccagagcc gttgttttta tcagaagtac ctttcagctc cagcttgtcg               50

<210> SEQ ID NO 66
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 66
acggttgcga tgagatcgta cttgccgttc ttgtcttttt ctttgctcac               50

<210> SEQ ID NO 67
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 67
cagaaccttc atttcaccgg gcagatctac agaaacggaa ccaatagact               50

<210> SEQ ID NO 68
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 68
cagcaccttt ctgtgcgcag ccgatcagag ccagcgccag agcaaagccg atcaacagac   60
gca                                                                  63

<210> SEQ ID NO 69
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 69
agcttacgat ctctgacgat ctcggtcaga ccac                                34

<210> SEQ ID NO 70
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 70
gctggaagtt ttcaaagagg atggcaagac cctcgtgtcc aaaaaagtaa               50

<210> SEQ ID NO 71
<211> LENGTH: 50
```

```
<212> TYPE: DNA
<213> ORGANISM: Artificial Sequence
<220> FEATURE:
<223> OTHER INFORMATION: Synthetic oligonucleotide

<400> SEQUENCE: 71
cttccaaaga caagtcctct acggaagaaa aattcaacga aaaaggtgag            50

<210> SEQ ID NO 72
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 72
gtgtctgaaa agatcatcac catggcagac ggcacccgtc                       40

<210> SEQ ID NO 73
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 73
ttgaatacac cggtattaaa agcgatggta c                                31

<210> SEQ ID NO 74
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 74
catcgctttt aataccggtg tattcaagac gggtgccgtc tgccatg               47

<210> SEQ ID NO 75
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 75
gtgatgatct tttcagacac ctcacctttt tcgttgaatt tttcttccgt            50

<210> SEQ ID NO 76
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 76
agaggacttg tctttggaag ttactttttt ggacacgagg gtcttgccat            50

<210> SEQ ID NO 77
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 77
cctctttgaa aacttccagc gtggtctgac cgagatcgtc agagatcgta            50
```

```
<210> SEQ ID NO 78
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 78
cggtaaagcg aaatatgttc tgaaaaactt cactctgga                           39

<210> SEQ ID NO 79
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 79
aggcaaagtg gctaatgata aaccaccttt ggaagtcaag gaaggcaccg               50

<210> SEQ ID NO 80
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 80
ttactctgag catgaatatc tccaaatctg gtgaagtttc cgttgaactg               50

<210> SEQ ID NO 81
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 81
aacgacactg acagcagcgc tgcgactaaa aaaactgcag cgtgg                    45

<210> SEQ ID NO 82
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 82
aattccacgc tgcagttttt ttagtcgca                                      29

<210> SEQ ID NO 83
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 83
gcgctgctgt cagtgtcgtt cagttcaacg gaaacttcac cagatttgga               50

<210> SEQ ID NO 84
<211> LENGTH: 50
<212> TYPE: DNA
<213> ORGANISM: Artificial Sequence
<220> FEATURE:
<223> OTHER INFORMATION: Synthetic oligonucleotide
```

```
<400> SEQUENCE: 84
gatattcatg ctcagagtaa cggtgccttc cttgacttcc aaggtggttt              50

<210> SEQ ID NO 85
<211> LENGTH: 63
<212> TYPE: DNA
<213> ORGANISM: Artificial Sequence
<220> FEATURE:
<223> OTHER INFORMATION: Synthetic oligonucleotide

<400> SEQUENCE: 85
tatcattagc cactttgcct tccagagtga agtttttcag aacatatttc gctttaccgg   60
tac                                                                63

<210> SEQ ID NO 86
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 86
aattccaaaa cttctacttt aaccattagc gttaacagca aaaa                   45

<210> SEQ ID NO 87
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 87
actacccagc tggtgttcac taaacaagac acgatcactg tgcagaaata              50

<210> SEQ ID NO 88
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 88
cgactccaac ggcaccaact tagaaggcac ggcagtcgaa attaaaccc               50

<210> SEQ ID NO 89
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 89
ttgatgaact gaaaacgcg ctgaaataag ctgagcg                            37

<210> SEQ ID NO 90
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 90
gatccgctca gcttatttca gcgcgttttt cagttcatca agggttttaa tttcgactgc   60
c                                                                  61
```

<210> SEQ ID NO 91
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 91
gtgccttcta agttggtgcc gttggagtcg tatttctgca cagtgatcgt        50

<210> SEQ ID NO 92
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 92
gtcttgttta gtgaacacca gctgggtagt tttttgctg ttaacgctaa         50

<210> SEQ ID NO 93
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 93
tggttaaagt agaagttttg g                                       21

<210> SEQ ID NO 94
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 94
tatgcgtctg ttgatcggct ttgctttggc gctggcttta atcggctg          48

<210> SEQ ID NO 95
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 95
tgcacagaaa ggtgctgagt ctattggttc cgtttctgta gatctgcccg        50

<210> SEQ ID NO 96
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 96
ggggtatgaa agttctggta agcaaagaaa aagacaaaaa cggtaaatac        50

<210> SEQ ID NO 97
<211> LENGTH: 50
<212> TYPE: DNA
<213> ORGANISM: Artificial Sequence
<220> FEATURE:
<223> OTHER INFORMATION: Synthetic oligonucleotide

```
<400> SEQUENCE: 97
agcctgatgg caaccgtaga aaagctggag cttaaaggca cttctgataa        50

<210> SEQ ID NO 98
<211> LENGTH: 53
<212> TYPE: DNA
<213> ORGANISM: Artificial Sequence
<220> FEATURE:
<223> OTHER INFORMATION: Synthetic oligonucleotide

<400> SEQUENCE: 98
aaacaacggt tctggcaccc tggaaggtga aaaaactaac aaaagcaaag taa    53

<210> SEQ ID NO 99
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 99
agctttactt tgcttttgtt agttttttca ccttcca                      37

<210> SEQ ID NO 100
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 100
gggtgccaga accgttgttt ttatcagaag tgcctttaag ctccagcttt        50

<210> SEQ ID NO 101
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 101
tctacggttg ccatcaggct gtatttaccg ttttgtctt tttctttgct         50

<210> SEQ ID NO 102
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 102
taccagaact ttcataccc cgggcagatc tacagaaacg gaaccaatag         50

<210> SEQ ID NO 103
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 103
actcagcacc tttctgtgca cagccgatta                              30

<210> SEQ ID NO 104
<211> LENGTH: 36
```

```
<212> TYPE: DNA
<213> ORGANISM: Artificial Sequence
<220> FEATURE:
<223> OTHER INFORMATION: Synthetic oligonucleotide

<400> SEQUENCE: 104
aagccagcgc caaagcaaag ccgatcaaca gacgca                              36

<210> SEQ ID NO 105
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 105
agcttactat tgctgaggat ctgagcaaaa ccacctttga aatcttc                  47

<210> SEQ ID NO 106
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 106
aaagaagatg gcaaaactct ggtatctaaa aaagtaaccc tgaaagacaa               50

<210> SEQ ID NO 107
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 107
gtcttctacc gaagaaaaat tcaacgaaaa gggtgaaatc                          40

<210> SEQ ID NO 108
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 108
tctgaaaaaa ctatcgtaat ggcaaatggt ac                                  32

<210> SEQ ID NO 109
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 109
aaggtggttt tgctcagatc ctcagcaata gta                                 33

<210> SEQ ID NO 110
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 110
agagttttgc catcttcttt gaagatttca                                     30
```

<210> SEQ ID NO 111
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 111
atttttcttc ggtagaagac ttgtctttca gggttacttt tttagatacc            50

<210> SEQ ID NO 112
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 112
catttgccat tacgatagtt ttttcagaga tttcacccct ttcgttga              48

<210> SEQ ID NO 113
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 113
ccgtctggaa tacaccgaca tcaaaagcga taaaaccggc aaagctaa              48

<210> SEQ ID NO 114
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 114
atacgttctg aaagacttta ctctggaagg cactctggct gctgacggca            50

<210> SEQ ID NO 115
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 115
aaaccactct gaaagttacc gaaggcactg ttactctgag catgaacatt            50

<210> SEQ ID NO 116
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 116
tctaaatccg gcgaaatcac cgttgcactg gatgacactg actctagcgg            50

<210> SEQ ID NO 117
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 117
caataaaaaa tccggcacct gggattctga tacttctact ttaaccatta                50

<210> SEQ ID NO 118
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 118
gcaaaaacag ccagaaaact aaacagctgg g                                    31

<210> SEQ ID NO 119
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 119
gcttttgatg tcggtgtatt ccagacgggt ac                                   32

<210> SEQ ID NO 120
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 120
ccttccagag taaagtcttt cagaacgtat ttagctttgc cggttttatc                50

<210> SEQ ID NO 121
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 121
cagtgccttc ggtaactttc agagtggttt tgccgtcagc agccagagtg                50

<210> SEQ ID NO 122
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 122
cagtgcaacg gtgatttcgc cggatttaga aatgttcatg ctcagagtaa                50

<210> SEQ ID NO 123
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 123
tcagaatccc aggtgccgga ttttttattg ccgctagagt cagtgtcatc                50

<210> SEQ ID NO 124
<211> LENGTH: 55

```
<212> TYPE: DNA
<213> ORGANISM: Artificial Sequence
<220> FEATURE:
<223> OTHER INFORMATION: Synthetic oligonucleotide

<400> SEQUENCE: 124
aattcccagc tgtttagttt tctggctgtt tttgctaatg gttaaagtag aagta        55

<210> SEQ ID NO 125
<211> LENGTH: 45
<212> TYPE: DNA
<213> ORGANISM: Artificial Sequence
<220> FEATURE:
<223> OTHER INFORMATION: Synthetic oligonucleotide

<400> SEQUENCE: 125
aattcaaaca gctggtattc accaaagaaa acactatcac cgtac                   45

<210> SEQ ID NO 126
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 126
agaactataa ccgtgcaggc aatgcgctgg aaggcagccc                         40

<210> SEQ ID NO 127
<211> LENGTH: 54
<212> TYPE: DNA
<213> ORGANISM: Artificial Sequence
<220> FEATURE:
<223> OTHER INFORMATION: Synthetic oligonucleotide

<400> SEQUENCE: 127
ggctgaaatt aaagatctgg cagagctgaa agccgctttg aaataagctg agcg         54

<210> SEQ ID NO 128
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 128
gatccgctca gcttatttca aagcggct                                      28

<210> SEQ ID NO 129
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 129
ttcagctctg ccagatcttt aatttcagcc gggctgcctt ccagcgcatt              50

<210> SEQ ID NO 130
<211> LENGTH: 61
<212> TYPE: DNA
<213> ORGANISM: Artificial Sequence
<220> FEATURE:
<223> OTHER INFORMATION: Synthetic oligonucleotide

<400> SEQUENCE: 130
gcctgcacgg ttatagttct gtacggtgat agtgttttct ttggtgaata ccagctgttt   60
```

```
g                                                              61

<210> SEQ ID NO 131
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 131
tatgcgtctg ttgatcggct tgctctggc gctggctctg atcggctg          48

<210> SEQ ID NO 132
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 132
cgcacagaaa ggtgctgagt ctattggttc cgtttctgta gatctgcccg        50

<210> SEQ ID NO 133
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 133
gtggcatgac cgttctggtc agcaaagaaa aagacaaaaa cg                42

<210> SEQ ID NO 134
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 134
gtaaatacag cctcgaggcg accgtcgaca                              30

<210> SEQ ID NO 135
<211> LENGTH: 56
<212> TYPE: DNA
<213> ORGANISM: Artificial Sequence
<220> FEATURE:
<223> OTHER INFORMATION: Synthetic oligonucleotide

<400> SEQUENCE: 135
agcttgtcga cggtcgcctc gaggctgtat ttaccgtttt tgtcttttc tttgct  56

<210> SEQ ID NO 136
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 136
gaccagaacg gtcatgccac cgggcagatc tacagaaacg                   40

<210> SEQ ID NO 137
<211> LENGTH: 50
<212> TYPE: DNA
<213> ORGANISM: Artificial Sequence
```

```
<220> FEATURE:
<223> OTHER INFORMATION: Synthetic oligonucleotide

<400> SEQUENCE: 137
gaaccaatag actcagcacc tttctgtgcg cagccgatca gagccagcgc            50

<210> SEQ ID NO 138
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 138
cagagcaaag ccgatcaaca gacgca                                      26

<210> SEQ ID NO 139
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 139
agcttgagct gaaaggcacc tctgataaaa acaacggttc cggcaccctg            50

<210> SEQ ID NO 140
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 140
gaaggtgaaa aaactaacaa aagcaaagtg aaactgacca ttgctgat              48

<210> SEQ ID NO 141
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 141
gacctcagcc agaccaaatt cgaaattttc aaagaagatg ccaaaacctt            50

<210> SEQ ID NO 142
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 142
agtatccaaa aaagtgaccc tgaaagacaa gtcctctacc gaagaaaat             50

<210> SEQ ID NO 143
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 143
tcaacgaaaa gggtgaaacc tctgaaaaaa ccatcgtaat ggcaaatggt ac         52
```

```
<210> SEQ ID NO 144
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 144
catttgccat tacgatggtt ttttcaga                                    28

<210> SEQ ID NO 145
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 145
ggtttcaccc ttttcgttga atttttcttc ggtagaggac                       40

<210> SEQ ID NO 146
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 146
ttgtctttca gggtcacttt tttggatact aaggttttgg catcttcttt            50

<210> SEQ ID NO 147
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 147
gaaaatttcg aatttggtct ggctgaggtc atcagcaatg gtcagtttca            50

<210> SEQ ID NO 148
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 148
ctttgctttt gttagttttt tcaccttcca gggtgccgga                       40

<210> SEQ ID NO 149
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 149
accgttgttt ttatcagagg tgcctttcag ctca                             34

<210> SEQ ID NO 150
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 150
```

```
ccgtctggaa tacaccgaca tcaaaagcga tggctccggc aaagccaa          48
```

<210> SEQ ID NO 151
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 151

```
atacgttctg aaagacttca ccctggaagg caccctcgct gccgacgg          48
```

<210> SEQ ID NO 152
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 152

```
caaaaccacc ttgaaagtta ccgaaggcac tgttgtttta ag                42
```

<210> SEQ ID NO 153
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 153

```
catgaacatc ttaaaatccg gtgaaatcac cgttgcgctg                   40
```

<210> SEQ ID NO 154
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 154

```
gatgactctg acaccactca ggccactaaa aaaaccggca aatgggattc        50
```

<210> SEQ ID NO 155
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 155

```
taacacttcc actctgacca tcagcgtg                                28
```

<210> SEQ ID NO 156
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 156

```
aattcacgct gatggtcaga gtggaagtgt tagaatccca tttgccg           47
```

<210> SEQ ID NO 157
<211> LENGTH: 55
<212> TYPE: DNA
<213> ORGANISM: Artificial Sequence

```
<220> FEATURE:
<223> OTHER INFORMATION: Synthetic oligonucleotide

<400> SEQUENCE: 157 gttttttag tggcctgagt ggtgtcagag tcatccagcg caacggtgat ttcac        55

<210> SEQ ID NO 158
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 158 cggatttaa gatgttcatg cttaaaacaa cagtgccttc ggtaactttc              50

<210> SEQ ID NO 159
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 159
aaggtggttt tgccgtcggc agcgagggtg ccttccaggg                        40

<210> SEQ ID NO 160
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 160
tgaagtcttt cagaacgtat ttggctttgc cggagccatc                        40

<210> SEQ ID NO 161
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 161
gcttttgatg tcggtgtatt ccagacgggt ac                                32

<210> SEQ ID NO 162
<211> LENGTH: 52
<212> TYPE: DNA
<213> ORGANISM: Artificial Sequence
<220> FEATURE:
<223> OTHER INFORMATION: Synthetic oligonucleotide

<400> SEQUENCE: 162
aattccaaaa aaactaaaaa catcgtgttc accaagaag acaccatcac cg           52

<210> SEQ ID NO 163
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 163
tccagaaata cgactctgcg ggcaccaacc tcgaaggcaa cgcagtcgaa             50
```

```
<210> SEQ ID NO 164
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 164
atcaaaaccc tggatgaact gaaaaacgct ctgaaataag ctgagcg            47

<210> SEQ ID NO 165
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 165
gatccgctca gcttatttca gagcgttttt cagttcatcc agggttttga tttcgactgc   60
gttgccttcg a                                                       71

<210> SEQ ID NO 166
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 166
ggttggtgcc cgcagagtcg tatttctgga cggtgatggt gtcttctttg            50

<210> SEQ ID NO 167
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 167
gtgaacacga tgtttttagt tttttttgg                                   28

<210> SEQ ID NO 168
<211> LENGTH: 822
<212> TYPE: DNA
<213> ORGANISM: Artificial Sequence
<220> FEATURE:
<223> OTHER INFORMATION: Synthetic oligonucleotide

<400> SEQUENCE: 168
atgaaaaaat atttattggg aataggtcta atattagcct taatagcatg taagcaaaat   60
gttagcagcc ttgacgagaa aaacagcgtt tcagtagatt tgcctggtga aatgaaagtt  120
cttgtaagca agaaaaaaaa caaagacggc aagtacgatc taattgcaac agtagacaag  180
cttgagctta aggaacttc tgataaaaac aatggatctg gagtacttga aggcgtaaaa  240
gctgacaaaa gtaaagtaaa attaacaatt tctgacgatc taggtcaaac cacacttgaa  300
gttttcaaag aagatggcaa aacactagta tcaaaaaaag taacttccaa agacaagtca  360
tcaacagaag aaaaattcaa tgaaaaaggt gaagtatctg aaaaaataat aacaagagca  420
gacggaacca gacttgaata cacaggaatt aaaagcgatg gatctggaaa agctaaagag  480 gtttttaaaaa actttactct tgaaggaaaa gtagctaatg ataaagtaac attggaagta  540
aaagaaggaa ccgttacttt aagtaaaaat atttcaaaat ctggggaagt ttcagttgaa  600
cttaatgaca ctgacagtag tgctgctact aaaaaaactg cagcttggaa ttcaaaaact  660
```

```
tctactttaa caattagtgt taacagcaaa aaaactacac aacttgtgtt tactaaacaa      720
gacacaataa ctgtacaaaa atacgactcc gcaggtacca atttagaagg cacagcagtc      780
gaaattaaaa cacttgatga acttaaaaac gctttaaaat ag                         822
```

<210> SEQ ID NO 169  
<211> LENGTH: 273  
<212> TYPE: PRT  
<213> ORGANISM: Artificial Sequence  
<220> FEATURE:  
<223> OTHER INFORMATION: Synthetic peptide

<400> SEQUENCE: 169

```
Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Glu Met Lys Val Leu Val Ser Lys Glu Lys Asn Lys
        35                  40                  45

Asp Gly Lys Tyr Asp Leu Ile Ala Thr Val Asp Lys Leu Glu Leu Lys
    50                  55                  60

Gly Thr Ser Asp Lys Asn Asn Gly Ser Gly Val Leu Glu Gly Val Lys
65                  70                  75                  80

Ala Asp Lys Ser Lys Val Lys Leu Thr Ile Ser Asp Asp Leu Gly Gln
                85                  90                  95

Thr Thr Leu Glu Val Phe Lys Gly Asp Gly Lys Thr Leu Val Ser Lys
            100                 105                 110

Lys Val Thr Ser Lys Asp Lys Ser Ser Thr Glu Glu Lys Phe Asn Glu
        115                 120                 125

Lys Gly Glu Val Ser Glu Lys Ile Ile Thr Arg Ala Asp Gly Thr Arg
    130                 135                 140

Leu Glu Tyr Thr Gly Ile Lys Ser Asp Gly Ser Gly Lys Ala Lys Glu
145                 150                 155                 160

Val Leu Lys Asn Phe Thr Leu Glu Gly Lys Val Ala Asn Asp Lys Val
                165                 170                 175

Thr Leu Glu Val Lys Glu Gly Thr Val Thr Leu Ser Lys Asn Ile Ser
            180                 185                 190

Lys Ser Gly Glu Val Ser Val Glu Leu Asn Asp Thr Asp Ser Ser Ala
        195                 200                 205

Ala Thr Lys Lys Thr Ala Ala Trp Asn Ser Lys Thr Ser Thr Leu Thr
    210                 215                 220

Ile Ser Val Asn Ser Lys Lys Thr Thr Gln Leu Val Phe Thr Lys Gln
225                 230                 235                 240

Asp Thr Ile Thr Val Gln Lys Tyr Asp Ser Ala Gly Thr Asn Leu Glu
                245                 250                 255

Gly Thr Ala Val Glu Ile Lys Thr Leu Asp Glu Leu Lys Asn Ala Leu
            260                 265                 270

Lys
```

<210> SEQ ID NO 170  
<211> LENGTH: 825  
<212> TYPE: DNA  
<213> ORGANISM: Artificial Sequence  
<220> FEATURE:  
<223> OTHER INFORMATION: Synthetic oligonucleotide

<400> SEQUENCE: 170

-continued

```
atgaaaaaat atttattggg aataggtcta atattagcct aatagcatg taagcaaaat      60 gttagcacgc ttgatgaaaa aaatagcgtt tcagtagatt tacctggtgg aatgacagtt    120
cttgtaagta aagaaaaaga caaagacggt aaatacagtc tagaggcaac agtagacaag    180
cttgagctta aaggaacttc tgataaaaac aacggttctg gaacacttga aggtgaaaaa    240
actgacaaaa gtaaagtaaa attaacaatt gctgatgacc taagtcaaac taaatttgaa    300
attttcaaag aagatgccaa aacattagta tcaaaaaaag taaccettaa agacaagtca    360 tcaacagaag aaaaattcaa cgaaagggt gaaacatctg aaaaaacaat agtaagagca     420
aatggaacca gacttgaata cacagacata aaaagcgatg gatccggaaa agctaaagaa    480
gttttaaaag actttactct tgaaggaact ctagctgctg acggcaaaac aacattgaaa    540
gttacagaag gcactgttgt tttaagcaag aacattttaa aatccggaga ataacagtt     600 gcacttgatg actctgacac tactcaggct actaaaaaaa ctggaaaatg ggattcaaat    660
acttccactt taacaattag tgtgaatagc aaaaaaacta aaaacattgt atttacaaaa    720
gaagacacaa taacagtaca aaaatacgac tcagcaggca ccaatctaga aggcaacgca    780
gtcgaaatta aaacacttga tgaacttaaa aacgctttaa aataa                    825
```

<210> SEQ ID NO 171
<211> LENGTH: 274
<212> TYPE: PRT
<213> ORGANISM: Artificial Sequence
<220> FEATURE:
<223> OTHER INFORMATION: Synthetic peptide

<400> SEQUENCE: 171

```
Met Lys Lys Tyr Leu Leu Gly Ile Gly Leu Ile Leu Ala Leu Ile Ala
1               5                   10                  15

Cys Lys Gln Asn Val Ser Thr Leu Asp Glu Lys Asn Ser Val Ser Val
                20                  25                  30

Asp Leu Pro Gly Gly Met Thr Val Leu Val Ser Lys Glu Lys Asp Lys
            35                  40                  45

Asp Gly Lys Tyr Ser Leu Glu Ala Thr Val Asp Lys Leu Glu Leu Lys
        50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Asp Asp Leu Ser Gln
                85                  90                  95

Thr Lys Phe Glu Ile Phe Lys Glu Asp Ala Lys Thr Leu Val Ser Lys
                100                 105                 110

Lys Val Thr Leu Lys Asp Lys Ser Ser Thr Glu Glu Lys Phe Asn Glu
            115                 120                 125

Lys Gly Glu Thr Ser Glu Lys Thr Ile Val Arg Ala Asn Gly Thr Arg
        130                 135                 140

Leu Glu Tyr Thr Asp Ile Lys Ser Asp Gly Ser Gly Lys Ala Lys Glu
145                 150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Val Leu Ser Lys Asn Ile
                180                 185                 190

Leu Lys Ser Gly Glu Ile Thr Val Ala Leu Asp Asp Ser Asp Thr Thr
            195                 200                 205

Gln Ala Thr Lys Lys Thr Gly Lys Trp Asp Ser Asn Thr Ser Thr Leu
        210                 215                 220
```

```
Thr Ile Ser Val Asn Ser Lys Lys Thr Lys Asn Ile Val Phe Thr Lys
225                 230                 235                 240

Glu Asp Thr Ile Thr Val Gln Lys Tyr Asp Ser Ala Gly Thr Asn Leu
            245                 250                 255

Glu Gly Asn Ala Val Glu Ile Lys Thr Leu Asp Glu Leu Lys Asn Ala
            260                 265                 270

Leu Lys

<210> SEQ ID NO 172
<211> LENGTH: 822
<212> TYPE: DNA
<213> ORGANISM: Artificial Sequence
<220> FEATURE:
<223> OTHER INFORMATION: Synthetic oligonucleotide

<400> SEQUENCE: 172
atgaaaaaat atttattggg aataggtcta atattagcct taatagcatg taagcaaaat      60
gttagcagcc ttgatgaaaa aaatagcgtt tcagtagatt tacctggtgg aatgaaagtt     120
cttgtaagta agaaaaaga caaagatggt aaatacagtc taatggcaac agtagaaaag     180
cttgagctta aggaacttc tgataaaaac aacggttctg gaacacttga aggtgaaaaa     240
actgacaaaa gtaaagtaaa attaacaatt gctgaggatc taagtaaaac cacatttgaa     300
atcttcaaag aagatggcaa acattagta tcaaaaaaag taaccttaa agacaagtca      360 tcaacagaag aaaaattcaa cgaaagggt gaaatatctg aaaaaacaat agtaagagca     420
aatggaacca gacttgaata cacagacata aaaagcgata aaaccggaaa agctaaagaa     480
gttttaaaag actttactct tgaaggaact ctagctgctg acggcaaaac aacattgaaa     540
gttacagaag gcactgttac tttaagcaag aacatttcaa aatccggaga ataacagtt     600 gcacttgatg acactgactc tagcggcaat aaaaaatccg gaacatggga ttcagatact     660
tctactttaa caattagtaa aaacagtcaa aaaactaaac aacttgtatt cacaaaagaa     720
aacacaataa cagtacaaaa ctataacaga gcaggcaatg cgcttgaagg cagcccagct     780
gaaattaaag atcttgcaga gcttaaagcc gctttaaaat aa                        822

<210> SEQ ID NO 173
<211> LENGTH: 273
<212> TYPE: PRT
<213> ORGANISM: Artificial Sequence
<220> FEATURE:
<223> OTHER INFORMATION: Synthetic peptide

<400> SEQUENCE: 173

Met Lys Lys Tyr Leu Leu Gly Ile Gly Leu Ile Leu Ala Leu Ile Ala
1               5                   10                  15

Cys Lys Gln Asn Val Ser Ser Leu Asp Glu Lys Asn Ser Val Ser Val
            20                  25                  30

Asp Leu Pro Gly Gly Met Lys Val Leu Val Ser Lys Glu Lys Asp Lys
        35                  40                  45

Asp Gly Lys Tyr Ser Leu Met Ala Thr Val Glu Lys Leu Glu Leu Lys
    50                  55                  60

Gly Thr Ser Asp Lys Asn Asn Gly Ser Gly Thr Leu Glu Gly Glu Lys
65                  70                  75                  80

Thr Asp Lys Ser Lys Val Lys Leu Thr Ile Ala Glu Asp Leu Ser Lys
                85                  90                  95

Thr Thr Phe Glu Ile Phe Lys Glu Asp Gly Lys Thr Leu Val Ser Lys
            100                 105                 110
```

```
Lys Val Thr Leu Lys Asp Lys Ser Ser Thr Glu Glu Lys Phe Asn Glu
        115                 120                 125

Lys Gly Glu Ile Ser Glu Lys Thr Ile Val Arg Ala Asn Gly Thr Arg
        130                 135                 140

Leu Glu Tyr Thr Asp Ile Lys Ser Asp Lys Thr Gly Lys Ala Lys Glu
145                     150                 155                 160

Val Leu Lys Asp Phe Thr Leu Glu Gly Thr Leu Ala Ala Asp Gly Lys
                165                 170                 175

Thr Thr Leu Lys Val Thr Glu Gly Thr Val Thr Leu Ser Lys Asn Ile
            180                 185                 190

Ser Lys Ser Gly Glu Ile Thr Val Ala Leu Asp Asp Thr Asp Ser Ser
        195                 200                 205

Gly Asn Lys Lys Ser Gly Thr Trp Asp Ser Asp Thr Ser Thr Leu Thr
        210                 215                 220

Ile Ser Lys Asn Ser Gln Lys Thr Lys Gln Leu Val Phe Thr Lys Glu
225                 230                 235                 240

Asn Thr Ile Thr Val Gln Asn Tyr Asn Arg Ala Gly Asn Ala Leu Glu
                245                 250                 255

Gly Ser Pro Ala Glu Ile Lys Asp Leu Ala Glu Leu Lys Ala Ala Leu
            260                 265                 270

Lys
```